US010213451B2

(12) United States Patent
Chan et al.

(10) Patent No.: US 10,213,451 B2
(45) Date of Patent: *Feb. 26, 2019

(54) METHODS AND COMPOUNDS FOR MODULATING THE SECRETION OR EXPRESSION OF ADHESION PROTEINS OR ANGIOPOIETINS OF CELLS

(71) Applicant: PACIFIC ARROW LIMITED, Hong Kong (CN)

(72) Inventors: Pui-Kwong Chan, Sugarland, TX (US); May Sung Mak, Hong Kong (CN); Yun Wang, Dunedin (NZ)

(*) Notice: Subject to any disclaimer, the term of this patent is extended or adjusted under 35 U.S.C. 154(b) by 0 days.

This patent is subject to a terminal disclaimer.

(21) Appl. No.: 15/181,631

(22) Filed: Jun. 14, 2016

(65) Prior Publication Data
US 2016/0354397 A1    Dec. 8, 2016

Related U.S. Application Data

(66) Continuation of application No. 13/841,053, filed on Mar. 15, 2013, now Pat. No. 9,382,285, which is a continuation-in-part of application No. 13/718,575, filed on Dec. 18, 2012, now abandoned, which is a continuation-in-part of application No. PCT/US2009/034115, filed on Feb. 13, 2009, and a continuation-in-part of application No. 12/344,682, filed on Dec. 29, 2008, now Pat. No. 8,841,265, and a continuation-in-part of application No. PCT/US2008/002086, filed on Feb. 15, 2008, which is a continuation-in-part of application No. PCT/US2007/077273, filed on Aug. 30, 2007, and a continuation-in-part of application No. 11/683,198, filed on Mar. 7, 2007, now Pat. No. 8,614,197, and a continuation-in-part of application No. PCT/US2006/016158, filed on Apr. 27, 2006, and a continuation-in-part of application No. 11/289,142, filed on Nov. 28, 2005, now Pat. No. 7,488,753, and a continuation-in-part of application No. 11/267,523, filed on Nov. 4, 2005, now abandoned, and a continuation-in-part of application No. PCT/US2005/031900, filed on Sep. 7, 2005, and a continuation-in-part of application No. 11/131,551, filed on May 17, 2005, now Pat. No. 7,262,285, and a continuation-in-part of application No. 11/117,760, filed on Apr. 27, 2005, now Pat. No. 7,727,561, said application No. 13/841,053 is a continuation-in-part (Continued)

(51) Int. Cl.
| | |
|---|---|
| *A61K 31/22* | (2006.01) |
| *A61K 31/704* | (2006.01) |
| *A61K 31/216* | (2006.01) |
| *A61K 31/343* | (2006.01) |
| *A61K 31/365* | (2006.01) |
| *A61K 31/7048* | (2006.01) |

(52) U.S. Cl.
CPC .......... *A61K 31/704* (2013.01); *A61K 31/216* (2013.01); *A61K 31/22* (2013.01); *A61K 31/343* (2013.01); *A61K 31/365* (2013.01); *A61K 31/7048* (2013.01)

(58) Field of Classification Search
None
See application file for complete search history.

(56) References Cited

U.S. PATENT DOCUMENTS

| | | | | |
|---|---|---|---|---|
| 6,616,943 B2* | 9/2003 | Wang | ..................... | A61K 36/77 424/451 |
| 7,262,285 B2* | 8/2007 | Chan | ..................... | A61K 36/77 536/18.1 |

(Continued)

FOREIGN PATENT DOCUMENTS

WO    WO2005/063273    *    7/2005    ............. A61K 35/78

OTHER PUBLICATIONS

Sirtori, "Aescin: Pharmacology, Pharmacokinetics, and Therapeutic Profile" Pharmacological Research (2001) vol. 44 No. 3 pp. 183-193 (Year: 2001).*

(Continued)

*Primary Examiner* — Eric Olson
(74) *Attorney, Agent, or Firm* — Law Offices of Albert Wai-Kit Chan, PLLC

(57) ABSTRACT

This invention provides methods, processes, compounds and compositions for modulating the gene expression or secretion of adhesion proteins, angiopoietins or their receptors to cure diseases, for anti-angiogenesis and for treating parasites, wherein the adhesion proteins or receptors comprise fibronectin, integrins family, myosin, vitronectin, collagen, laminin, glycosylation cell surface proteins, polyglycans, cadherin, heparin, tenascin, CD 54, CAM, elastin and FAK; wherein the angiopoietins comprise angiopoietin 1, angiopoietin 2, angiopoietin 3, angiopoietin 4, angiopoietin 5, angiopoietin 6, angiopoietin 7, angiopoietin-like 1, angiopoietin-like 2, angiopoietin-like 3, angiopoietin-like 4, angiopoietin-like 5, angiopoietin-like 6, and angiopoietin-like 7; wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphatic cancer, pancreas cancer, stomach cancer and thyroid cancer.

18 Claims, 45 Drawing Sheets

Figure 1:
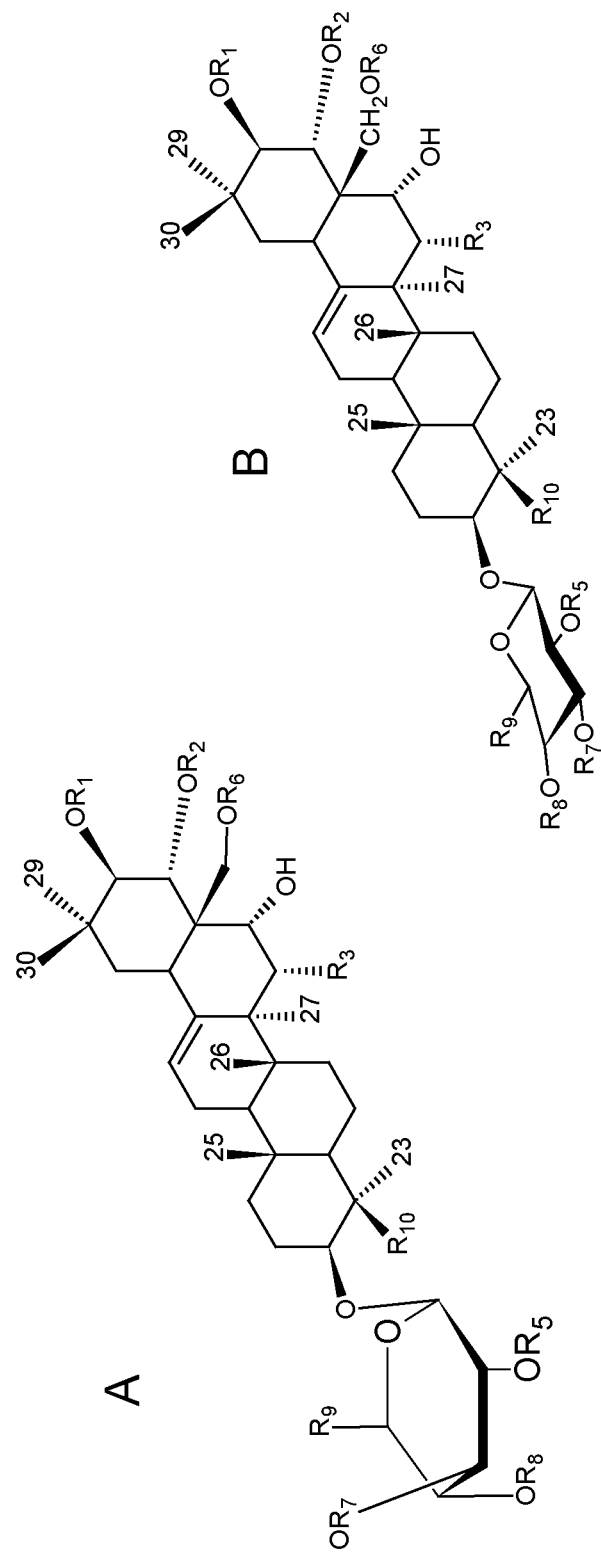

Related U.S. Application Data of application No. 11/412,659, filed on Apr. 27, 2006, now abandoned, and a continuation-in-part of application No. 10/906,303, filed on Feb. 14, 2005, now Pat. No. 7,524,824, and a continuation-in-part of application No. 11/117,745, filed on Apr. 27, 2005, now Pat. No. 7,514,412, and a continuation-in-part of application No. 12/195,112, filed on Aug. 20, 2008, now abandoned, and a continuation-in-part of application No. 12/392,795, filed on Feb. 25, 2009, now Pat. No. 8,334,269, and a continuation-in-part of application No. 12/541,713, filed on Aug. 14, 2009, now Pat. No. 8,735,558, and a continuation-in-part of application No. 12/714,598, filed on Mar. 1, 2010, now Pat. No. 8,859,012, Substitute for application No. 61/038,277, filed on Mar. 20, 2008.

(60) Provisional application No. 61/054,308, filed on May 19, 2008, provisional application No. 60/890,380, filed on Feb. 16, 2007, provisional application No. 60/947,750, filed on Jul. 3, 2007, provisional application No. 60/795,417, filed on Apr. 27, 2006, provisional application No. 60/841,727, filed on Sep. 1, 2006, provisional application No. 60/890,380, filed on Feb. 16, 2007, provisional application No. 60/675,282, filed on Apr. 27, 2005, provisional application No. 60/675,284, filed on Apr. 27, 2005, provisional application No. 60/617,379, filed on Oct. 8, 2004, provisional application No. 60/613,811, filed on Sep. 27, 2004, provisional application No. 60/607,858, filed on Sep. 7, 2004.

(56) References Cited

U.S. PATENT DOCUMENTS

| | | | | |
|---|---|---|---|---|
| 7,488,753 | B2* | 2/2009 | Chan | A61K 31/7012 514/510 |
| 7,514,412 | B2* | 4/2009 | Chan | A61K 36/77 514/33 |
| 7,524,824 | B2* | 4/2009 | Chan | A61K 36/77 514/33 |
| 7,727,561 | B2* | 6/2010 | Chan | A23L 1/3002 424/725 |
| 8,586,719 | B2* | 11/2013 | Chan | C07H 15/256 536/18.1 |
| 8,614,197 | B2* | 12/2013 | Chan | C07H 15/24 514/33 |
| 8,735,558 | B2* | 5/2014 | Chan | A61K 9/0019 536/18.1 |
| 8,785,405 | B2* | 7/2014 | Chan | A61K 31/704 514/33 |
| 8,841,265 | B2* | 9/2014 | Chan | A61K 31/7012 514/33 |
| 8,859,012 | B2* | 10/2014 | Chan | A23L 1/3002 424/725 |
| 9,382,285 | B2* | 7/2016 | Chan | A61K 31/56 |
| 9,434,677 | B2* | 9/2016 | Chan | C07H 15/24 |
| 2004/0138151 | A1* | 7/2004 | Maes | A61K 36/185 514/33 |
| 2005/0245470 | A1* | 11/2005 | Chan | A61K 36/77 514/33 |
| 2006/0122129 | A1* | 6/2006 | Chan | A61K 31/7012 514/33 |
| 2008/0058273 | A1* | 3/2008 | Yang | C07J 63/00 514/26 |
| 2017/0022246 | A1* | 1/2017 | Chan | C07J 63/008 |

OTHER PUBLICATIONS

Voutquenne et al., "Structure-Activity Relationships of Haemolytic Saponins" Pharmaceutical Biology (2002) vol. 40 No. 4 pp. 253-262 (Year: 2002).*

Germonprez et al., "In Vitro and in Vivo Anti-Leishmanial Activity of Triterpenoid Saponins Isolated from Maesa balansae and Some Chemical Derivatives" Journal of Medicinal Chemistry (2005) vol. 48 pp. 32-37 (Year: 2005).*

Aurada et al., "Struktur der Triterpen-Sapogenine von Aesculus glabra" Planta Medica (1984) pp. 391-394 (Year: 1984).*

Li et al., "Two New Triterpenes From the Husks of Xanthoceras Sorbifolia" Planta Medica vol. 71 pp. 1068-1070 (Year: 2005).*

Hoppe et al., "Structure of the Principal Aglycon of Horse Chestnut Saponin" Angew. Chem. internat. Edit vol. 7 No. 7 pp. 547-548 (Year: 1968).*

Voutquenne et al., "Triterpenoid saponins and acylated prosapogenins from Harpullia austro-caledonica" Phytochemistry vol. 59 pp. 825-832 (Year: 2002).*

Dizes et al., "Harpuloside A Triterpenoid Saponin From Harpullia Ramiflora" Phytochemistry vol. 48 No. 7 pp. 1229-1232 (Year: 1998).*

* cited by examiner

Anticancer activity of Compounds Y, Y1, Y2, Y8, Y9 and Y10.

Structure of Y, X, ACH-Y, AKOH-Y and B-Escin

Figure 7
Y1 activities 1

Figure 8

Y1 activities 2

Y1 activities 3

Y1 activities 4

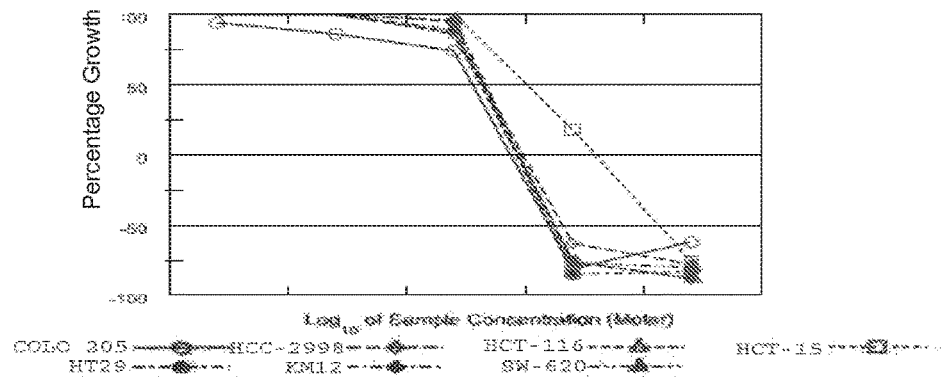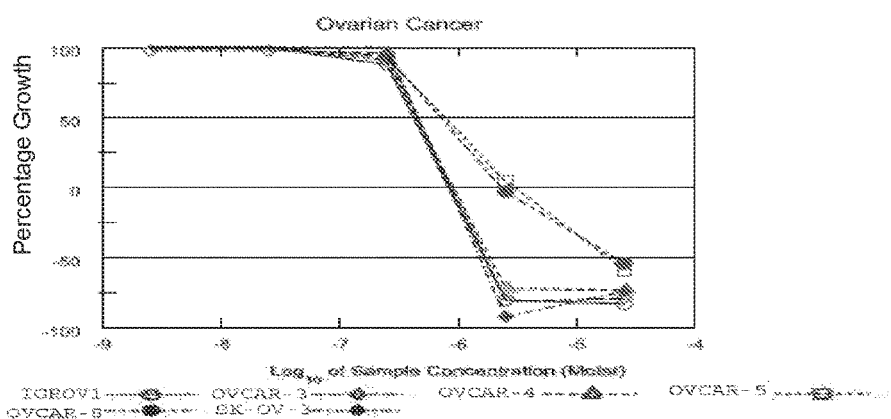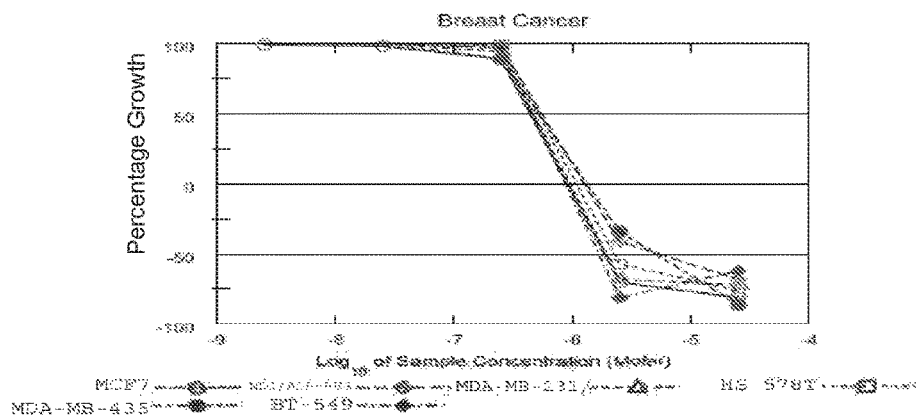
Figure 14
Y1 activities 8

Figure 15
Y2 activities 1

Figure 16
Y2 activities 2

Y2 activities 3

Y2 activities 4

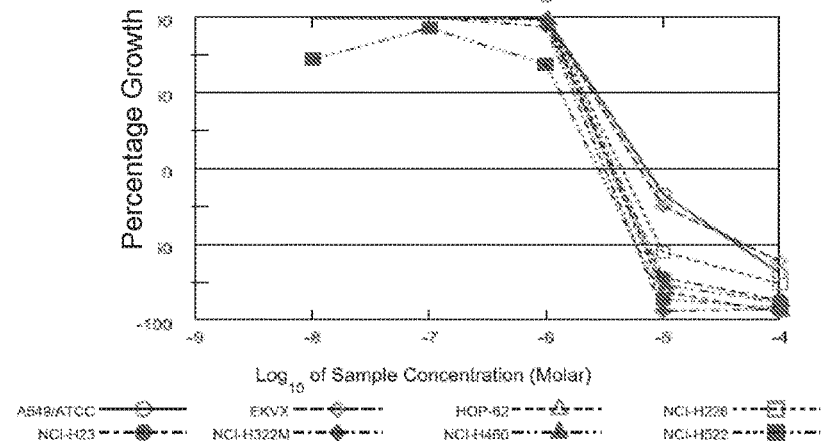
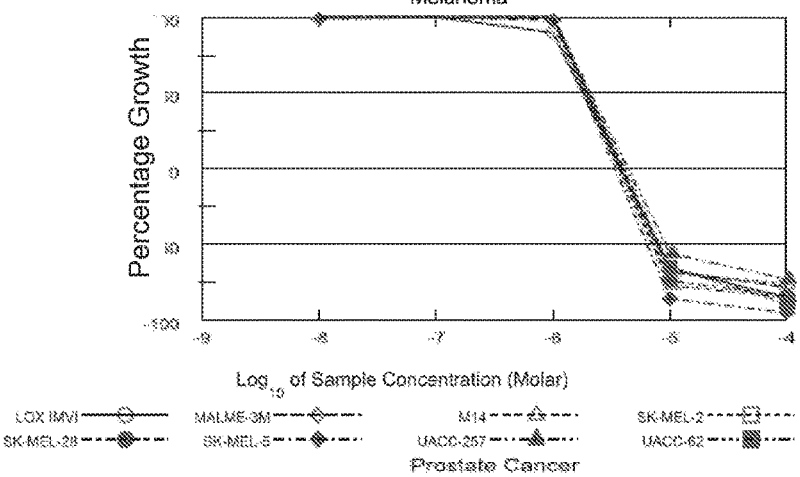
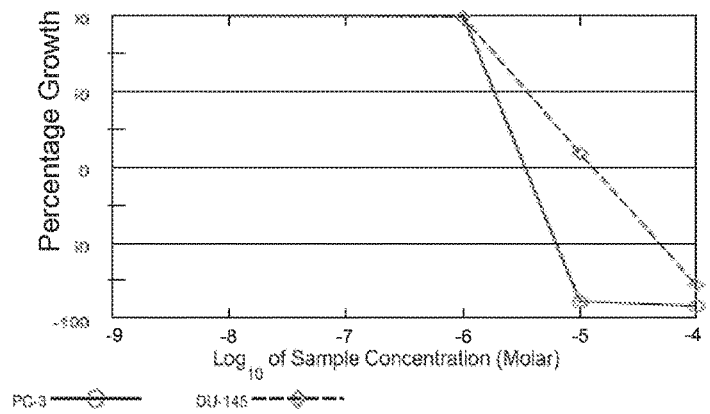
Figure 21
Y2 activities 7

Animal Studies

Survival Test (AS-3)

Animal experiment of solid tumor

Apoptosis of xanifolia

EM study the effect of Xanifolia on membrane

Inhibition effect of Xanifolia and Paclitaxel on cancer cell

Activity of Ys

Animal survival experiment

Determination of Aquaporin

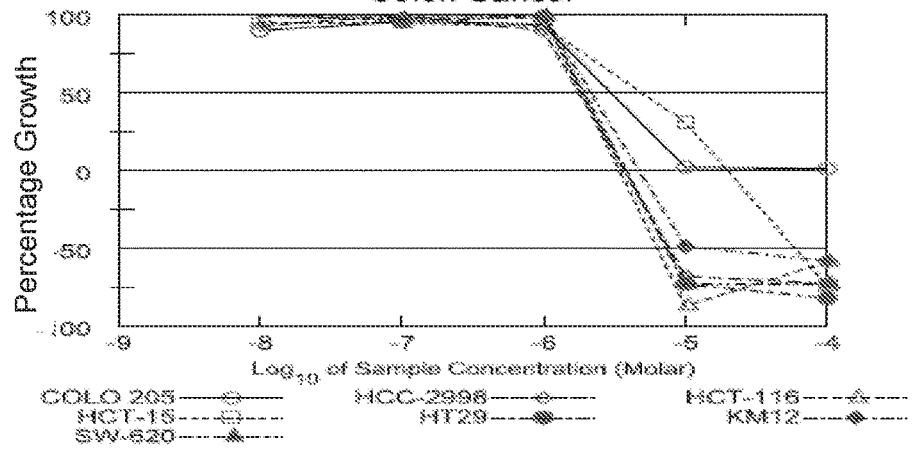
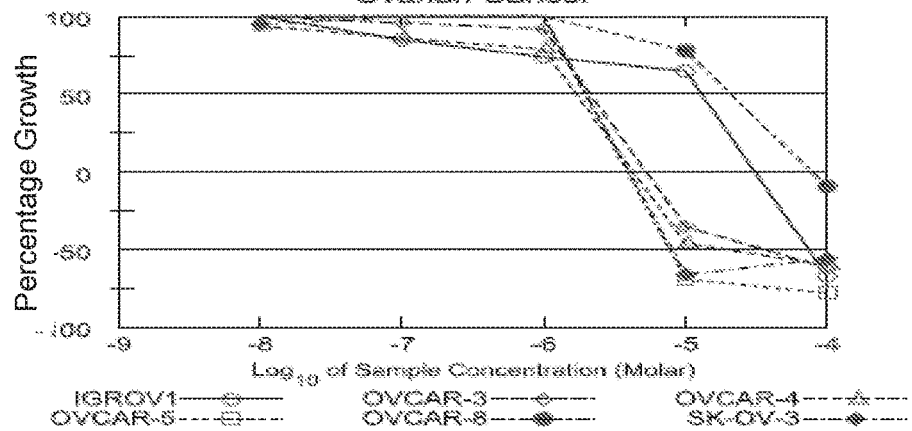
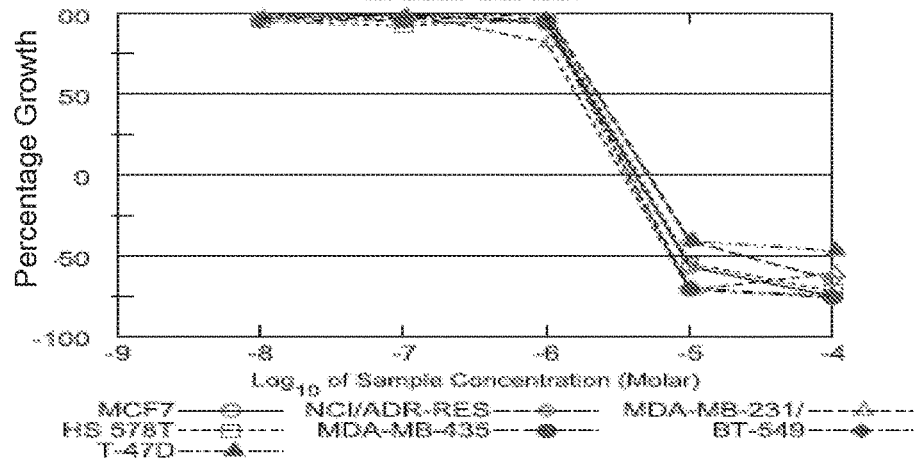
Figure 35
Y0 Activities (3)

Figure 36
Y9 Activities (1)
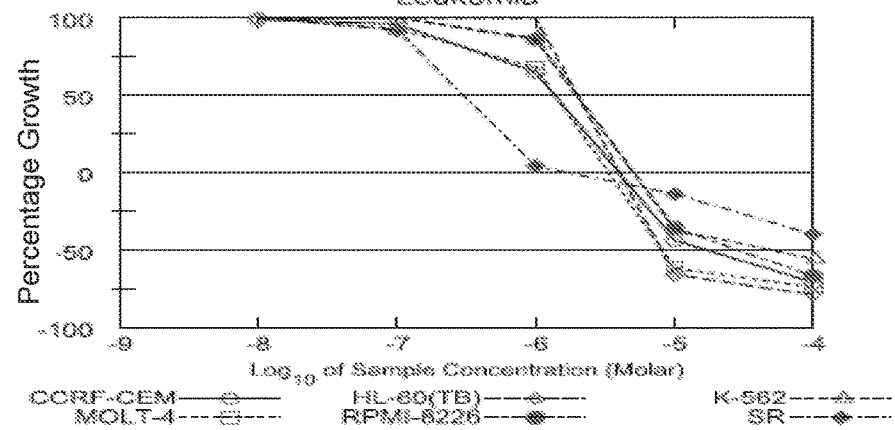
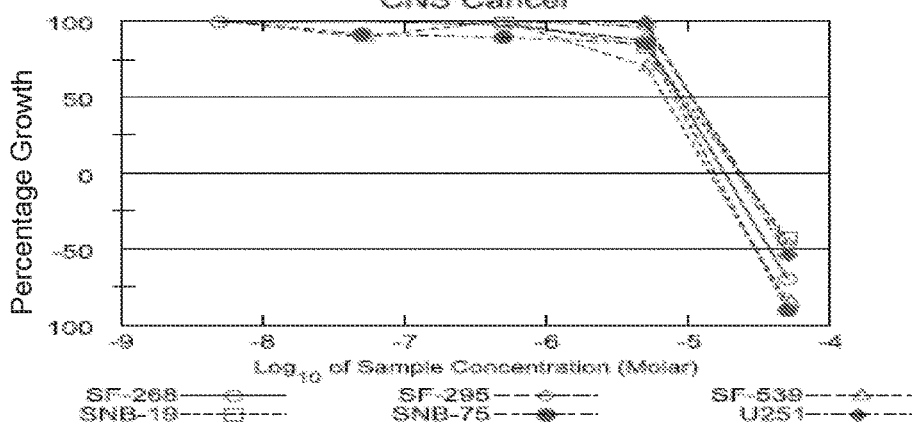
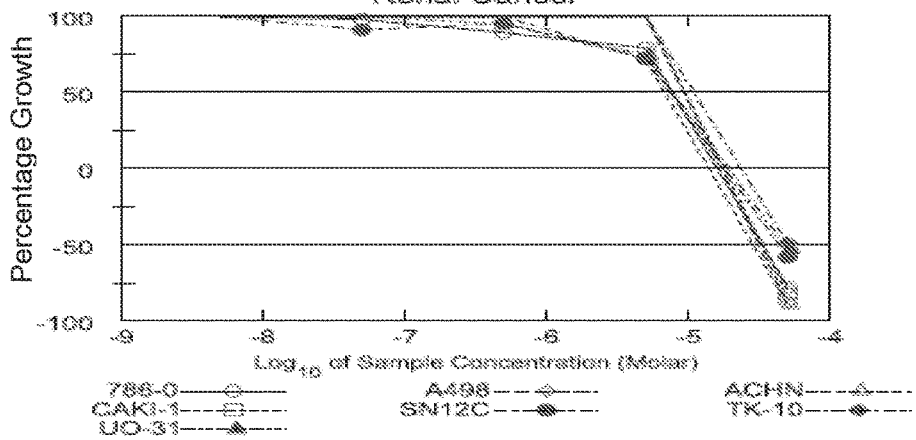

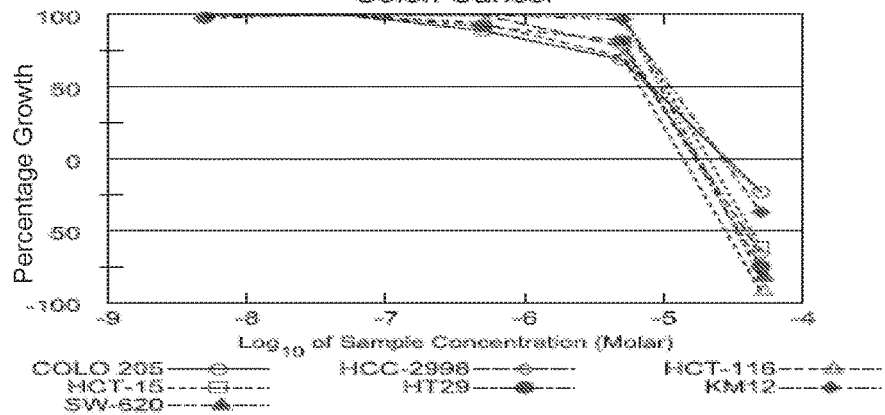
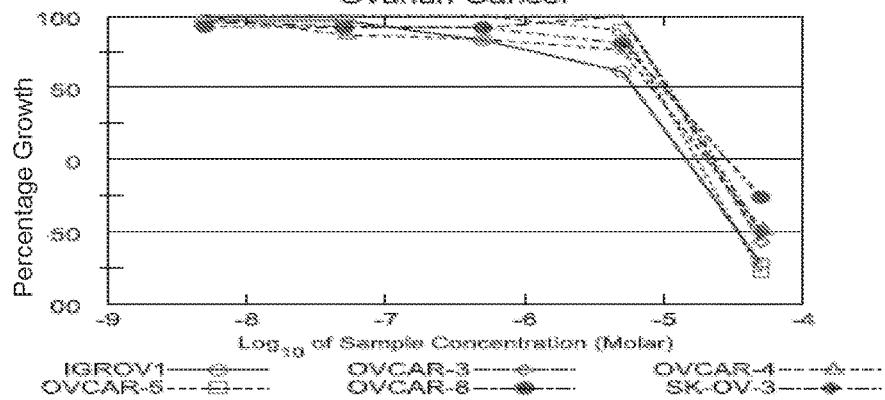
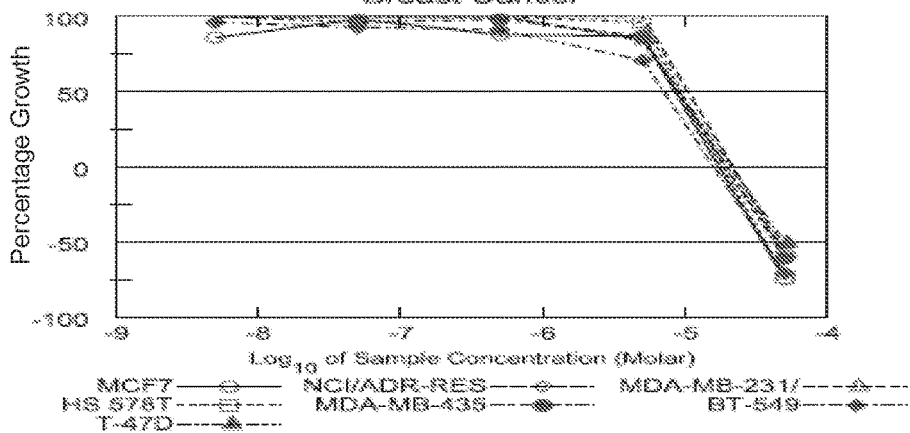
Figure 38

Inhibition of Fibronectin Secretion by Xanifolia-Y (Western blot) F 1

Figure 40
Inhibition of Fibronectin Secretion by Xanifolia-Y (Western blot)

A: Experiment (F5)

D  Y  D  Y  D  Y

B: Experiment (F7)

D  Y  T10  T50  D  Y  T10  T50

C: Experiment (F8)

D  Y  D  Y  D  Y

D: Experiment (F11)

D1  D2  Y10  Y20  D1  D2  Y10  Y20

E: Experiment (F12)

D1  D2  Y10

F: Experiment (F13)

D1  Y10  ES10  ES20

G: Experiment (F14B)

D  ES  X  D  Y1  Y3  AKOH  Y7

H: Experiment (F14C)

ES  X  Y1  D  AKOH  Y3  D  Y7

Inhibition of Fibronectin Secretion by Xanifolia-Y (Western blot)

A: Experiment (F23)

D

Figure 42
Inhibition of Fibronectin Secretion by Xanifolia-Y (Western blot)

A: Experiment (F30) (HTB9))

D1  D2  Y3-5  Y3-10  Y5-5  ACH  Y1-10

B: Experiment (F31) (T98G)

D-10  Y0-10  Y1-10  Y3-10  Y7-10  ACH-20

Increase Synthesis of Angiopoietin-2 in ES2 cells by Xanifolia-Y Treatment

Figure 44
Tumor Section
Micro blood vessel (enhanced RBC stain)
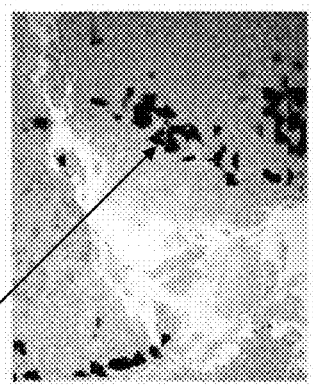
Control ES#1
Control ES#3
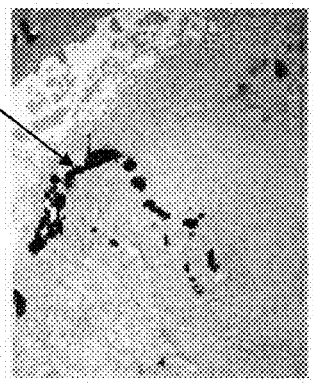
Day10 ES#2
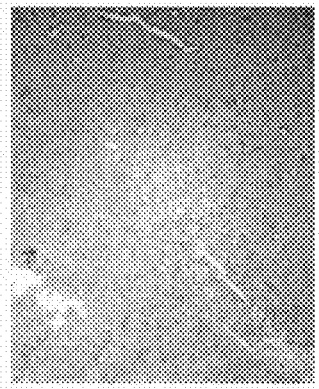
Day10 ES#5
A
B
C
D

METHODS AND COMPOUNDS FOR MODULATING THE SECRETION OR EXPRESSION OF ADHESION PROTEINS OR ANGIOPOIETINS OF CELLS

This application is a Continuation-in-part of International App'l No. PCT/US2009/034115, filed Feb. 13, 2009, which claims benefit of U.S. Ser. No. 61/038,277 filed Mar. 20, 2008, U.S. Ser. No. 61/054,308, filed May 19, 2008, and is a Continuation-in-part of U.S. Ser. No. 12/344,682, filed Dec. 29, 2008 and International App'l No. PCT/US2008/002086, filed Feb. 15, 2008, which is a continuation-in-part of International App'l No. PCT/US2007/077273, filed Aug. 30, 2007, which claims benefit of U.S. Ser. No. 60/890,380, filed on Feb. 16, 2007, U.S. Ser. No. 60/947,705, filed on Jul. 3, 2007, and is a continuation-in-part of U.S. Ser. No. 11/683,198, filed on Mar. 7, 2007, which claims benefit of U.S. Ser. Nos. 60/795,417, filed on Apr. 27, 2006, 60/841,727, filed on Sep. 1, 2006, 60/890,380, filed on Feb. 16, 2007, and is a continuation-in-part of International Application No. PCT/US2006/016158, filed Apr. 27, 2006, which claims benefit of U.S. Ser. Nos. 60/675,282, filed Apr. 27, 2005 and U.S. Ser. No. 60/675,284, filed Apr. 27, 2005 and is a continuation-in-part of the following applications (1) U.S. Ser. No. 11/289,142, filed Nov. 28, 2005; (2) U.S. Ser. No. 11/267,523, filed Nov. 4, 2005; (3) International Application No. PCT/US05/31900, filed Sep. 7, 2005 (which claims the benefit of U.S. Ser. Nos. 60/617,379, filed Oct. 8, 2004, 60/613,811, filed Sep. 27, 2004, and 60/607,858, filed Sep. 7, 2004); (4) U.S. Ser. No. 11/131,551, filed May 17, 2005; and (5) U.S. Ser. No. 11/117,760, filed Apr. 27, 2005. This application is also a continuation-in-part of U.S. Ser. No. 11/412,659, filed Apr. 27, 2006, Ser. No. 10/906,303, filed Feb. 14, 2005, Ser. No. 11/117,745, filed Apr. 27, 2005, Ser. No. 12/192,112, filed Aug. 20, 2008, Ser. No. 12/392,795, filed Feb. 25, 2009, Ser. No. 12/541,713, filed Aug. 14, 2009, and Ser. No. 12/714,598, filed Mar. 1, 2010. The contents of these preceding applications are hereby incorporated in their entireties by reference into this application.

FIELD OF THE INVENTION

This invention identifies Xanifolia-Y's cellular target(s). Xanifolia-Y is an alternate or supplemental anticancer agent to other DNA-inhibition or microtubule-targeting drugs.

In an embodiment, Xanifolia-Y binds adhesion proteins to blocks the migration, metastasis angiogenesis of cancer cells. It inhibits the growth of cancers. The compounds in this application have effects on cell membrane structure and cell's adhesion process. This invention relates to the inhibiting cancer through regulating aquaporin in cancer cells and/or interacting with aquaporin with compounds comprise of a triterpene with two angeloyl groups. In an embodiment, the compound may be a saponin wherein comprises at least one angeloyl, preferable two angeloyl groups. In an embodiment, the compound may comprise more than two angeloyl groups, acetyl group, tigloyl group, senecioyl group, or an acid having two to five carbons or combination thereof. This invention relates to saponins and compounds with angeloyl groups isolated from plants, their uses and functions. A composition comprises a diangeloyl group compound for inhibiting hemorrhoids, venous insufficiency and swelling. The compounds and compositions in this invention inhibit tumor or cancer growth. This invention provides methods and compositions for affecting the gene expression in cells as a result that cure diseases, wherein the methods comprise reducing the syndrome of diseases. In an embodiment the method comprise inhibition of gene expression. In an embodiment the method comprises stimulating the gene expression. This invention provides methods, processes, compounds and compositions for modulating the gene expression or secretion of adhesion proteins or their receptors to cure disease, wherein the modulating comprises positive and negative regulating; wherein comprises inhibiting cancer growth, wherein the adhesion proteins or receptors comprise fibronectin, integrins family, Myosin, vitronectin, collagen, laminin, Glycosylation cell surface proteins, polyglycans, cadherin, heparin, tenascin, CD 54, CAM, elastin and FAK; wherein the cancers comprise cancer of breast, leukocyte, liver, ovarian, bladder, prostate, skin, bone, brain, leukemia, lung, colon, CNS, melanoma, renal, cervix, esophagus, testis, spleen, kidney, lymph, pancreas, stomach and thyroid.

BACKGROUND OF THE INVENTION

We have identified an herbal extract that inhibits cancer cell's growth. The active compounds were purified and their structures identified to be novel triterpenoid saponins. Varicose veins are swollen and knotted veins that can occur in any part of the body, especially in the calf, inside leg or around the anus. Escin has been satisfactorily used for treating Varicose veins and chronic venous insufficiency for many years. Escin is a mixture of saponins found in the seed of the horse chestnut tree, Aesculus hippocastanum L., Hippocastanaceae. Escin is the major active ingredient prepared from Aesculus hippocastanum (Hippocastanaceae), the horse chestnut tree. In one controlled trial study, aescin was shown to be as effective as compression therapy as an alternative to medical treatment for CVI. The therapeutic benefit is well supported by a number of experimental investigations in different animal models. See Department of Pharmacological Sciences, University of Milano, Via Balzaretti 9, 20133 Milano, Italy. New saponin compounds with two angeloyls have been provided in International PCT Application No. PCT/US04/33359, filed Oct. 8, 2004, and U.S. Ser. No. 10/906,303. Yingjie Chen, Tadahiro Takeda and Yukio Ogihara reported four new saponin compounds that were isolated from the fruits of Xanthoceras sorbifolia Bunge in Chem. Pharm. Bull., 33(1)127-134, 1985; 33(3) 1043-1048, 1985 and 33(4)1387-1394, 1985. Other related studies on saponin compounds include: triterpenoid saponins and acylated prosapogenins from Harpullia austrocaledonica (Voutquenne et al. 2002); six triterpennoid saponins from Maesa laxiflora (Zhong et al. 1999); new triterpene saponin from Pittosporum viridiflorum from the Madagascar rainforest (Young et al. 2002); anti-HIV-1 protease triterpenoid saponins from the seeds of Aesculus chinensis (Yang et al. 1999); triterpenoid saponins from the roots of Camellia sinensis var. assamica (Lu et al. 2000); new acylated triterpenoid saponins from Maesa laceceolata (Apers et al. 1999); isolation and structure elucidation of four new triterpenoid estersaponins from fruits of the Pittosporumtobira AIT (D'Acquarica et al. 2002) and method for the prevention and treatment of chronic venous insufficiency (U.S. Pat. No. 6,210,680). The contents of the above-mentioned references are hereby incorporated by reference.

Human cells are surrounded by aquatic environments. Aquaporins is a family of transmembrane water-channel transporting proteins that play a major role in trans-cellular and transepithelial water movement. This invention shows that the triterpene saponins with two angeloyls have stronger activity for inhibiting cancer cell growth by affecting membrane functions. In an embodiment they affect the aquaporin and permeability of cell membrane.

SUMMARY OF THE INVENTION

In accordance with these and other objects of the invention, a brief summary of the present invention is presented. Some simplifications and omissions may be made in the following summary, which is intended to highlight and introduce some aspects of the present invention, but not to limit its scope. Detailed descriptions of a preferred exemplary embodiment adequate to allow those of ordinary skill in the art to make and use the invention's concepts will follow in later sections.

This invention provides the uses of compounds comprising a triterpene or other sapongenin with two angeloyl groups, or at least two side groups selected from the following groups: angeloyl, tigloyl and/or senecioyl groups, wherein the side groups are attached to carbon 21, 22 or/and 28 of triterpenoidal saponin, triterpenoid, triterpenoidal compounds or other sapongenin backbones. The methods of purification and determination of structures of the compounds are detailed in the International Application No. PCT/US05/31900, filed Sep. 7, 2005, and U.S. Ser. No. 11/289,142, filed Nov. 28, 2005. Details also in U.S. Ser. No. 11/131,551, filed May 17, 2005

We have identified an herbal extract from *Xanthoceras sorbifolia* that inhibits cancer cell's growth. The active compounds were purified and their structures identified to be a novel triterpenoid saponin. We named them as Xanifolia-Y and family. Details in U.S. Ser. No. 10/906,303 and Intl App'l No. PCT/US04/33359

In vivo studies with Xanifolia-Y employing human ovarian carcinoma xenografts in mouse indicate that Xanifolia-Y is capable of extending the life span of animals bearing human tumors. These results show that it can be useful in treating cancers in mammal. In an embodiment it can be use in treating human cancers, preferably ovarian cancer. Xanifolia-Y prolongs the life span of mice bearing of human tumor. It blocks the migration or metastasis of cancer cells. In an embodiment it binds with adhesion proteins or interferes with the function of molecules on carcinoma cells or on the mesothelial cells. It inhibits the tumor growth in mammal. It is useful in cancer therapy. See Experiment 7, 8, 9

Xanifolia-Y binds with adhesion proteins or signaling proteins in cancer cells. Xanifolia-Y is radioactive labeled with $^3$H and use it as ligand to search for target molecules. With the labeled Xanifolia-Y, we study the cellular binding location with autoradiography; determine binding affinity to adhesion proteins or target protein with RIA, investigate its associated proteins with co-IP and verify them with competition assay. In an embodiment, Xanifolia-Y binds to adhesion proteins comprising integrins family, CD44, fibronectin, Myosin VI or FAK. We identify the target proteins by 2D gel blotting and MALDI-TOF peptide mapping techniques. Xanifolia-Y is inhibiting nodule formation and/or growth in the peritoneal cavity of mouse. Cancer cell is inoculated into the peritoneal cavity of nude mice. Drug treatment starts at different stages of tumor progression. At the end of the drug-treatment, the change in the number and weight of tumor nodules are measured. Xanifolia-Y is inhibiting solid tumor growth. Details are in Experiment 10.

Xanifolia-Y has effects on cell membrane structure and adhesion process. This invention identifies Xanifolia-Y's cellular target(s). It is an alternate or supplemental anticancer agent to other DNA-inhibition or microtubule-targeting drugs. In an embodiment, this invention provides a method of binding with adhesion proteins to blocks the migration, metastasis of cancer cells, anti-angiogenesis and inhibits the growth of cancers.

This invention discloses saponin compounds having the specific structures are capable of inhibiting cancer or tumor cell growth and anti-angiogenesis. This invention provides a method for treating cancer wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer. This invention provides a method for treating cancer by binding with adhesion proteins to blocks the migration, metastasis of cancer cells, growth of cancers wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer. This invention relates to the mechanism of inhibiting cancer by regulating aquaporin in cancer cell and the interacting of aquaporin with compounds comprise a triterpene and two angeloyl groups. In an embodiment, the compound may be a saponin wherein comprises at least one angeloyl, preferable two angeloyl groups.

This invention relates to the aquaporin pathway that is influenced by saponins with angeloyl groups in inhibiting cancer. This invention relates to a method for curing enuresis, frequent micturition, urinary incontinence by regulating the aquaporin with a compound wherein comprises a triterpene, angeloyl group(s) and sugar moiety. Varicose veins are enlarged veins that can be flesh colored, dark purple or blue. They often look like cords and appear twisted and bulging. They are swollen and raised above the surface of the skin. Varicose veins are commonly found on the backs of the calves or on the inside of the leg. During pregnancy, varicose veins called hemorrhoids can form in the vagina or around the anus. This invention provides the uses of compositions for treating or preventing chronic venous insufficiency, peripheral edema, antilipemic, chronic venous disease, varicose vein disease, varicose syndrome, venous stasis, expectorant, peripheral vascular disorders, cerebro-organic convulsion, cerebral circulation disorder, cerebral edema, psychoses, dysmenorrheal, hemorrhoids, episiotomies, peripheral edema formation or postoperative swelling; for reducing symptoms of pain; for reducing symptoms of stomach pain; for reducing symptoms of leg pain; for treating pruritis, lower leg volume, thrombosis, thromophlebitis and for treating or preventing gastric ulcers or use for antispasmotic. This invention also provides a composition for inhibiting tumor cell growth. This invention further provides a composition for preventing tumor formation or killing tumor cells. This invention further comprises the composition of an effective amount of compound used for manufacture of a medicament for the treatment of varicose vein disease, chronic venous insufficiency, hemorrhoids or inhibition of leg swelling.

This invention provide methods and compositions for modulating the secretion, expression, or synthesis of adhesion protein or angiopoietin of cancer cell and block their migration, metastasis or inhibit the growth of cancers or anti-angiogenesis, wherein the adhesion protein and their receptors comprise fibronectin, integrins family, Myosin, vitronectin, collagen, laminin, Glycosylation cell surface proteins, polyglycans, cadherin, heparin, tenascin, CD 54, CAM, elastin and FAK.

This invention provides a method of reducing the adhesion protein in cell and blocks the migration, metastasis of cancer cells or inhibits the growth of cancers or antiangiogenesis, wherein the adhesion proteins or its receptors comprise fibronectin, integrins family, Myosin, vitronectin, collagen, laminin, Glycosylation cell surface proteins, polyglycans, cadherin, heparin, tenascin, CD 54, CAM, elastin and FAK. In an embodiment, this invention provides a method of reducing the secretion of fibronectin. In an embodiment, this invention provides a method for inhibiting the expression of adhesion proteins, wherein the adhesion proteins comprise fibronectin, integrins family, Myosin, vitronectin, collagen, laminin, Glycosylation cell surface proteins, polyglycans, cadherin, heparin, tenascin, CD 54, CAM, elastin and FAK. This invention provides a method of inhibiting the growth, migration, metastasis of cancer by altering the characteristics of membrane of cancer cells, wherein the characteristics comprise adhesion protein; wherein the cancers comprise breast, leukocyte, liver, ovarian, bladder, prostate, skin, bone, brain, leukemia, lung, colon, CNS, melanoma, renal and cervix cancer.

DETAILED DESCRIPTION OF THE FIGURES

FIG. 1: Structures of saponins A and B.

R1=angeloyl, tigloyl, senecioyl, H, or a sugar moiety comprising angeloyls, tigloyl or senecioyl. R2=angeloyl, tigloyl, senecioyl, H, or a sugar moiety comprising angeloyls, tigloyl or senecioyl. R6=angeloyl, tigloyl, senecioyl, acetyl, H, or a sugar moiety comprising angeloyls, tigloyl or snecioyl; R3=H or OH. R10=$CH_3$, $CH_2OH$, or CHO; R5=D-glucose, D-galactose, L-rhamnose, L-arabinose, D-xylose, alduronic acid, D-glucuronic acid, D-galacturonic acid or H. R7=D-glucose, D-galactose, L-rhamnose, L-arabinose, D-xylose, alduronic acid, D-glucuronic acid, D-galacturonic acid or H; R8=D-glucose, D-galactose, L-rhamnose, L-arabinose, D-xylose, alduronic acid, D-glucuronic acid, D-galacturonic acid or H. R9=COOH or $CH_2OH$.

Figure 2:
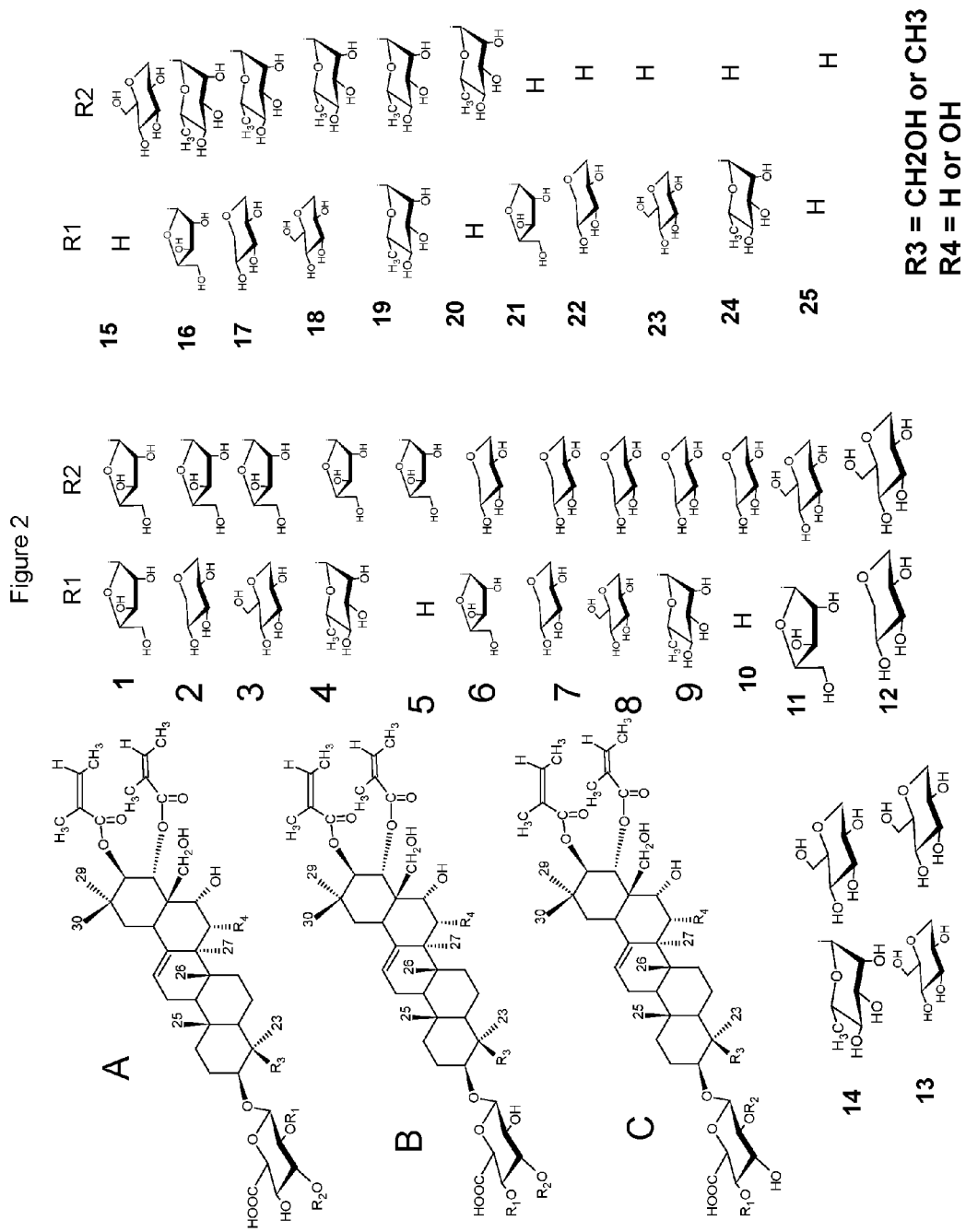

FIG. 2: Structures of saponins A, B, and C.

Figure 3:
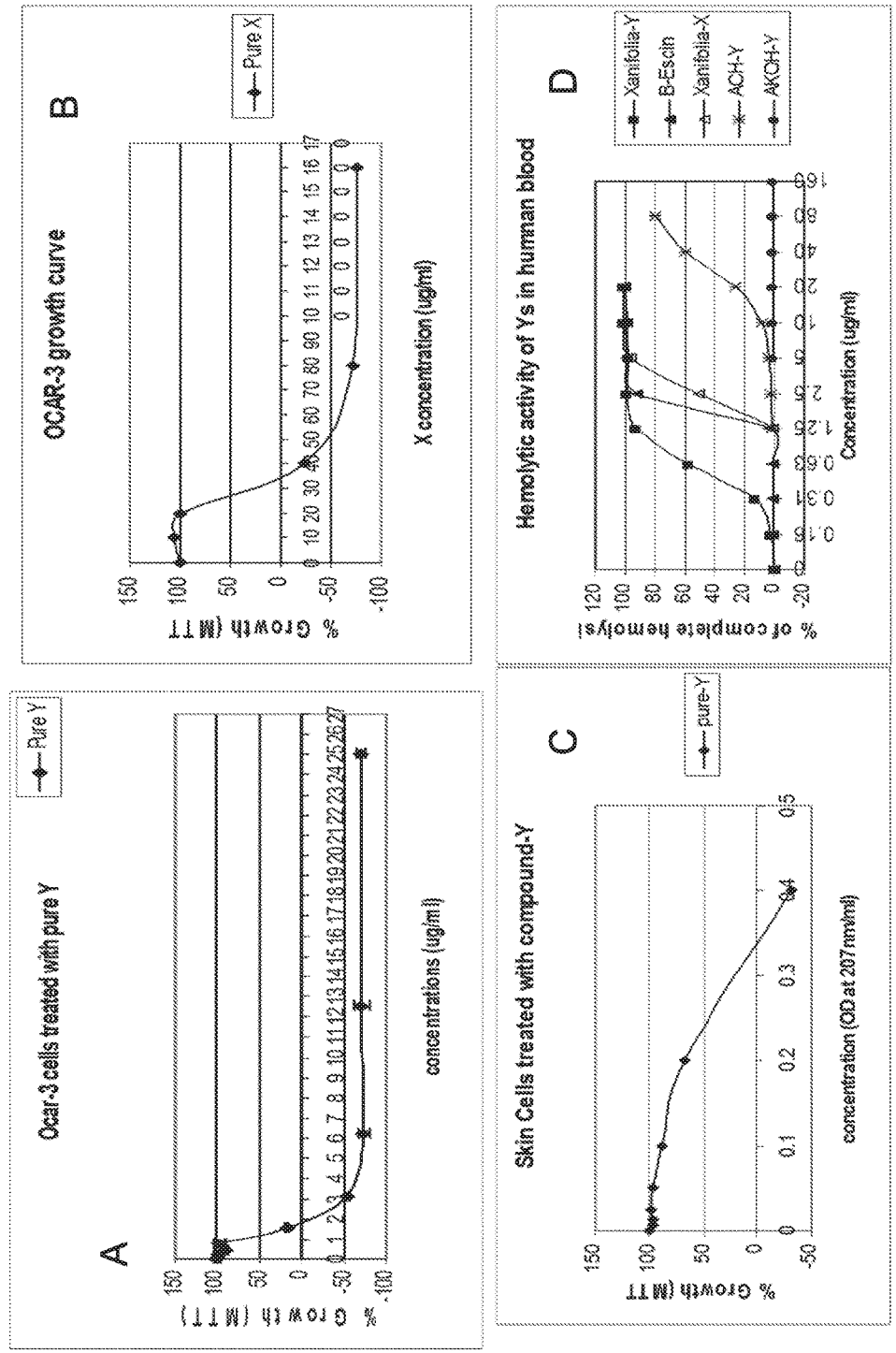

FIGS. 3: 3A and 3B: Comparison of potency of compound Y (saponin with 2 angeloyl groups) and compound X (saponin with 1 angeloyl) in inhibiting growth of ovarian cancer cells. The IC50 for Compound Y is about 1.5 µg/ml while 30 µg/ml for compound X. 3C: Inhibition of growth of skin cancer cells by the purified compound Y. The IC50 is 0.23 µg/ml. 3D: Hemolytic activity of Xanifolia-Y, B-Escin, Xanifolia-X, ACH-Y and AKOH-Y.

Figure 4:
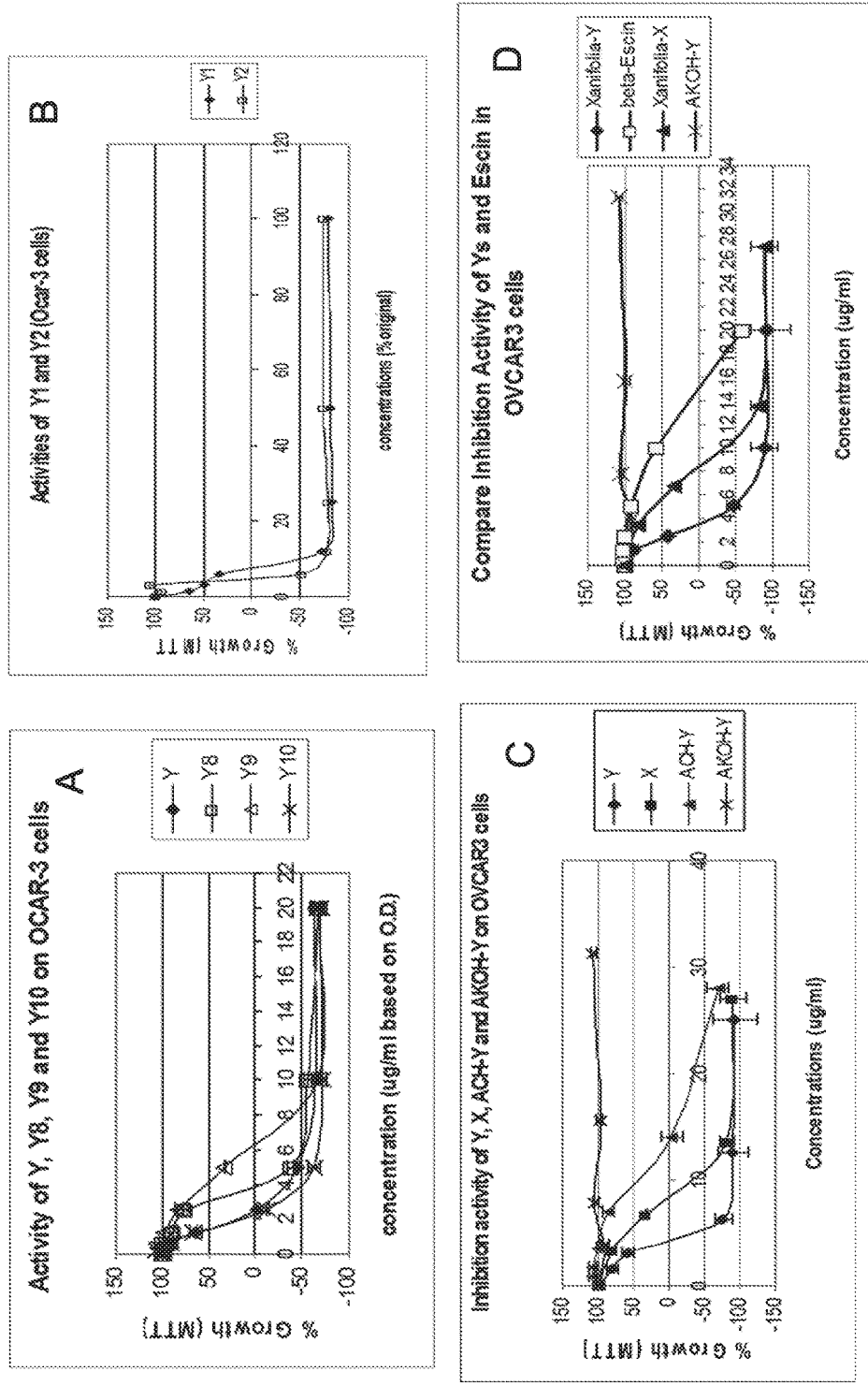

FIG. 4: 4A: Anticancer activities of Y, Y8, Y9 and Y10, determined by MTT assay on ovarian cancer cells. 4B: The purified compound Y1 and compound Y2 show inhibition of growth of ovarian cancer cells. 4C: Compound Y inhibits tumor growth (IC50=4 µg/ml). Compound X which has a similar structure to Y but with only one angeloyl group at C22, has less anticancer activity (IC50=6 µg/ml). Removal of sugars from Y (ACH-Y) but retaining the diangeloyl group retains 40% of the anticancer activity (IC50=9.5 µg/ml). However, removal of both angeloyl groups from Y (AKOH-Y) completely abolishes its anticancer activity (even at 120 µg/ml). The results indicate that diangeloyl groups in compound Ys are important for anti-tumor activity. 4D: Compare inhibition activity of Xanifolia-Y, B-Escin, Xanifolia-X and AKOH-Y.

Figure 5:
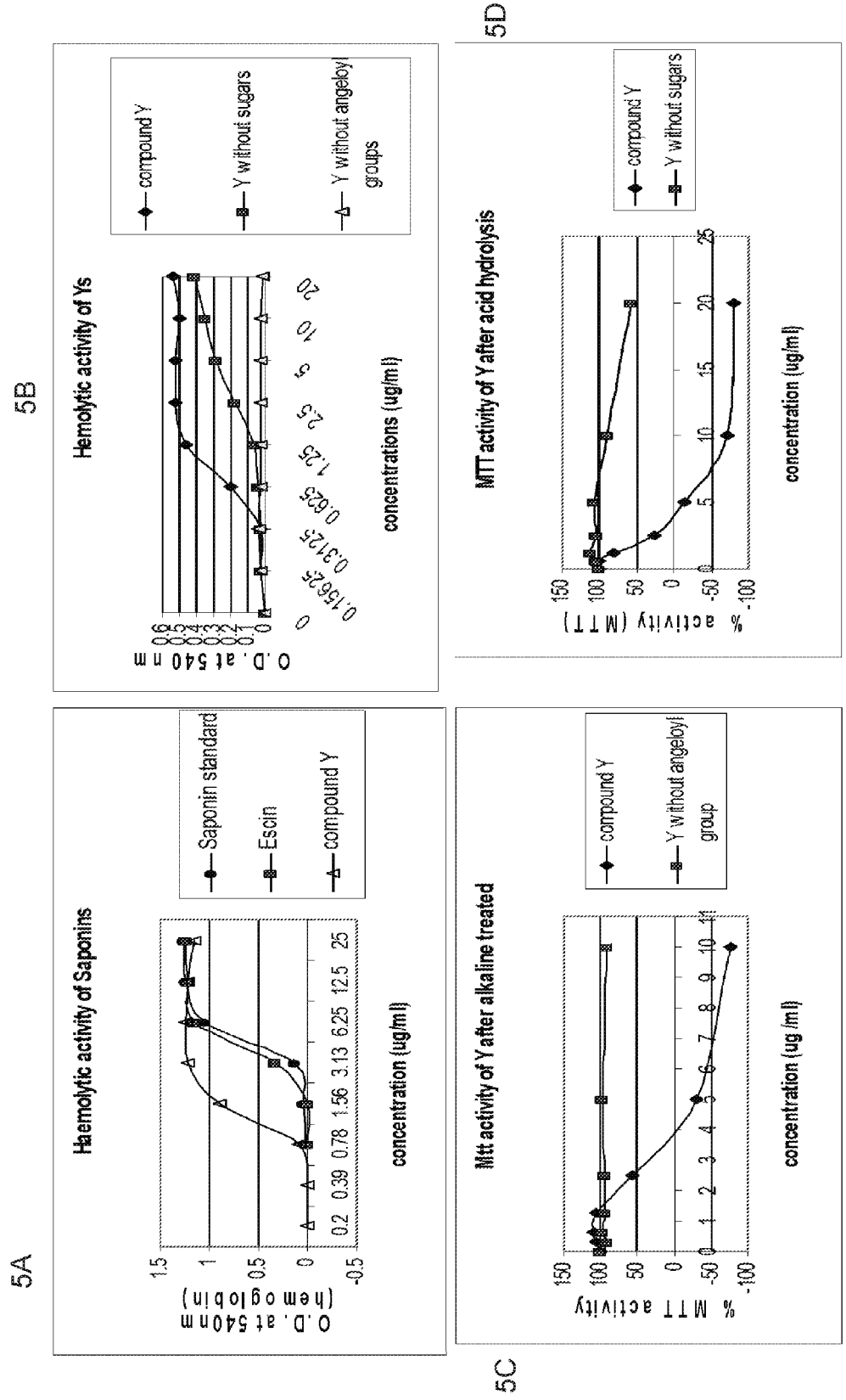

FIG. 5: Comparison of MTT and hemolytic activities of saponin compound and compound Ys. (5A) and (5B). Hemolytic activities; (5C) and (5D). MTT activities.

Figure 6:
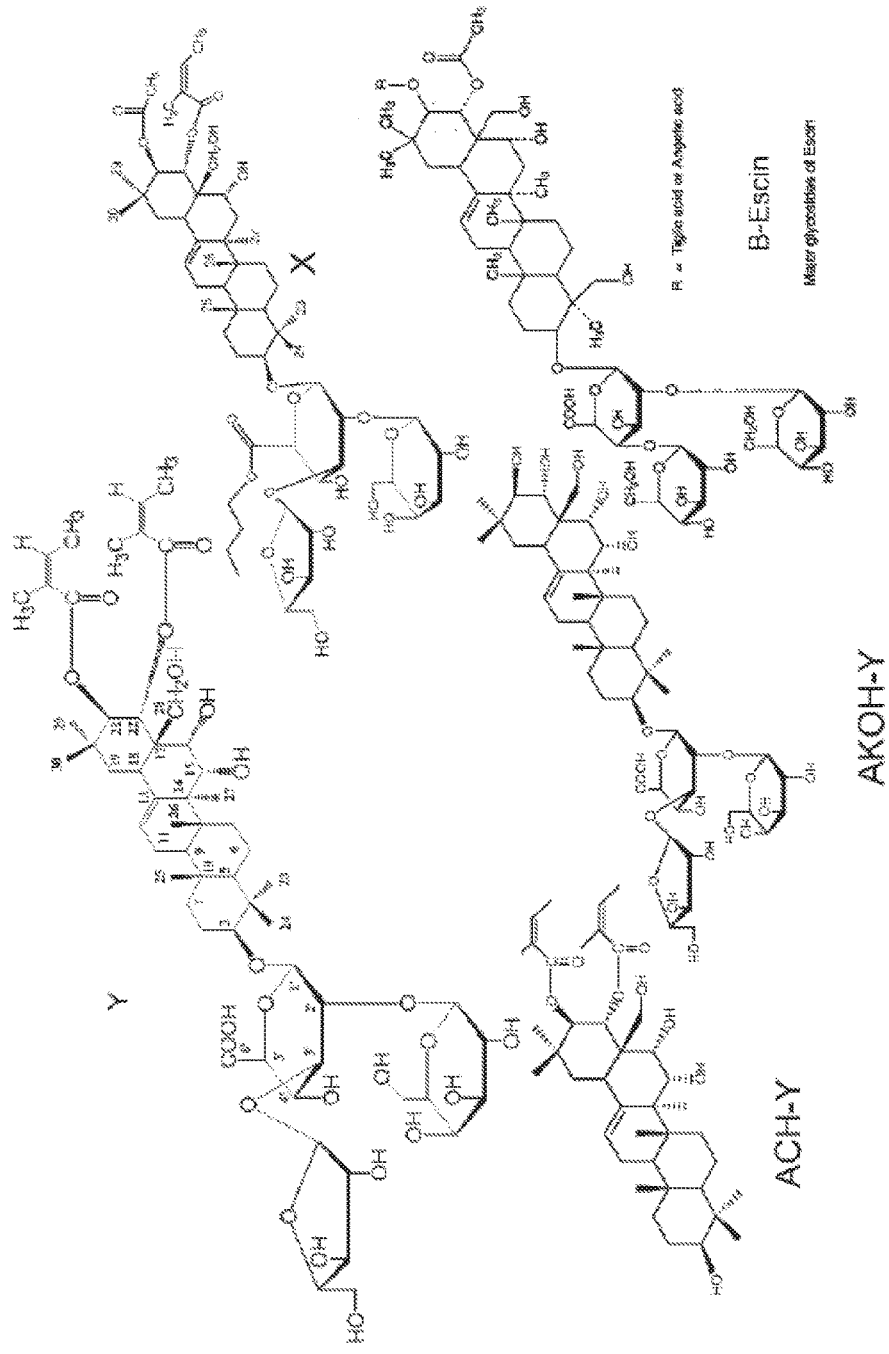

FIG. 6: Saponin compound Y, X, ACH-Y, AKOH-Y and B-Escin. These compounds are purified and their structures were verified by NMR and MS. These compounds are then used for MTT test.

Figure 7:
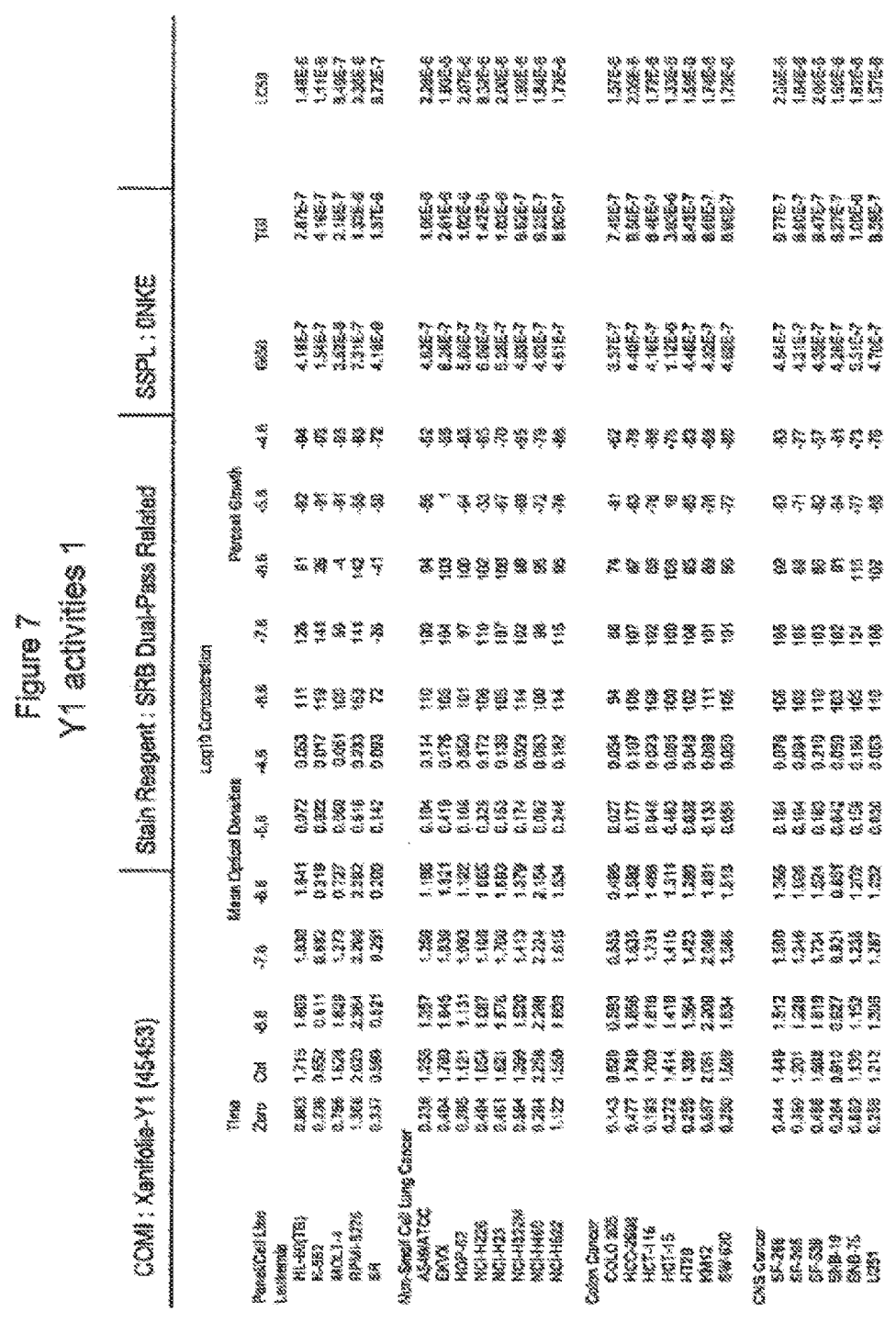

FIG. 7: Y1 activities 1, shows Xanifolia Y1 inhibits Leukemia cancer, Lung cancer, Colon cancer and CNS cancer activities.

Figure 8:
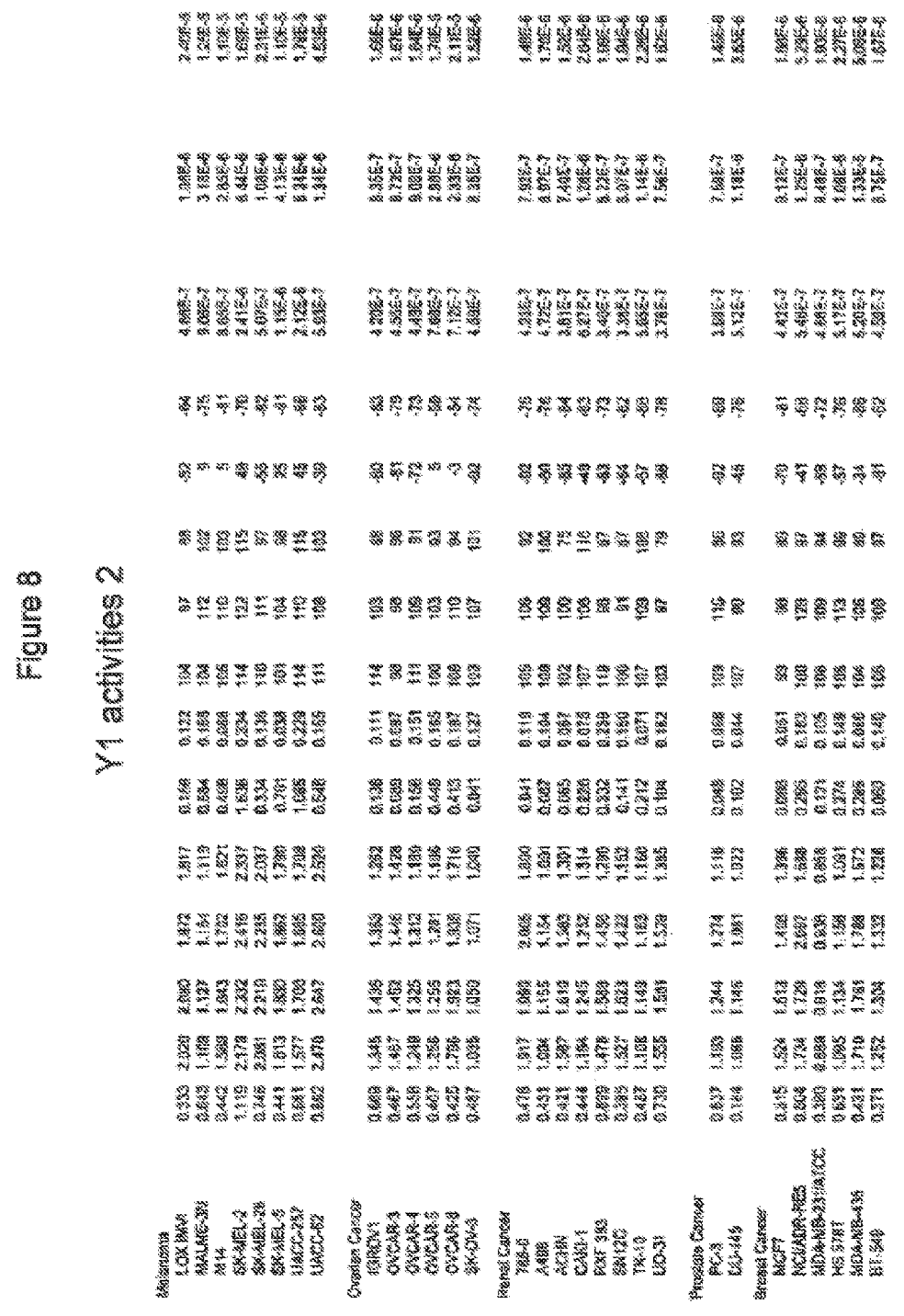

FIG. 8: Y1 activities 2, shows Xanifolia Y1 inhibits Melanoma, Ovarian cancer, Renal cancer, Prostate cancer and Breast cancer activities.

Figure 9:
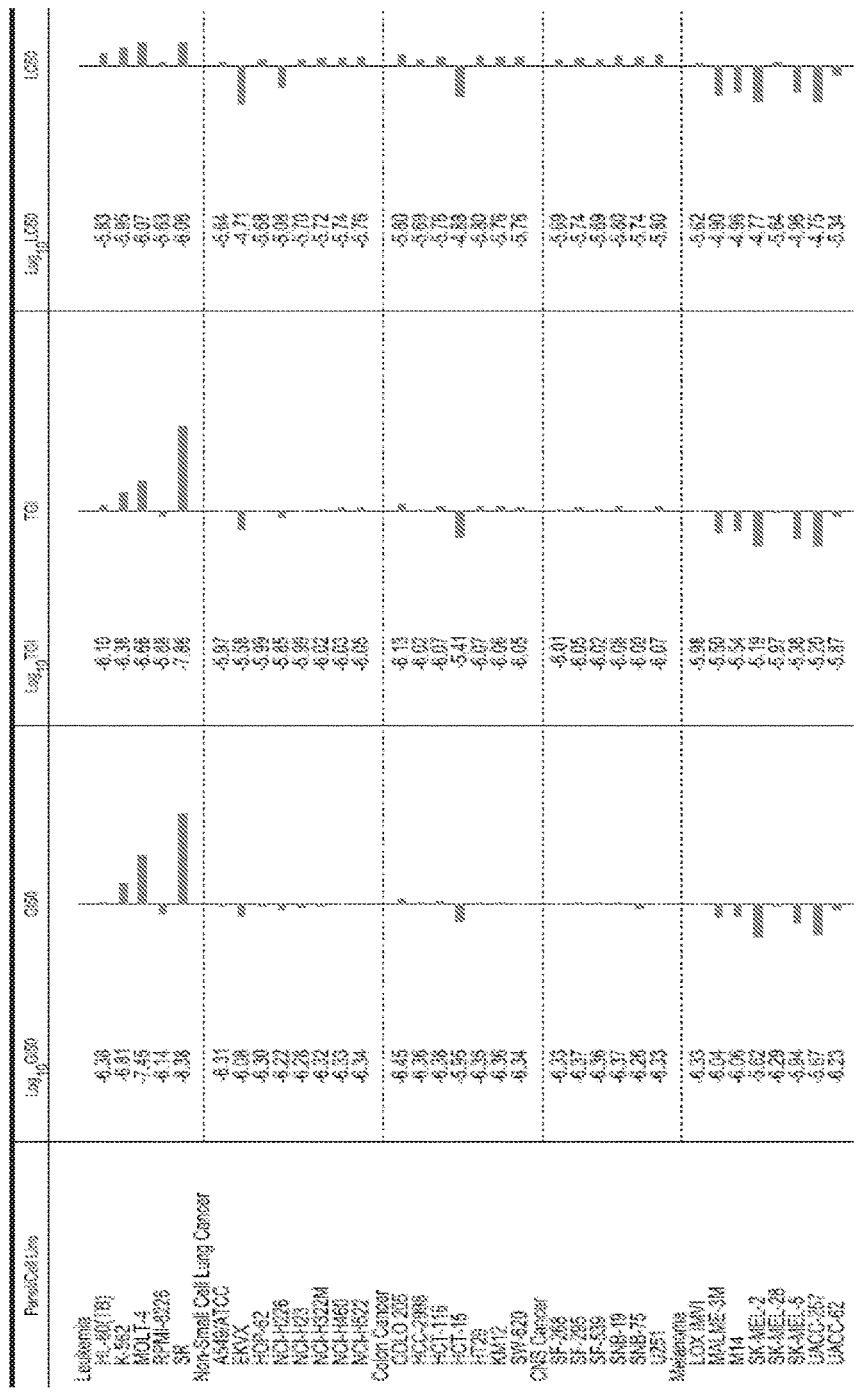

FIG. 9: Y1 activities 3, shows Xanifolia Y1 inhibits Leukemia cancer, Lung cancer, Colon cancer, CNS cancer and Melanoma activities.

Figure 10:
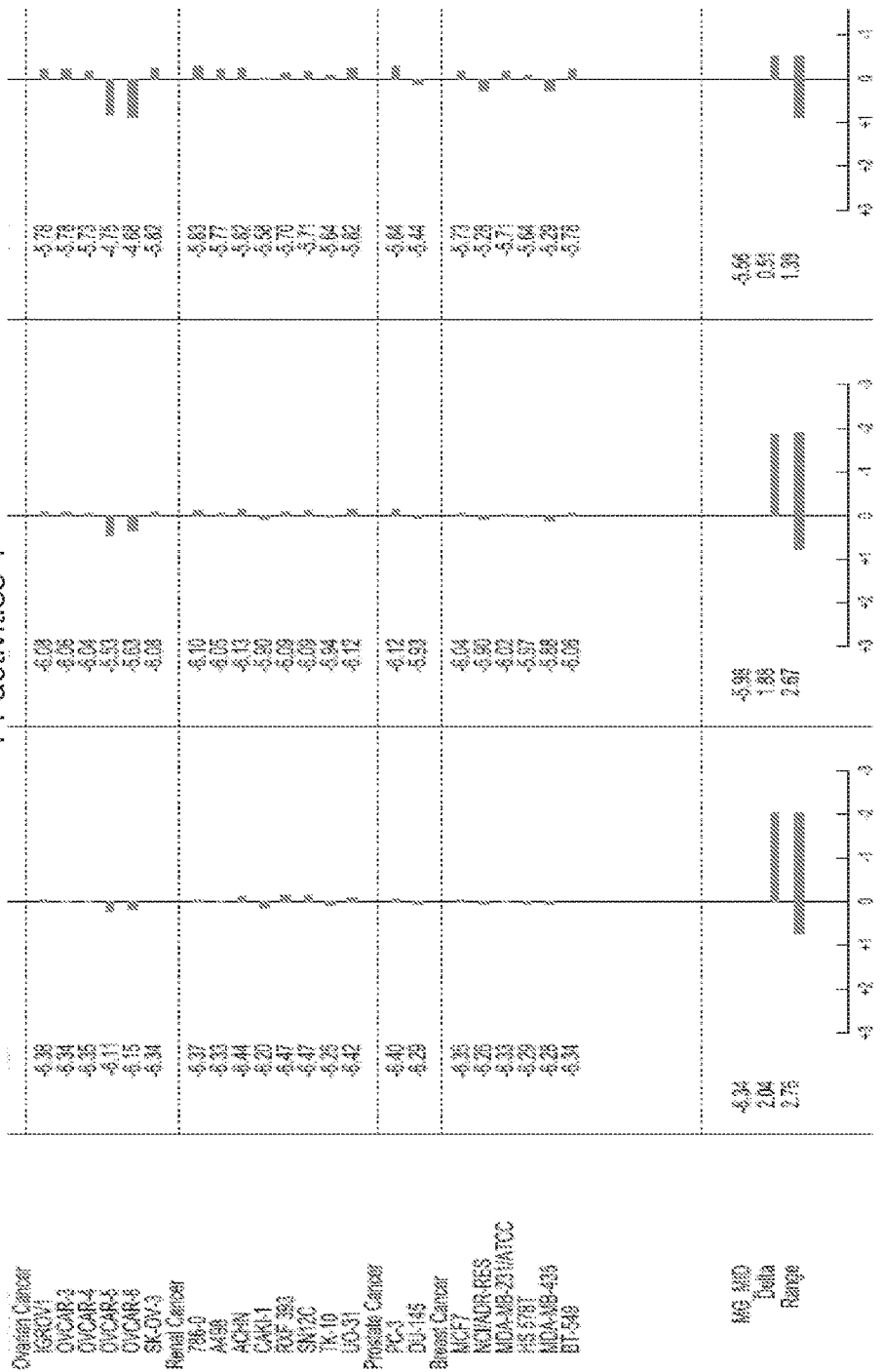

FIG. 10: Y1 activities 4, shows Xanifolia Y1 inhibits Ovarian cancer, Renal cancer, Prostate cancer and Breast cancer activities.

Figure 11:
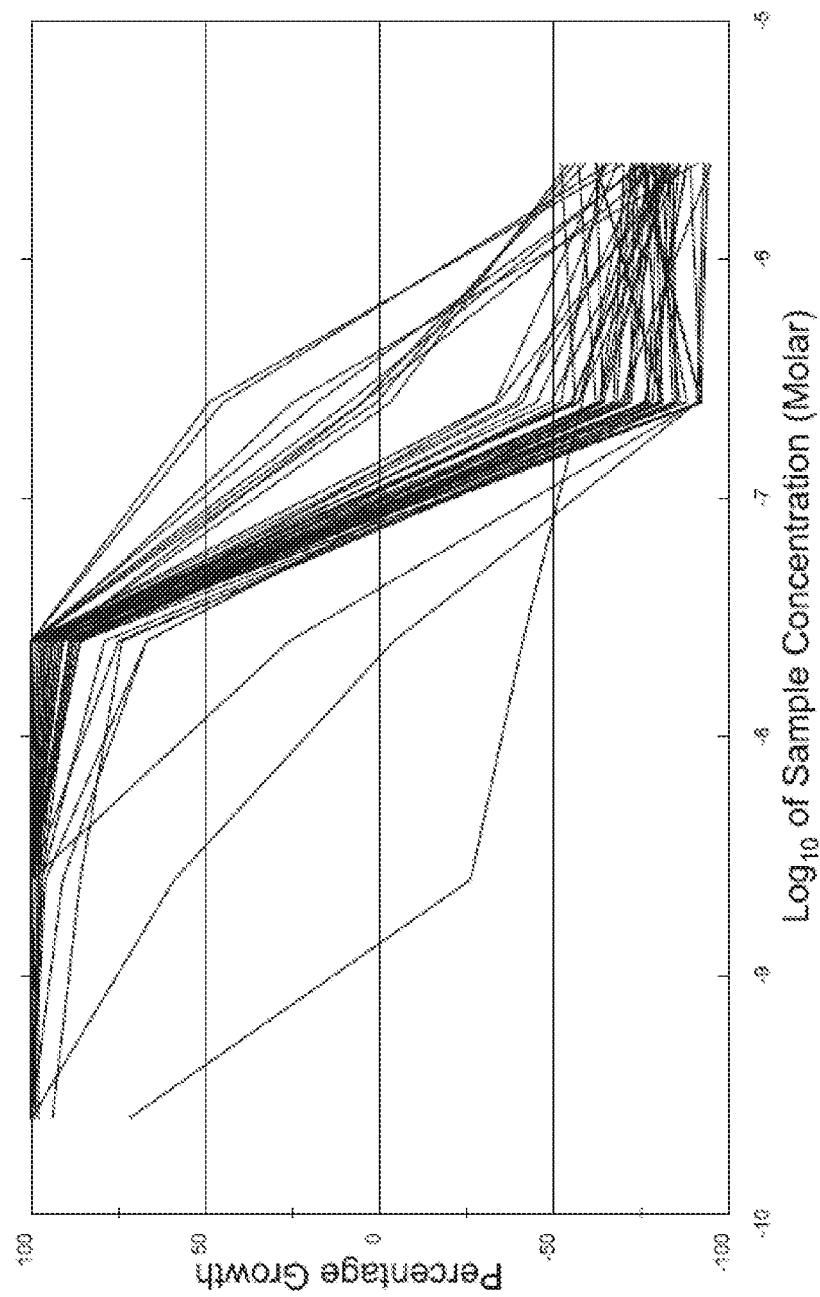

FIG. 11: Y1 activities 5, shows Xanifolia Y1 inhibits Leukemia cancer, Lung cancer, Colon cancer, CNS cancer, Melanoma, Ovarian cancer, Renal cancer, Prostate cancer and Breast cancer activities.

Figure 12:
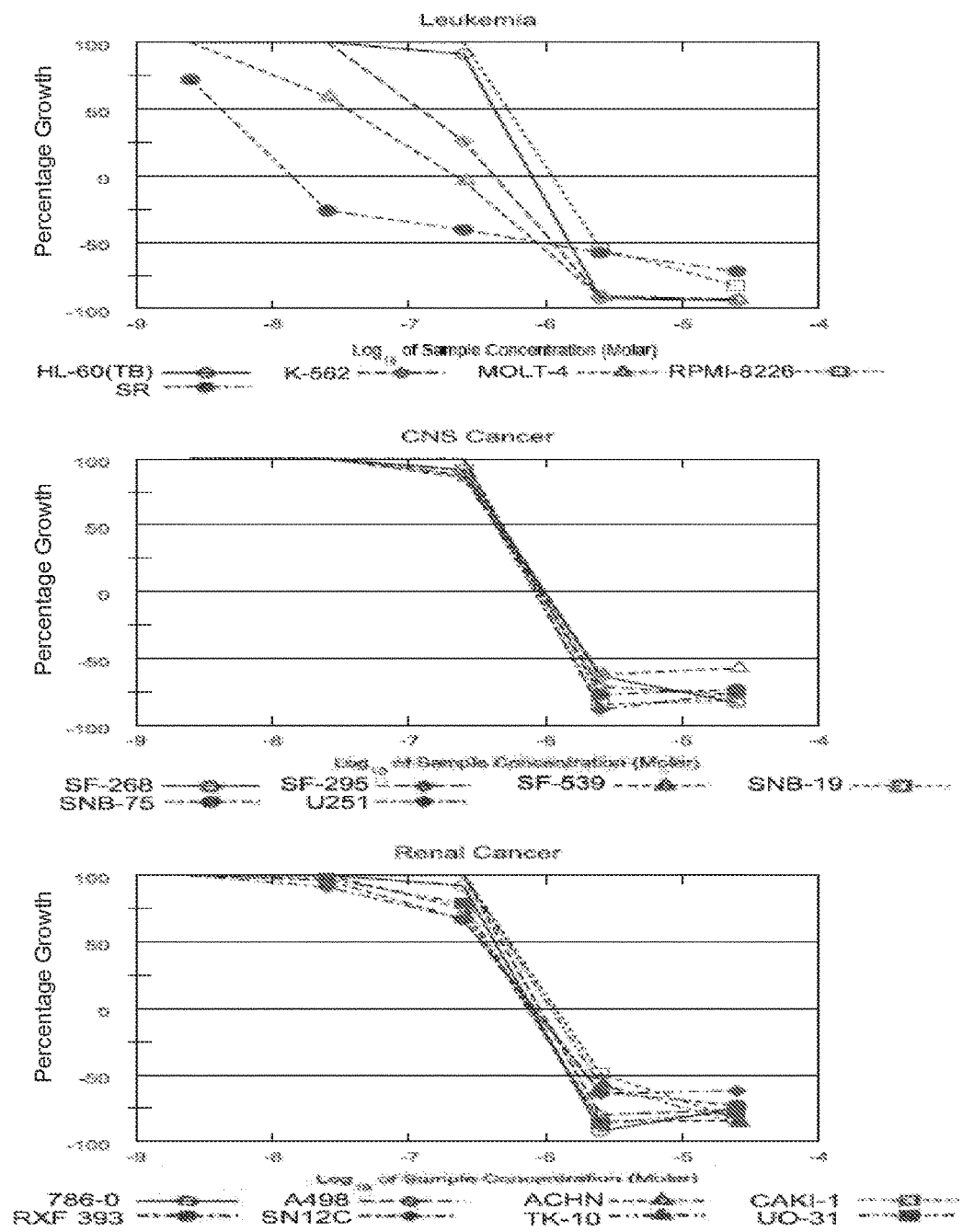

FIG. 12: Y1 activities 6, shows Xanifolia Y1 inhibits Leukemia cancer, CNS cancer and Renal cancer activities.

Figure 13:
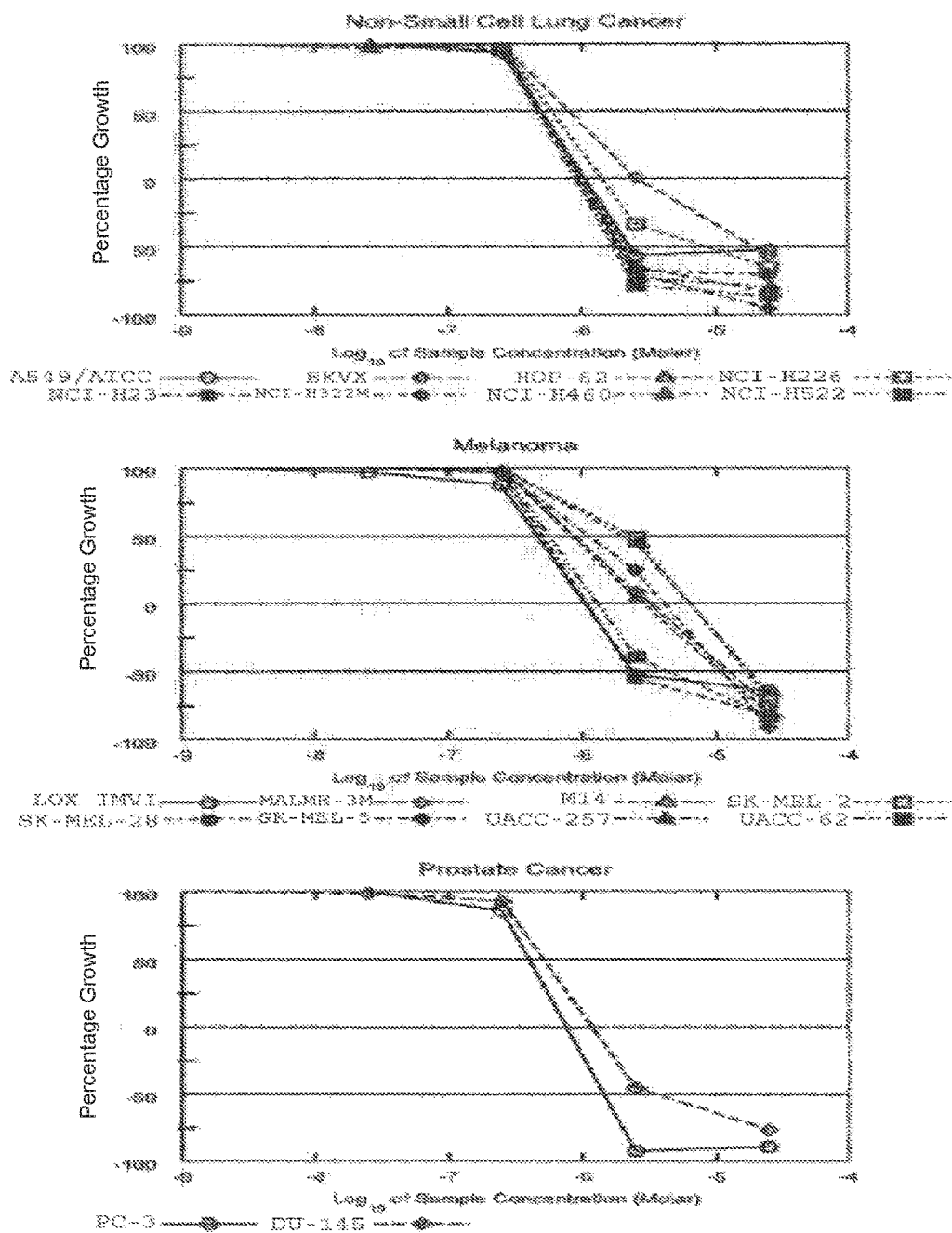

FIG. 13: Y1 activities 7, shows Xanifolia Y1 inhibits Lung cancer, Melanoma and Prostate cancer activities.

FIG. 14: Y1 activities 8, shows Xanifolia Y1 inhibits Colon cancer, Ovarian cancer and Breast cancer activities.

Figure 15:
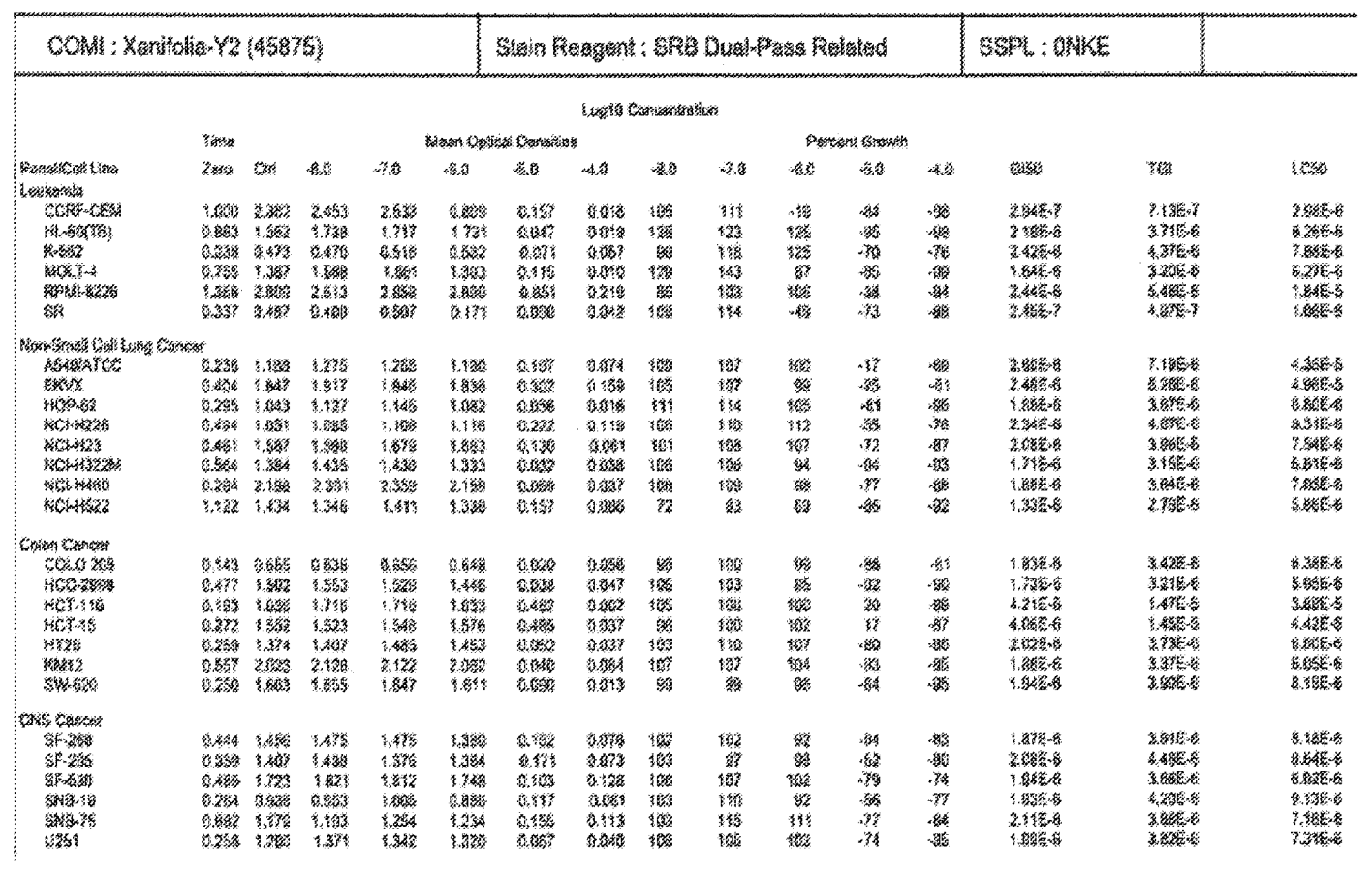

FIG. 15: Y2 activities 1, shows Xanifolia Y2 inhibits Leukemia cancer, Lung cancer, Colon cancer and CNS cancer activities.

Figure 16:
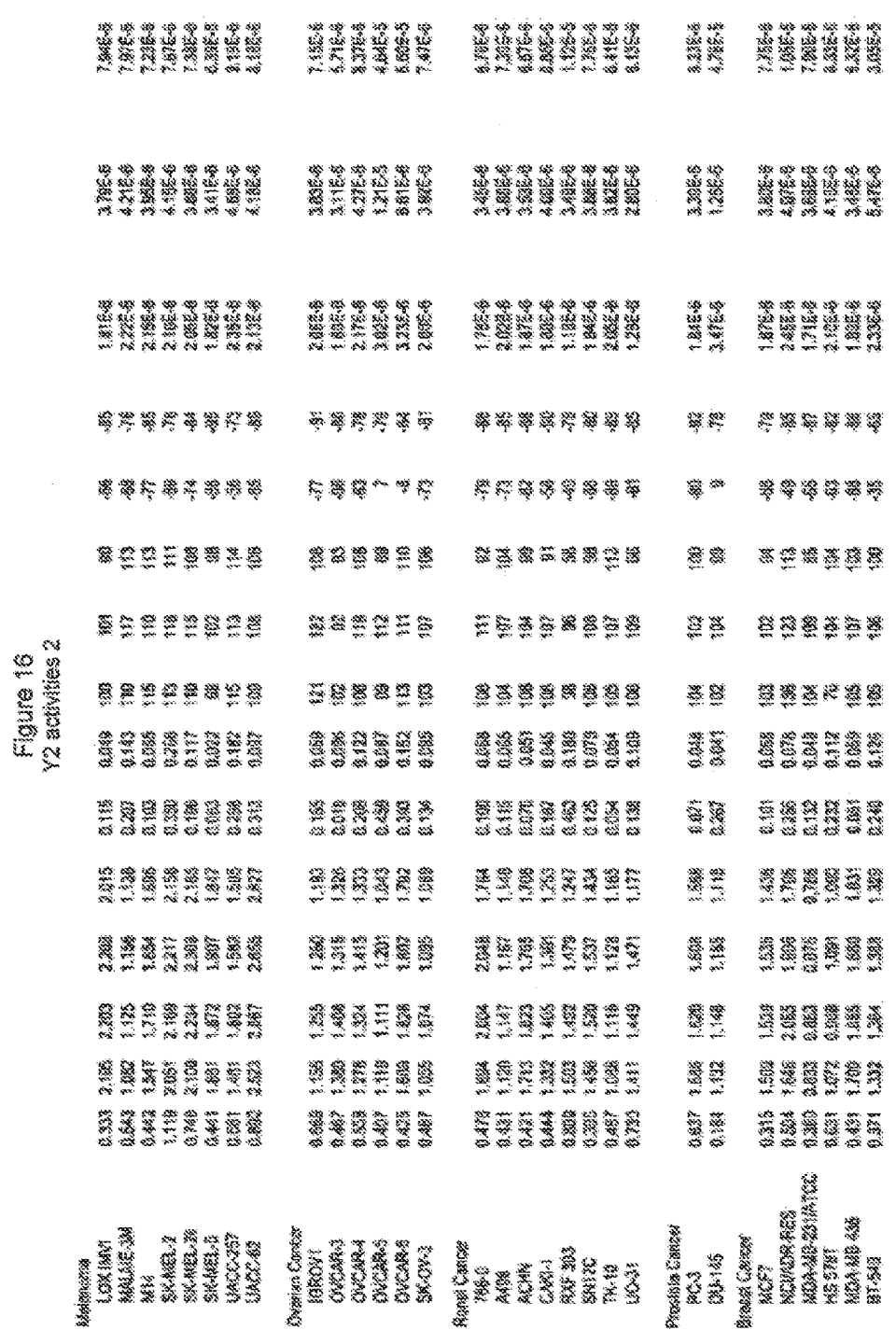

FIG. 16: Y2 activities 2, shows Xanifolia Y2 inhibits Melanoma, Ovarian cancer, Renal cancer, Prostate cancer and Breast cancer activities.

Figure 17:
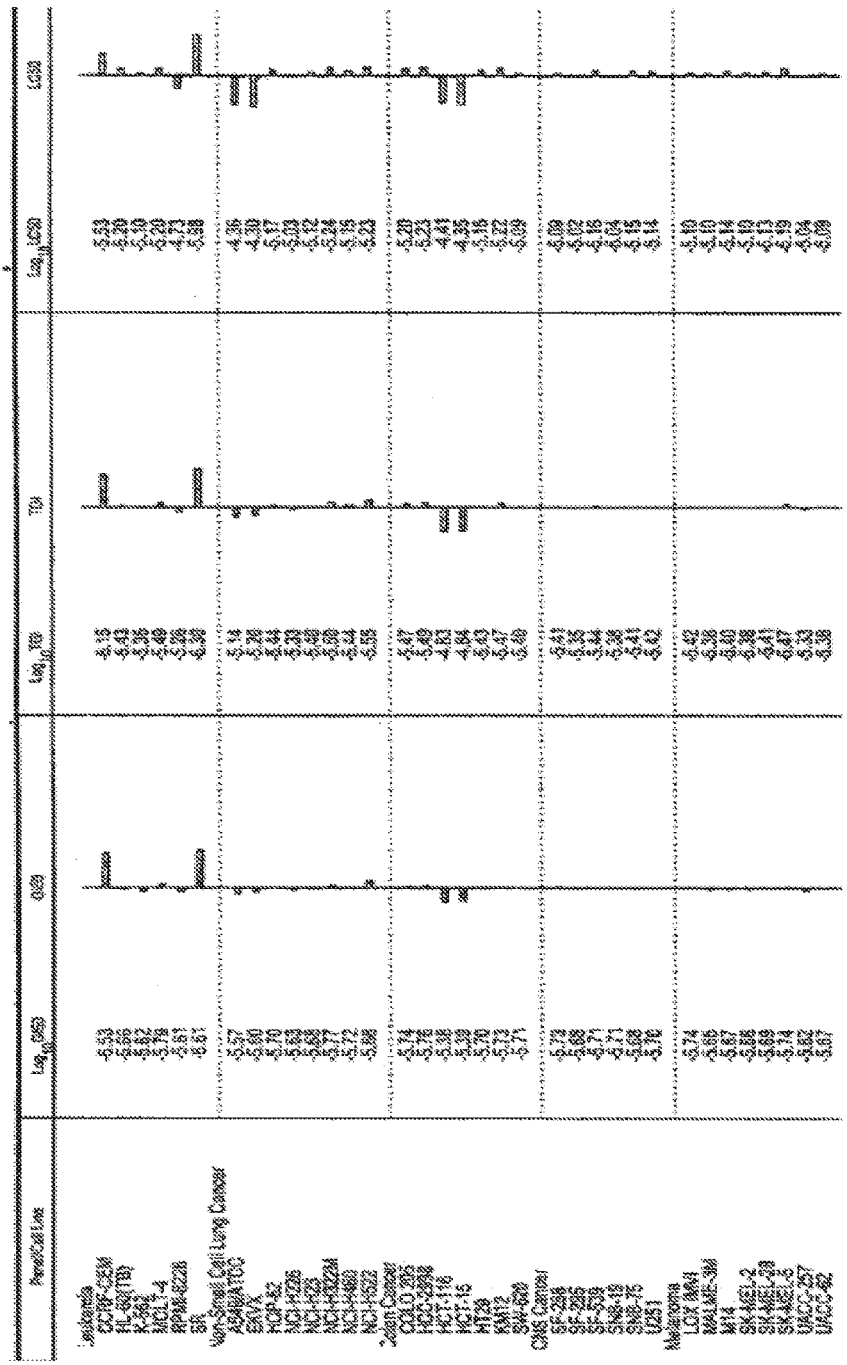

FIG. 17: Y2 activities 3, shows Xanifolia Y2 inhibits Leukemia cancer, Lung cancer, Colon cancer, CNS cancer and Melanoma activities.

Figure 18:
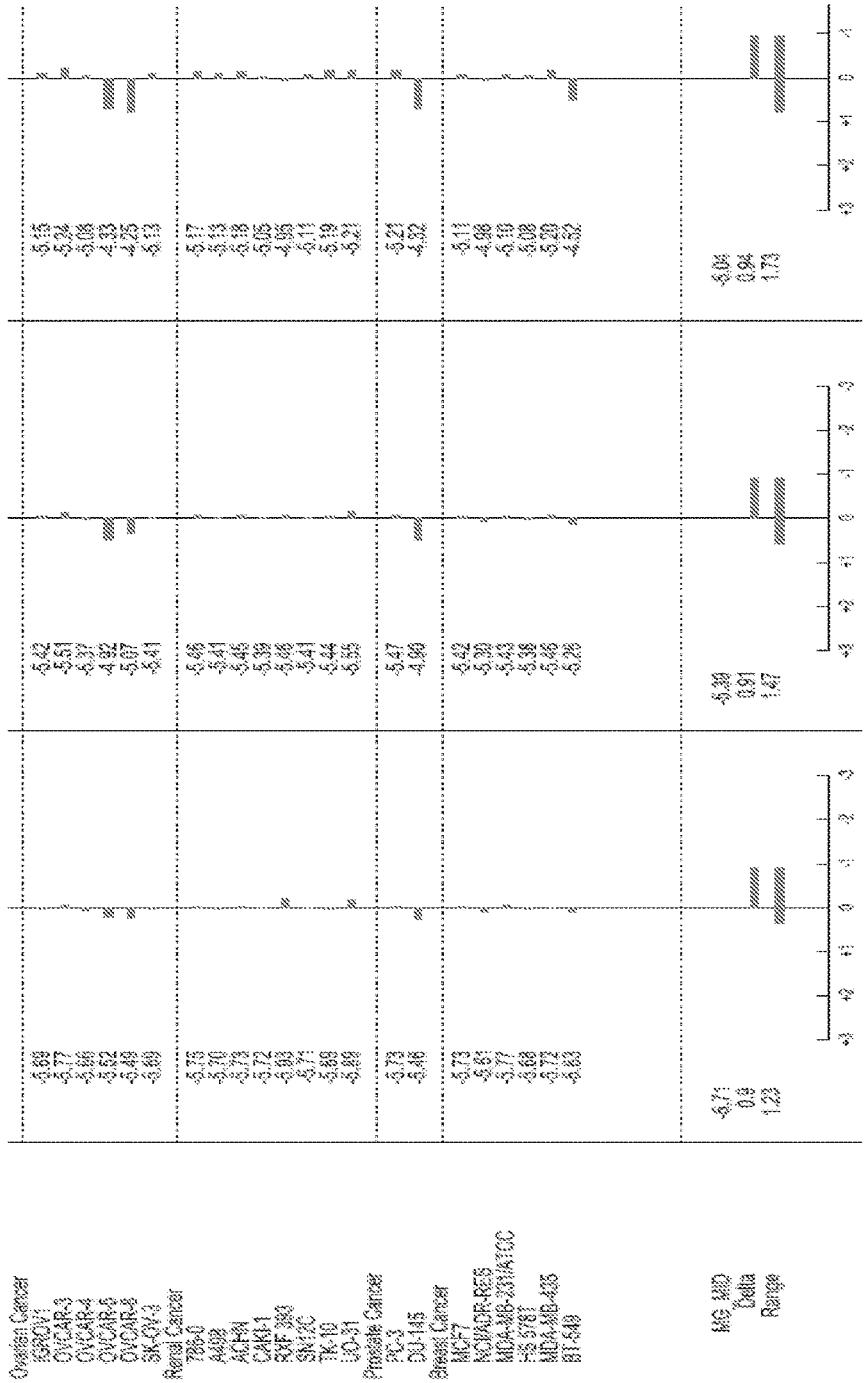

FIG. 18: Y2 activities 4, shows Xanifolia Y2 inhibits Ovarian cancer, Renal cancer, Prostate cancer and Breast cancer activities.

Figure 19:
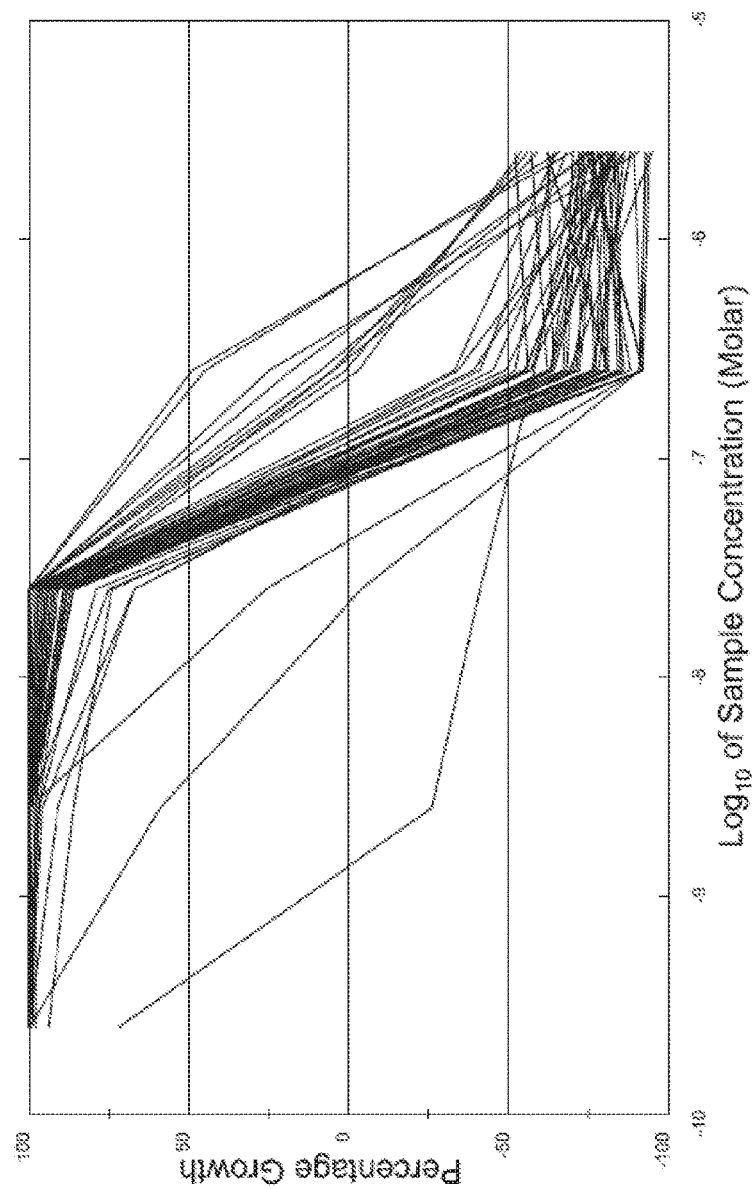

FIG. 19: Y2 activities 5, shows Xanifolia Y2 inhibits Leukemia cancer, Lung cancer, Colon cancer, CNS cancer, Melanoma, Ovarian cancer, Renal cancer, Prostate cancer and Breast cancer activities.

Figure 20:
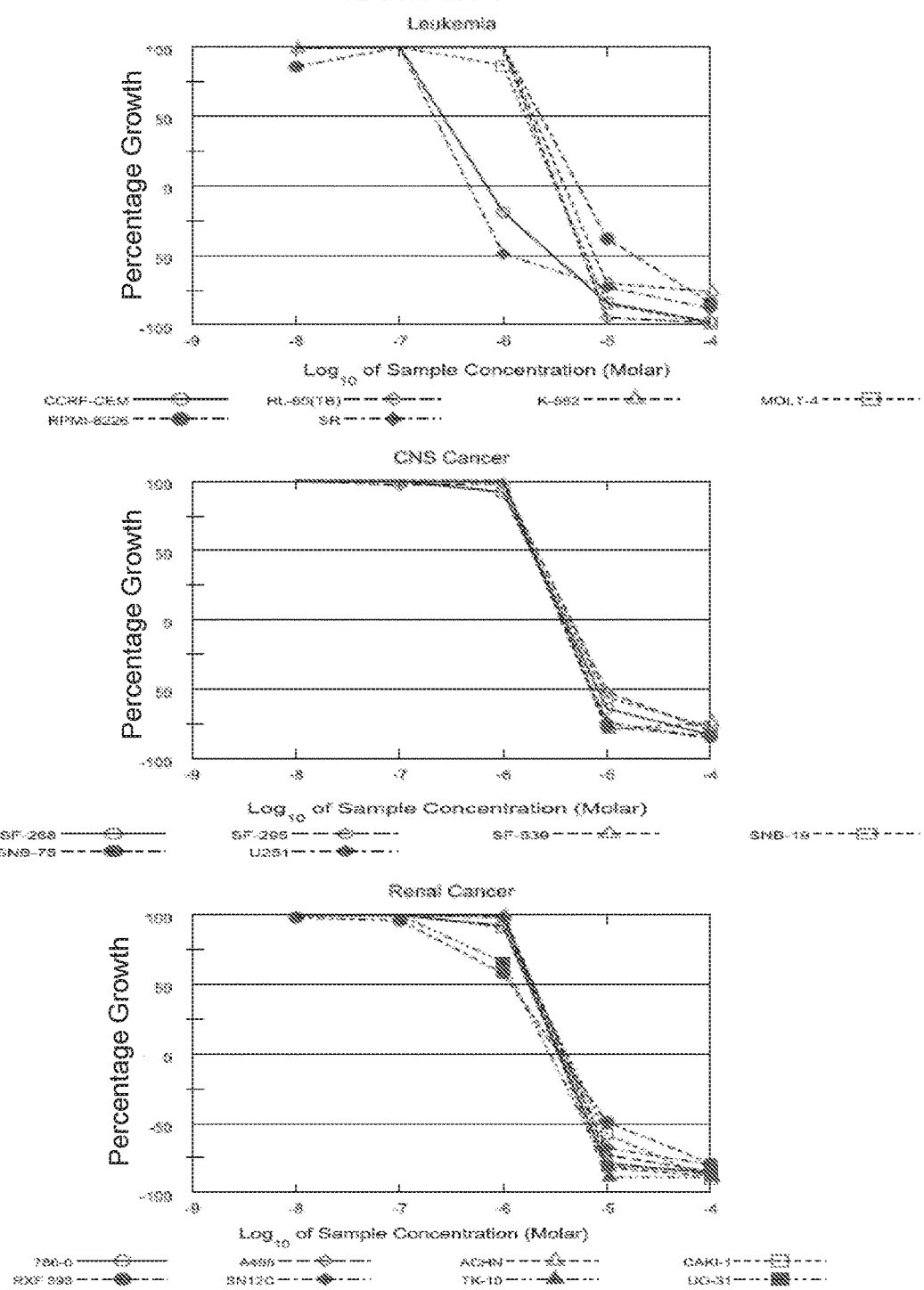

FIG. 20: Y2 activities 6, shows Xanifolia Y2 inhibits Leukemia cancer, CNS cancer and Renal cancer activities.

FIG. 21: Y2 activities 7, shows Xanifolia Y2 inhibits Lung cancer, Melanoma and Prostate cancer activities.

Figure 22:
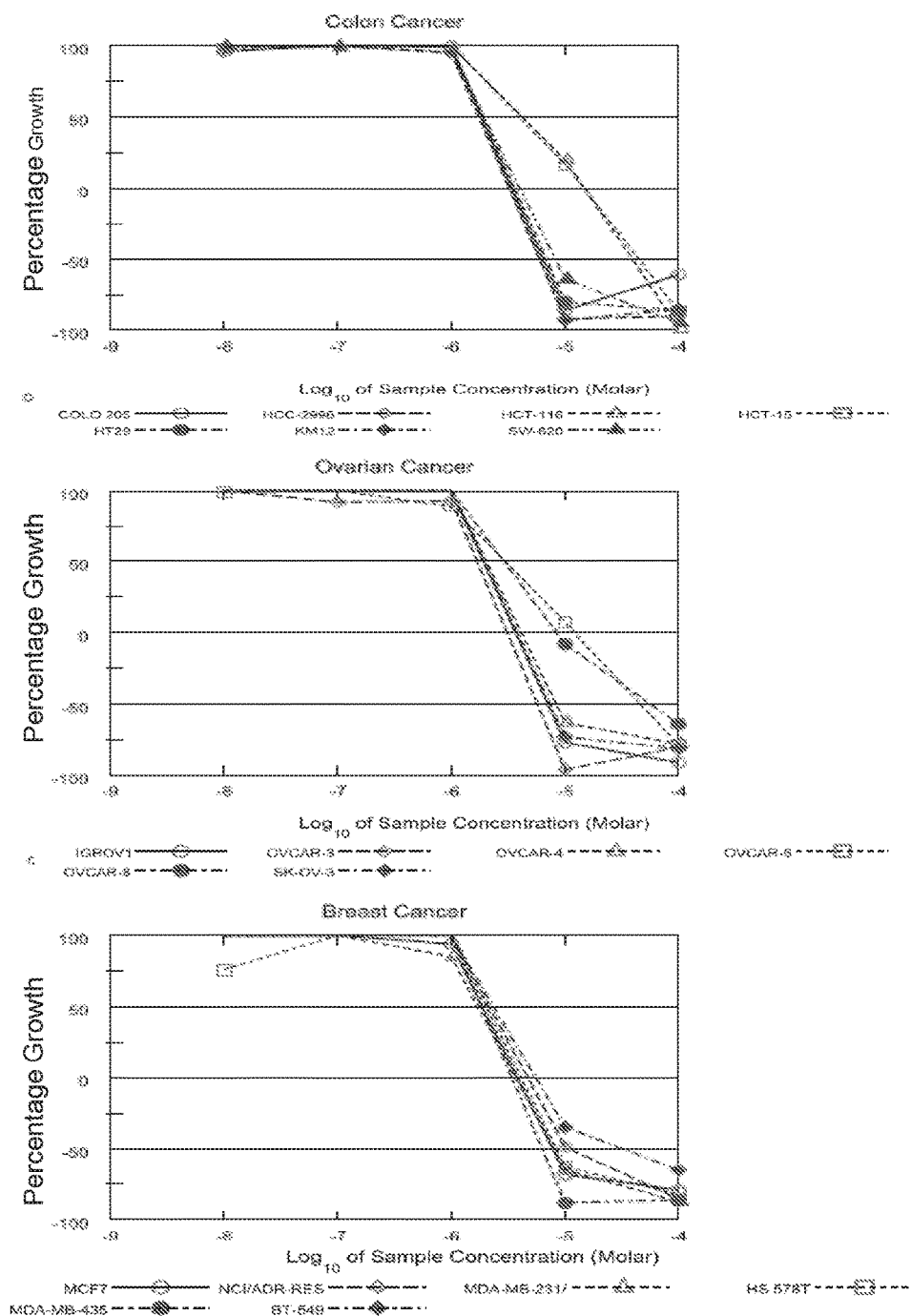

FIG. 22: Y2 activities 8, shows Xanifolia Y2 inhibits Colon cancer, Ovarian cancer and Breast cancer activities.

Figure 23:
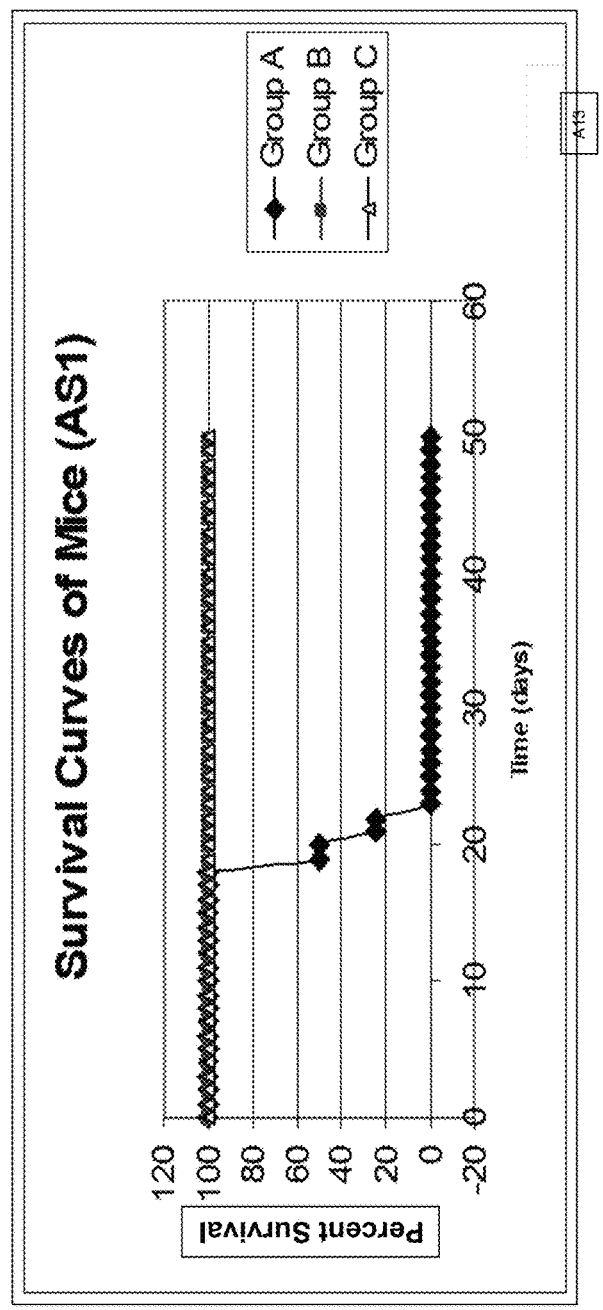

FIG. 23: Animal study result shows Group A Mice—Implanted tumor and no drug, Died on day 19-22; Group B Mice—Implanted tumor and with drug, survived over 50 days; Group C Mice—No tumor and with drug, survived over 50 days.

Figure 24:
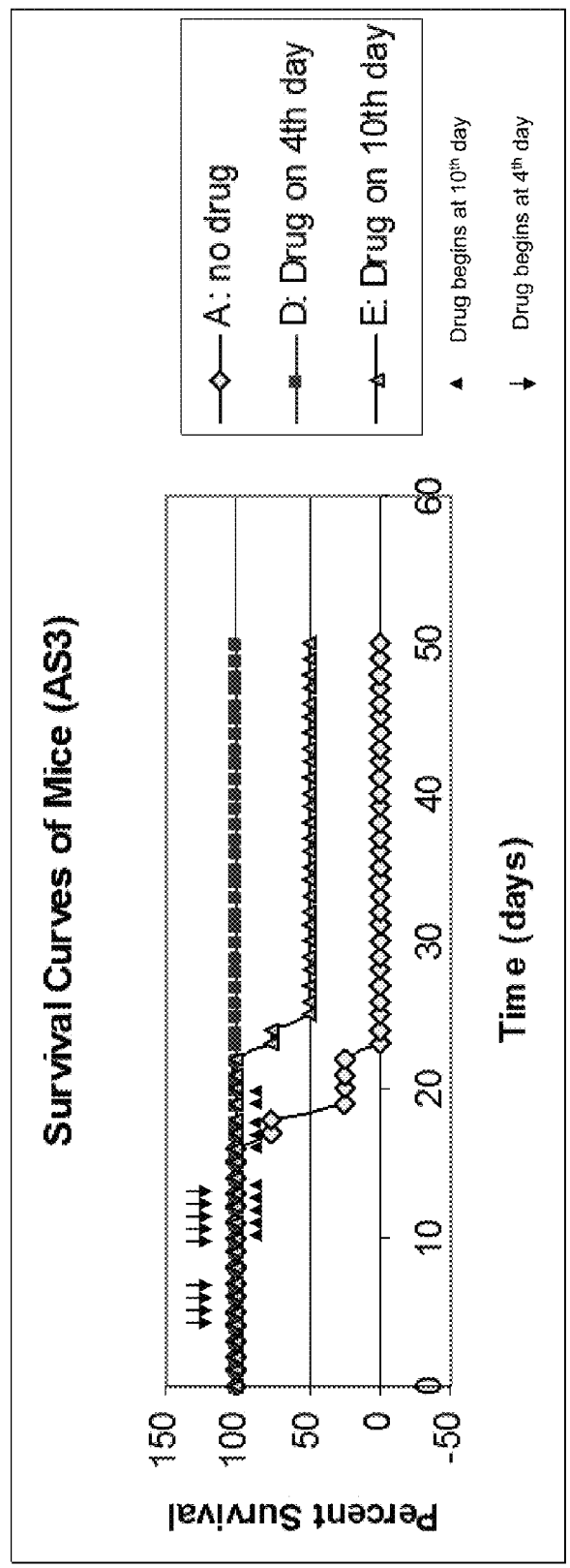

FIG. 24: Animal study result shows Group A Mice implanted with tumor and no drug, all died within 24 days; Group D Mice implanted with tumor and were given drug 9 times from 4th day, all survived; Group E Mice implanted with tumor and were given drug 10 times from 10th day, half the number of mice survived.

Figure 25:
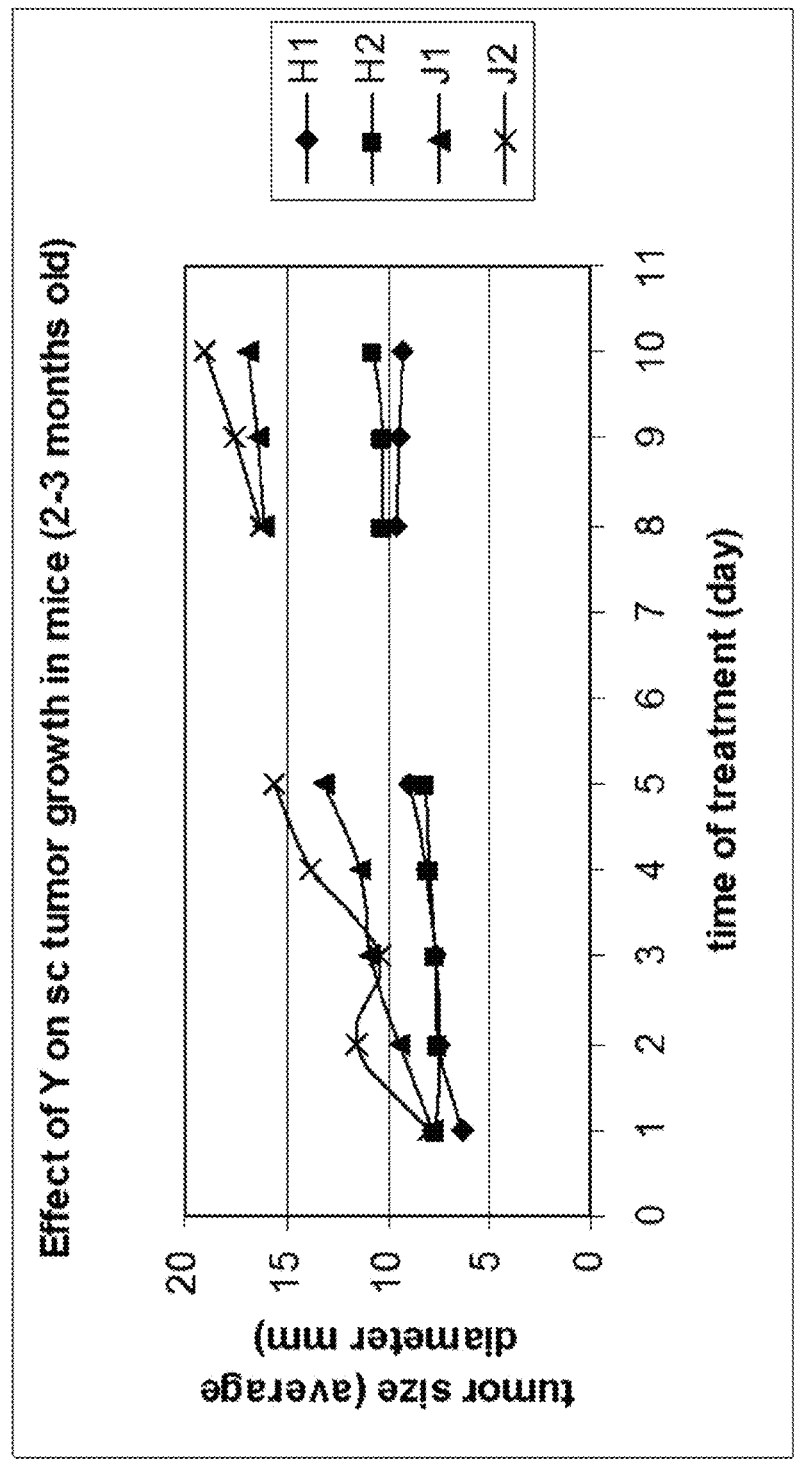

FIG. 25: Animal study shows that the tumor size is 45% smaller in mice with drug than the mice with no drug in 10 days period.

Figure 26:
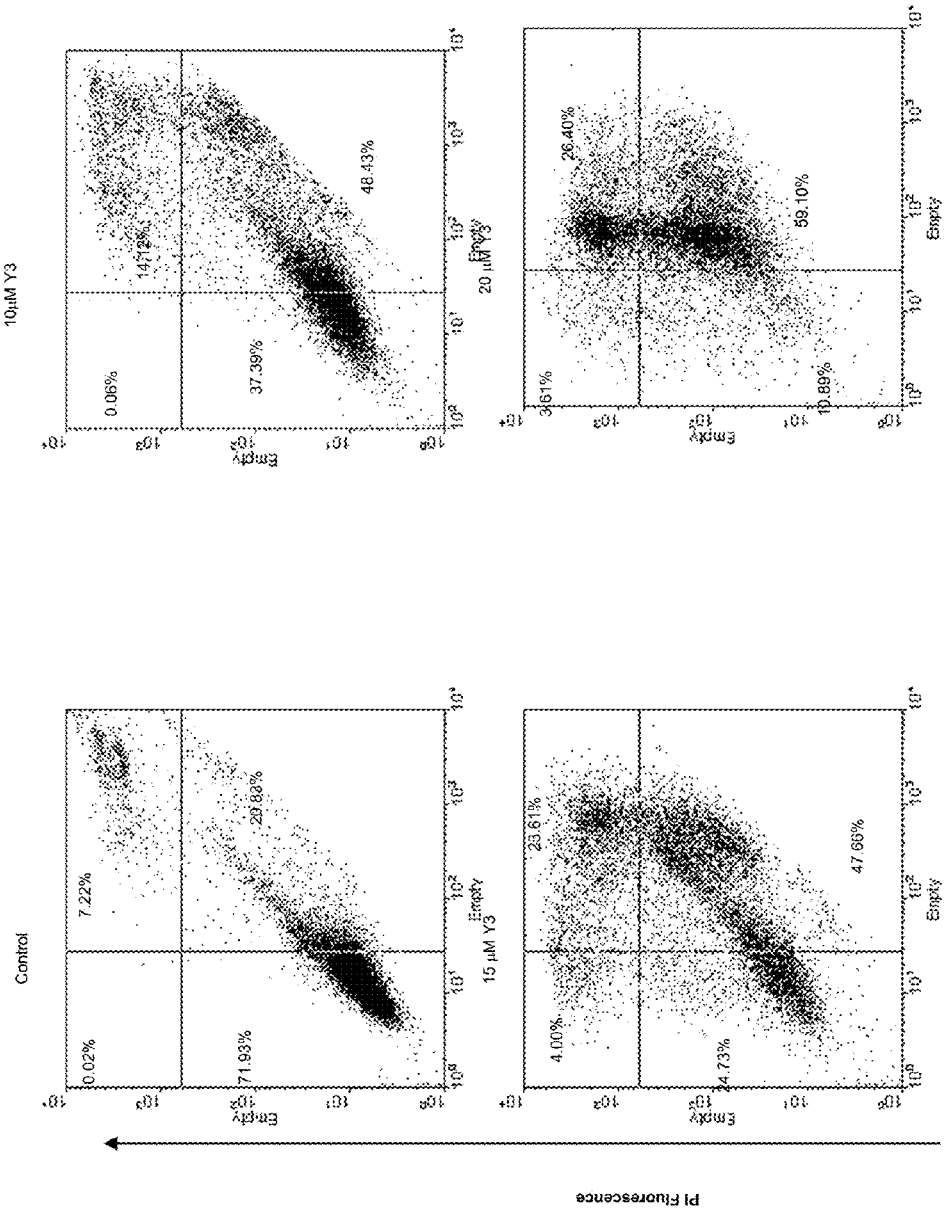

FIG. 26: Study apoptosis induced by Xanifolia-Y that apoptosis is a major form of cell death induced by Xanifolia-Y.

Figure 27:
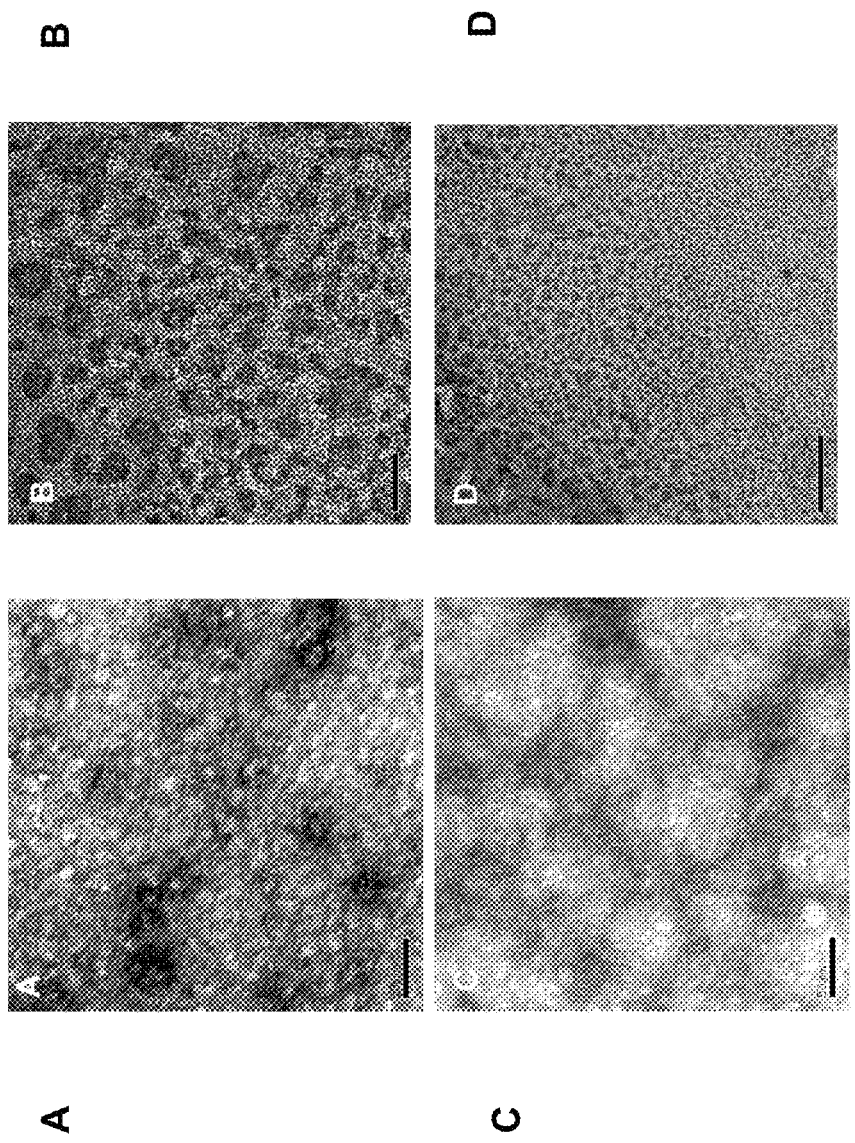

FIG. 27: EM study the effect of Xanifolia on membrane show that patches of pits were found in the membrane of Xanifolia-Y treated cells (B) but not in cells treated with the DMSO (A) or AKOH-Y (C) controls. These pits have the size from 80 A to 500 A (in diameter). The pits represent holes formed in the membrane. The pits are arranged in a characteristic pattern with smaller pits (80 A in diameter) located in the periphery and the bigger ones (500 A in diameter) in the center. The bigger holes are resulted from fusing of the smaller holes (D). Membrane image of cells treated with A: DMSO solvent control, 60 min (magnification: ×60,000); B: Xanifolia-Y 5 uM, 60 min. (×60000); C: AKOH-Y, 20 uM, 60 min. (×60000); D: Xanifolia-Y 5 uM, 60 min. (×20000).

Figure 28:
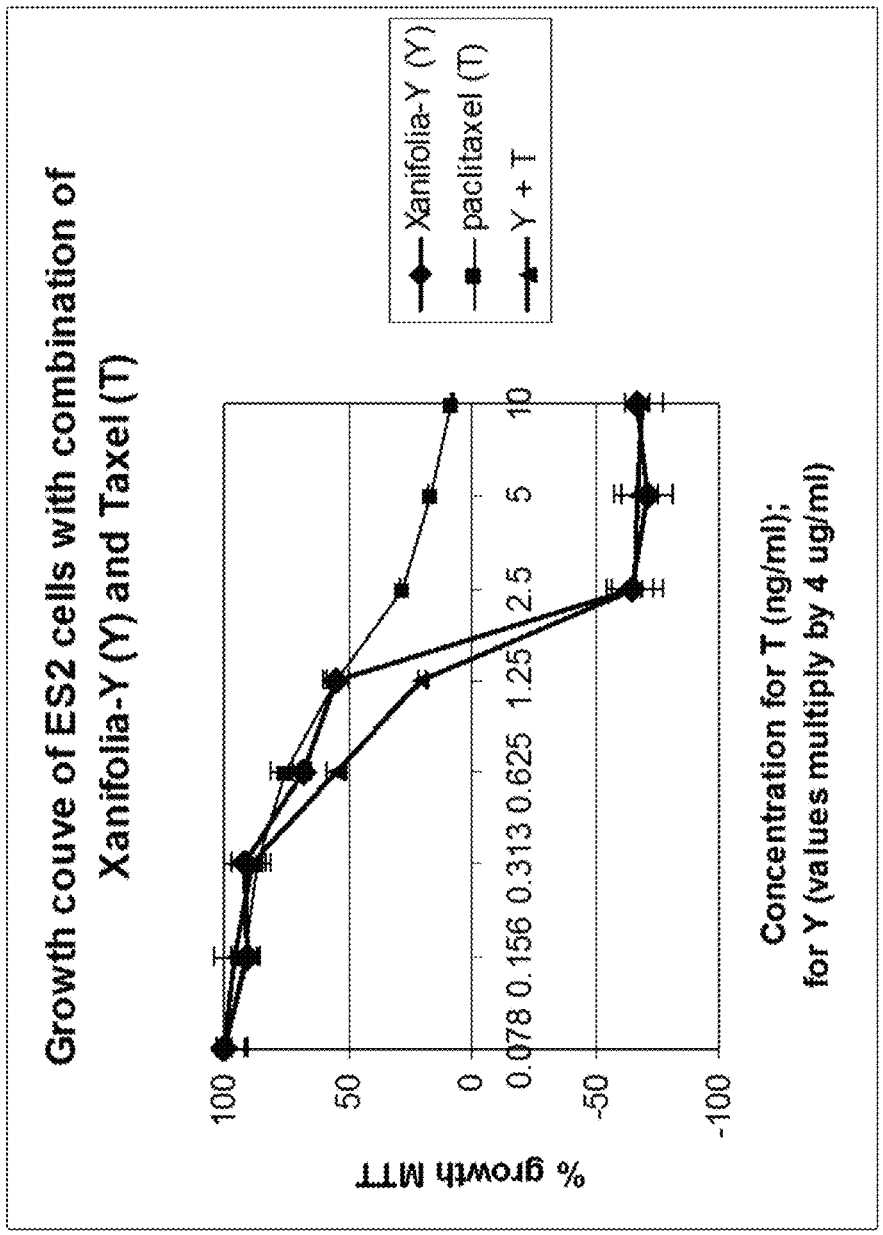

FIG. 28: Inhibition effect of Xanifolia and Paclitaxel on cancer cell.

Figure 29:
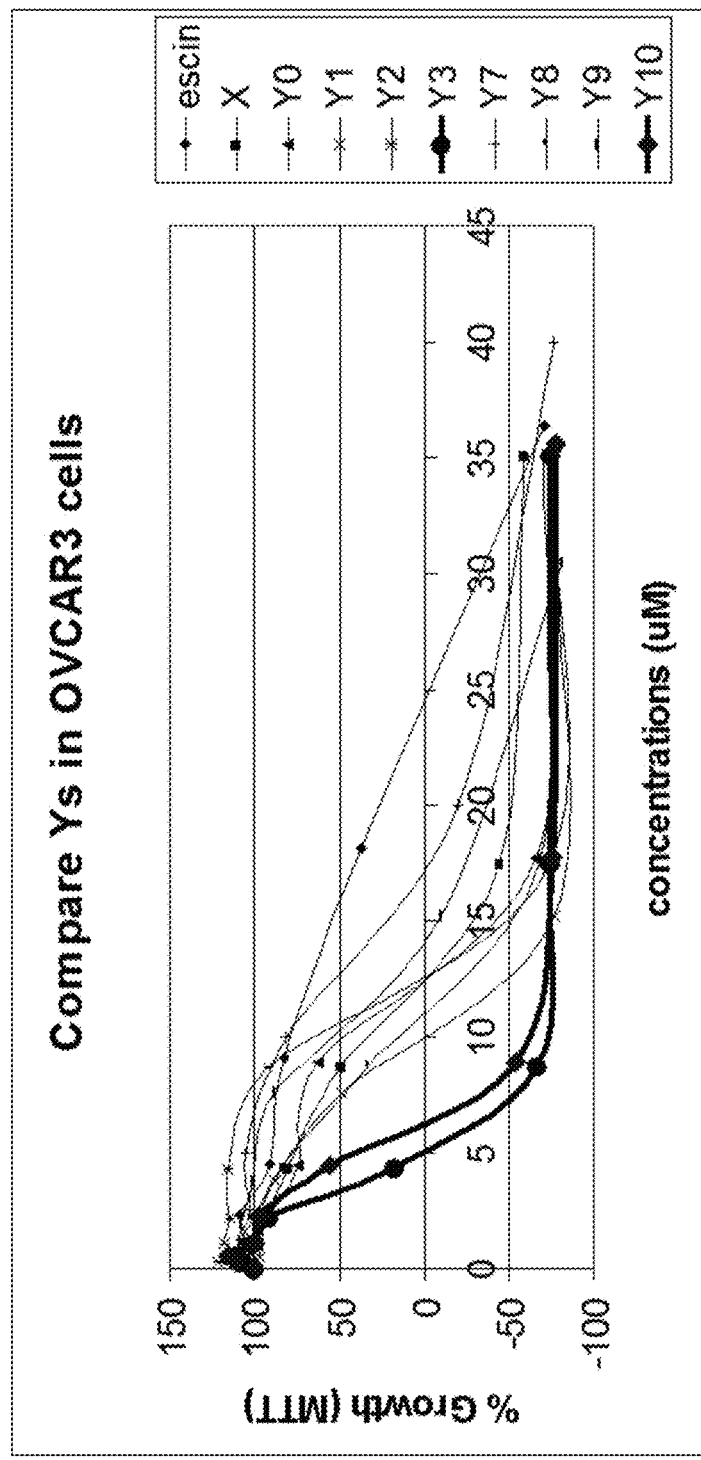

FIG. 29: Activities of Ys.

Figure 30:
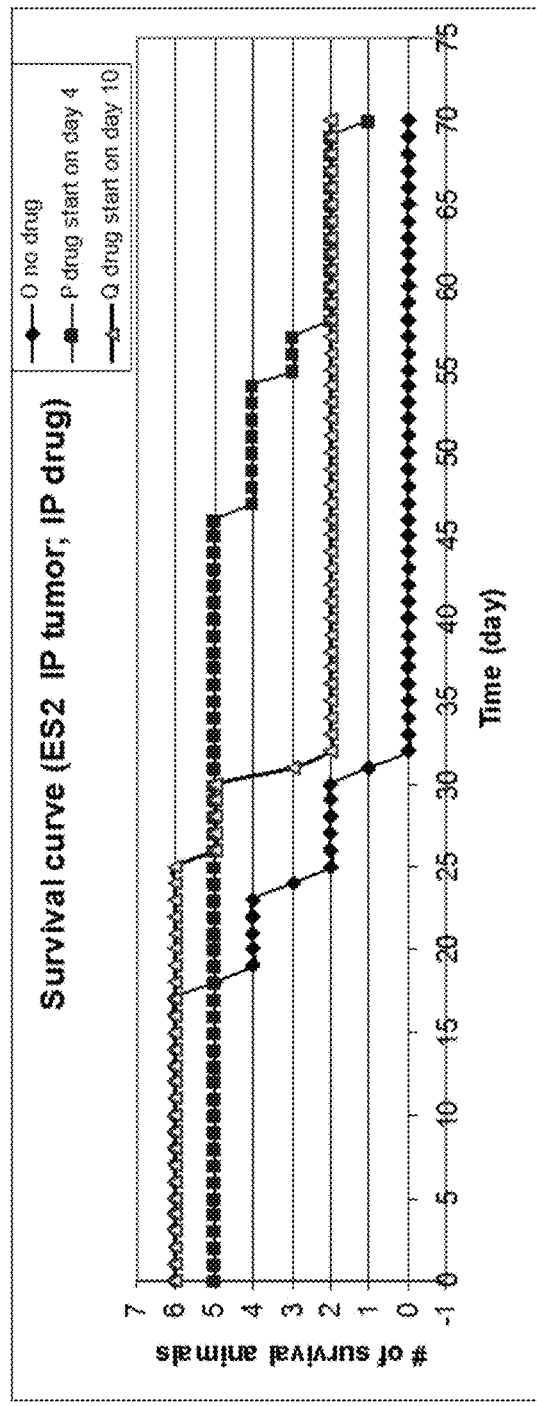

FIG. 30: Animal survival experiment.

Figure 31:
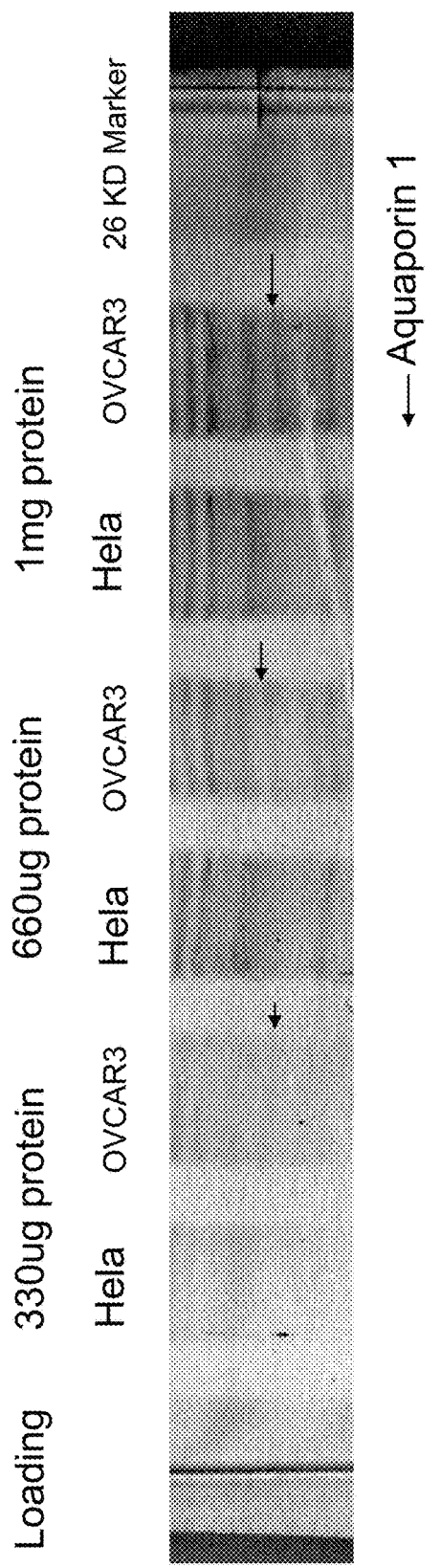

FIG. 31: Determination of Aquaporin.

Figure 32:
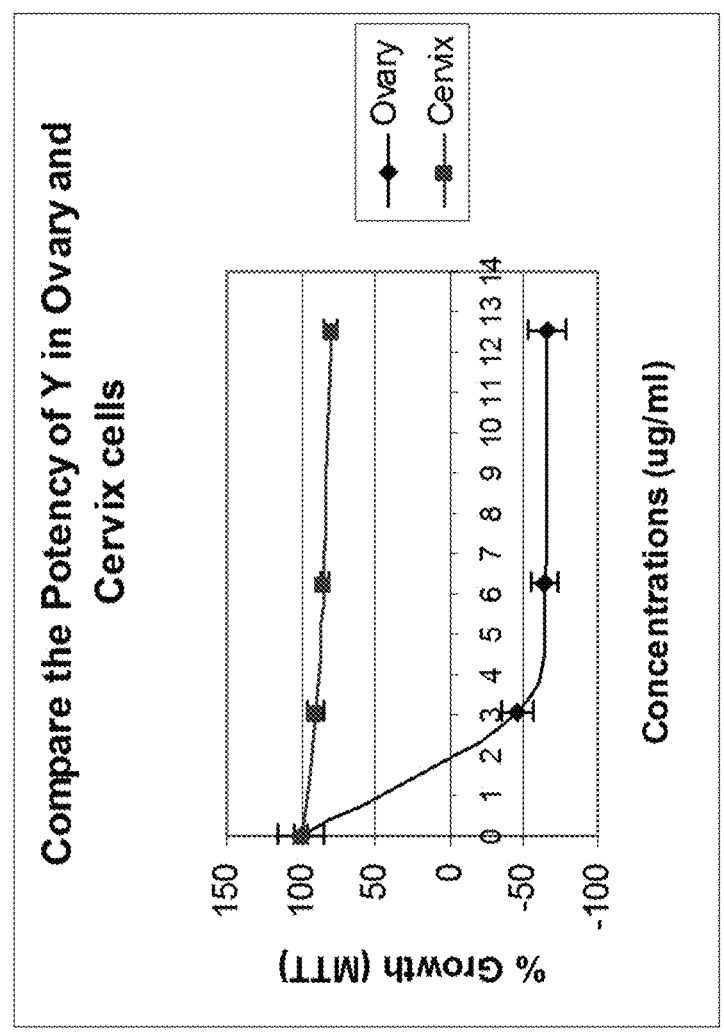

FIG. 32: Compare the potency of Xanifolia Y in ovary and cervix cell.

Figure 33:
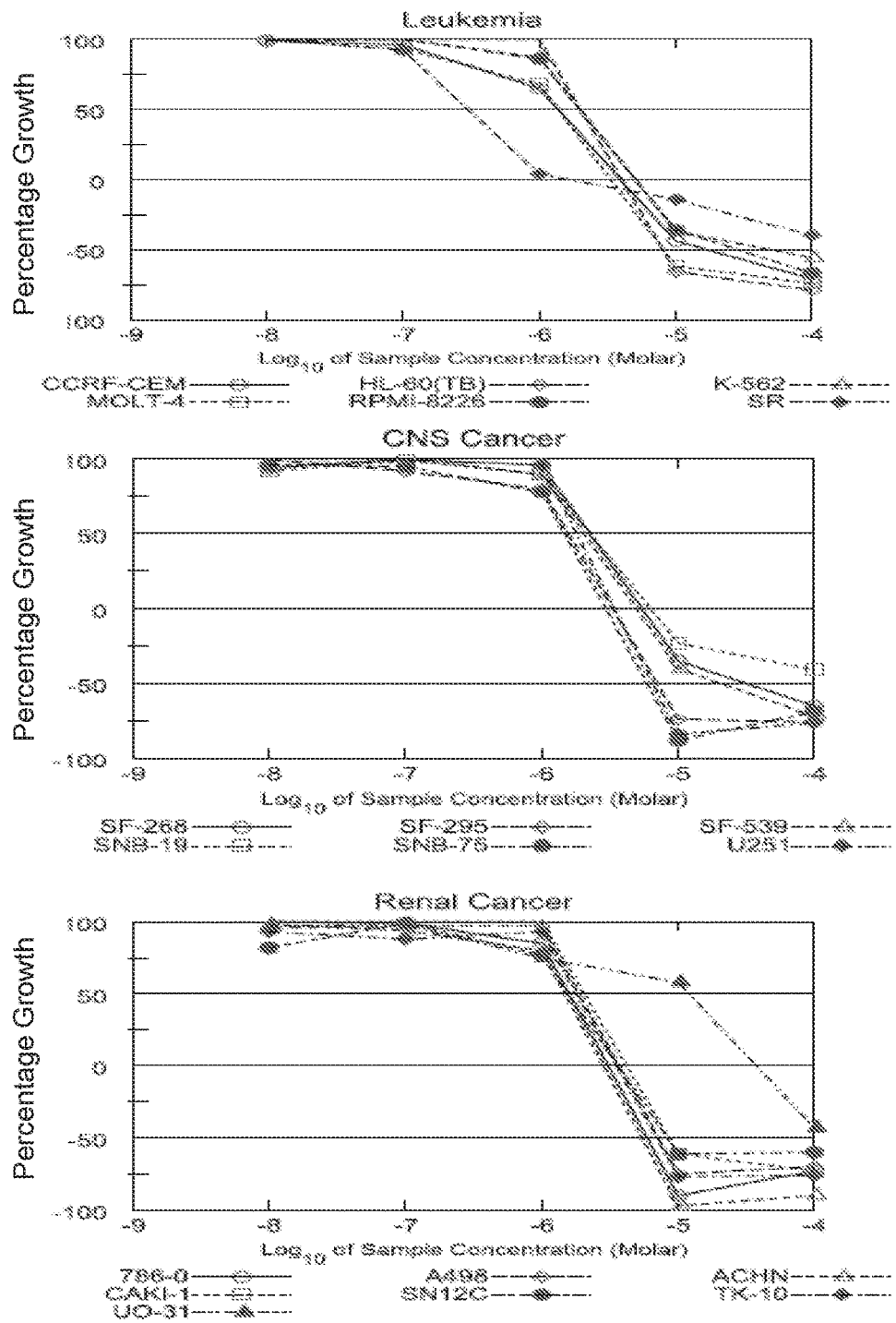

FIG. 33: show Xanifolia Y0 inhibits Leukemia cancer, CNS cancer, Renal cancer activities.

Figure 34:
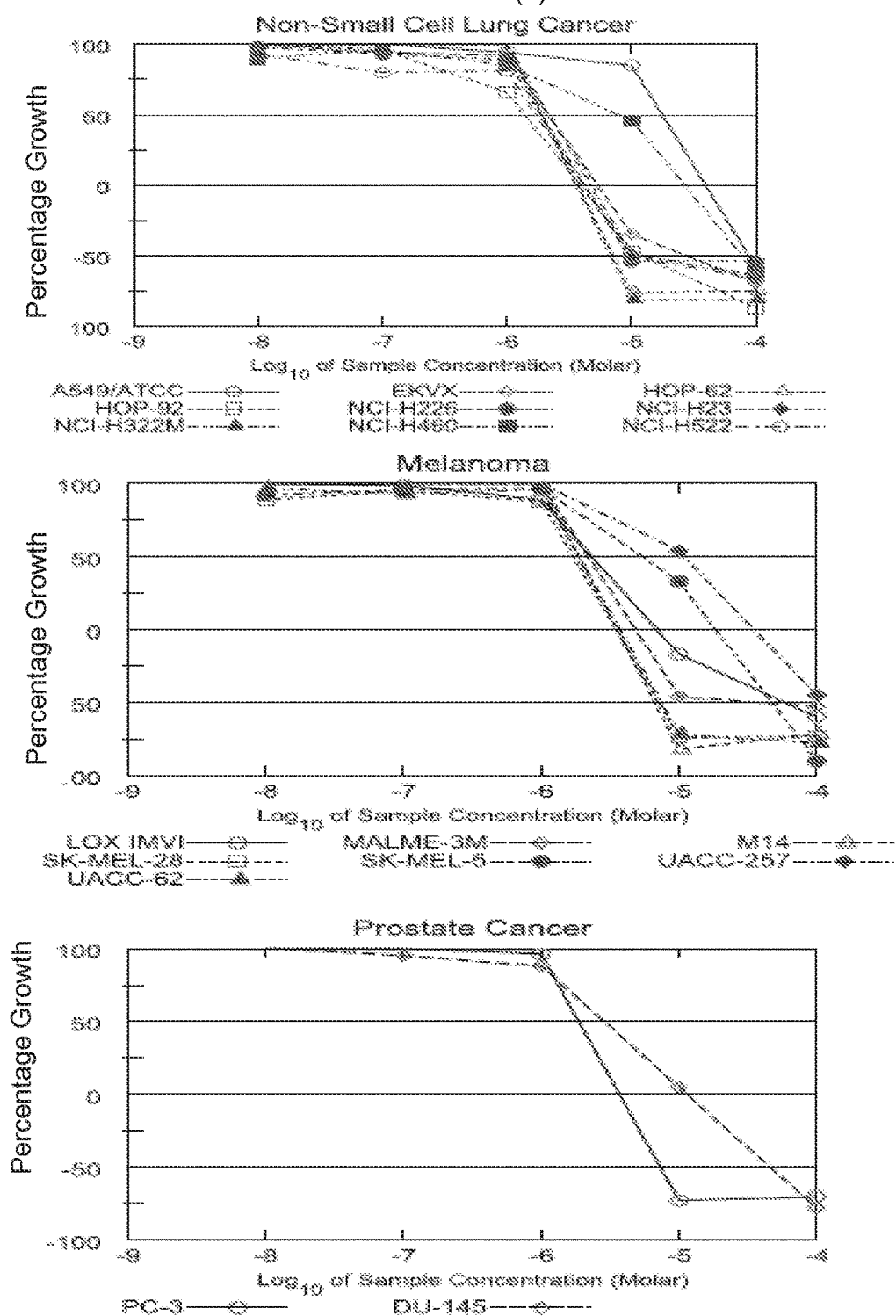

FIG. 34: show Xanifolia Y0 inhibits Lung cancer, Melanoma, Prostate cancer activities.

FIG. 35: show Xanifolia Y0 inhibits Colon cancer, Ovarian cancer, Breast cancer activities.

FIG. 36: show Xanifolia Y9 inhibits Leukemia cancer, CNS cancer, Renal cancer activities.

Figure 37:
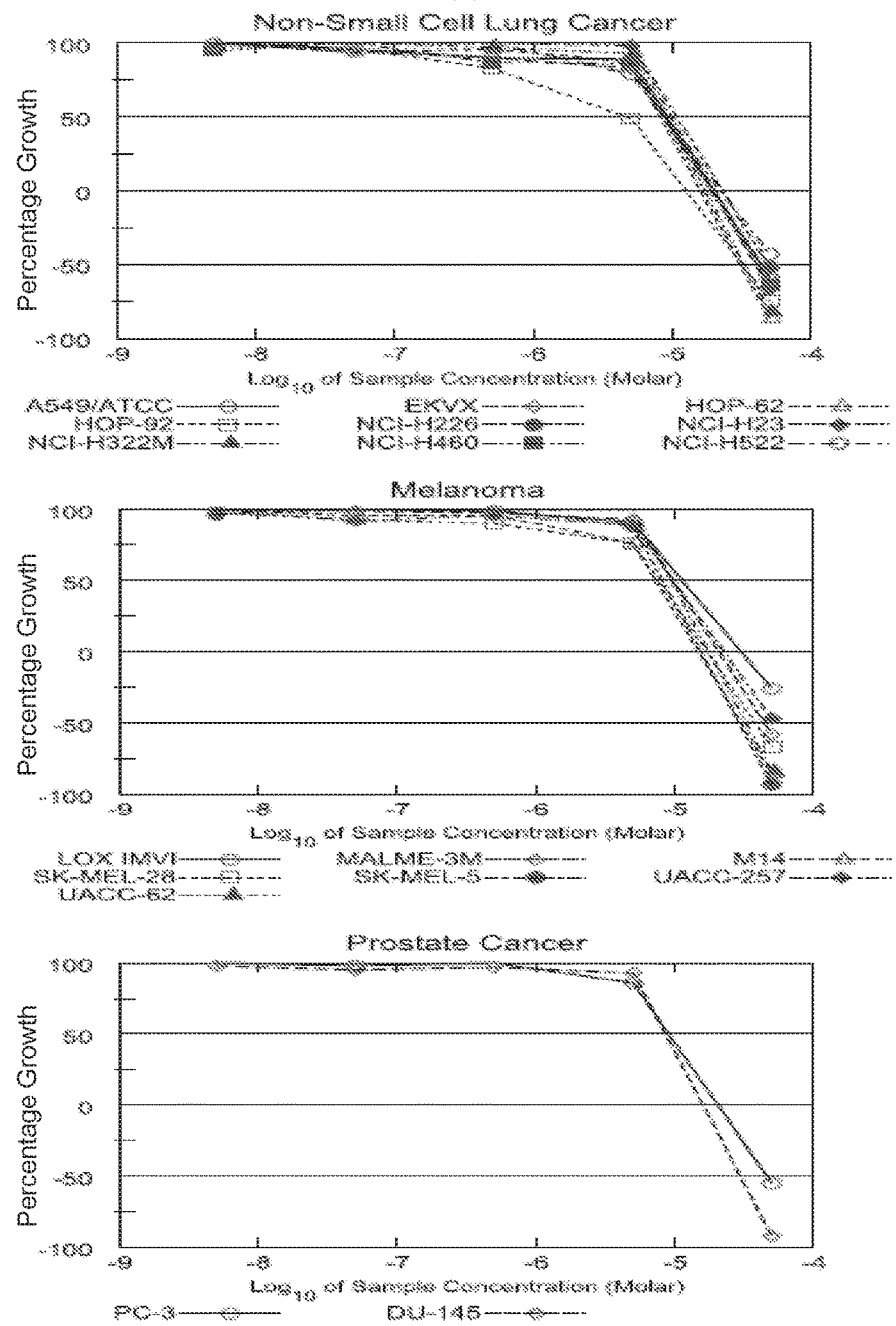

FIG. 37: show Xanifolia Y9 inhibits Lung cancer, Melanoma, Prostate cancer activities.

FIG. 38: show Xanifolia Y9 inhibits Colon cancer, Ovarian cancer, Breast cancer activities.

Figure 39:
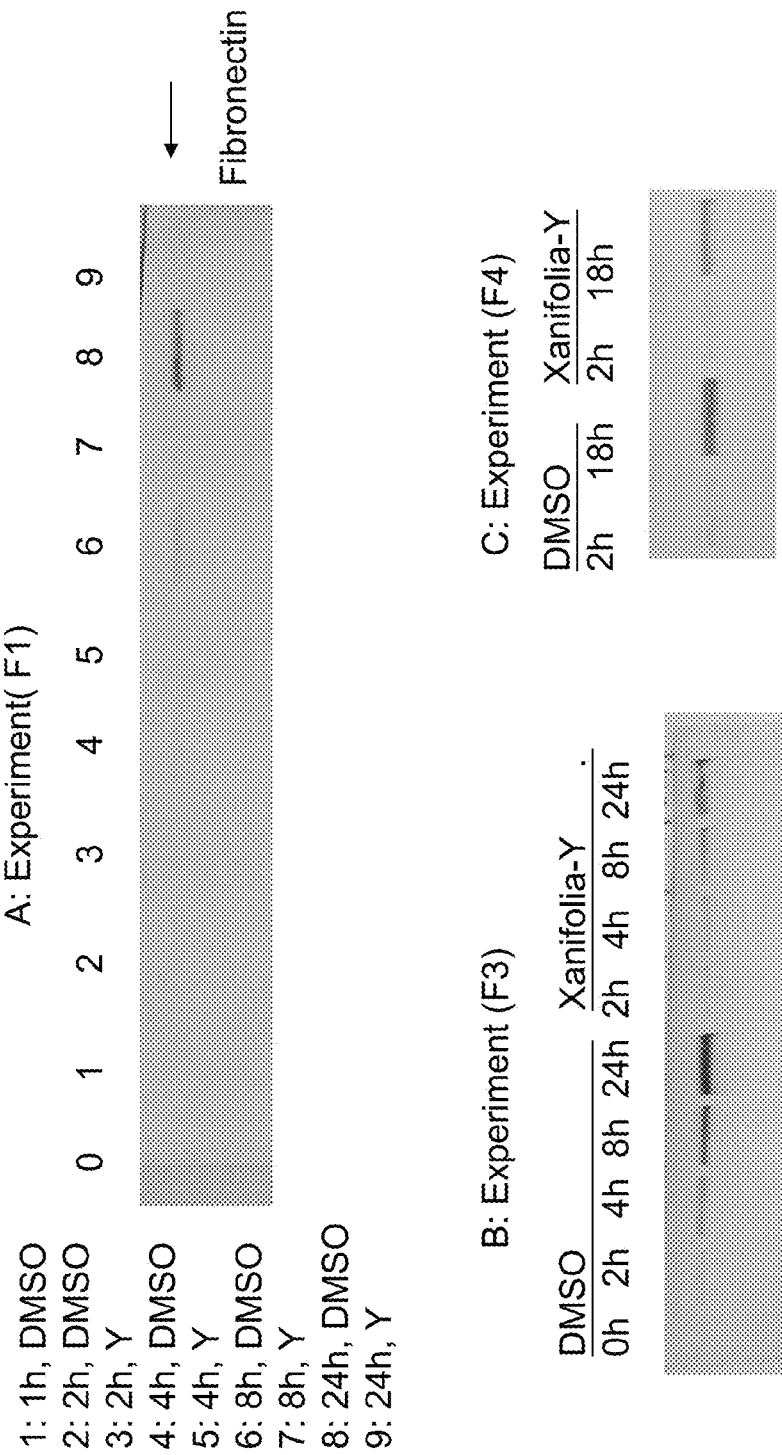

FIG. 39: Time studies of inhibition of Fibronectin secretion from cancer cells (ES2) after incubation of Xanifolia-Y. Fibronectin released in culture medium was determined by Western blot. A: (results of experiment F1) Y is Xanifolia compound Y; B: (results of experiment F3); C: (results of experiment F4).

FIG. 40: Inhibition of Fibronectin Secretion by Xanifolia-Y (Western Blot). A: result of experiment F5; B: result of experiment F7; C: result of experiment F8; D: result of experiment F11; E: result of experiment F12; F: result of experiment F13; G: result of experiment F14B; H: result of experiment 14C.

Figure 41:
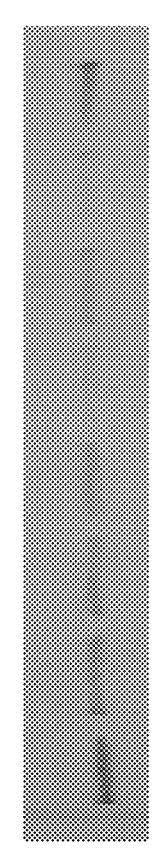

FIG. 41: Inhibition of Fibronectin Secretion by Xanifolia-Y (Western Blot). A: result of experiment F23; B: result of experiment F24; C: result of experiment F26; D: result of experiment F27; E: result of experiment F29; F: result of experiment F28.

FIG. 42: Inhibition of Fibronectin Secretion by Xanifolia-Y (Western Blot). A: result of experiment F30; B: result of experiment F31; C: result of experiment F32; D: result of experiment F33A; E: result of experiment F20.

Figure 43:
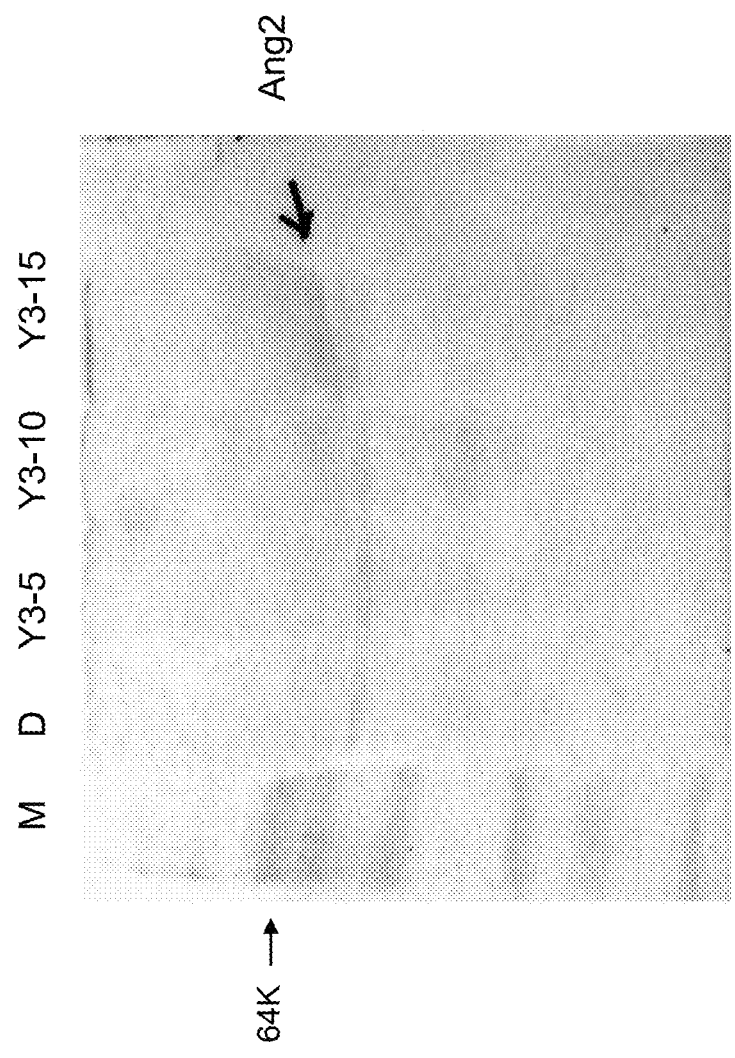

FIG. 43: Increase synthesis of Angiopoietin-2 in ES2 cells by Xanifolia-Y treatment.

FIG. 44: Analysis of genesis of blood vessel in xenograft tumor treated with compound Y. A and B show the tumor sections taking from mice without Xanifolia Y treatment. C and D show the tumor sections taking from mice with Xanifolia Y treatment. More blood vessels were observed in the control Group 1 than those in the drug-treated Group 2.

Figure 45:
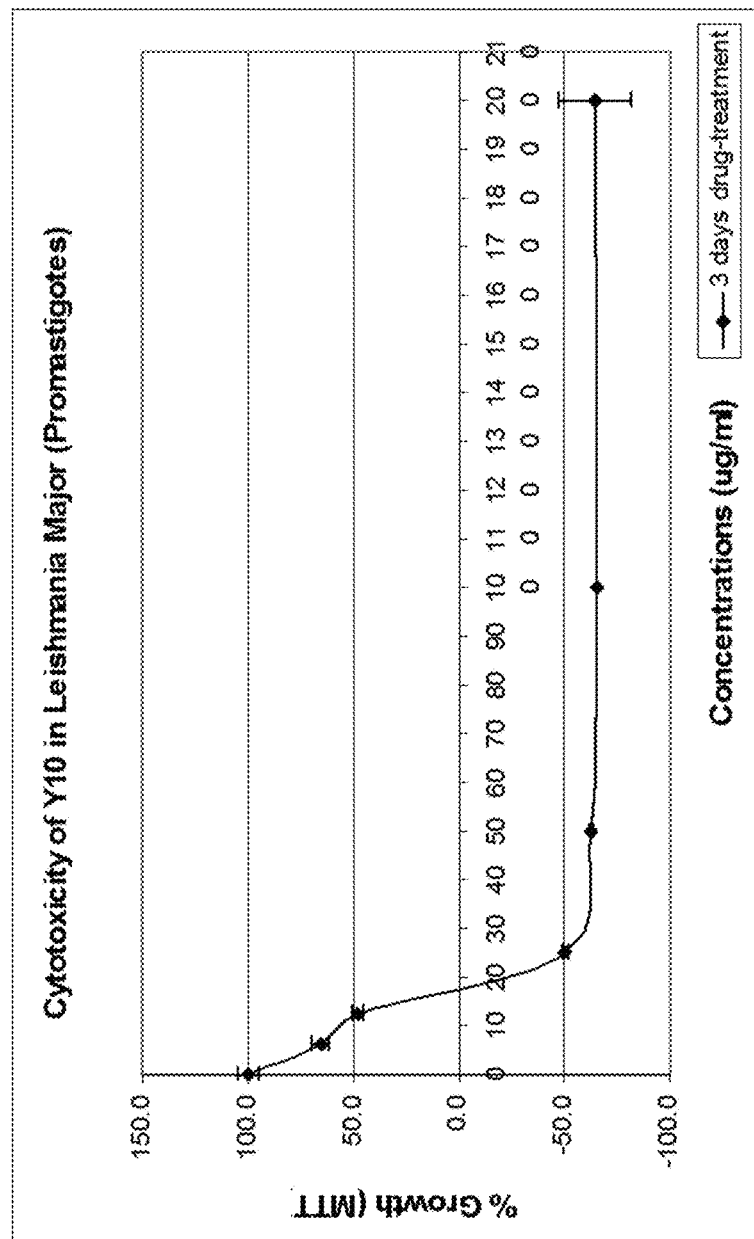

FIG. 45: Experiment shows that Y10 is cytotoxic to *Leishmania Major* (promastigotes) with IC50 approximately equal to 15 ug/ml.

DETAILED DESCRIPTION OF THE INVENTION

This invention provides the results of a program for screening the bioactive compounds from natural plants. The majority of the plants are from the Sapindaceae family, which has 140-150 genera with 1400-2000 species. The program is based on our purification methods and biological assays including the MTT assay See International Application No. PCT/US05/31900, filed Sep. 7, 2005 and U.S. Ser. No. 11/289,142, filed Nov. 28, 2005. Details also in U.S. Ser. No. 11/131,551, filed May 17, 2005

The invention provides compositions comprising triterpenoidal saponins may be isolated from plants in the following genus: *Acer, Aesculus, Alectryon, Allophylus, Allosanthus, Amesiodendron, Aphania, Aporrhiza, Arfeuillea, Arytera, Atalaya, Athyana, Averrhoidium, Blighia, Boniodendron, Camellia, Camptolepis, Cardiospermum, Castanospora, Chonopetalum, Chouxia, Chytranthus, Conchopetalum, Cossinia, Cubilia, Cupania, Cupaniopsis, Deinbollia, Delavaya, Diatenopteryx, Dictyoneura, Dilodendron, Dimocarpus, Diploglottis, Diplokelepa, Diplopeltis, Dipteronia, Distichostemon, Dodonaea, Doratoxylon, Elattostachys, Eriocoelum, Erioglossum, Erythrophysa, Euchorium, Euphorianthus, Eurycorymbus, Exothea, Filicium, Ganophyllum, Glenniea, Gloeocarpus, Gongrodiscus, Gongrospermum, Guindilia, Guioa, Handeliodendron, Haplocoelum, Harpullia, Hippobromus, Hornea, Houssayanthus, Hypelate, Hypseloderma, Jagera, Koelreuteria, Laccodiscus, Lecaniodiscus, Lepiderema, Lepidopetalum, Lepisanthes, Litchi, Llagunoa, Lophostigma, Loxodiscus, Lychnodiscus, Macphersonia, Maesa, Magonia, Majidea, Matayba, Melicoccus, Mischocarpus, Molinaea, Negundo, Neotina, Nephelium, Otonephelium, Otophora, Pappea, Paranephelium, Pauffinia, Pavieasia, Pentascyphus, Phyllotrichum, Pittosporum, Placodiscus, Plagioscyphus, Podonephelium, Pometia, Porocystis, Pseudima, Pseudopancovia, Pseudopteris, Ptelea, Radlkofera, Rhysotoechia, Sapindus, Sarcopteryx, Sarcotoechia, Scyphonychium, Serjania, Sisyrolepis, Smelophyllum, Stadmania, Stocksia, Storthocalyx, Synima, Talisia, Thinouia, Thouinia, Thouinidium, Tina, Tinopsis, Toechima, Toulicia, Trigonachras, Tripterodendron, Tristira, Tristiropsis, Tsingya, Ungnadia, Urvillea, Vouarana, Xanthoceras, Xeropspermum, Zanha, Zollingeria.*

This invention provides the uses of compositions comprising a triterpenoidal saponin. In an embodiment, the saponin has triterpenoid, triterpenoidal or other sapongenin, one or more sugar moieties and two angeloyl groups, or at least two side groups selected from the following groups: angeloyl groups, tigloyl groups or senecioyl groups, wherein the side groups are attached to the sapongenin backbone at carbon 21 and 22. In an embodiment, at least two of angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl attached to the side groups; wherein the sugar moiety in the saponin comprises at least one or more of the following sugars and alduronis acids: glucose, galactose, rhamnose, arabinose, xylose, fucose, allose, altrose, gulose, idose, lyxose, mannose, psicose, ribose, sorbose, tagatose, talose, fructose, glucuronic acid, galacturonic acid; or their derivatives thereof, or the combination thereof; wherein the sugar preferably comprises glucuronic acid, arabinose and galactose.

This invention further provides a composition comprising the structures comprising at least two side groups selected from the following groups: angeloyl, tigloyl or senecioyl groups, wherein the side groups are attached to a triterpenoidal, triterpenoid, triterpenoidal or other sapongenin backbone. These compositions are obtainable from the above-identified plants or synthesis. This invention provides a method of preparing the saponins, comprising the steps of:

(a) Extracting roots, kernels, leaves, bark, stem, husks, seeds, seed shells or fruits of the above plant, or combinations thereof with organic solvents such as ethanol or methanol to obtain an organic extract; (b) Collecting the organic extracts; (c) Refluxing the organic extract to obtain a second extract; (d) Removing the organic solvent from the second extract to obtain a third extract; (e) Drying and sterilizing the third extract to obtain a crude extract powder; (f) Fractionating the crude extract powder into fractions or components. Fractionation may be achieved by HPLC and FPLC chromatography with silica gel, C18 or other equivalent solid phase materials; (g) Monitoring the fractionating, if using HPLC or FPLC, the absorption wavelength at 207 nm to 500 nm may be used; (h) Identifying the bioactive components of the crude extract; (i) Purifying one or more bioactive components of the crude extract with FPLC to obtain one or more fractions of the bioactive component; and (j) isolating the bioactive components with chromatographic techniques that employ preparative columns and HPLC. In an embodiment, this invention provides the method of MTT Assay to test the bioactivities of the saponins or other compounds.

Cells. Human cancer cell lines were obtained from American Type Culture Collection: HTB-9 (bladder), HeLa-S3 (cervix), DU145 (prostate), H460 (lung), MCF-7 (breast), K562 (leukocytes), HCT116 (colon), HepG2 (liver), U2OS (bone), T98G (brain), SK-MEL-5 (Skin) and OVCAR-3 (ovary). The cells were grown in following culture media: HeLa-53, DU145, MCF-7, Hep-G2 and T98G are in MEN (Earle's salts); HTB-9, H460, K562 and OVCAR-3 in RPMI-1640; HCT-116 and U2OS in McCoy-5A. They are supplemented with 10% fetal calf serum, glutamine and antibiotics, and incubated in an incubator with 5% $CO_2$ humidified at 37° C.

MTT Assay. The procedure for MTT assay followed the method described by Carmichael et al. (1987) with modifications. The cells were seeded into a 96-well plate at concentration of 10,000/well for HTB-9, HeLa, H460, HCT116, T98G and OVCAR-3), 15,000/well for DU145, MCF-7, HepG2 and U2OS), and 40,000/well for K562 for 24 hours before drug-treatment. The cells were then exposed to the drugs for 48 hours (72 hours for HepG2 and U2OS, and 96 hours for MCF-7). After the drug-treatment, MTT (0.5 mg/mL) was added to cultures and incubated for an hour. The formazan (product of the reduction of tetrazolium by viable cells) formed and was dissolved with DMSO and the O.D. at 490 nm, and was measured by an ELISA reader. The MTT level of the cells before drug-treatment was also measured (T0). The % cell-growth (% G) is calculated as: % G=(TD−T0/TC−T0)×100(1), where TC or TD represents O.D. readings of control or drug-treated cells. When T0>TD, then the cytotoxicity (LC) expressed as % of the control is calculated as: % LC=(TD−T0/T0)×100(2).

This invention provides a composition that effectively reduced or inhibitied the cancer cell growth, wherein the cancer includes but is not limited to bladder cancer, bone cancer and ovary cancer. This invention provides a composition comprising an effective amount of triterpenoidal saponins named as Xanifolia Y1, Y2, Y, Y7, Y8, Y9, Y10, Y0 or their derivatives for treating chronic venous insufficiency, peripheral edema, antilipemic, chronic venous disease, varicose vein disease, varicose syndrome, venous stasis, expectorant, peripheral vascular disorders, cerebroorganic convulsion, cerebral circulation disorder, cerebral edema, psychoses, dysmenorrheal, hemorrhoids, episiotomies, peripheral edema formation or postoperative swelling; for reducing symptoms of pain; for reducing symptoms of stomach pain; for reducing symptoms of leg pain; for treating pruritis, lower leg volume, thrombosis, thromophlebitis; for treating rheumatism; for preventing gastric ulcers antispasmotic and inhibiting tumor growth.

This invention provides a method of inhibiting cancer cell growth by affecting the aquaporin protein. This invention provides a method of inhibiting tumor growth in a subject comprising administering contracting an effective amount of compounds in this invention to the subject affecting or interacting the aquaporin protein at the surface of cancer cell. The compound comprises two angeloyl groups. In an embodiment the compound may be selected from formula (1), (1A), (1B), (1C) and (1D). In an embodiment, the compound comprises a triterpene backbone, two angeloyl groups and sugar moiety. In an embodiment the compound(s) are selected from Xanifolia (Y0, Y1, Y2, Y, Y7, Y8, Y9, and Y10). In an embodiment the compound(s) are selected from Xanifolia (x), Escin or Aescin. In an embodiment the compound(s) are selected from Compound A to X and A1 to X1 in the application.

This invention provides a method of inhibiting cancer cell growth by increasing the static charge of the cell, wherein increase water flow in the cell. In an embodiment the compounds open the channel protein or ion gates of the cells. The charged molecules or ions pass cell membrane through channel protein and kill cancer cell. As used herein, the term "inhibit" encompasses prevent, and killing of the said cancer or tumor cell This invention provides a method interacting with aquaporin protein for regulating the water channel, modulating the secretion, regulating the water metabolism of body, reducing the amount of urine, reducing urinate times, treating enuresis, treating frequent urination. The method comprises administering contracting an effective amount of compounds to the subject affecting or interacting with the aquaporin protein at the surface of cancer cell. The compound comprises two angeloyl groups. In an embodiment the compound may be selected from formula (1), (1A), (1B) and (1D). In an embodiment, the compound comprises a triterpene backbone, two angeloyl groups and sugar moiety. In an embodiment, the compound comprises a triterpene backbone, two acetyl groups with 2 or more carbon and sugar moiety. In an embodiment the compound(s) are selected from Xanifolia (Y0, Y1, Y2, Y, Y7, Y8, Y9, and Y10). In an embodiment the compound(s) are selected from Xanifolia (x), Escin or Aescin. In an embodiment the compound(s) are selected from Compound A to X and A1 to X1 in the application.

This invention provides uses compound comprises a triterpene and angeloyl groups interacting with aquaporin protein for regulating the water channel, modulating the secretion, treating enuresis, inhibiting tumor growth, stopping cancer cell proliferate.

In an embodiment, compound interacting with aquaporin protein for regulating the water channel, modulating the secretion, destroying the cancer cell. This invention provides a composition interacting with aquaporin protein for regulating the water channel, modulating the secretion, treating enuresis, inhibiting tumor growth. A composition comprising an effective amount of the compound of any one of Y0, Y1, Y2, Y, Y7, Y8, Y9, Y10, or a salt, ester, metabolite or derivative thereof as a medicament for inhibiting tumor or cancer cell growth and for treating cancer, wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer.

The aquaporins (AQPs) are a family of homologous water channels expressed in many epithelial and endothelial cell types involved in fluid transport. The family of mammalian AQPs consists of 11 members, AQP0-10, each with a distinct tissue. Functional measurements indicate that mammalian AQPs 1, 2, 4, 5, and 8 are probably water selective, whereas AQPs 3, 7, 9, and 10 also transport glycerol and other small solutes. They are expressed at part of membrane of cell. AQP1 protein is strongly expressed in most microvessel endothelia outside of the brain, as well as in endothelial cells in cornea, intestinal lacteals, and in other tissues. AQP1 protein was strongly expressed in the membrane of microvessels and small vessels in all ovarian epithelial tumors, but less at the cytoplasm of tumor cells. In addition, AQP1 protein was also observed in the membrane of interstitial cells of ovarian carcinoma. Incorporated by reference of: The influence of aquaporin-1 and microvessel density on ovarian carcinogenesis and ascites formation, J. H. Yang et al., 2006 IGCS, International Journal of Gynecological Cancer 16 (suppl. 1)

Structural determinants of water permeation through aquaporin-1, by Kazuyoshi Murata, et al., Nature, Vol. 407, Oct. 5, 2000

The distribution amount of AQPs 1, 2, 3, 4, 5, 6, 7, 8, 9, 10 are varied at membrane of different cells. In different tumor cell, certain type of Aquaporin proteins is overexpressed. An increasing number of disturbances have been found associated to abnormal function of these proteins. The compounds Xanifolia can interact with the aquaporin and inhibit the tumor cell growth. We can use Western blot analysis and identified expression of aquaporin in cell lines. Detail of Xanifolia in PCT/US05/31900, filed Sep. 7, 2005

A Western blot is a common method in molecular biology/biochemistry/immunogenetics to detect protein in a given sample of tissue homogenate or extract. It uses gel electrophoresis to separate proteins by mass. The proteins are then transferred out of the gel and onto a membrane, where they are "probed" using antibodies specific to the aquaporin protein. As a result, we can examine the amount of aquaporin protein in a given sample and compare levels between several groups. Other techniques which allow detection of proteins in tissues (immunohistochemistry) and cells (immunoctochemistry) are used. Other methods such as Bradford protein assay, UV spectroscopy, Biuret protein assay, Lowry protein assay, Bicinchonic acid protein assay may also be used. There are many publications about the studies of the aquaporin as a maker for cancer cells but none of them mention the regulating or affecting the aquaporin as method to facilitate the blockage, inhibition or destroying the cancer cells.

This invention describes a method of destroying cancer cell or inhibiting the cancer cell proliferates by regulating or affecting the aquaporin. In an embodiment, the saponin with two angeloyl groups can interacts with the aquaporin in order inhibiting the cancer cell growth. In an embodiment the compound may be selected from formula (1), (1A), (1B) (1C) and (1D). In an embodiment, the compound comprises a triterpene backbone, two angeloyl groups and sugar moiety. In an embodiment, the compound comprises a triterpene backbone, two acetyl groups with 2 or more carbon and sugar moiety. In an embodiment the compound(s) are selected from Xanifolia (Y0, Y1, Y2, Y, Y7, Y8, Y9, and Y10). In an embodiment the compound(s) are selected from Xanifolia (x), Escin or Aescin. In an embodiment the compound(s) are selected from Compound A to X and A1 to X1 in the application. In embodiment the method is blocking the cancer cell proliferates by regulating, interacting or affecting the aquaporin. In embodiment, the method is increase the water permeability of the cell membrane by regulating or affecting the aquaporin in order to kill the cell. In an embodiment, the method is affecting the aquaporin permitting extra water into the cell to damage the cancer cell. In an embodiment, the method is affecting the aquaporin permitting Glycerol related solute into the cell to damage the cancer cell. In an embodiment, the method is affecting the aquaporin regulating water into the cell to damage the cancer cell, wherein the method comprise compound selecting from Xanifolia (Y0, Y1, Y2, Y, Y7, Y8, Y9, and Y10). In embodiment, the method is adjusting the fluid density outside the cell in order to damage the cancer cell by regulating the fluid pass in the cell wherein the aquaporin is overexpressed. In an embodiment this invention makes use of the change of cell membrane permeability to damage the cancer cells. The cell membrane permeability can be changed by the overexpression of some aquaporins.

The potency of Xanifolia(Y) is difference in different cancer cells of ovary, cervix, lung, skin and breast because they have variation of Aquaporin (AQPs 1, 2, 3, 4, 5, 6, 7, 8, 9, 10) at the membrane. Amount of Aquarpoin (AQP 1, 2, 3, 4, 5, 6, 7, 8, 9, 10) at the membrane in various types of ovarian cancer cells such as OVCAR3, SKOV3, TOV21G and ES2 is different, therefore they show different inhibition activity when treated with Xanifolia (Y). Xanifolia (Y) is a saponin comprises a triterpene, two angeloyl groups and sugar moiety. Xanifolia (Y) inhibits tumor growth (IC50=1.5-4.5 ug/ml). Xanifolia (X) which has a similar structure to Y but with only one angeloyl group at C22, has less anticancer activity (IC50=6 ug/ml). Removal of sugars from Y (ACH-Y) but retaining the diangeloyl group retains 40% of the anticancer activity (IC50=9.5 ug/ml). However, removal of both angeloyl groups from Y (AKOH-Y) completely abolishes its anticancer activity (even at 120 ug/ml). The results indicate that diangeloyl groups in compound Ys are important for anti-tumor activity. The diangeloyl groups pay an important role in interacting with the aquaporin for inhibiting cancer growth. The hemolytic activities of human red blood cells by Xanifolia-Y (#63Y), Escin and SIGMA saponin standard were compared. Y contains two angeloyl groups, Escin has one angeloyl group and SIGMA saponin standard is a mixture of saponins from *Quillaia* bark. The results show that #63Y (compound Y) has higher hemolytic activity (IC50=1 ug/ml) than Escin or SIGMA saponin standard (IC50=5 ug/ml). See application PCT/US2006/016158, filed Apr. 27, 2006, Dkt#804-K-PCT, FIG. 6 A. In embodiment, the compounds of this invention interact with cancer cells and increase the static charge of the cells. The static charge increase water flow into the cells. The cancer cells are collaped.

This invention describes a method interacting or regulating the protein on the surface of a cell or altering the functional properties of intracellular membranes or regulating the fluid passage through the cell wall or softening the skin or improving the skin structure, comprising administering to a subject. This invention describes a method of regulating or affecting the aquaporin, wherein the method comprising the uses of compositions comprising a triterpenoidal saponin. In an embodiment, the saponin has triterpenoid, triterpenoidal or other sapongenin, one or more sugar moieties and two angeloyl groups, or at least two side groups selected from the following groups: angeloyl groups, tigloyl groups or senecioyl groups, wherein the side groups are attached to the sapongenin backbone at carbon 21 and 22. Wherein the sugar moiety comprises at least one or more of the following sugars and alduronis acids: glucose, galactose, rhamnose, arabinose, xylose, fucose, allose, altrose, gulose, idose, lyxose, mannose, psicose, ribose, sorbose, tagatose, talose, fructose, glucuronic acid, galacturonic acid; or their derivatives thereof, or the combination thereof; wherein the sugar comprises glucuronic acid, arabinose and galactose.

The compounds provided in the invention can be used for accelerating the growth of bladder, suppressing deep sleep, increasing alertness in a sleeping subject, modulating the release, breakdown and uptake of antidieuretic hormone (ADH) and its receptors; modulating the secretion, breakdown and uptake of adrenocorticotropic hormone (ACTH) and its receptors, modulating the release, breakdown and uptake of 5-hydroxytryptamine, acetylcholine (Ach), adrenaline (AD), dopamine (DA), norepinephrine (NE) and their receptors; for preventing sleep paralysis, for modulating the formation, release, breakdown and activity of neuropeptides and their receptors. This invention provides a method comprising compounds in this invention modulating the secretion, breakdown or uptake of adrenocorticotropic hormone (ACTH) or its receptors. This invention provides a composition regulating the protein on the surface of the cell or alters the functional properties of intracellular membranes. The compounds and compositions provided in this invention can regulate the water passing through the cell wall to soften the skin or improve the skin structure.

This invention provides a composition comprising the compounds provided in the invention for treating cancers; for inhibiting virus; for preventing cerebral aging; for improving memory; improving cerebral functions, for curing enuresis, frequent micturition, urinary incontinence, dementia, Alzheimer's disease, autism, brain trauma, Parkinson's disease or other diseases caused by cerebral dysfunctions; for treating arthritis, rheumatism, poor circulation, arteriosclerosis, Raynaud's syndrome, angina pectoris, cardiac disorder, coronary heart disease, headache, dizziness, kidney disorder; cerebrovascular diseasea; inhibiting NF-Kappa B activation; for treating brain edema, sever acute respiratory syndrome, respiratory viral diseases, chronic venous insufficiency, hypertension, chronic venous disease, anti-oedematous, anti inflammatory, hemonhoids, peripheral edema formation, varicose vein disease, flu, post traumatic edema and postoperative swelling; for inhibiting blood clot, for inhibiting ethanol absorption; for lowering blood sugar; for regulating the adrenocorticotropin and corticosterone level; and for treating impotence or premature ejaculation or diabetes (See PCT/US05/31900, filed Sep. 7, 2006; U.S. Ser. No. 10/906,303, filed Feb. 14, 2005; International Application No. PCT/US04/43465, filed Dec. 23, 2004; International Application No. PCT/US04/33359, filed Oct. 8, 2004 and U.S. Ser. No. 11/131,551, filed May 17, 2005, the contents of which are incorporated herein by reference).

This invention provides a composition for AntiMS, anti-aneurysm, antiasthmatic, antibradykinic, anticapillarihemorrhagic, anticephalagic, anticervicobrachialgic, antieclamptic, antiedemic, antiencaphalitic, antiepiglottitic, antiexudative, antiflu, antifracture, antigingivitic, antihematomic, antiherpetic, antihistaminic, antihydrathritic, antimeningitic, antioxidant, antiperiodontic, antiphlebitic, antipleuritic, antiraucedo, antirhinitic, antitonsilitic, antiulcer, antivaricose, antivertiginous, cancerostatic, corticosterogenic, diuretic, fungicide, hemolytic, hyaluronidase inhibitor, lymphagogue, natriuretic, pesticide, pituitary stimulant, thymolytic, vasoprotective, and venotonic treatment.

A composition comprising an effective amount of the compound of any one of Y0, Y1, Y2, Y, Y7, Y8, Y9, Y10, or a salt, ester, metabolite or derivative thereof as a medicament for inhibiting tumor or cancer cell growth and for treating cancer, wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer.

This composition can be administered orally or in a particular embodiment, it can be administered through intraperitoneal (I.P.), intravenous (I.V.) injection or intravenous drip. In an embodiment, the medicine can be administered with glucose solution or NaCl solution. The administration of the medicine can be as intravenous injection or intravenous drip. Example 1: Intravenous drip: 0.05-0.2 mg/kg medicine dissolved in 250 ml of 10% glucose solution or in 250 ml of 0.9% NaCl solution. Example 2: Intravenous injection: 0.05-0.2 mg/kg/day medicine dissolved in 10-20 ml of 10% glucose solution or of 0.9% NaCl solution. Course of treatment: 7-10 days. Example 3: Intravenous drip: 0.1-0.2 mg/kg/day medicine dissolved in 250 ml of 10% glucose solution or in 250 ml of 0.9% NaCl solution. Course of treatment: 7-10 days. Example 4: Intravenous injection: 0.1-0.2 mg/kg/day medicine dissolved in 10-20 ml of 10% glucose solution or of 0.9% NaCl solution. Course of treatment: 7-10 days. Example 5: Intraperitoneal (I.P.): 2.5 mg/kg/day medicine dissolved in 10% glucose solution or of 0.9% NaCl solution. Course of treatment: 7-10 days.

The composition can be administered orally wherein the dosage of mammal is 1-10 mg/Kg. The composition can be administered orally wherein the dosage is 10-30 mg/Kg. The composition can be administered orally wherein the dosage is 30-60 mg/Kg. The composition can be administered orally wherein the dosage is 60-90 mg/Kg. The composition can be administered intravenous injection or intravenous drip wherein the dosage of mammal is 0.01-0.1 mg/Kg. The composition can be administered intravenous injection or intravenous drip wherein the dosage is 0.1-0.2 mg/Kg. The composition can be administered intravenous injection or intravenous drip wherein the dosage is 0.2-0.4 mg/Kg. The composition can be administered intravenous injection or intravenous drip wherein the dosage is 0.4-0.6 mg/Kg. The composition can be administered intraperitoneal (I.P.) wherein the dosage of mammal is 1-3 mg/Kg. The composition can be administered intraperitoneal (I.P.) wherein the dosage is 3-5 mg/Kg. The composition can be administered intraperitoneal (I.P.) wherein the dosage is 4-6 mg/Kg. The composition can be administered intraperitoneal (I.P.) wherein the dosage is 6-10 mg/Kg. This invention provides a method of treating a mammal for treating cancers; for inhibiting virus; for preventing cerebral aging; for improving memory; improving cerebral functions, for curing enuresis, frequent micturition, urinary incontinence, dementia, Alzheimer's disease, autism, brain trauma, Parkinson's disease or other diseases caused by cerebral dysfunctions; for treating arthritis, rheumatism, poor circulation, arteriosclerosis, Raynaud's syndrome, angina pectoris, cardiac disorder, coronary heart disease, headache, dizziness, kidney disorder; cerebrovascular diseasea; inhibiting NF-Kappa B activation; for treating brain edema, sever acute respiratory syndrome, respiratory viral diseases, chronic venous insufficiency, hypertension, chronic venous disease, anti-oedematous, anti inflammatory, hemonhoids, peripheral edema formation, varicose vein disease, flu, post traumatic edema and postoperative swelling; for inhibiting ethanol absorption; for lowering blood sugar; for regulating the adrenocorticotropin and corticosterone level comprising administering to said mammal a therapeutically effective amount of a pharmaceutical composition comprising a composition comprises the molecular formula or compound in this invention.

This invention provides a method of treating a mammal for treating cancers comprising administering to said mammal a therapeutically effective amount of a pharmaceutical composition comprising a composition comprises the molecular formula or compound in this invention. The cancers are included but not limited to: Leukemia cancer, Lung cancer, Colon cancer, CNS cancer, Melanoma cancer, Ovarian cancer, Renal cancer, Prostate cancer, Breast cancer, bladder cancer, cervix cancer, liver cancer, bone cancer, brain cancer and Skin cancer. The compounds comprise Xanifolia Y0, Y1, Y2, Y, Y7, Y8, Y9, Y10, or a salt, ester, metabolite or derivative thereof. This invention provides a method comprising the compounds interacting with cancer cells and increases the static charge of the cells, which increase water flow into the cells. The cancer cells are collaped. The compounds comprise Xanifolia Y0, Y1, Y2, Y, Y7, Y8, Y9, Y10, X or a salt, ester, metabolite or derivative thereof. This invention also provides a method for treating cancers comprising administering to said mammal a therapeutically effective amount of a pharmaceutical composition comprising a composition comprises the molecular formula or compound in this invention. The cancers comprise Leukemia cancer, Lung cancer, Colon cancer, CNS cancer, Melanoma cancer, Ovarian cancer, Renal cancer, Prostate cancer, Breast cancer, bladder cancer, cervix cancer, liver cancer, bone cancer, brain cancer and Skin cancer. The compounds comprise Xanifolia Y0, Y1, Y2, Y, Y7, Y8, Y9, Y10, or a salt, ester, metabolite or derivative thereof.

This invention describes a method interacting or regulating the protein on the surface of a cell or altering the functional properties of intracellular membranes or regulating the fluid passage through the cell wall to kill the cancer cells. The method comprising administering contacting an effective amount of compound selected from formula (1), (1A), (1B), (1C), (1D) preferable Xanifolia Y0, Y, Y1, Y2, Y7, Y8, Y9, Y10. In an embodiment the compound select from Xanifolia Y0, Y, Y1, Y2, Y7, Y8, Y9, and Y10 interact with the protein in the membrane and open up the channel for water or solute particle. The cell takes in water or solute particle and bursts. In an embodiment the components of the compound select from Xanifolia Y0, Y, Y1, Y2, Y7, Y8, Y9, and Y10 combine with the protein in the membrane and open up the channel for water or solute particle. The cell takes in water or solute particle and bursts.

One or more aquaporin AQPs 1, 2, 3, 4, 5, 6, 7, 8, 9, 10 in the cancer cell membrane is overexpressed. So as providing more chance react with Xanifolia compound. Water or ion particle pass through the cell membrane the cancer cells. The compound select from Xanifolia Y0, Y, Y1, Y2, Y7, Y8, Y9, and Y10 dilute the solution outside the cancer to make more water pass in the cell. The overexpress of Aquaporin of AQPs 1, 2, 3, 4, 5, 6, 7, 8, 9 or 10 provide more channel for water or ion particle which causes cancer cell die. This invention provides a method of inhibiting cancer growth by destroys the cancer cell wherein aquaporin is overexpressed; wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer. In an embodiment, the cancer is ovarian cancer. This invention provides a method of treating a mammal for treating cancers comprising administering to said mammal a therapeutically effective amount of a pharmaceutical composition comprising a composition comprises the molecular formula or compound in this invention. The cancers are included but not limited to Leukemia cancer, Lung cancer, Colon cancer, CNS cancer, Melanoma cancer, Ovarian cancer, Renal cancer, Prostate cancer, Breast cancer, bladder cancer, cervix cancer, liver cancer, bone cancer, brain cancer and Skin cancer. The compounds comprise Xanifolia Y0, Y1, Y2, Y, Y7, Y8, Y9, Y10, or a salt, ester, metabolite or derivative thereof.

To investigate the anti-tumor activity of *Xanthoceras sorbifolia*, we employed cancer cell lines derived from different human organs and tested the effect on growth activity. In these preliminary studies, we found that the plant extract inhibits the growth of certain cell lines. We studied 10-15 cell-lines (derived from different human organs) with a MTT cell-growth assay, and found that OVCAR3 cells (from ovary) to be the most sensitive (with IC50=14.5 ug/ml). Intl App'l No. PCT/US04/33359 and U.S. Ser. No. 10/906,303. The active compound was then purified and named Xanifolia-Y. Its chemical structure was determined by 2D NMR and MS analysis. Xanifolia-Y is a novel triterpenoid saponin with a diangeloyl group attached at one end and carbohydrates or sugar moieties at another end of the triterpene structure. In an embodiment, the diangeloyl attached at C21, C22 positions and carbohydrates or sugar moieties at C3 position of a triterpene structure. The diangeloyl group is important for its activity. The purified compound has been tested with 60 cancer cell lines. Test results show inhibition towards most cell lines tested with GI50 values ranging from 0.1-1 uM.

OVCAR3 cells, cancer cells derived from ovary, are the most sensitive to Xanifolia-Y among cell lines tested in our early studies. We subsequently tested 10 additional human ovarian cancer cell lines and found all of them to be susceptible to inhibition by Xanifolia-Y with IC50 values ranging from 2-12 uM. See experiment 10

In vivo studies employing human ovarian carcinoma xenografts in nude mice were performed. The human ovarian cancer cells (ES2) were inoculated into the peritoneal cavity of nude mice and subsequently received Xanifolia-Y. (Experiment 7, 8, 9). The tumor bearing mice received the drug (by i.p. route) for 10 days starting from either day 1, day 4, or day 10 after inoculations. The results show that the median survival time for tumor bearing mice without drug-treatment is approximately 20-24 days. However, there was no death for tumor bearing mice with drug-treatment starting on day 1 after tumor inoculation. The median survival time for tumor bearing mice with drug-treatment starting on day 4 after tumor inoculation is no death in 50 days; and tumor bearing mice with drug-treatment started on day 10 after tumor inoculation is half of the mice survive in 50 days. These results indicate that the compounds of this invention are capable of increasing the survival rate of mammal. The median survival time for tumor bearing mice with drug-treatment starting on day 4 after tumor inoculation is 58 days (extension of life span of 141%); and tumor bearing mice with drug-treatment started on day 10 after tumor inoculation is 31 days (extension of life span of 29%). These results indicate that Xanifolia-Y is capable of extending the life span of mammal bearing tumors. It is useful in treating ovarian cancer in humans. These results indicate that Xanifolia-Y is capable of extending the life span of mammal bearing tumors. It is useful in treating ovarian cancer in humans.

Among gynecological malignancies, ovarian cancer has the highest rate of mortality in women in the United States with an estimated 22,220 new cases in 2005 and over 16,000 deaths (NIH web info). The disease is often missed in diagnosis in the early stage due to asymptomatic and the lack of reliable diagnostic marker. As a result, most of the ovarian cancer patients being diagnosed are already at advanced stages. The standard treatment of ovarian cancer is a combination of a platinum analogue with paclitaxel (McGuire et al., 1996; Ozols et al., 2003). Improved patients survival time was observed in patients with intraperitoneal administration of these agents (Armstrong et al., 2006). The peritoneal cavity is the principal site of disease in ovarian cancer. The improved efficacy of these agents could be due to a more direct interaction with cancer cells. However, the increase of median survival from 49.7 to 65.6 months is still far from satisfactory. As mentioned above, our in vivo animal experiments mimicking the human situation showed that Xanifolia-Y is effective in prolonging mammal life span. Mice were inoculated with human ovarian carcinoma (ES2) in the peritoneal cavity. Starting from the mid-way (time to mortality) point of tumor progression (considered as a late stage of disease in human), drug was then administered into the peritoneal cavity. It was found that Xanifolia-Y treatment is beneficial to tumor bearing mice by prolonging their life span. Depending on the stage of the disease progression, the sooner the start of the drug-treatment, the better the results are. Based on our results, it can prolonged the life-span of tumor bearing mice after Xanifolia-Y-treatment is due to blockage of the migration or metastasis of inoculated cancer cells into the mesothelium lining in the peritoneal cavity. In vitro studies show that Xanifolia-Y inhibits cell adhesion to culture flasks (See Experiment 38). It is known that adhesive molecules play an important role in the migration and metastasis of ovarian cancer (Skubitz, 2002, Schaller, 1996; Zetter, 1993). A major route for the spread of ovarian cancer is by the attachment of tumor cells to the mesothelium lining in the peritoneal cavity (Gardner et al., 1995). Xanifolia-Y blocks the function of these adhesive molecules on cells. In an embodiment, Xanifolia-Y blocks the function of these adhesive molecules on carcinoma cells. In an embodiment, Xanifolia-Y blocks the function of these adhesive molecules on ovarian carcinoma cells. In an embodiment, Xanifolia-Y blocks the function of these adhesive molecules on the mesothelial cells. In an embodiment, Xanifolia-Y binds to the adhesive proteins (by masking) on the membrane and inhibits the interaction of adhesion proteins with their receptors. In an embodiment, Xanifolia-Y action on membrane affects adhesion proteins' function in membrane. The lost of adhesion activity of cancer cells is result from direct or indirect action of Xanifolia-Y on membrane proteins. Most of the adhesion proteins are glycoproteins. The carbohydrate moiety in adhesion proteins interact with carbohydrates from other molecules, such as saponin or Xanifolia-Y. Xanifolia-Y has a trisaccharide at the C3 position and it was found that a loss of carbohydrates reduces its activity (FIGS. 3D and 4C). Our EM studies show that Xanifolia-Y affects membrane structure and makes holes. Damage to the membrane structure could alter adhesion protein's conformation and interfere with their binding with other molecules or even cause them to lose their anchorage on membrane. Our studies of Xanifolia-Y indicate it can be used in cancer therapy, especially as a benefit to patients with late stage ovarian cancer. They indicate that our determined saponins and formulas are useful in cancer therapy by demonstrating its inhibition of tumor growth in mammal systems.

We labeled Xanifolia-Y as ligands and used it to confirm its bindings, such as its location on cells, binding to adhesion proteins or other target protein with RIA, investigate its associated proteins with co-IP and verify them with competition assay. We confirm Xanifolia-Y as an anticancer agent. Specifically we determine tumor nodule growth in peritoneal cavity during Xanifolia-Y treatment.

Xanifolia-Y blocks cancer migration and metastasis. In an embodiment, it blocks ovarian cancer migration and metastasis. Xanifolia-Y has effect on membrane and adhesion proteins.

To study the effect of Xanifolia-Y on membrane structure, the morphology of cell membrane treated with Xanifolia-Y was examined with EM. In this experiment, K562 cells were treated with 5 uM of Xanifolia-Y for 60 min. Solvent DMSO and AKOH-Y (a derivative of Xanifolia-Y without the angeloyl group and it has no activity) served as controls. Cells were negative stained with 1% UAc and subsequently examined with EM. FIG. 27 show that patches of pits were found in the membrane of Xanifolia-Y treated cells (FIG. 27B) but not in cells treated with the DMSO (FIG. 27A) or AKOH-Y (FIG. 27C) controls. These pits have the size from 80 A to 500 A (in diameter). The pits represent holes formed in the membrane. The pits are arranged in a characteristic pattern with smaller pits (80 A in diameter) located in the periphery and the bigger ones (500 A in diameter) in the center. The bigger holes are resulted from fusing of the smaller holes (FIG. 27D). Membrane image of cells treated with A: DMSO solvent control, 60 min (magnification: ×60,000); B: Xanifolia-Y 5 uM, 60 min. (×60000); C: AKOH-Y, 20 uM, 60 min. (×60000); D: Xanifolia-Y 5 uM, 60 min. (×20000). This experiments results show that the Xanifolia-Y alters the membrane of cell. In an embodiment, it damage the membrane of cancer cell. See FIG. 27

Xanifolia-Y can be used for inhibiting cancers cell growth or treating cancers wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer, wherein the cancer is preferably ovarian cancer. Among the different cell lines tested in our studies, carcinoma cells derived from ovary proved to be the most sensitive, a finding which is substantiated with more human ovarian cancer cell lines. The results of animal studies with human tumor xenograft in mice show that it can extend the life span of mice bearing tumors. The compounds of this application can extend the life span of mammal bearing human cancer. Cancer drugs that target on membrane or membrane constituents are not explored. Xanifolia-Y is a new drug. It has effects on cell membrane, a target that differs from current anticancer drugs.

This invention provides a method of altering the characteristic of cancer cell membrane to block the migration, metastasis of cancer cells or inhibit the growth of cancers or anti-angiogenesis.

This invention provides a method of inhibiting the growth, migration, metastasis of cancer by altering the characteristic of membrane of cancer cell, wherein the characteristic comprise adhesion protein; wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer, wherein the method is administering contacting Xanifolia Y0, Y1, Y2, Y, Y7, Y8, Y9, Y10, or a salt, ester, metabolite thereof.

This invention provides a method of inhibiting the growth, migration, metastasis of cancer by altering the adhesion characteristic of membrane of cancer cell, wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer, wherein the method is administering contacting Xanifolia Y0, Y1, Y2, Y, Y7, Y8, Y9, Y10, or a salt, ester, metabolite thereof. In an embodiment the method is administering contacting the compound selected from formula in this application.

This invention provides a composition for inhibiting the growth, migration, metastasis of cancer by altering the adhesion characteristic of membrane of cancer cell, wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer. This application shows Xanifolia-Y is an alternate or supplemental agent to DNA-inhibition or microtubule-targeting drugs. It could be beneficial if it is used singly or in combination with other drugs of different mechanisms (block M-phase progression or DNA synthesis). Our inventions show combined effect of Xanifolia-Y and paclitaxel on inhibition of ES2 cells' growth (Detail in Experiment 15) Identify the binding target of Xanifolia-Y of adhesion proteins and signaling proteins in ovarian cancer cells. In our animal studies, it was shown that Xanifolia-Y extended the life span of tumor bearing mice. (See Experiments 7, 8, 9). The animals died sooner if the treatment of Xanifolia-Y was delayed (comparing results of treatments started from 1, 4 or 10 days after tumor inoculation). The results show that Xanifolia-Y inhibits migration or metastasis of the inoculated cancer cells. Ovarian carcinoma cells express high levels of adhesion molecules. Adhesion proteins are present in both cancer cells and mesothelial cells. While the lost of adhesion is blocking of the protein accessibility due to direct binding to Xanifolia-Y, In an embodiment, the interaction of Xanifolia-Y with membrane alter indirectly the adhesion protein's binding site(s).

We have shown that Xanifolia-Y are cytotoxic to tumor cells, In an embodiment it kills ovarian cancer cells. Our inventions show that Xanifolia-Y inhibits cancer cell growth and prolongs life-span of tumor bearing mice. Our studies also indicate that the sooner the drug-treatment, the longer the life-span of the tumor bearing animals is extended. Xanifolia-Y also has an effect in blocking or inhibiting migration or metastasis. The delay of Xanifolia-Y-treatment allows more chances for cancer cells to metastasize to the mesothelium lining in the peritoneal cavity which resulted in more tumor growth and shorter life span. Adhesive molecules play an important role in cell migration and metastasis. It was shown in our studies that Xanifolia-Y inhibits cell attachment to culture flasks. Xanifolia-Y interferes with the function of the adhesive molecules. In embodiment Xanifolia-Y blocks the function of the adhesive molecules. In an embodiment, Xanifolia-Y binds directly to adhesive proteins. It is masking the adhesive proteins. In an embodiment, Xanifolia-Y indirectly alters membrane structure that cause changes in protein conformation, or locations and result in loss of adhesion process.

This invention provides methods and compositions for modulating gene expression to cure diseases or reduce the syndrome of diseases, wherein the modulating comprises positive and negative regulating. In an embodiment, the method comprises inhibiting gene expression. In an embodiment the method comprises stimulating gene expression. This invention provides methods and compositions for inhibiting the migration, metastasis or growth of cancers or anti-angiogenesis, wherein the methods comprise affecting the gene expression, wherein the method comprises affecting adhesion proteins or their receptors, reducing adhesion proteins, or inhibiting the expression or secretion of adhesion proteins, wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK.

This invention provides methods and compositions for inhibiting the migration, metastasis or growth of cancers or anti-angiogenesis, wherein the methods comprise affecting the gene expression, wherein the method comprises stimulating gene expression. This invention provides a method for altering the characteristics of cancer cell membranes resulting in blocking the migration, metastasis of cancer cells or inhibiting the growth of cancers or anti-angiogenesis, wherein the method comprises reducing adhesion proteins or their receptors, wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK.

This invention provides methods, processes, compounds and compositions of reducing expression or secretion of adhesion proteins of cells, wherein the adhesion proteins comprise fibronectin, integrins family, myosin, vitronectin, collagen, laminin, glycosylation cell surface proteins, polyglycans, cadherin, heparin, tenascin, CD54, CAM, elastin and FAK. In an embodiment, methods comprise inhibiting gene expression. In an embodiment, this invention provides a method of reducing the secretion of fibronectin. In an embodiment the method can block the migration, metastasis of cancer cells or inhibit the growth of cancers or anti-angiogenesis, wherein the cancers comprise breast, leukocyte, liver, ovarian, bladder, prostate, skin, bone, brain, leukemia, lung, colon, CNS, melanoma, renal, cervix, esophagus, testis, spleen, kidney, lymph, pancreas, stomach and thyroid cancer. In an embodiment, the method comprises contacting the cell with compound selected from Mb1, Mb2, Mb2.1, Mb3, Mb4, Mb5, Mb6, Mb7, Mb8, Mb9, Mb10, Mb11, Mb12 and Mb13, ACH-Z4, ACH-Y10, ACH-Y2, ACH-Y8, ACH-Y7, ACH-Y0, ACH-X, ACH-E, Ba1, Ba2, Ba3, Ba4, Ba5, Ba6, Ba7, Ba8, Ba9, Ba10, Ba11, Ba12, Ba13, Ba14, Ba15, Ba16, Ba17, Xanifolia Y0, Y1, Y2, Y, Y5, Y7, Y8, Y9, Y10, Xanifolia (x), Escin or Aescin or a salt, ester, metabolite thereof and Compound A to X and A1 to X1 in the application.

This invention provides a method of altering the characteristics of cancer cell membranes, wherein the method comprises altering the secretion of adhesion proteins, wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK. In an embodiment, the methods, processes, compounds and compositions comprise blocking, suppressing or inhibiting the expression or secretion of adhesion protein, wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK. In an embodiment, the methods, processes, compounds and compositions is interacting with adhesion proteins, wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK. In an embodiment the methods, processes, compounds or compositions can block the migration, metastasis of cancer cells or inhibit the growth of cancers or anti-angiogenesis, wherein the cancers comprise cancers of breast, leukocyte, liver, ovarian, bladder, prostate, skin, bone, brain, leukemia, lung, colon, CNS, melanoma, renal, cervix, esophagus, testis, spleen, kidney, lymph, pancreas, stomach and thyroid. In an embodiment, the method comprises contacting the cell with compound selected from Mb1, Mb2, Mb3, Mb4, Mb5, Mb6, Mb7, Mb8, Mb9, Mb10, Mb11, Mb12 and Mb13, ACH-Z4, ACH-Y10, ACH-Y2, ACH-Y8, ACH-Y7, ACH-Y0, ACH-X, ACH-E, Ba1, Ba2, Ba3, Ba4, Ba5, Ba6, Ba7, Ba8, Ba9, Ba10, Ba11, Ba12, Ba13, Ba14, Ba15, Ba16, Ba17, Xanifolia Y0, Y1, Y2, Y, Y7, Y8, Y9, Y10, Xanifolia (x), Escin or Aescin or a salt, ester, metabolite thereof and Compound A to X and A1 to X1 in the application.

The adhesion proteins help cancer cell adhesion, invasion or metastasis, wherein the cancers comprise ovarian cancer. Reducing the adhesion proteins will reduce the metastasis of cancers. Fibronectin is one of the key factors in the biology of epithelial ovarian cancers. Reduction of fibronectin will inhibit the metastasis of cancer cells. This invention provides a method and composition for inhibiting the expression or secretion of adhesion proteins comprising fibronectin in order to cure diseases, wherein the diseases comprise inhibiting cancer growth, wherein the cancers comprise breast, leukocyte, liver, ovarian, bladder, prostate, skin, bone, brain, leukemia, lung, colon, CNS, melanoma, renal, cervix, esophagus, testis, spleen, kidney, lymph, pancreas, stomach and thyroid cancer. In an embodiment, the method comprises contacting the cell with compound selected from Mb1, Mb2, Mb3, Mb4, Mb5, Mb6, Mb7, Mb8, Mb9, Mb10, Mb11, Mb12 and Mb13, ACH-Z4, ACH-Y10, ACH-Y2, ACH-Y8, ACH-Y7, ACH-Y0, ACH-X, ACH-E, ACH-Mb5, ACH-Mb13, Ba1, Ba2, Ba3, Ba4, Ba5, Ba6, Ba7, Ba8, Ba9, Ba10, Ba11, Ba12, Ba13, Ba14, Ba15, Ba16, Ba17, Xanifolia Y0, Y1, Y2, Y, Y7, Y8, Y9, Y10, Xanifolia (x), Escin or Aescin or a salt, ester, metabolite thereof and Compound A to X and A1 to X1 in the application.

This invention provides a use of compound or a composition for manufacture of medicament for inhibiting the growth, migration, metastasis of cancer or altering the characteristics of membranes of cancer cell, wherein the characteristics comprise adhesion of proteins; wherein comprising the secretion of proteins or the adhesion of cells; wherein the characteristics comprise adhesion ability; wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK; wherein the cancers comprise cancers of breast, leukocyte, liver, ovarian, bladder, prostate, skin, bone, brain, leukemia, lung, colon, CNS, melanoma, renal, cervix, esophagus, testis, spleen, kidney, lymph, pancreas, stomach and thyroid; wherein the method comprises administering to the subject or contacting the cells with the extract, compositions, saponins or compounds from *Xanthoceras Sorbifolia, Harpullia, Aesculus hippocastanum, Maesa balansae* and *Barringtonia acutangula* for inhibiting cancer metastasis, wherein the cancers comprise cancers of breast, leukocyte, liver, ovarian, bladder, prostate, skin, bone, brain, leukemia, lung, colon, CNS, melanoma, renal, cervix, esophagus, testis, spleen, kidney, lymph, pancreas, stomach and thyroid cancers; wherein extracts, compositions, saponins or compounds are prepared from the husks, branches, stems, leaves, kernels, roots, barks, fruit, seeds or seed shells of the herb or plant.

The present invention provides vaccines for cancer immunotherapy. The vaccines comprise extract, compositions, compounds and saponins from *Xanthoceras Sorbifolia, Harpullia, Aesculus hippocastanum, Maesa balansae* and/or *Barringtonia acutangula*. In embodiment, the compounds can be obtained from synthesis, semi-synthesis or modification. The method comprises administering to the subject an effective amount of vaccine for enhancing the immune response. The vaccines comprise saponins isolated from *Xanthoceras Sorbifolia, Harpullia, Aesculus hippocastanum, Maesa balansae* and/or *Barringtonia acutangula*.

The present invention provides adjuvant compositions for cancer curing. The adjuvant compositions comprise extract, compositions, compounds and saponins from *Xanthoceras Sorbifolia, Harpullia, Aesculus hippocastanum, Maesa balansae* and/or *Barringtonia acutangula*. The method comprises administering to the subject an effective amount of the above adjuvant compositions for enhancing the immune response. The use of vaccine compositions comprise inhibiting cancer metastasis, wherein the cancers comprise breast, leukocyte, liver, ovarian, bladder, prostate, skin, bone, brain, leukemia, lung, colon, CNS, melanoma, renal, cervix, esophagus, testis, spleen, kidney, lymph, pancreas, stomach and thyroid cancers.

The present invention provides a use of compound for manufacture of medicament or methods for making a vaccine, wherein the vaccine comprises compounds or saponins from *Xanthoceras Sorbifolia, Harpullia, Aesculus hippocastanum, Maesa balansae* and/or *Barringtonia acutangula*, wherein the vaccine can be used for inhibiting cancer growth, wherein the vaccine is having immune adjuvant activity, wherein the saponins comprise Xanifolia Y0, Y1, Y2, Y, Y5, Y7, Y8, Y9, Y10, Xanifolia (x), Escin or Aescin or a salt, ester, metabolite thereof. In an embodiment the saponin may be selected from formulas (1A), (1B), (1C), (1D), (1E), (1F), (1G), (1H), (1J), (1K), (1L). In an embodiment the compound(s) are selected from Compound Z1 to Z13 in the application. In an embodiment the saponin(s) comprise Mb1, Mb2, Mb3, Mb4, Mb5, Mb6, Mb7, Mb8, Mb9, Mb10, Mb11, Mb12 and Mb13. In an embodiment, the compound comprises a triterpene backbone, two angeloyl groups and sugar moiety. In an embodiment the compound(s) are selected from Compound A to X and A1 to X1 in the application. In an embodiment the compound(s) are selected from ACH-Z4, ACH-Y10, ACH-Y2, ACH-Y8, ACH-Y7, ACH-Y0, ACH-X, ACH-E, ACH-Mb5, and ACH-Mb12. In an embodiment the saponins comprise Ba1, Ba2, Ba3, Ba4, Ba5, Ba6, Ba7, Ba8, Ba9, Ba10, Ba11, Ba12, Ba13, Ba14, Ba15, Ba16 and Ba17. In an embodiment the compound(s) are selected from Xanifolia Y0, Y1, Y2, Y, Y5, Y7, Y8, Y9, Y10, Xanifolia (x), Escin or Aescin or a salt, ester, metabolite thereof. This invention provides a method of treating protozoal infections. In an embodiment, this invention provides a method for treating parasites by using the above compounds, wherein the method comprises inhibiting leishmaniases, amoebiasis, trypanosomiasis, toxoplasmosis or malaria; wherein the method comprises contacting cells with an effective amount of an isolated, purified or synthesized compound, or its salt, or ester thereof, selected from the above compounds.

This invention provides a use of compound for manufacture of medicament or a method for pharmaceutical composition useful for inducing an immune response to an antigen in an individual comprising a saponin composition from *Xanthoceras Sorbifolia, Harpullia, Aesculus hippocastanum, Maesa balansae* or *Barringtonia acutangula* or synthesis. The present invention provide methods for enhancing an immune response to an antigen in an individual comprising administering an effective amount of saponins/compositions from *Xanthoceras Sorbifolia, Harpullia, Aesculus hippocastanum, Maesa balansae* and/or *Barringtonia acutangula*, or saponins comprising Xanifolia Y0, Y1, Y2, Y, Y5, Y7, Y8, Y9, Y10, Xanifolia (x), Escin or Aescin or a salt, ester, metabolite thereof, or the saponin may be selected from formulas (1A), (1B), (1C), (1D), (1E), (1F), (1G), (1H), (1J), (1K), (1L). In an embodiment the compound(s) are selected from Compound Z1 to Z13 in the application. In an embodiment the saponin comprise Mb1, Mb2, Mb3, Mb4, Mb5, Mb6, Mb7, Mb8, Mb9, Mb10, Mb11, Mb12 and Mb13. In an embodiment the compound(s) are selected from Compound A to X and A1 to X1 in the application. In an embodiment the composition(s) are selected from ACH-Z4, ACH-Y10, ACH-Y2, ACH-Y8, ACH-Y7, ACH-Y0, ACH-X, ACH-E, ACH-Mb5, and ACH-Mb12. In an embodiment the saponins comprise Ba1, Ba2, Ba3, Ba4, Ba5, Ba6, Ba7, Ba8, Ba9, Ba10, Ba11, Ba12, Ba13, Ba14, Ba15, Ba16, Ba17.

This invention provides methods or a use of compound for manufacture of medicament for modulating adhesion or angiogenesis of cancer cells, antiparasitics, enhancing an immune response, providing adjuvant activities or providing vaccine activities, inhibiting cancer metastasis or growth, wherein the cancers comprise breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphatic cancer, pancreatic cancer, stomach cancer and thyroid cancer; In an embodiment the method comprises modulating the phosphatidylinositol signaling system and regulating the gene expression of RGS4, LEPR, ICFBP3, ANGPT2, GPNMB, NUPR1 or LOC100126784. The compounds can be purified from natural resource comprising *Xanthoceras Sorbifolia, Harpullia, Aesculus hippocastanum, Maesa balansae* or *Barringtonia acutangula*, or synthesized. The compounds comprise the following:

(Our purification methods and biological assays including the MTT assay in International Application No. PCT/US05/31900, filed Sep. 7, 2005, U.S. Ser. No. 11/289,142, filed Nov. 28, 2005, and U.S. Ser. No. 11/131,551, filed May 17, 2005, and PCT/US2008/002086, 1188-ALA-PCT, filed Feb. 15, 2008, the contents of which are incorporated herein by reference)

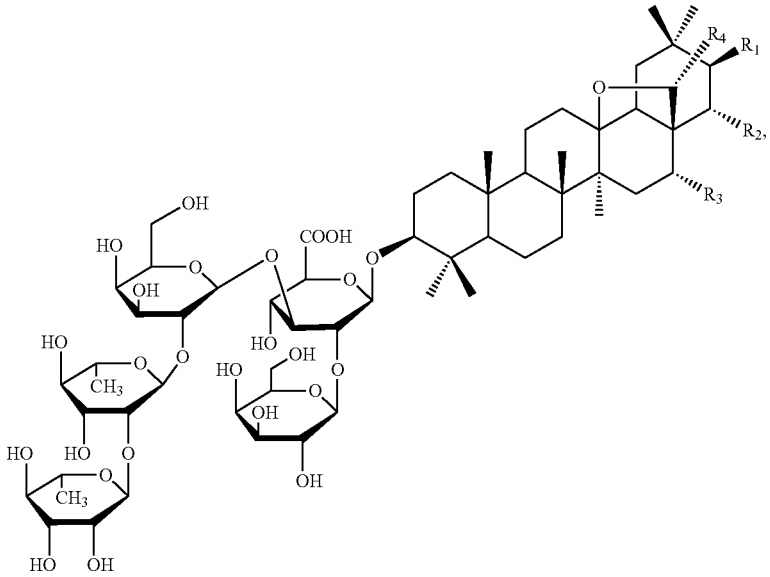

wherein R1 is O(C=O)C(CH3)=CH(CH3), R2 is (E) O(C=O)CH=CH—C6H5, R3 is OH, R4 is OH, also named Mb1; or wherein R1 is O(C=O)C(CH3)=CH(CH3), R2 is (Z)—O(C=O)CH=CH—C6H5, R3 is OH, R4 is OH, also named Mb2; or wherein R1 is O(C=O)C(CH3)=CH(CH3), R2 is (Z)—O(C=O)C(CH3)=CH-C6H5, R3 is OH, R4 is OH, also named Mb2.1; or wherein R1 is O(C=O)C6H5, R2 is (E)-O(C=O)CH=CH—C6H5, R3 is OH, R4 is OH, also named Mb3; or wherein R1 is O(C=O)C6H5, R2 is (Z)—O(C=O)CH=CH—C6H5, R3 is OH, R4 is OH, also named Mb4; or wherein R1, R2, are O(C=O)C(CH3)=CH(CH3), R3 is OH, R4 is OH, also named Mb5; or wherein R1 is O(C=O)C6H5, R2 is O(C=O)C(CH3)=CH(CH3), R3 and R4 are OH, also named Mb6; or

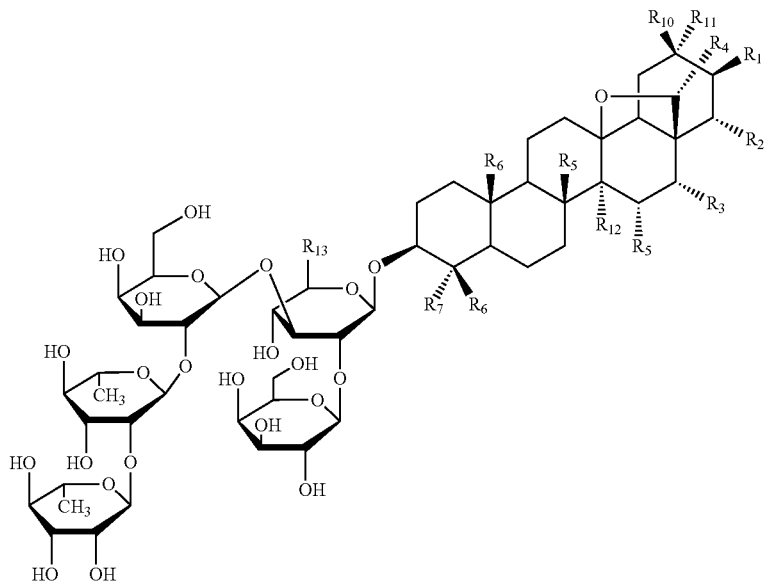

wherein R1 is O(C=O)C6H5, R2 is O(C=O)CH=CH—C6H5, R3, R4, R5 are OH, R6, R7,R8, R9, R10, R11, R12 are CH3, R13 is COOH also named Mb7; or wherein R1 is O(C=O)C6H5, R2 is O(C=O)CH=CH—C6H5, R3, R4, R5 are OH, R6 is CH2OH, R7, R8, R9, R10, R11, R12 are CH3, R13 is COOH also named Mb8; or wherein R1 is O(C=O)C(CH3)=CH(CH3), R2 is O(C=O)CH=CH-C6H5, R3, R4 are OH, R6, R7, R8, R9, R10, R11, R12 are CH3, R13 is COOH also named Mb9; or wherein R1 is O(C=O)C(CH3)=CH(CH3), R2 is O(C=O)CH=CH—C6H5, R3, R4 are OH, R6 is CH2OH, R7, R8, R9, R10, R11, R12 are CH3, R13 is COOH, also named Mb10; or wherein R1, R2, are O(C=O)C(CH3)=CH(CH3), R3 is OH, R4 is CH2OH, R5 is H, R6, R7, R8, R9, R10, R11, R12 are CH3, R13 is COOH, also named Mb11; or wherein R1 is O(C=O)C(CH3)=CH(CH3), R2 is O(C=O)CH=CH—C6H5, R3, R4 are OH, R6, R7, R8, R9, R10, R11, R12 are CH3, R13 is COOCH3, also named Mb12; or wherein R1 is O(C=O)C(CH3)=CH(CH3), R2 is (Z)—O(C=O)C(CH3)=CH—C6H5, R3 is OH, R4 is OH, R5 is H, and R6, R7, R8, R9, R10, R11, R12 are CH3, R13 is COOH, also named Mb13; or

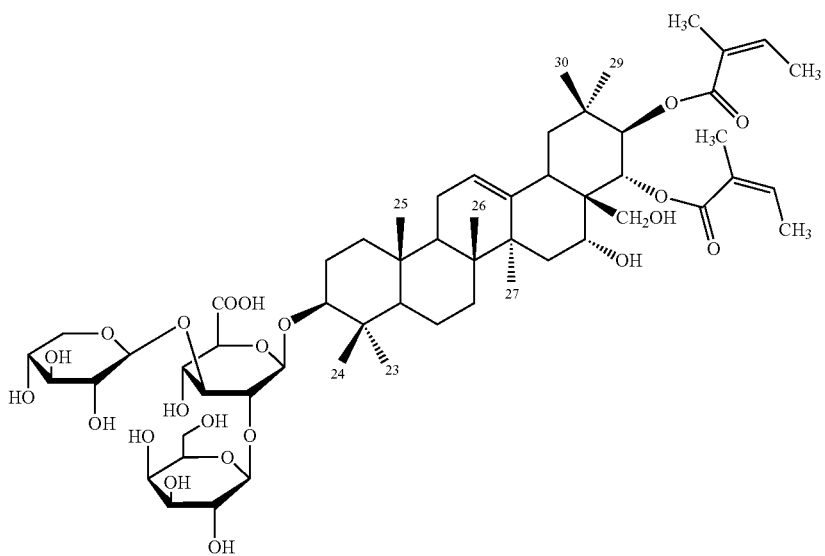

3-O-[β-D-galactopyranosyl(1→2)]-β-D-xylopyranosyl (1→3)-β-D-glucuronopyranosyl-21-O-angeloyl, 22-O-angeloyl-3β, 15α, 21β, 22α, 28-pentahydroxyolean-12-ene, named Ba 1

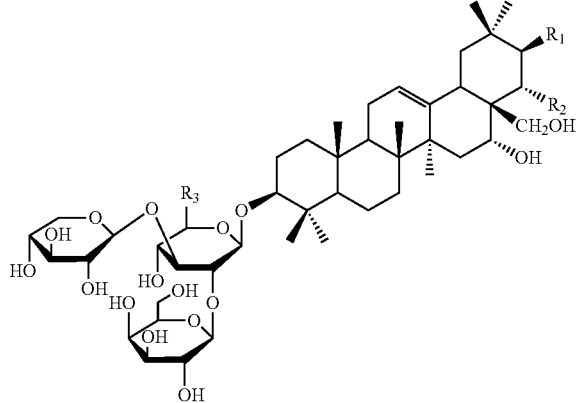

wherein R1 is O(C=O)C(CH3)=CH(CH3), R2 is O(C=O)C(CH3)=CH(CH3), R3 is COOCH3, formula is 3-O-[β-D-galactopyranosyl(1→2)]-β-D-xylopyranosyl (1→3)-β-D-methylglucuronopyranosyl-21-O-angeloyl, 22-O-angeloyl-3β, 15α, 21β, 22α, 28-pentahydroxyolean-12-ene, named Ba 2; or wherein R1 is O(C=O)C6H5, R2 is O(C=O)C(CH3)=CH(CH3), R3 is COOH, formula is: 3-O-[β-D-galactopyranosyl(1→2)]-β-D-xylopyranosyl (1→3)-β-D-glucuronopyranosyl-21-O-benzoyl, 22-O-angeloyl-3β, 15α, 21β, 22α, 28-pentahydroxyolean-12-ene, named Ba 3; or wherein R1 is O(C=O)C6H5, R2 is O(C=O)C(CH3)=CH(CH3), R3 is COOCH3, formula is: 3-O-[β-D-galactopyranosyl(1→2)]-β-D-xylopyranosyl (1→3)-β-D-methylglucuronopyranosyl-21-O-benzoyl, 22-O-angeloyl-3β, 15α, 21β, 22α, 28-pentahydroxyolean-12-ene, named Ba 4; or wherein R1 is O(C=O)C6H5, R2 is O(C=O)C6H5, R3 is COOH, formula is:

3-O-[β-D-galactopyranosyl(1→2)]-β-D-xylopyranosyl (1→3)-β-D-glucuronopyranosyl-21-O-benzoyl, 22-O-benzoyl-3β, 15α, 21β, 22α, 28-pentahydroxyolean-12-ene, named Ba 5; or wherein R1 is O(C=O)C6H5, R2 is O(C=O)C6H5, R3 is COOCH3, formula is:

3-O-[β-D-galactopyranosyl(1→2)]-β-D-xylopyranosyl (1→3)-β-D-methylglucuronopyranosyl-21-O-benzoyl, 22-O-benzoyl-3β, 15α, 21β, 22α, 28-pentahydroxyolean-12-ene, named Ba 6; or wherein R1 is O(C=O)C6H5, R2 is O(C=O)CH3CH3, R3 is COOH, formula is:

3-O-[β-D-galactopyranosyl(1→2)]-β-D-xylopyranosyl (1→3)-β-D-glucuronopyranosyl-21-O-benzoyl, 22-O-isobutyryl-3β, 15α, 21β, 22α, 28-pentahydroxyolean-12-ene, named Ba 7; or wherein R1 is O(C=O)C6H5, R2 is OH, R3 is COOH, formula is: 3-O-[β-D-galactopyranosyl(1→2)]-β-D-xylopyranosyl (1→3)-β-D-glucuronopyranosyl-21-O-benzoyl-3β, 15α, 21β, 22α, 28-pentahydroxyolean-12-ene, named Ba 8

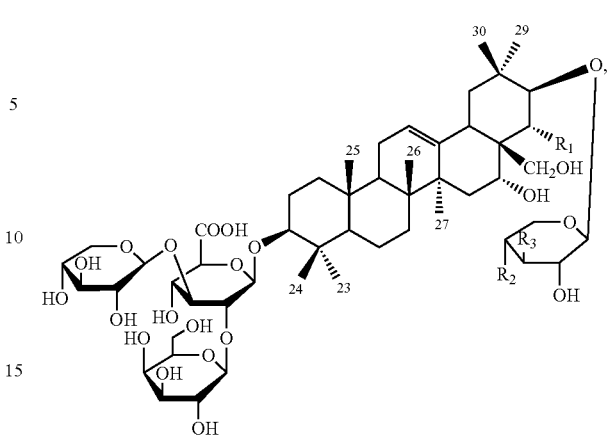

wherein R1 is OH, R2 is O-benzoyl, R3 is O-benzoyl,
3-O-[β-D-galactopyranosyl(1→2)]-β-D-xylopyranosyl (1→3)-β-D-glucuronopyranosyl-21-O-[3,4-dibenzoyl-β-D-xylopyranosyl]-3β, 15α, 21β, 22α, 28-pentahydroxyolean-12-ene, named Ba9;

R1 is O-acetyl, R2 is O-benzoyl, R3 is O-benzoyl
3-O-[β-D-galactopyranosyl(1→2)]-β-D-xylopyranosyl (1→3)-β-D-glucuronopyranosyl-21-O-[3,4-dibenzoyl-β-D-xylopyranosyl]-22-O-acetyl-3β, 15α, 21β, 22α, 28-pentahydroxyolean-12-ene, named Ba10;

3-O-[β-D-galactopyranosyl(1→2)]-β-D-xylopyranosyl (1→3)-β-D-glucuronopyranosyl-21-O-[3-angeloyl, 4-benzoyl-β-D-xylopyranosyl]-3β, 15α, 21β, 22α, 28-pentahydroxyolean-12-ene, named Ba11;

3-O-[β-D-galactopyranosyl(1→2)]-β-D-xylopyranosyl (1→3)-β-D-glucuronopyranosyl-21-O-[3,4-diangeloyl-β-D-xylopyranosyl]-3β, 15α, 21β, 22α, 28-pentahydroxyolean-12-ene, named Ba12;

3-O-[β-D-galactopyranosyl(1→2)]-β-D-xylopyranosyl (1→3)-β-D-glucuronopyranosyl-21-O-[3-angeloyl, 4-tigloyl-β-D-xylopyranosyl]-3β, 15α, 21β, 22α, 28-pentahydroxyolean-12-ene, named Ba13;

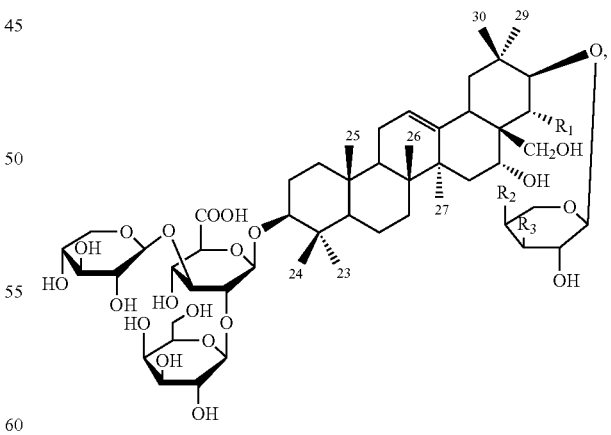

wherein R1 is OH, R2 is O-benzoyl, R3 is O-benzoyl
3-O-[β-D-galactopyranosyl(1→2)]-β-D-xylopyranosyl (1→3)-β-D-glucuronopyranosyl-21-O-[3,4-dibenzoyl-α-L-arabinopyranosyl]-3β, 15α, 21β, 22α, 28-pentahydroxyolean-12-ene, named Ba14;

wherein R1 is O-acetyl, R2 is O-benzoyl, R3 is O-benzoyl

3-O-[β-D-galactopyranosyl(1→2)]-β-D-xylopyranosyl(1→3)-β-D-glucuronopyranosyl-21-O-[3,4-dibenzoyl-α-L-arabinopyranosyl]-22-O-acetyl-3β, 15α, 21β, 22α, 28-pentahydroxyolean-12-ene, named Ba15;

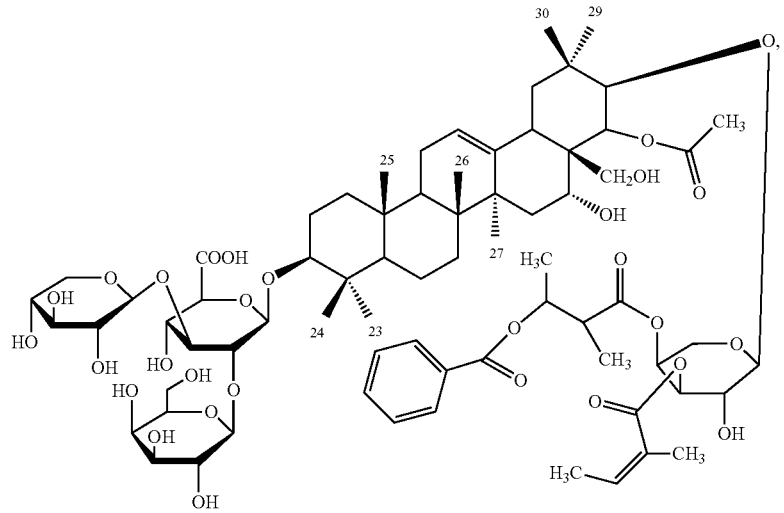

3-O-[β-D-galactopyranosyl(1→2)]-β-D-xylopyranosyl(1→3)-β-D-glucuronopyranosyl-21-O-[3-angeloyl-4-(3-benzoyl-2-methylbutyryl)-α-L-arabinopyranosyl]-22-O-acetyl-3β, 15α, 21β, 22α, 28-pentahydroxyolean-12-ene. named Ba16:

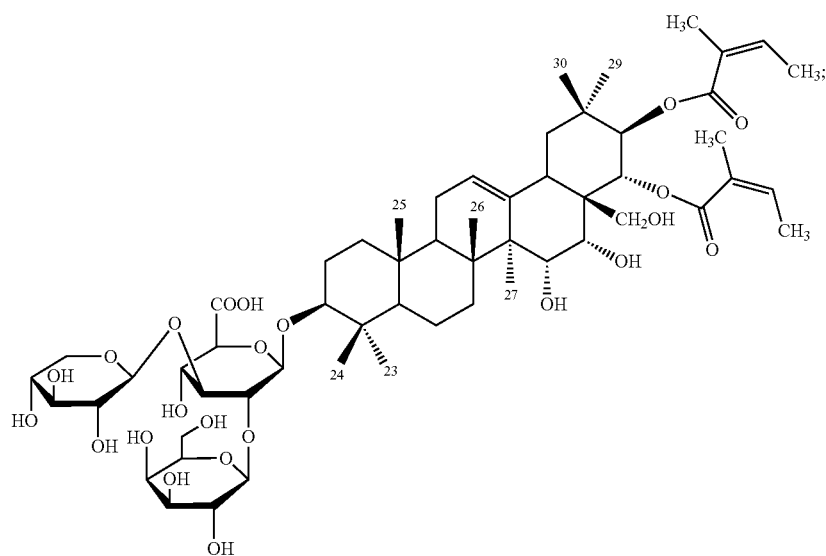

3-O-[β-D-galactopyranosyl(1→2)]-β-D-xylopyranosyl(1→3)-β-D-glucuronopyranosyl-21-O-angeloyl, 22-O-angeloyl-3β, 15α, 16α, 21β, 22α, 28-hexahydroxyolean-12-ene, also named Ba 17.

Anti-Cancer Activities:

The anti-cancer activity of Mb's compounds with ES2 cell: the IC50 of Mb1 is 8 ug/ml, Mb2 is/ml, Mb3 is 8 ug/ml, Mb4 is 15 ug/ml, Mb5 is 6.5 ug/ml, and Mb6 is 10 ug/ml, Mb7 is 12 ug/ml, Mb8 is 20 ug/ml, Mb9 is 18 ug/ml, Mb12 is 10 ug/ml.

The anti-cancer activity of ACH's compounds with ES2 cell: the IC50 of ACH-Z4 is 40 ug/ml, ACH-Y3 is 20 ug/ml, ACH-Y10 is 20 ug/ml, ACH-Y2 is 35 ug/ml, ACH-Y8 is 35 ug/ml, ACH-Y7 is 65 ug/ml, ACH-Y0 is 20 ug/ml, ACH-X is 40 ug/ml, ACH-E is 60 ug/ml The anti-cancer activity of Ba compounds with ES2 cell: Ba1 is 5 ug/ml, Ba2 is 5 ug/ml, Ba3 is 8 ug/ml, Ba 5 is 16 ug/ml, Ba7 is 11 ug/ml, Ba8 is 20 ug/ml, Ba9 is 12 ug/ml, Ba17 is 5 ug/ml.

The anti-cancer activity of Xanifolia Y with cells: the IC50 of Y on (bladder)TB9 cells is 5 ug/ml; IC50 of Y on (lung)H460 cells is 7.5 ug/ml; IC50 of Y on HeLa cells is 20 ug/ml; IC50 of Y on skin cells is 12 ug/ml; IC50 of Y on ES2(ovarian) cells is 5 ug/ml;

IC50 of pure Y on (Mouth) KB cells is 6 ug/ml;

IC50 of Z12 on ES2(ovarian) cells is 16 ug/ml; Z4 is 20 ug/ml

IC50 of Mb5: (bladder)TB9 is 6.5 ug/ml, (Prostate) DU145 is 7.6 ug/ml, (Lung) H460 is 12 ug/ml (Liver) HepG2 is 6.5 ug/ml, (brain) T98G is 12 ug/ml, (Skin) SK-MELS is 25 ug/ml, (Ovary)ES2 is 6.5 ug/ml, (Breast) MCF7 is 11 ug/ml.

IC 50 of ACH-Mb5: (bladder)TB9 is 5.7 ug/ml, (Prostate) DU145 is 6.4 ug/ml, (Lung) H460 is 6.5 ug/ml (Liver) HepG2 is 4 ug/ml, (brain) T98G is 6 ug/ml, (Skin) SK-MELS is 22 ug/ml, (Ovary)ES2 is 8 ug/ml, (Breast)MCF7 is 13 ug/ml.

This invention provides a method or composition for reducing the expression and secretion of adhesion proteins to cure diseases, wherein the diseases comprise cancer growth, leg swelling, symptoms of chronic venous insufficiency, peripheral edema, lipemic, chronic venous disease, varicose vein disease, varicose syndrome, venous stasis, expectorant, peripheral vascular disorders, cerebro-organic convulsion, cerebral circulation disorder, cerebral edema, psychoses, dysmenorrheal, hemorrhoids, episiotomies, peripheral edema formation or postoperative swelling; leg pain; for pruritis, lower leg volume, symptoms of pain; thrombosis, thromophlebitis or for preventing gastric ulcers, spasms, comprising administering to a subject, in need thereof, an effective amount of the composition of this invention.

In an embodiment, the method comprises interacting with adhesion proteins, wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK. In an embodiment, this invention provides a method of reducing the secretion of fibronectin.

In an embodiment, the method comprises reducing the adhesion ability of adhesion proteins; wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK.

In an embodiment, the method comprises modulating the expression or secretion of adhesion proteins, wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK. In an embodiment, the method comprises blocking the secretion of adhesion proteins, wherein the adhesion proteins comprise fibronectin. In an embodiment the method comprises administering to a subject or contacting the cell with an effective amount of the compound selected from formulas in this application.

In an embodiment, this invention provides a method and composition for modulating adhesion or angiogenesis of cancer cells, antiparasitics or manufacturing an adjuvant composition. In an embodiment, this invention provides a method of treating protozoal infections including leishmaniases, amoebiasis, trypanosomiasis, toxoplasmosis and malaria infections.

This invention provides a use of compound for manufacture of medicament, a method and a composition for altering the characteristics of adhesion proteins to cure diseases, wherein the characteristics comprising adhesion ability, wherein the method comprises reducing the secretion of fibronectin, wherein the diseases comprise cancer growth, leg swelling, symptoms of chronic venous insufficiency, peripheral edema, lipemic, chronic venous disease, varicose vein disease, varicose syndrome, venous stasis, expectorant, peripheral vascular disorders, cerebro-organic convulsion, cerebral circulation disorder, cerebral edema, psychoses, dysmenorrheal, hemorrhoids, episiotomies, peripheral edema formation or postoperative swelling; symptoms of leg pain; pruritis, lower leg volume, symptoms of pain; thrombosis, thromophlebitis; for preventing gastric ulcers antispasmotic, comprising administering to a subject, in need thereof, an effective amount of the composition of this invention; wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK. In an embodiment the method is administering contacting an effective amount in a subject with the compound selected from formulas in this application.

This invention provides a process and method for administration of the composition, wherein administration is by intravenous injection, intravenous drip, intraperitoneal injection or oral administration; wherein administration is by intravenous drip: 0.05-0.2 mg/kg compound dissolved in 250 ml of 10% glucose solution or in 250 ml of 0.9% NaCl solution, or by intravenous injection: 0.05-0.2 mg/kg/day compound dissolved in 10-20 ml of 10% glucose solution or of 0.9% NaCl solution, or by intravenous drip: 0.1-0.2 mg/kg/day compound dissolved in 250 ml of 10% glucose solution or in 250 ml of 0.9% NaCl solution, or by intravenous injection: 0.1-0.2 mg/kg/day compound dissolved in 10-20 ml of 10% glucose solution or of 0.9% NaCl solution, or by intraperitoneal injection(I.P.): 2.5 mg/kg/day compound dissolved in 10% glucose solution or of 0.9% NaCl solution, or by oral administration wherein the dosage in mammal is 1-10 mg/Kg, 10-30 mg/Kg, 30-60 mg/Kg, or 60-90 mg/Kg compound, or by intravenous injection or intravenous drip wherein the dosage in mammal is 0.01-0.1 mg/Kg, 0.1-0.2 mg/Kg, 0.2-0.4 mg/Kg, or 0.4-0.6 mg/Kg compound, or by intraperitoneal injection (I.P.) wherein the dosage in mammal is 1-3 mg/Kg, 3-5 mg/Kg, 4-6 mg/Kg, or 6-10 mg/Kg compound.

The methods and uses of an isolated, purified or synthesized compound or its salt, ester, metabolite or derivative thereof, having the formula of:

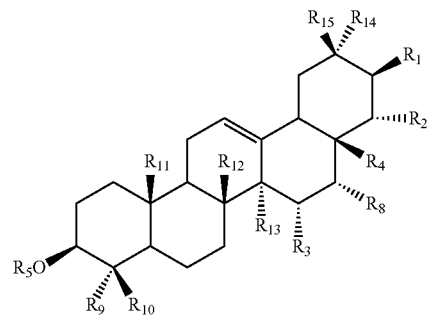

also named (1A), wherein R1 is selected from hydrogen, hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, and derivatives thereof;

R2 is selected from hydrogen, hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, and derivatives thereof;

R4 represents CH$_2$R6 or CORE, wherein R6 is selected from a group consisting of hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, and derivatives thereof; R3 is H or OH; R8 is H or OH;

R5 is a hydrogen, heterocyclic or sugar moiety(ies), wherein the sugar moiety(ies) is/are selected from a group consisting of glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, and derivatives or combination thereof; wherein R9, R10, R11, R12, R13, R14, R15 are independently attached a group selecting from CH$_3$, CH$_2$OH, CHO, COOH, COO-alkyl, COO-aryl, COO-heterocyclic, COO-heteroaryl, CH$_2$Oaryl, CH$_2$O— heterocyclic, CH$_2$O— heteroaryl, alkyls group, hydroxyl, acetyl group; wherein at least two of R1, R2 and R6 are comprising a group selected from O-angeloyl, O-tigloyl, O-senecioyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, and derivatives thereof; or at least one of R1, R2, and R4 is a sugar moiety substituted with at least two groups selected from a group consisting of angeloyl, acetyl, tigloyl, senecioyl, benzoyl, dibenzoyl, alkanoyl, alkenoyl, benzoyl alkyl substituted alkanoyl, O-alkanoyl substituted phenyl, O-alkenoyl substituted phenyl, aryl, acyl, heterocylic, heteroraryl, and a derivative thereof; or wherein R4 is CH$_2$R6; wherein R1 and R2 independently consists an O-angeloyl group, or at least two of R1, R2 and R6 are O-angeloyl or at least one of R1, R2 or R6 is a sugar moiety with two O-angeloyls; or wherein R5 is/are the sugar moiety(ies) selected from the following sugars and alduronic acids: glucose, galactose, rhamnose, arabinose, xylose, fucose, allose, altrose, gulose, idose, lyxose, mannose, psicose, ribose, sorbose, tagatose, talose, fructose, glucuronic acid, galacturonic acid; or their derivatives thereof, or the combination thereof; wherein the sugar comprises glucuronic acid, arabinose and galactose. In an embodiment, wherein R5 is/are sugar moiety(ies) selected from a group consisting of glucose, galactose, arabinose, alduronic acid, glucuronic acid, galacturonic acid, and a derivative or combination thereof; in embodiment, the acyl has 2 to 10 carbons.

In an embodiment the method is administering contacting the compounds, wherein the compound is selected from the following:

a) An isolated, purified or synthesized compound having structure Xanifolia(Y),

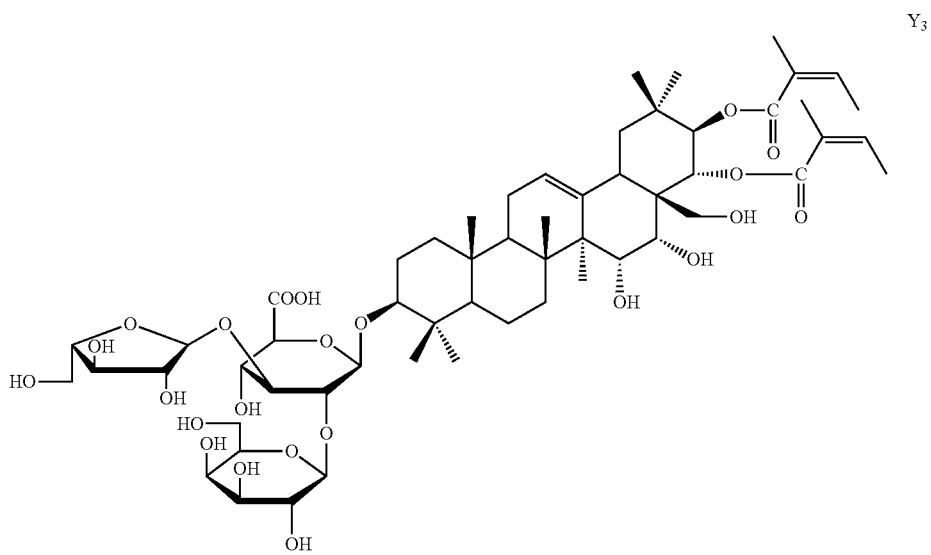

or chemical name: 3-O-[β-D-galactopyranosyl (1→2)]-α-L-arabinofuranosy (1→3)-β-D-glucuronopyranosyl-21,22-O-diangeloyl-3β, 15α, 16α, 21β, 22α, 28-hexahydroxyolean-12-ene;

b) An isolated, purified or synthesized compound having structure Xanifolia (Y1),

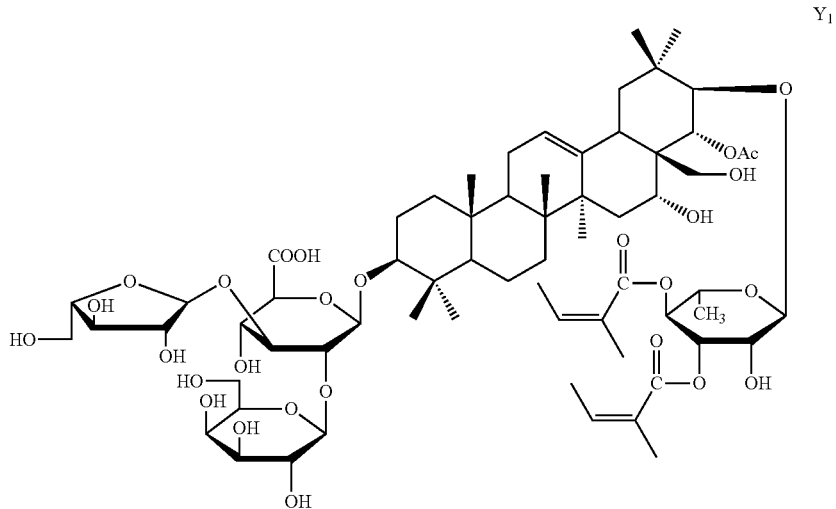

or chemical name: 3-O-[β-D-galactopyranosyl (1→2)]-α-L-arabinofuranosyl (1→3)-β-D-glucuronopyranosyl-21-O-(3,4-diangeloyl)-α-L-rhamnophyranosyl-22-O-acetyl-3β,16α,21β, 22α, 28-pentahydroxyolean-12-ene;

c) An isolated, purified or synthesized compound having structure Xanifolia (Y2),

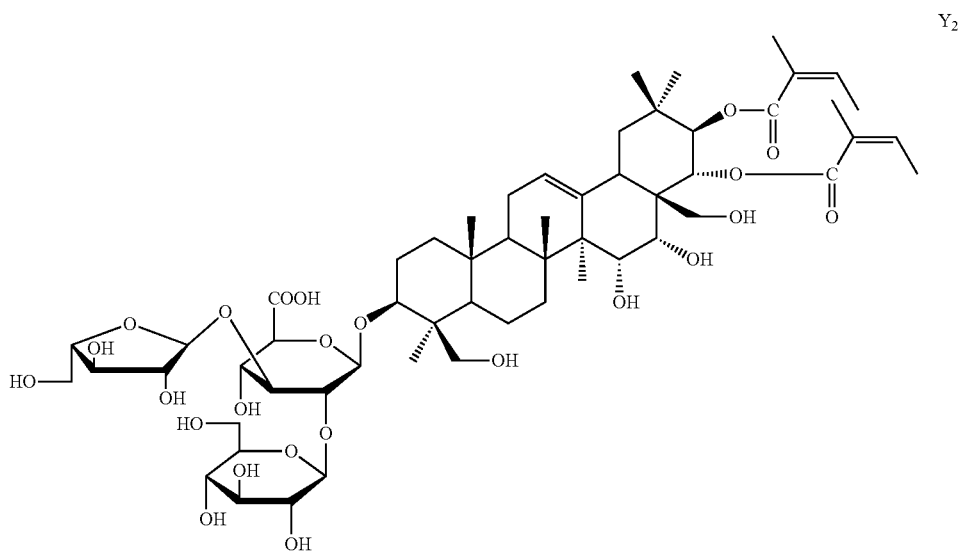

or chemical name: 3-O-[β-D-glucopyranosyl-(1→2)]-α-L-arabinofuranosy (1→3)-β-D-glucuronopyranosyl-21,22-O-diangeloyl-3β, 15α, 16α, 21β, 22α, 24β, 28-heptahydroxy-olean-12-ene;

d) An isolated, purified or synthesized compound having structure Xanifolia (Y8),

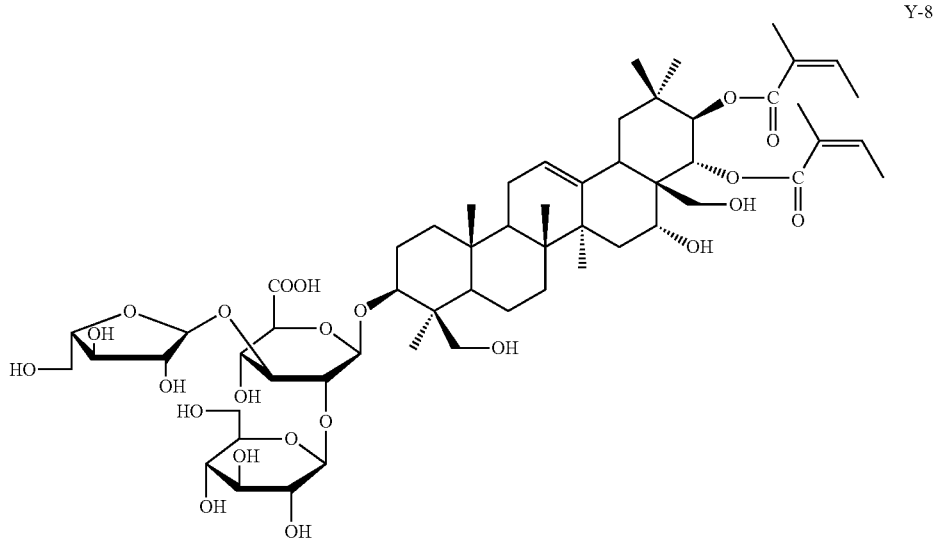

or chemical name: 3-O-[β-glucopyranosyl (1→2)]-α-arabinofuranosyl (1→3)-β-glucuronopyranosyl-21, 22-O-diangeloyl-3β, 16α, 21β, 22α, 24β, 28-hexahydroxyolean-12-ene;

e) An isolated, purified or synthesized compound having structure Xanifolia (Y9),

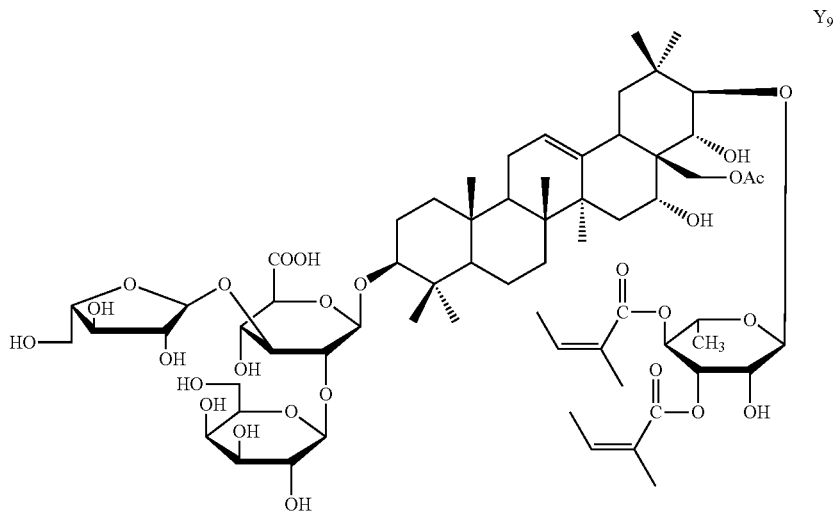

or chemical name: 3-O-[β-galactopyranosyl (1→2)]-α-arabinofuranosyl (1→3)-β-glucuronopyranosyl-21-O-(3,4-diangeloyl)-α-rhamnopyranosyl-28-O-acetyl-3β, 16α, 21β, 22α, 28-pentahydroxyolean-12-ene; and f) An isolated, purified or synthesized compound having structure Xanifolia (Y10),

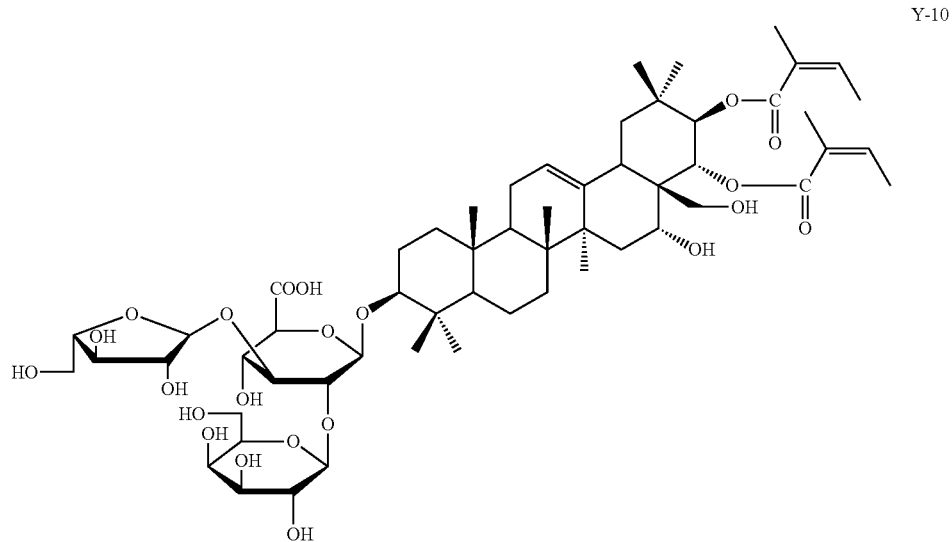

or chemical name:
3-O-[β-galactopyranosyl (1→2)]-α-arabinofuranosyl (1→3)-β-glucuronopyranosyl-21, 22-O-diangeloyl-3β, 16α, 21β, 22α, 28-pentahydroxyolean-12-ene;

g) An isolated, purified or synthesized compound having structure Xanifolia (Y0),

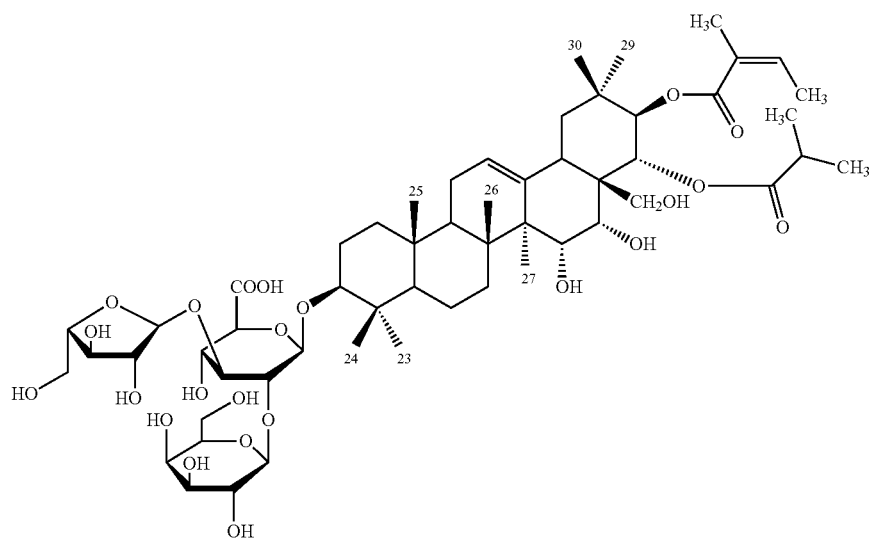

or chemical name: 3-O-[β-D-galactopyranosyl(1→2)]-α-L-arabinofuranosyl(1→3)-β-D-glucuronopyranosyl-21-O-angeloyl, 22-O-(2-methylpropanoyl)-3β, 15α, 16α, 21β, 22α, 28-hexahydroxyolean-12-ene;

h) An isolated, purified or synthesized compound having structure Xanifolia (X),

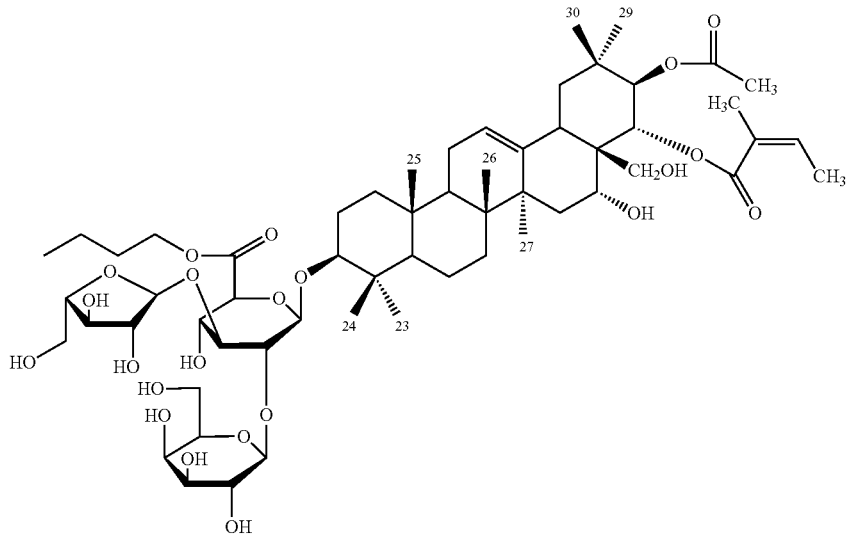

or chemical name: 3-O-{[β-D-galactopyranosyl (1→2)]-[α-L-arabinofuranosyl (1→3)]-β-D-glucuronopyranoside butyl ester}-21-O-acetyl-22-O-angeloyl-3β,16α,21β,22α,28-pentahydroxyolean-12-ene;

i) An isolated, purified or synthesized compound having structure (Y7),

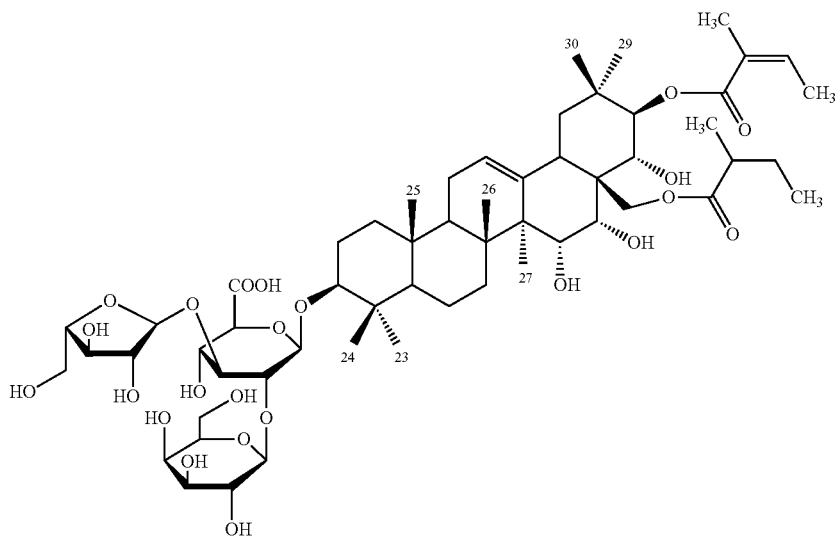

or chemical name: 3-O-[β-D-galactopyranosyl-(1→2)]-α-L-arabinofuranosyl-(1→3)-β-D-glucuronopyranosyl-21-O-angeloyl-28-O-2-methylbutanoyl-3β, 15α, 16α, 21β, 22α, 28-hexahydroxyolean-12-ene;

j) An isolated, purified or synthesized compound having structure (ACH):
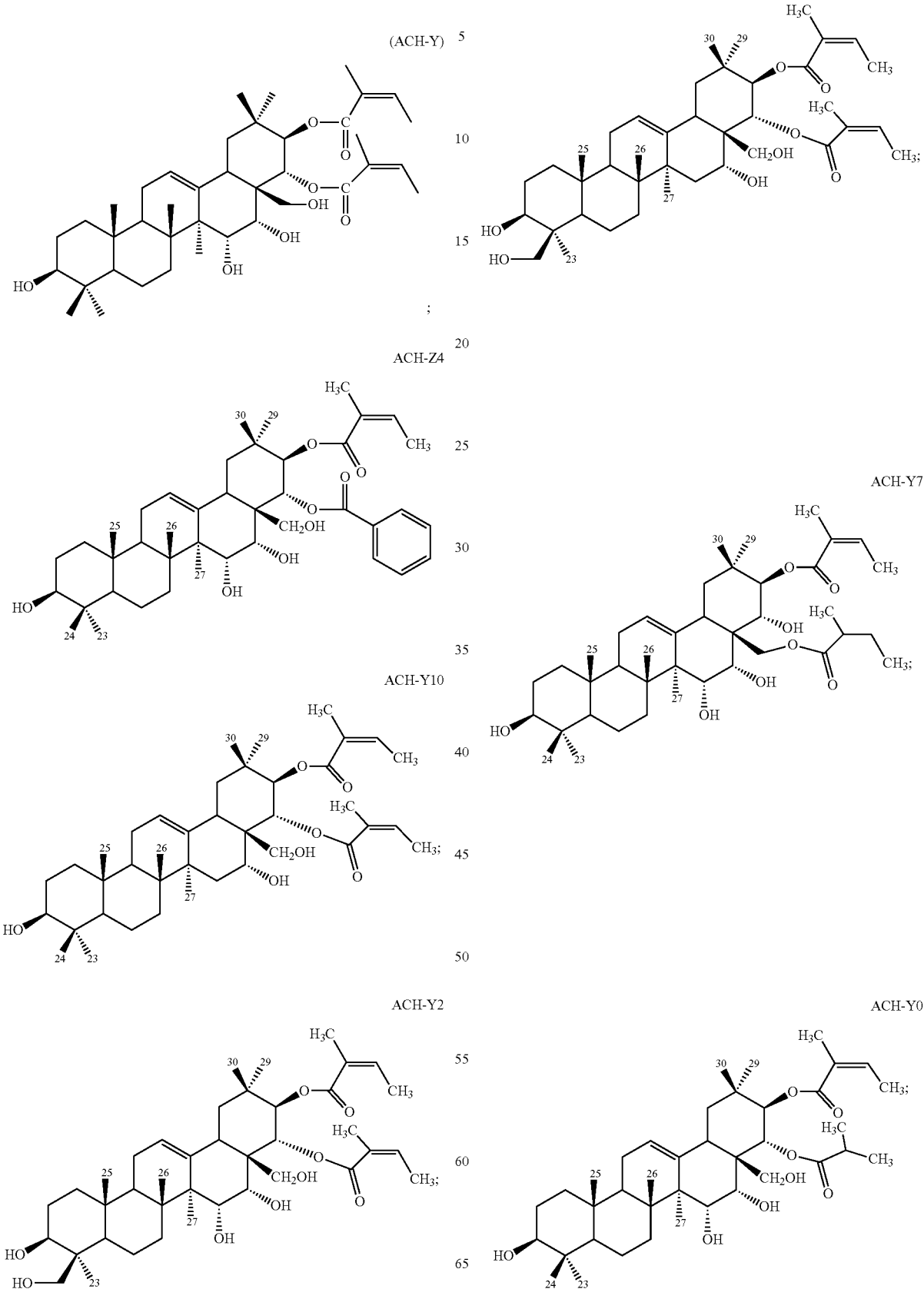

ACH-E
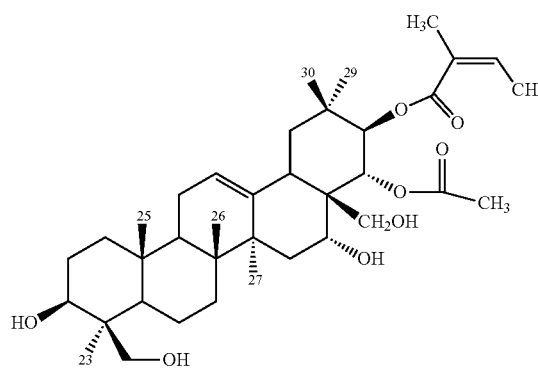
ACH-X
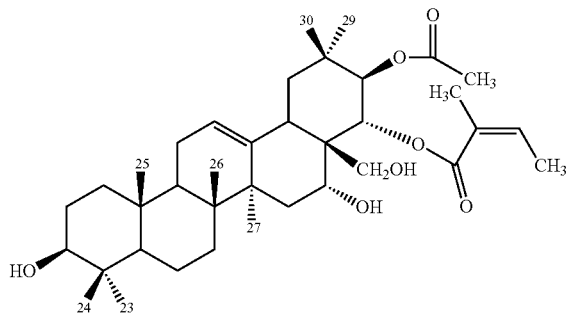
ACH-Mb5
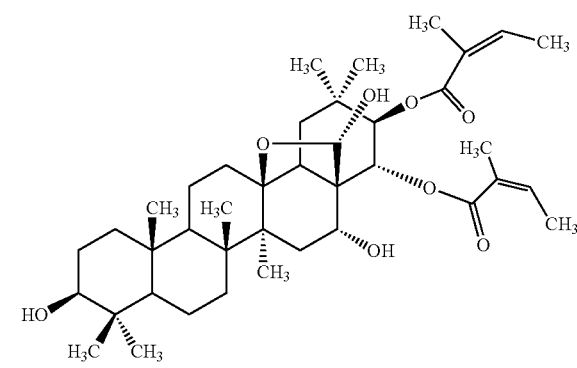
ACH-Mb12
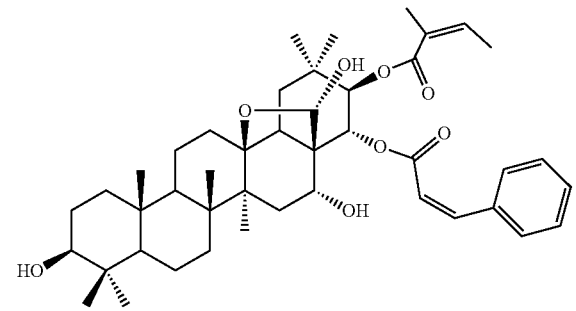
In an embodiment the method is administering contacting the compound, wherein the compound is selected from the following:
k) An isolated, purified or synthesized compound having a structure:
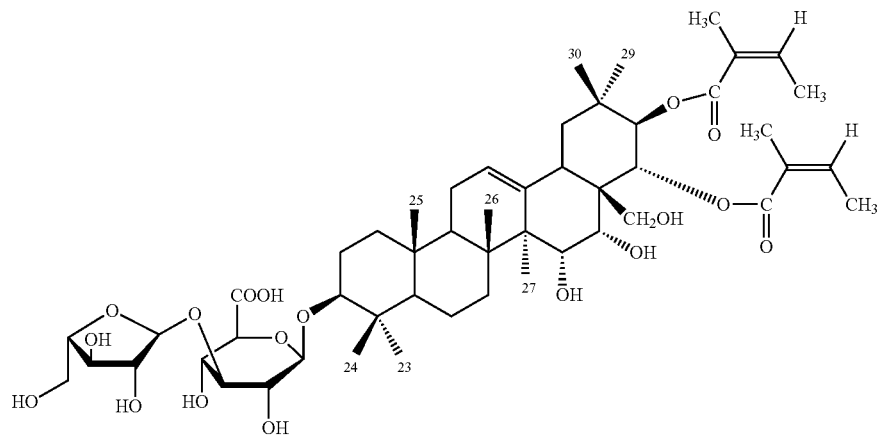

l) An isolated, purified or synthesized compound having a structure(Y5):

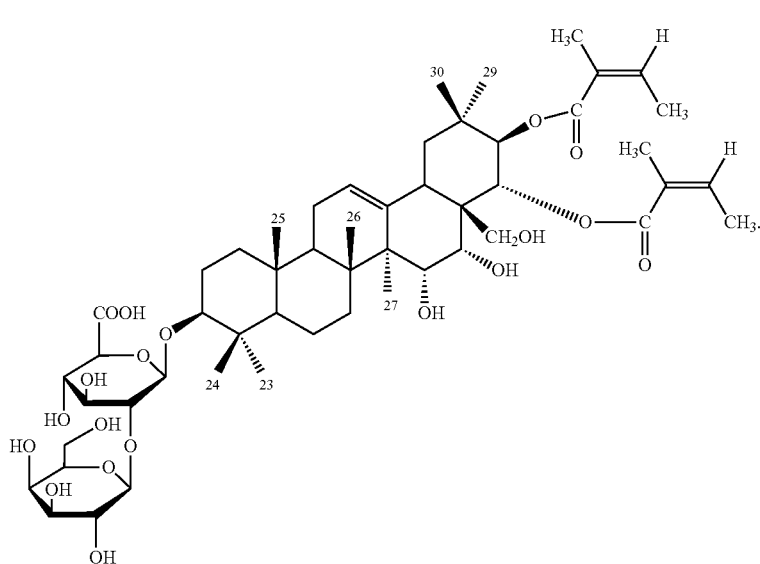

In an embodiment the method comprises administering to a subject or contacting the cell with the compound, wherein the compound is isolated, purified or synthesized having a structure selected from following formulae:

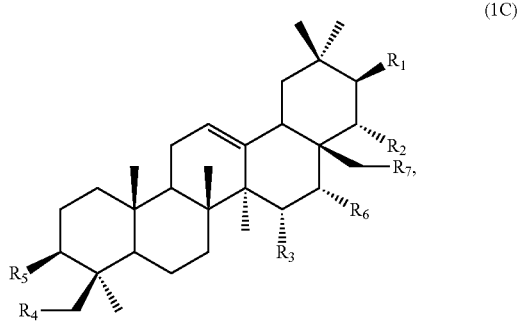

(1C)

wherein R1, R2 are individually selected of an O-acetyl or O-angeloyl; wherein the R3, R4, R5, R6, R7 is hydrogen or hydroxyl.

In an embodiment the method comprises administering to a subject or contacting the cell with compound in this application comprising Xanifolia Y0, Y1, Y2, Y, Y5, Y7, Y8, Y9, Y10, Xanifolia (x), Escin or Aescin or a salt, ester, metabolite thereof. In an embodiment the compounds may be selected from formulas (1A), (1B), (1C), (1D), (1E), (1F), (1G), (1H), (1J), (1K), (1L), In an embodiment, the compound comprises a triterpene backbone, two angeloyl groups and sugar moiety. In an embodiment the compound(s) are selected from Compound A to X and A1 to X1 in the application. In an embodiment the compound(s) are selected from Compound Z1 to Z13 in the application. In an embodiment the method comprises administering to a subject or contacting the cell with compound comprising of a triterpene wherein the carbon position 21, 21 has an unsaturated group and sugar moieties at carbon 3.

In an embodiment, methods and compounds of this application reduce the ability of bacteria, in colonization and tropism of cells. In an embodiment, methods and compounds of this application reduce the adhesive ability of cells or viruses in order to inhibit viruses binding to host cells, wherein the viruses comprise HIV.

This invention provides a use of compound for manufacture of medicament, a method and a composition for modulating adhesion or anti-angiogenesis of cancer tumor, antiparasitics or manufacturing an adjuvant composition, wherein the modulating adhesion of cancer cell comprising modulating the secretion or expression of adhesion protein, wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK; wherein the modulating comprises reducing, inhibiting and stimulating, wherein modulating adhesion protein comprises reducing the fibronectin for inhibiting the metastasis or growth of cancer cells, wherein the cancer is selected from breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphatic cancer, pancreatic cancer, stomach cancer and thyroid cancer; wherein modulating adhesion of cancer cells comprises modulating the secretion or expression of adhesion protein, wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK; wherein modulating comprises reducing, inhibiting and stimulating; wherein modulating angiogenesis comprises inhibiting and stimulating angiopoietin, wherein comprising angiopoietin1, angiopoietin 2, angiopoietin 3, angiopoietin 4, angiopoietin 5, angiopoietin 6 and angiopoietin 7; wherein the angiopoietin comprising angiopoietin-like 1, angiopoietin-like 2, angiopoietin-like 3, angiopoietin-like 4, angiopoietin-like 5, angiopoietin-like 6 and angiopoietin-like 7; wherein the modulating comprises positive and negative regulating; wherein modulating angiopoietin comprises stimulating angiopoietin 2 in order to inhibit angiogenesis; wherein modulating angiopoietin comprises inhibiting angiopoietin 1 in order to inhibit angiogenesis; wherein modulating angiopoietin comprises inhibiting angiopoietin-like 1; wherein modulating angiopoietin comprises inhibiting angiopoietin-like 4; wherein the antiparasitics comprise inhibiting leishmaniases, amoebiasis, trypanosomiasis, toxoplasmosis or malaria, wherein the method comprises administering to a subject or contacting the cell with the compound in this application comprising Xanifolia Y0, Y1, Y2, Y, Y5, Y7, Y8, Y9, Y10, Xanifolia (x), Escin or Aescin or a salt, ester, metabolite thereof. In an embodiment the compound may be selected from formulas (1A), (1B), (1C), (1D), (1E), (1F), (1G), (1H), (1J), (1K), (1L). In an embodiment, the compound comprises a triterpene backbone, two angeloyl groups and sugar moiety. In an embodiment the compound(s) are selected from Compound A to X and A1 to X1 in the application. In an embodiment the compound(s) are selected from Compound Z1 to Z13 in the application. In an embodiment the compound(s) are selected from ACH-Z4, ACH-Y10, ACH-Y2, ACH-Y8, ACH-Y7, ACH-Y0, ACH-X, ACH-E, ACH-Mb5 and ACHMb12. In an embodiment the saponins comprise Ba1, Ba2, Ba3, Ba4, Ba5, Ba6, Ba7, Ba8, Ba9, Ba10, Ba11, Ba12, Ba13, Ba14, Ba15, Ba16, and Ba17. In an embodiment the saponins comprise Mb1, Mb2, Mb3, Mb4, Mb5, Mb6, Mb7, Mb8, Mb9, Mb10, Mb11, Mb12, and Mb13.

In an embodiment, the methods and compositions of this application can be used for manufacturing an adjuvant vaccine, wherein the methods and compositions are used for manufacturing an adjuvant vaccine in a subject, wherein the method comprises administering to a subject or contacting the cell with the compound in this application comprising Xanifolia Y0, Y1, Y2, Y, Y5, Y7, Y8, Y9, Y10, Xanifolia (x), Escin or Aescin or a salt, ester, metabolite thereof. In an embodiment the compound may be selected from formulas (1A), (1B), (1C), (1D), (1E), (1F), (1G), (1H), (1J), (1K), (1L). In an embodiment, the compound comprises a triterpene backbone, two angeloyl groups and sugar moiety. In an embodiment the compound(s) are selected from Compound A to X and A1 to X1 in the application. In an embodiment the compound(s) are selected from Compound Z1 to Z13 in the application. In an embodiment the compound(s) are selected from ACH-Z4, ACH-Y10, ACH-Y2, ACH-Y8, ACH-Y7, ACH-Y0, ACH-X, ACH-E, ACH-Mb5 and ACH-Mb12. In an embodiment the saponins comprise Ba1, Ba2, Ba3, Ba4, Ba5, Ba6, Ba7, Ba8, Ba9, Ba10, Ba11, Ba12, Ba13, Ba14, Ba15, Ba16, and Ba17. In an embodiment the saponins comprise Mb1, Mb2, Mb3, Mb4, Mb5, Mb6, Mb7, Mb8, Mb9, Mb10, Mb11, Mb12 and Mb13. In an embodiment, this application provides an adjuvant composition comprising a saponin or compound selecting from above; wherein the composition is comprised of an immunostimulatory oligonucleotide.

In an embodiment, the methods and compositions of this application can be used for manufacture of medicament for vaccine or antiviral agent for Enterovirus comprising EV71, wherein the method comprises administering to a subject or contacting the cell with compounds selected in this application comprising Mb1, Mb2, Mb3, Mb4, Mb5, Mb6, Mb7, Mb8, Mb9, Mb10, Mb11, Mb12 and Mb13.

The composition comprises bioactive compounds from natural plants or synthesis. The majority of the plants are from the Sapindaceae family, which has 140-150 genera with 1400-2000 species. The program is based on our purification methods and biological assays including the MTT assay See International Application No. PCT/US05/31900, filed Sep. 7, 2005, U.S. Ser. No. 11/289,142, filed Nov. 28, 2005, and U.S. Ser. No. 11/131,551, filed May 17, 2005, and PCT/US2008/002086, 1188-ALA-PCT, filed Feb. 15, 2008, the contents of which are incorporated herein by reference. The details of Analysis of gene expression of ES2 cells after Y-treatment by Microarray, Data Analysis Methods and Western blot in PCT/US2008/002086, 1188-ALA-PCT, filed Feb. 15, 2008, the contents of which are incorporated herein by reference.

This invention provides a composition comprising an effective amount of triterpenoidal saponins named as Xanifolia Y1, Y2, Y, Y5, Y7, Y8, Y9, Y10, and Y0 or their salt or their derivatives. In an embodiment the saponins comprise Ba1, Ba2, Ba3, Ba4, Ba5, Ba6, Ba7, Ba8, Ba9, Ba10, Ba11, Ba12, Ba13, Ba14, Ba15, Ba16, and Ba17 or their salt or their derivatives. In an embodiment the saponins comprise Mb1, Mb2, Mb3, Mb4, Mb5, Mb6, Mb7, Mb8, Mb9, Mb10, Mb11, Mb12 and Mb13, or their salt or their derivatives for modulating expression or secretion of adhesion proteins, reducing expression or secretion of adhesion proteins or reducing the expression or secretion of fibronectin, for treating chronic venous insufficiency, peripheral edema, antilipemic, chronic venous disease, varicose vein disease, varicose syndrome, venous stasis, expectorant, peripheral vascular disorders, cerebro-organic convulsion, cerebral circulation disorder, cerebral edema, psychoses, dysmenorrheal, hemorrhoids, episiotomies, peripheral edema formation or postoperative swelling; for reducing symptoms of pain; for reducing symptoms of stomach pain; for reducing symptoms of leg pain; for treating pruritis, lower leg volume, thrombosis, thromophlebitis; for treating rheumatism; for preventing gastric ulcers antispasmotic; blocking the migration, metastasis of cancer cells or inhibiting tumor growth. In an embodiment the method comprises administering to a subject or contacting the cell with compounds in this application comprising Xanifolia Y0, Y1, Y2, Y, Y5, Y7, Y8, Y9, Y10, Xanifolia (x), Escin or Aescin or a salt, ester, metabolite thereof. In an embodiment the compound may be selected from formulas (1A), (1B), (1C), (1D), (1E), (1F), (1G), (1H), (1J), (1K), (1L). In an embodiment, the compound comprises a triterpene backbone, two angeloyl groups and sugar moiety. In an embodiment the compound(s) are selected from Compound A to X and A1 to X1 in the application. In an embodiment the compound(s) are selected from Compound Z1 to Z13 in the application. In an embodiment the compound(s) are selected from ACH-Z4, ACH- Y10, ACH-Y2, ACH-Y8, ACH-Y7, ACH-Y0, ACH-X, ACH-E, ACH-Mb5 and ACH-Mb12. The compounds of this invention can be isolated from natural sources or synthesized.

See experiments results in this application and see PCT/US05/31900, filed Sep. 7, 2006; U.S. Ser. No. 10/906,303, filed Feb. 14, 2005; International Application No. PCT/US04/43465, filed Dec. 23, 2004; International Application No. PCT/US04/33359, filed Oct. 8, 2004 and U.S. Ser. No. 11/131,551, filed May 17, 2005, PCT/US2007/077273, filed Aug. 30, 2007, PCT/US2008/002086, 1188-ALA-PCT, filed Feb. 15, 2008, U.S. 61/038,277 filed Mar. 20, 2008, U.S. 61/054,308, filed May 19, 2008, the contents of which are incorporated herein by reference.

Acid Hydrolysis of Saponin 15 mg Xanifolia-Y was dissolved in 1 ml of Methanol. 1 ml of 2N HCl was then added. The mixture was refluxed in 80 C water bath for 5 hours. The solution was then neutralized by adding 2 ml of 1N NaOH (to final pH 4-6). The aglycone was then extracted with ethylacetate 3 ml×2. The extracts were collected and pooled. Further isolation of aglycone (ACH-Y) was achieved by HPLC with isocratic elution of 80-100% acetonitrile. Repeat the experiment with compound Z4, Y10, Y2, Y8, Y7, Y0, X, and ESCIN were obtained compounds ACH-Z4, ACH-Y10, ACH-Y2, ACH-Y8, ACH-Y7, ACH-Y0, ACH-X, ACH-E, ACH-Mb12, ACH-Mb5. In mild conditions, the saponin will be partially hydrolyzed to a mixture of products. The products can be separated by HPLC. Also, specific partial hydrolysis can be achieved with enzymes. The β-glucosidase is a good enzyme for cleaving the β-glucose from saponins.

Removal of the Acyl Group by Alkaline Hydrolysis 20 mg of Xanifolia-Y was dissolved in 0.5 ml of 1M NaOH. The solution was incubated in 80 C water bath for 4 hours. It was cooled to room temperature before neutralized with 0.5 ml 1 N HCl (adjust pH to about 3). The mixture was extracted with 2 ml 1-butanol 3 times. The butanol fractions were collected and lyophilized. The hydrolyzed saponin with further purified with HPLC in a C-18 column eluted with 25% acetonitrile.

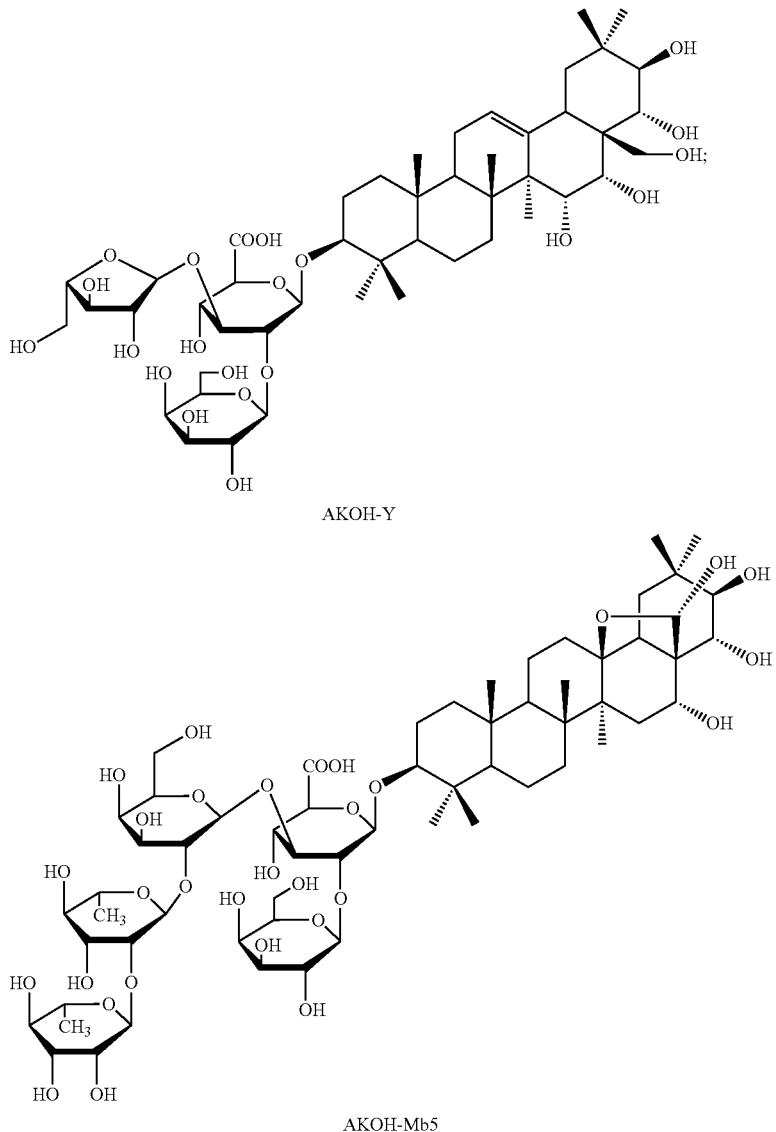

AKOH-Y

AKOH-Mb5

Compounds AKOH-Y and AKOH-Mb5 have lost anti-cancer activity.

This invention provides a use of compound for manufacture of medicament or a method of modulating adhesion proteins or their receptors, reducing the adhesive ability of the cancer cells, wherein the modulating comprises positive or negative regulating. In an embodiment, the adhesion proteins comprise fibronectin, integrins family, myosin, vitronectin, collagen, laminin, glycosylation cell surface proteins, polyglycans, cadherin, heparin, tenascin, CD 54, CAM, elastin and FAK. In an embodiment, the method comprises reducing the secretion of fibronectin. This invention provides a method of blocking the migration, metastasis of cancer cells or inhibiting cancer cell growth or inhibiting leishmaniases modulating adhesion or inhibiting angiogenesis of cancer tumor, antiparasitics or manufacturing an adjuvant composition comprising administering an effective amount of a pharmaceutical composition comprising a composition comprises the molecular formula or compound in this invention. The cancers comprise comprise breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphhatic cancer, pancreatic cancer, stomach cancer and thyroid cancer. The compounds of this invention can be isolated from natural sources or synthesized. In an embodiment the method comprises administering to a subject or contacting a cell with the compounds, wherein the compound is selected from the following:

(Z1) 3-O-[β-D-galactopyranosyl(1→2)]-α-L-arabinofuranosyl(1→3)-β-D-glucuronopyranosyl-21-O-angeloyl, 22-O-(2-methylpropanoyl)-3β, 15α, 16α, 21β, 22α, 28-hexahydroxyolean-12-ene;

(Z2) 3-O-[β-D-galactopyranosyl-(1→2)]-α-L-arabinofuranosyl-(1→3)-β-D-glucuronopyranosyl-21-O-angeloyl-22-O-(angeloyl-2-methylbutanoyl)-3β, 15α, 16α, 21β, 22α, 28-hexahydroxyolean-12-ene;

(Z3) 3-O-[β-D-galactopyranosyl(1→2)]-α-L-arabinofuranosyl(1→3)-β-D-glucuronopyranosyl-21-O-(2-methylpropanoyl), 22-O-(2-methylpropanoyl)-3β, 15α, 16α, 21β, 22α, 28-hexahydroxyolean-12-ene;

(Z4) 3-O-[β-D-galactopyranosyl(1→2)]-α-L-arabinofuranosyl(1→3)-β-D-glucuronopyranosyl-21-O-angeloyl, 22-O-benzoyl-3β, 15α, 16α, 21β, 22α, 28-hexahydroxyolean-12-ene;

(Z5) 3-O-[β-D-galactopyranosyl(1→2)]-α-L-arabinofuranosyl(1→3)-β-D-glucuronopyranosyl-21-O-angeloyl, 22-O-angeloyl-3β, 15α, 16α, 21β, 22α, 28-hexahydroxyolean-12-ene;

(Z6) 3-O-[β-D-galactopyranosyl(1→2)]-α-L-arabinofuranosyl(1→3)-β-D-glucuronopyranosyl-21-O-(2-methylpropanoyl)-O-benzoyl, 22-O-(2-methylpropanoyl)-3β, 15α, 16α, 21β, 22α, 28-hexahydroxyolean-12-ene;

(Z7) 3-O-[β-D-galactopyranosyl(1→2)]-α-L-arabinofuranosyl(1→3)-β-D-glucuronopyranosyl-21-O-(2-methylpropanoyl)-O-angeloyl, 22-O-(2-methylbutanoyl)-3β, 15α, 16α, 21β, 22α, 28-hexahydroxyolean-12-ene;

(Z8) 3-O-[β-D-galactopyranosyl(1→2)]-α-L-arabinofuranosyl(1→3)-β-D-glucuronopyranosyl-21-O-benzoyl, 22-O-benzoyl-3β, 15α, 16α, 21β, 22α, 28-hexahydroxyolean-12-ene;

(Z9) 3-O-[β-D-galactopyranosyl(1→2)]-β-D-xylopyranosyl(1→3)-β-D-glucuronopyranosyl-21-O-angeloyl, 22-O-benzoyl-3β, 15α, 16α, 21β, 22α, 28-hexahydroxyolean-12-ene;

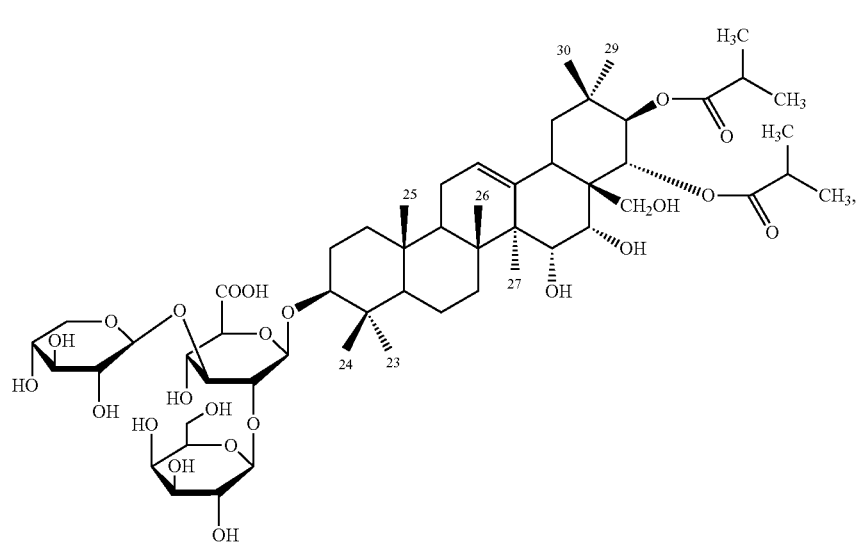

Z10

3-O-[β-D-galactopyranosyl(1→2)]-β-D-xylopyranosyl-(1→3)-β-D-glucuronopyranosyl-21-O-(2-methylpropanoyl), 22-O-(2-methylpropanoyl)-3β, 15α, 16α, 21β, 22α, 28-hexahydroxyolean-12-ene;
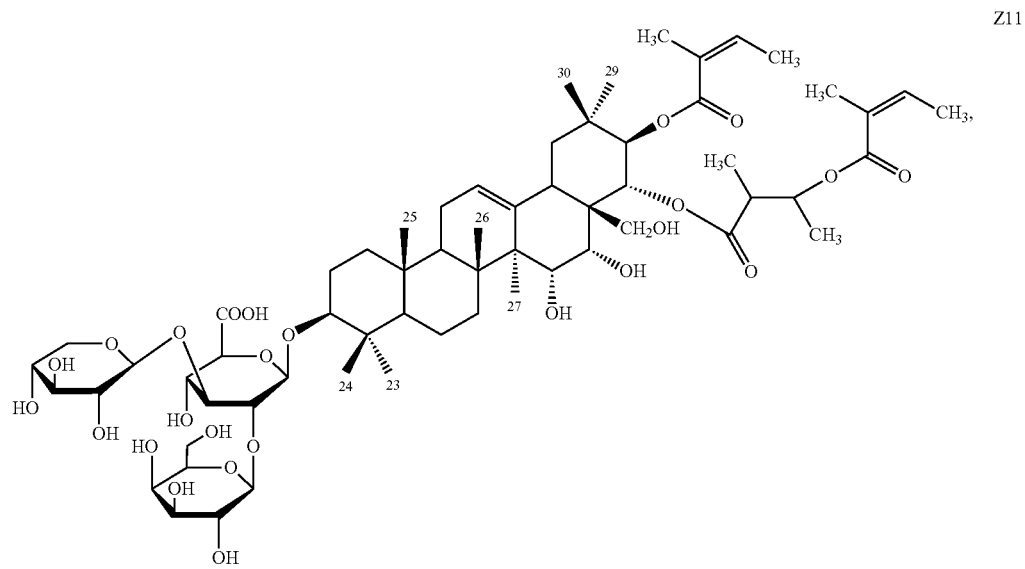
3-O-[β-D-galactopyranosyl-(1→2)]-13-D-xylopyranosyl-(1→3)-β-D-glucuronopyranosyl-21-O-angeloyl-22-O-(angeloyl-2-methylbutanoyl)-3β, 15α, 16α, 21β, 22α, 28-hexahydroxyolean-12-ene;
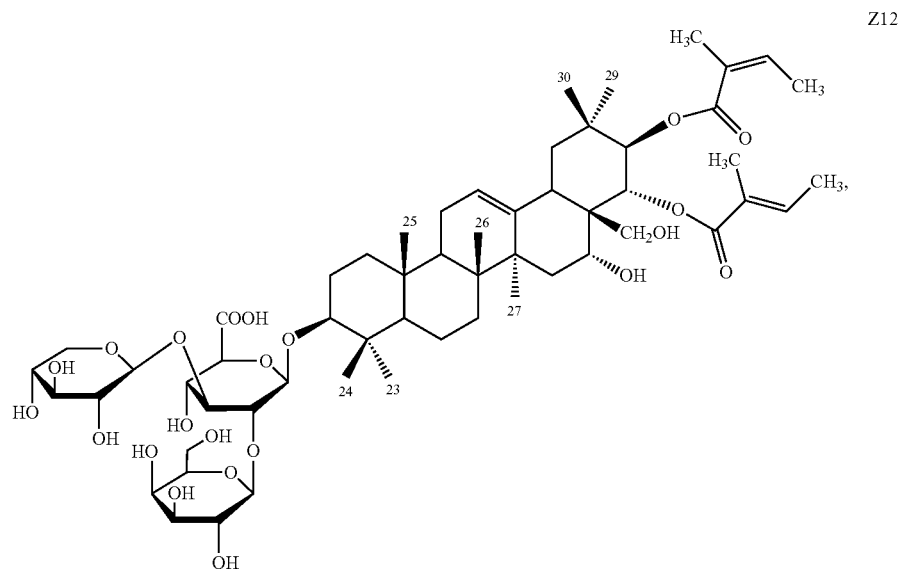

3-O-[β-D-galactopyranosyl(1→2)]-β-D-xylopyranosyl (1→3)-β-D-glucuronopyranosyl-21-O-angeloyl, 22-O-tigloyl-3β, 16α, 21β, 22α, 28-pentahydroxyolean-12-ene;

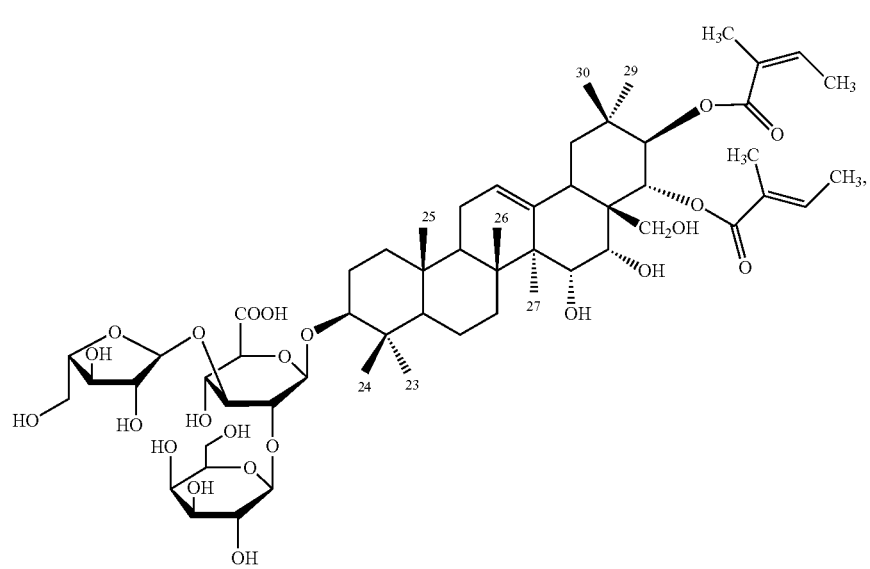

3-O-[β-D-galactopyranosyl(1→2)]-α-L-arabinofuranosyl (1→3)-β-D-glucuronopyranosyl-21-O-angeloyl, 22-O-tigloyl-3β, 15α, 16α, 21β, 22α, 28-hexahydroxyolean-12-ene.

This invention provides uses of a compound for manufacture of medicament selected from formula (1B), for modulating, regulating or interacting with the adhesion protein, wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK. In an embodiment, this invention provides a method of reducing the expression or secretion of fibronectin, modulating adhesion or angiogenesis of cancer cells, antiparasitics, enhancing an immune response, providing adjuvant activities or providing vaccine activities, inhibiting cancer metastasis or growth, using the compounds selected for the following:

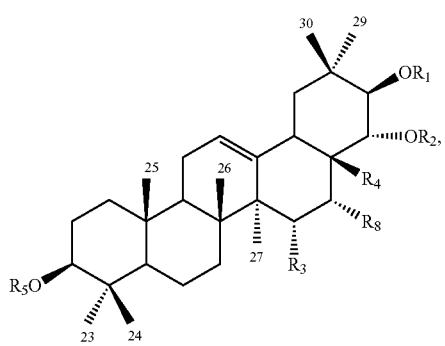

also named as (1B),
or a salt, ester, metabolite or derivative thereof, wherein R1 comprises a group selected from hydrogen, angeloyl, acetyl, tigloyl, senecioyl, alkyl, dibenzoyl, benzoyl, alkanoyl, alkenoyl, benzoyl alkyl substituted alkanoyl, acyl, aryl, heterocylic, heteroraryl, alkenylcarbonyl and derivatives thereof; R2 comprises a group selected from hydrogen, angeloyl, acetyl, tigloyl, senecioyl, alkyl, benzoyl, dibenzoyl, alkanoyl, alkenoyl, benzoyl alkyl substituted alkanoyl, aryl, acyl, heterocylic, heteroraryl, alkenylcarbonyl and derivative thereof; R4 represents $CH_2OR6$ or $COOR6$, wherein R6 is selected from hydrogen, angeloyl, acetyl, tigloyl, senecioyl, alkyl, benzoyl, dibenzoyl, alkanoyl, alkenoyl, benzoyl alkyl substituted alkanoyl, aryl, acyl, heterocylic, heteroraryl and derivative thereof; R3 is H or OH; wherein at least one of R1, R2, and R6 comprises a group selected from angeloyl, acetyl, tigloyl, senecioyl, benzoyl, dibenzoyl, alkanoyl, alkenoyl, benzoyl alkyl substituted alkanoyl, aryl, acyl, heterocylic, heteroraryl and derivative thereof; R5 comprises a hydrogen or sugar moiety, wherein the sugar moiety comprises at least one sugar of, but is not limited to, D-glucose, D-galactose, L-rhamnose, L-arabinose, D-xylose, alduronic acid: D-glucuronic acid, D-galacturonic acid or a derivative thereof, or the combination thereof. In an embodiment, R1 comprises a sugar moiety wherein substituted with two groups selecting from angeloyl, acetyl, tigloyl, senecioyl, benzoyl, dibenzoyl, alkanoyl, alkenoyl, benzoyl alkyl substituted alkanoyl, aryl, acyl, heterocylic heteroraryl and a derivative thereof. In an embodiment, R1 comprises a sugar moiety wherein substituted with at least one group selecting from angeloyl, acetyl, tigloyl, senecioyl, benzoyl, dibenzoyl, alkanoyl, alkenoyl, benzoyl alkyl substituted alkanoyl, aryl, acyl, heterocylic, heteroraryl and a derivative thereof. In an embodiment, R2 comprises a sugar moiety wherein at least one group is selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic, heteroraryl and a derivative thereof. In an embodiment, R2 comprises a sugar moiety or a side chain wherein at least two groups are selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic, heteroraryl and a derivative thereof. In an embodiment, R4 comprises $CH_2OR6$ or $COOR6$ wherein R6 is a sugar moiety which comprises at least one group selected from angeloyl, acetyl, tigloyl, senecioyl, benzoyl, dibenzoyl, alkanoyl, alkenoyl, benzoyl alkyl substituted alkanoyl, aryl, acyl, heterocylic, heteroraryl and a derivative thereof. In an embodiment, R4 comprises CH$_2$OR6 or COOR6, wherein R6 is a sugar moiety which comprises at least two groups selected from angeloyl, acetyl, tigloyl, senecioyl, benzoyl, dibenzoyl, alkanoyl, alkenoyl, benzoyl alkyl substituted alkanoyl, aryl, acyl, heterocylic, heteroraryl and a derivative thereof. In an embodiment, R4 comprises CH$_2$OR6 or COOR6, wherein R6 is a sugar moiety which comprises at least two groups selected from angeloyl, acetyl, tigloyl and senecioyl. In an embodiment, R4 comprises CH$_2$OR6 or COOR6 of formula (1B), at least two of R1, R2 and R6 comprise the group selected from angeloyl, acetyl, tigloyl, senecioyl, benzoyl, dibenzoyl, alkanoyl, alkenoyl, benzoyl alkyl substituted alkanoyl, aryl, acyl, heterocylic, heteroraryl and a derivative thereof. In an embodiment, R4 comprises CH$_2$OR6 or COOR6 of formula (1B), wherein at least two of R1, R2 and R6 comprise angeloyl, benzoyl, alkenoyl, or a derivative thereof. In an embodiment, R4 is a side chain comprising CH$_2$OCOCH$_3$, CH$_2$COO-alkyl, CH$_2$OH, COOH, angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl, alkanoyl substituted phenyl, alkenoyl substituted phenyl, or a derivative thereof. In a further embodiment, R5 comprises a sugar moiety, wherein the sugar moiety comprises one or more sugar of, but is not limited to glucose, galactose, rhamnose, arabinose, xylose, fucose, allose, altrose, gulose, idose, lyxose, mannose, psicose, ribose, sorbose, tagatose, talose, fructose, or alduronic acid: glucuronic acid, galacturonic acid, or derivatives thereof, or the combination thereof. In an embodiment, R5 comprises a sugar moiety or a group capable of performing the function of the sugar moiety. In an embodiment, the R5 represents H. In an embodiment, R4 represents H, OH or CH$_3$. In an embodiment, positions C23, C24, C25, C26, C29 and C30 of the compound independently comprise CH$_3$, CH$_2$OH, CHO, COOH, COOa-lkyl, COO-aryl, COO-heterocyclic, COO-heteroaryl, CH$_2$Oaryl, CH$_2$O-heterocyclic, CH$_2$O-heteroaryl, alkyls group, acetyl group or derivatives thereof. In an embodiment, R1 and R2 independently comprise an angeloyl group. In an embodiment, R1 is a sugar moiety or a side chain which comprises two angeloyl groups. In an embodiment, R1 and R2 independently comprise a benzoyl group. In an embodiment, R1 is a sugar moiety which is substituted with two benzoyl groups. In an embodiment, R3 represents H or OH. In an embodiment, R8 may be OH. In an embodiment, the O at C21, 22 may be replaced by NH. In an embodiment, this invention provides a method of reducing the secretion of fibronectin; wherein the medicament is for inhibiting tumor or cancer cell growth and for treating cancer, wherein the cancers comprise breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphatic cancer, pancreatic cancer, stomach cancer and thyroid cancer. Substitution, deletion and/or addition of any group in the above-described compounds by other group(s) will be apparent to one of ordinary skill in the art based on the teachings of this application. In a further embodiment, the substitution, deletion and/or addition of the group(s) in the compound of the invention does not substantially affect the biological function of the compound.

This invention provides uses, methods, processes, compounds and compositions for modulating adhesion or angiogenesis of cancer cells, antiparasitics, enhancing an immune response, providing adjuvant activities or providing vaccine activities, inhibiting cancer metastasis or growth, reducing adhesion protein of cells, wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK. In an embodiment, methods comprise inhibiting the gene expression. In an embodiment, this invention provides a method of reducing the expression or secretion of fibronectin. In an embodiment the method can block the migration, metastasis of cancer cells or inhibit the growth of cancers or anti-angiogenesis, wherein the cancers comprise breast cancer, leukocytic cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphatic cancer, pancreatic cancer, stomach cancer and thyroid cancer, In an embodiment the compounds are anti-angiogenic, inhibit cancer cell metastasis and inhibit cancer growth. In an embodiment the compounds promote angiopoietin 2. In an embodiment the compound is selected from the following formulas (1E). In an embodiment the method comprises administering to a subject or contacting the cells with the compounds, wherein the compound is selected from the formula (1E):

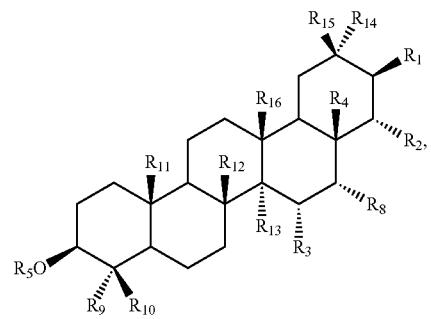

also named (1E), wherein
R1 is selected from hydrogen, hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof;
R2 is selected from hydrogen, hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof;
R4 represents CH3, CHO, CH$_2$R6 or CORE, wherein R6 is selected from hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof; R3 is H or OH; R8 is H or OH, particularly OH; R16 is H, or R4 and R16 may together form —CH2-X—, CH(OH)—X— or C(=O)—X—, wherein the —X— may be O or NH; wherein when the C12-13 of ring 3 of the triterpene has a double bond then R16 is absent; R5 is a hydrogen, heterocyclic or sugar moiety(ies), wherein the sugar moiety(ies) is/are selected from a group consisting of glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, and derivatives or combination thereof; wherein R9, R10, R11, R12, R13, R14, R15 are independently attached a group selecting from $CH_3$, $CH_2OH$, CHO, COOH, COO-alkyl, COO-aryl, COO-heterocyclic, COO-heteroaryl, $CH_2Oaryl$, $CH_2O$-heterocyclic, $CH_2O$-heteroaryl, alkyls group, hydroxyl, acetyl group; or wherein R9, R10, R11, R12, R13, R14, R15 are independently attached a $CH_3$; wherein R4 and R16 form a divalent radical of formula $CH_2O$, CH(OR7)O, or COOR7, wherein R7 is hydrogen, alkyl, angeloyl, tigloyl, senecioyl, dibenzoyl, benzoyl, alkanoyl, alkenoyl, benzoyl alkyl substituted alkanoyl, aryl, acyl, heterocylic, heteroraryl, and derivatives thereof; wherein at least two of R1, R2 and R6 individually comprises a group selected from O-angeloyl, O-tigloyl, O-senecioyl, O-dibenzoyl, O-benzoyl, O-alkanoyl, O-alkenoyl, O-benzoyl alkyl substituted O-alkanoyl, O-aryl, O-acyl, O-heterocylic, O-heteroraryl, and derivatives thereof; or at least one of R1, R2, and R4 is a sugar moiety substituted with at least two groups selected from a group consisting of angeloyl, acetyl, tigloyl, senecioyl, benzoyl, dibenzoyl, alkanoyl, alkenoyl, benzoyl alkyl substituted alkanoyl, aryl, acyl, heterocylic, heteroraryl, and a derivative thereof; or wherein R4 is $CH_2R6$; wherein R1 and R2 independently consists an O-angeloyl group, or at least two of R1, R2 and R6 are O-angeloyl or at least one of R1, R2 or R6 is a sugar moiety with two 0-angeloyls; wherein R5 is/are the sugar moiety(ies) selected from the following sugars and alduronic acids: glucose, galactose, rhamnose, arabinose, xylose, fucose, allose, altrose, gulose, idose, lyxose, mannose, psicose, ribose, sorbose, tagatose, talose, fructose, glucuronic acid, galacturonic acid; or their derivatives thereof, or the combination thereof; wherein the sugar preferably comprises glucuronic acid, arabinose and galactose. In an embodiment, wherein R5 is/are sugar moiety(ies) selected from a group consisting of glucose, galactose, arabinose, alduronic acid, glucuronic acid, galacturonic acid, and a derivative or combination thereof. In an embodiment, wherein R5 is 3-β-O-{[(α-L-rhamnopyranosyl-(1→2)]-α-L-rhamnopyranosyl-(1→2)-β-D-galactopyranosyl-(1→3)]-[β-D-galactopyranosyl-(1→2)]-β-D-glucuronopyranosyl}. In an embodiment, wherein the carbon ring 3 comprises a double bond when R16 is H; wherein the double bond in carbon ring 3 is reduced when R4 and R16 form a divalent radical. In an embodiment, the compound has no sugar moiety. In an embodiment, the compound has at least 1 sugar moiety (ies). In an embodiment, the compound has at least 2 sugar moiety(ies). In an embodiment, the compound has at least 3 sugar moieties. In an embodiment, the compound has at least 4 sugar moieties. In an embodiment, the compound has at least 5 sugar moieties. In an embodiment, the number of sugar moiety(ies) at R5 is(are) 1, 2, 3, 4, or 5. In an embodiment, the sugar moieties attach at R5 or other side bonds. In an embodiment, the sugar moiety may be in the form of alduronic acid. In an embodiment, the compound is attached an acid.

In an embodiment the method comprises administering to a subject or contacting the cells with the compounds, wherein the compound is selected from the formula (1F):

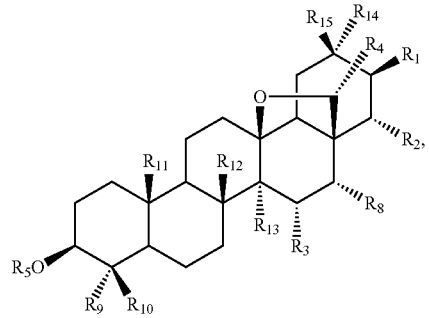

also named (1F), wherein
R1 is selected from hydrogen, hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof;
R2 is selected from hydrogen, hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof;
R4 is selected from hydrogen, hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof; R3 is H or OH; R8 is H or OH, particularly OH;
R5 is a hydrogen or sugar moiety(ies), wherein the sugar moiety(ies) is/are selected from a group consisting of glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, and derivatives or combination thereof; wherein R9, R10, R11, R12, R13, R14, R15 are independently attached a group selecting from $CH_3$, $CH_2OH$, CHO, COOH, COO-alkyl, COO-aryl, COO-heterocyclic, COO-heteroaryl, $CH_2Oaryl$, $CH_2O$-heterocyclic, $CH_2O$-heteroaryl, alkyls group, hydroxyl, acetyl group; or wherein R9, R10, R11, R12, R13, R14, R15 are independently attached a $CH_3$; wherein at least two of R1, R2 and R4 are comprising a group selected from O-angeloyl, O-tigloyl, O-senecioyl, O-dibenzoyl, O-benzoyl, O-alkanoyl, O-alkenoyl, O-benzoyl alkyl substituted O-alkanoyl, O-aryl, O-acyl, O-heterocylic, O-heteroraryl, and derivatives thereof; or at least one of R1, R2, and R4 is a sugar moiety substituted with at least two groups selected from a group consisting of angeloyl, acetyl, tigloyl, senecioyl, benzoyl, dibenzoyl, alkanoyl, alkenoyl, benzoyl alkyl substituted alkanoyl, aryl, acyl, heterocylic, heteroraryl, and a derivative thereof; or wherein R4, R1 and R2 independently consists an O-angeloyl group, or at least two of R1, R2 and R4 are O-angeloyl or at least one of R1, R2 or R4 is a sugar moiety with two O-angeloyls; wherein R5 is/are the sugar moiety(ies) selected from the following sugars and alduronic acids: glucose, galactose, rhamnose, arabinose, xylose, fucose, allose, altrose, gulose, idose, lyxose, mannose, psicose, ribose, sorbose, tagatose, talose, fructose, glucuronic acid, galacturonic acid; or their derivatives thereof, or the combination thereof; wherein the sugar preferably comprises glucuronic acid, arabinose and galactose. In an embodiment, wherein R5 is/are sugar moiety(ies) selected from a group consisting of glucose, galactose, arabinose, alduronic acid, glucuronic acid, galacturonic acid, and a derivative or combination thereof; In an embodiment, wherein R5 is 3-β-O-{[(α-L-rhamnopyranosyl-(1→2)]-α-L-rhamnopyranosyl-(1→2)-β-D-galactopyranosyl-(1→3)]-[β-D-galactopyranosyl-(1→2)]-β-D-glucuronopyranosyl}.

In an embodiment the method comprises administering to a subject or contacting the cells with the compounds of following:

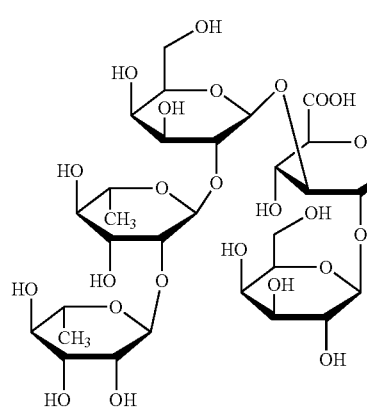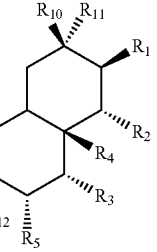

also named (1G), wherein
R1 is selected from hydrogen, hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof;
R2 is selected from hydrogen, hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof;

R4 represents CH3, CHO, CH2R6 or CORE, wherein R6 is selected from hydroxyl, 0-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof; R3 is H or OH; R5 is H or OH; wherein R6, R7, R8, R9, R10, R11, R12 are independently attached a group selecting from CH3, CH2OH, CHO, COOH, COO-alkyl, COO-aryl, COO-heterocyclic, COO-heteroaryl, CH2Oaryl, CH2O-heterocyclic, CH2O-heteroaryl, alkyls group, hydroxyl, acetyl group.

In an embodiment the method comprises administering to a subject or contacting the cells with the compounds of following:

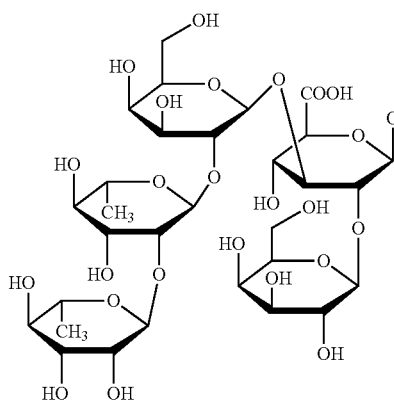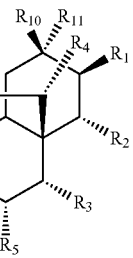

also named (1H), wherein
R1 is selected from hydrogen, hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof; R2 is selected from hydrogen, hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof; R4 is selected from hydroxyl, CH2OH, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof; R3 is H or OH; R5 is H or OH; wherein R6, R7, R8, R9, R10, R11, R12 are independently attached a group selecting from $CH_3$, $CH_2OH$, CHO, COOH, COO-alkyl, COO-aryl, COO-heterocyclic, COO-heteroaryl, $CH_2O$aryl, $CH_2O$-heterocyclic, $CH_2O$-heteroaryl, alkyls group, hydroxyl, acetyl group.

In an embodiment the method comprises administering to a subject or contacting the cells with the compounds of following:

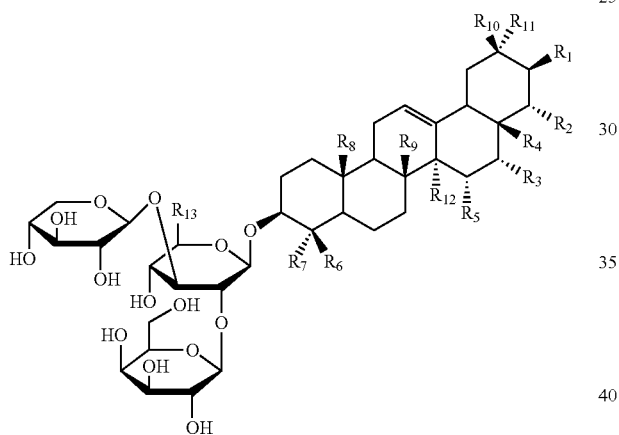

also named (1J), wherein

R1 is selected from hydrogen, hydroxyl, O-angeloyl, )-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof; R2 is selected from hydrogen, hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof; R4 represents CH3, CHO, $CH_2R6$ or COR6, wherein R6 is selected from hydroxyl, O-angeloyl, O-tigloyl, O-senecioyl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof; R3 is H or OH; R5 is H or OH, particularly OH; wherein R6, R7, R8, R9, R10, R11. R12 are independently attached a group selecting from $CH_3$, $CH_2OH$, CHO, COOH, COO-alkyl, COO-aryl, COO-heterocyclic, COO-heteroaryl, $CH_2O$aryl, $CH_2O$-heterocyclic, $CH_2O$- heteroaryl, alkyls group, hydroxyl, acetyl group;

R13 is COOH or COO-alkyl;

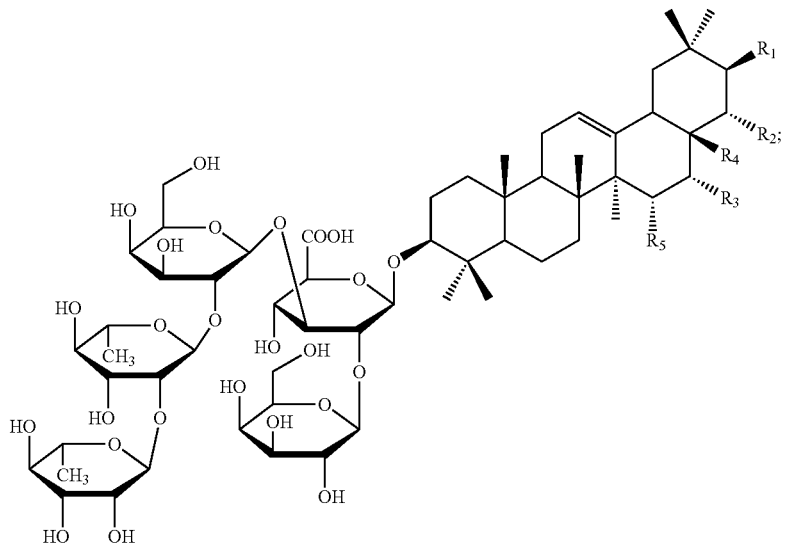

also named (1L),
wherein R1, R2 are angeloyl, R3 is OH, R4 is CH2OH, R5 is H or OH.

In an embodiment the method comprises administering to a subject or contacting the cells with the compounds of following:

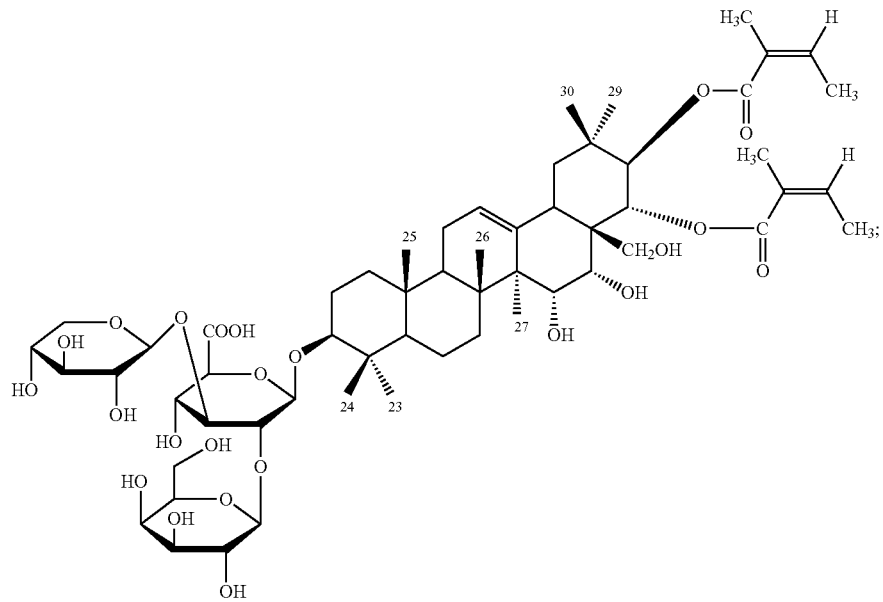

or
3-O-[β-D-galactopyranosyl(1→2)]-β-D-xyopyranosyl (1→3)-β-D-glucuronopyranosyl-21-O-angeloyl, 22-O-angeloyl-3β, 15α, 16α, 21β, 22α, 28-hexahydroxyolean-12-ene,

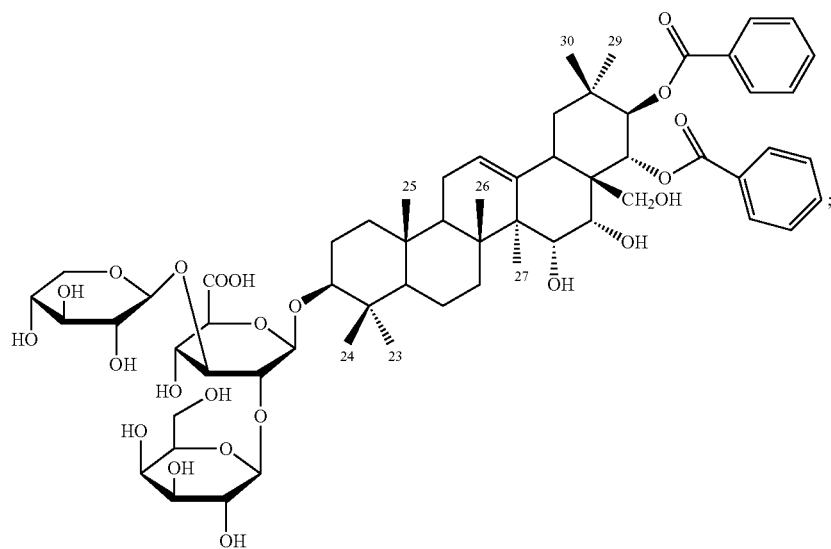

or
3-O-[β-D-galactopyranosyl(1→2)]-β-D-xyopyranosyl (1→3)-β-D-glucuronopyranosyl-21-O-benzoyl, 22-O-benzoyl-3β, 15α, 16α, 21β, 22α, 28-hexahydroxyolean-12-ene

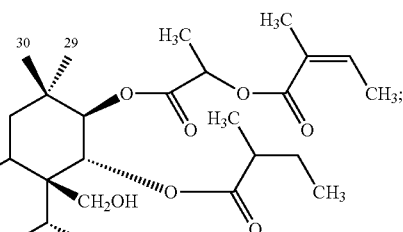
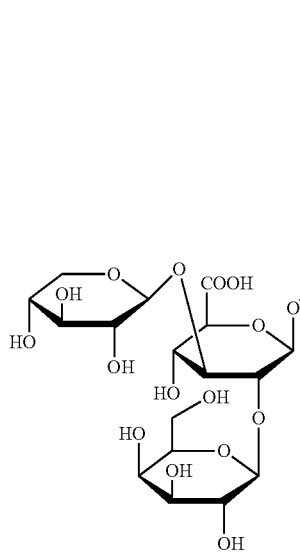

or
3-O-[β-D-galactopyranosyl(1→2)]-β-D-xyopyranosyl (1→3)-β-D-glucuronopyranosyl-21-O-(2-methylpropanoyl)-O-angeloyl, 22-O-(2-methylbutanoyl)-3β, 15α, 16α, 21β, 22α, 28-hexahydroxyolean-12-ene.

A sugar moiety is a segment of a molecule comprising one or more sugar groups. Substitution, deletion and/or addition of any group in the above-described compounds will be apparent to one of ordinary skill in the art based on the teaching of this application. In a further embodiment, the substitution, deletion and/or addition of the group(s) in the compound of the invention does not substantially affect the biological function of the compound.

This invention provides a method or a use of compound for manufacture of medicament for inhibiting venous insufficiency, particularly hemorrhoids or inhibiting leg swelling, or peripheral edema; antilipemic; for treating chronic venous disease, varicose vein disease, varicose syndrome, venous stasis, expectorant, peripheral vascular disorders, cerebro-organic convulsion, cerebral circulation disorder, cerebral edema, psychoses, dysmenorrheal, hemorrhoids, episiotomies, hamonhoids, peripheral edema formation or postoperative swelling; for reducing symptoms of pain; for reducing symptoms of stomach pain; for reducing symptoms of leg pain; for treating pruritis, lower leg volume, thrombosis, thromophlebitis; for preventing gastric ulcers antispasmotic comprising administering to a subject, in need thereof, an effective amount of the composition of any one of the above compounds or a compound comprises a triterpene which comprises any two of angeloyl, tigloyl, senecioyl, preferably two angeloyl groups, and a sugar moiety, glucose, galactose, rhamnose, arabinose, xylose, fucose, allose, altrose, gulose, idose, lyxose, mannose, psicose, ribose, sorbose, tagatose, talose, fructose, alduronic acid, glucuronic acid or galacturonic acid, or a derivative thereof, or combinations thereof, preferably selected from glucuronic acid, galacturonic acid, glucose, galactose and arabinose. The method regulates or interacts with adhesion protein, wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK. In an embodiment, the method comprises regulating the secretion of fibronectin. In an embodiment, the method comprises inhibiting leishmaniases, modulating adhesion or angiogenesis of cancer cells, antiparasitics or manufacturing an adjuvant composition. In an embodiment, antiparasitics comprise inhibiting leishmaniases, amoebiasis, trypanosomiasis, toxoplasmosis or malaria.

This invention provides a method for inhibiting the growth, migration, metastasis of cancer by altering the characteristics of membranes of cancer cell, wherein the method comprises reducing adhesion protein; wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK; wherein the method comprises inhibiting the secretion of fibronectin, wherein the methods comprises administering to a subject, in need thereof, an appropriate amount of triterpenoidal saponins comprising two or more angeloyl groups, or a compound comprising a triterpene which comprises of any two of angeloyl, tigloyl, senecioyl, preferably two angeloyl groups, and a sugar moiety, glucose, galactose, rhamnose, arabinose, xylose, fucose, allose, altrose, gulose, idose, lyxose, mannose, psicose, ribose, sorbose, tagatose, talose, fructose, alduronic acid, glucuronic acid or galacturonic acid, or a derivative thereof, or combinations thereof, preferably selected from glucuronic acid, galacturonic acid, glucose, galactose and arabinose. This invention provides a composition comprising an effective amount of the compound of any one of compound selected from the above formula or a salt, ester, metabolite or derivative thereof as a medicament for reducing expression and secretion of adhesion proteins; wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK, for inhibiting the growth, migration, metastasis of cancer, wherein the cancers comprise breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphatic cancer, pancreatic cancer, stomach cancer and thyroid cancer.

This invention also provides a composition comprising the above described compounds or their derivatives for reducing adhesion protein, wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK; wherein comprising inhibiting the secretion of fibronectin, wherein the composition is used for treating venous insufficiency, particularly hemorrhoids or inhibiting leg swelling, or peripheral edema, lipemic, chronic venous disease, varicose vein disease, varicose syndrome, venous stasis, Expectorant, peripheral vascular disorders, cerebro-organic convulsion, cerebral circulation disorder, cerebral edema, psychoses, dysmenorrheal, episiotomies, hemonhoids, peripheral edema formation or post-operative swelling; for reducing symptoms of pain; for reducing symptoms of stomach pain; for reducing symptoms of leg pain; for treating pruritis, lower leg volume, thrombosis, thromophlebitis; for preventing gastric ulcers antispasmotic, inhibiting leishmaniases; for modulating adhesion or angiogenesis of cancer cells; antiparasitics or manufacturing an adjuvant composition. In an embodiment of the above, the uses of compositions comprising any one of triterpenoid saponins with the following formula:

3-O-{[[β-D-galactopyranosyl (1→2)]-[α-L-arabinofuranosyl (1→3)]-β-D-glucuronopyranoside butyl ester}-21-O-acetyl-22-O-angeloyl-3β,16α,21β,22α,28-pentahydroxy-olean-12-ene, 3-O-[β-D-galactopyranosyl(1→2)]-α-L-arabinofuranosyl (1→3)-β-D-glucuronopyranosyl-21,22-O-diangeloyl-3β, 15α, 16α, 21β, 22α, 28-hexahydroxyolean-12-ene, 3-O-[β-D-galactopyranosyl(1→2)]-α-L-arabinofuranosyl (1→3)-β-D-glucuronopyranosyl-21-O-(3,4-diangeloyl)-α-L-rhamnophyranosyl-22-O-acetyl-3β,16α, 21β, 22α, 28-pentahydroxyolean-12-ene, 3-O-[β-D-glucopyranosyl-(1→2)]-α-L-arabinofuranosyl (1→3)-β-D-glucuronopyranosyl-21,22-O-diangeloyl-3β, 15α, 16α, 21β, 22α, 24β, 28-heptahydroxyolean-12-ene, 3-O-[β-glucopyranosyl (1→2)]-α-arabinofuranosyl (1→3)-β-glucuronopyranosyl-21, 22-O-diangeloyl-3β, 16α, 21β, 22α, 24β, 28-hexahydroxyolean-12-ene, 3-O-[β-galactopyranosyl (1→2)]-α-arabinofuranosyl (1→3)-β-glucuronopyranosyl-21-O-(3,4-diangeloyl)-α-rhamnopyranosyl-28-O-acetyl-3β, 16α, 21β, 22α, 28-pentahydroxyolean-12-ene, 3-O-[β-galactopyranosyl (1→2)]-α-arabinofuranosyl (1→3)-β-glucuronopyranosyl-21, 22-O-diangeloyl-3β, 16α, 21β, 22α, 28-pentahydroxyolean-12-ene, 3-O-[β-D-galactopyranosyl(1→2)]-α-L-arabinofuranosyl (1→3)-β-D-glucuronopyranosyl-21-O-angeloyl, 22-O-(2-methylpropanoyl)-3β, 15α, 16α, 21β, 22α, 28-hexahydroxyolean-12-ene, 3-O-[β-D-galactopyranosyl-(1→2)]-α-L-arabinofuranosyl-(1→3)-β-D-glucuronopyranosyl-21-O-angeloyl-28-O-2-methylbutanoyl-3β, 15α, 16α, 21β, 22α, 28-hexahydroxyolean-12-ene This invention also provides a composition for regulating or reducing adhesion proteins, wherein the adhesion proteins comprise fibronectin, integrins family, myosin, vitronectin, collagen, laminin, glycosylation cell surface proteins, polyglycans, cadherin, heparin, tenascin, CD 54, CAM, elastin and FAK; inhibiting venous insufficiency, particularly hemorrhoids or inhibition of leg swelling, or inhibiting cancer growth, inhibiting leishmaniases, modulating adhesion of cancer cells, modulating angiogenesis of cancer cells, antiparasitics or manufacturing an adjuvant composition, comprising any of compounds selected from the following compounds (A) to (X) and (A1) to (X1) incorporated here from PCT/US2008/002086, 1188-ALA-PCT:

In an embodiment, a triterpene comprising the following structure has activities of reducing adhesion proteins to block the migration, inhibiting metastasis of cancer cells, inhibiting growth of cancers, inhibiting leishmaniases, modulating adhesion or angiogenesis of cancer cells, antiparasitics, or manufacturing an adjuvant composition.

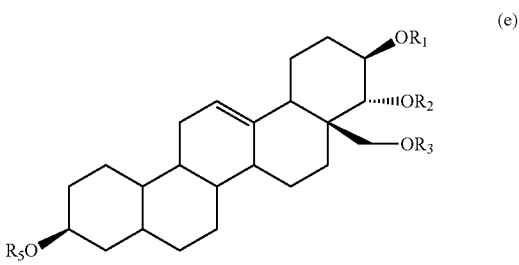

(e)

wherein at least two of R1, R2 and R3 comprise compounds selected from angeloyl, acetyl, tigloyl, senecioyl, benzoyl, dibenzoyl, alkanoyl, alkenoyl, benzoyl alkyl substituted alkanoyl, aryl, heterocylic, heteroraryl, alkanoyl substituted phenyl, alkenoyl substituted phenyl, alkenylcarbonyl or substituted with an C2-9 acid or derivative thereof. In an embodiment, at least one of R1, R2 and R3 comprise a sugar moiety comprising two compounds selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic, heteroraryl, alkanoyl substituted phenyl, alkenoyl substituted phenyl, alkenylcarbonyl or substituted with an C2-9 acid or derivative thereof. In embodiment, R1, R2 or R3 comprise angeloyl groups, tigloyl groups, senecioyl groups or acetyl group or their combinations, preferable wherein at least two of the R1, R2 and R3 comprise angeloyl groups. In an embodiment, R5 comprises sugar moiety. In an embodiment, the sugar moiety comprises at least one sugar, or glucose, or galactose, or rhamnose, or arabinose, or xylose, or alduronic acid, or glucuronic acid, or galacturonic acid, or their derivative thereof, or the combination thereof. In an embodiment, the sugar moiety comprises one or more sugar selected from, but is not limited to glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, or derivatives thereof, or the combination thereof. In an embodiment, the sugar moiety comprise glucose, galactose or arabinose, or combination thereof, or derivatives thereof. In an embodiment, the sugar moietiy comprise alduronic acids, galactose and arabinose, wherein the alduronic comprise glucuronic acid or galacturonic acid. In an embodiment, the sugar moiety comprise alduronic acids, glucose and arabinose, wherein the alduronic comprise glucuronic acid or galacturonic acid. In an embodiment, R5 is Hydrogen. In an embodiment, the R1, R 2 and R3 may be attached in other position of the structure. In an embodiment, the compound is a triterpenoid saponin comprising at least two angeloyl groups, tigloyl groups, senecioyl groups or acetyl group or their combinations, preferably with at least two angeloyl groups. In an embodiment, at least two groups are selected from angeloyl, acetyl, tigloyl, senecioyl, benzoyl, dibenzoyl, alkanoyl, alkenoyl, benzoyl alkyl substituted alkanoyl, aryl, acyl, heterocylic, heteroraryl, alkanoyl substituted phenyl, alkenoyl substituted phenyl, alkenylcarbonyl or substituted with an C2-9 acid or derivative thereof. In an embodiment, at least one of the side bonds of the compound comprises a sugar moiety comprising two compounds selected from angeloyl, acetyl, tigloyl, senecioyl, benzoyl, dibenzoyl, alkanoyl, alkenoyl, benzoyl alkyl substituted alkanoyl, aryl, acyl, heterocylic, heteroraryl, alkanoyl substituted phenyl, alkenoyl substituted phenyl, alkenylcarbonyl or substituted with an C2-9 acid or derivative thereof. In an embodiment, the compound comprises a sugar moiety. In a further embodiment, the sugar moiety comprises glucose, galactose or arabinose or combination thereof. In a further embodiment, the sugar moiety comprises at least one sugar, or glucose, or galactose, or rhamnose, or arabinose, or xylose, or alduronic acid, or glucuronic acid, or galacturonic acid, or their derivative thereof, or the combinations thereof. In a further embodiment, the sugar moiety comprises one or more sugars selected from, but is not limited to glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, or derivatives thereof, or combinations thereof.

A composition comprises an effective amount of compound selected from the above formula or a salt, ester, metabolite or derivative thereof as a medicament for regulating or reducing adhesion protein, blocking the migration, metastasis of cancer cells, inhibiting tumor or cancer cell growth and for treating cancer, wherein the cancers comprise breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphatic cancer, pancreatic cancer, stomach cancer and thyroid cancer.

In a further embodiment, a compound or sapongenin comprising the structure (d) or (e) has anti-cancer or virus inhibiting activities.

A composition for regulating or reducing adhesion proteins, blocking the migration or metastasis of cancer cells, treating cancers or inhibiting viruses, comprises a compound, wherein the compound is a triterpene, which comprises at least two side chains which comprise angeloyl groups, wherein the side chains are at adjacent carbon in trans position. In an embodiment, the side chains are at alternate carbon in cis position. In an embodiment, the side chains are at alternate carbon in trans position. In an embodiment, the side chains are attached to an acyl. In an embodiment, the side chains are attached to an unsaturated group. In an embodiment, the side chains are in non-adjacent carbon cis or trans position. In an embodiment, the side chains comprise a functional group capable of performing the function of angeloyl group.

The above compounds can be used for regulating or reducing adhesion proteins, blocking the migration or metastasis of cancer cells, inhibiting tumor cell growth, or reducing leg swelling, symptoms of chronic venous insufficiency, peripheral edema, antilipemic, chronic venous disease, varicose vein disease, varicose syndrome, venous stasis, expectorant, peripheral vascular disorders, by administering to a subject in need thereof, an effective amount of the above described compounds.

This invention provides a method for inhibiting tumor cell growth, regulating cell growth, reducing inflammation, inhibiting leishmaniases, modulating adhesion or angiogenesis of cancer cells, antiparasitics or manufacturing an adjuvant composition, comprising administering to a subject, in need thereof, an effective amount of the compound which comprises any of the above structures to said subject. The cancers are included but not limited to breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphatic cancer, pancreatic cancer, stomach cancer and thyroid cancer. This invention also provides a method for reducing swelling, reducing symptoms of chronic venous insufficiency, peripheral edema, chronic venous disease, varicose vein disease, varicose syndrome, venous stasis, Expectorant, peripheral vascular disorders, cerebro-organic convulsion, cerebral circulation disorder, cerebral edema, psychoses, dysmenorrheal, hemorrhoids, episiotomies, peripheral edema formation or postoperative swelling; for reducing symptoms of leg pain; for treating pruritus, lower leg volume, for reducing symptoms of pain; thrombosis, thromophlebitis; for preventing gastric ulcers antispasmotic, antilipemic, comprising administering to a subject, in need thereof, an effective amount of the composition of this invention.

This invention provides a composition comprising the compounds provided in the invention for treating cancers; for inhibiting virus; for preventing cerebral aging; for improving memory; improving cerebral functions, for curing enuresis, frequent micturition, urinary incontinence, dementia, Alzheimer's disease, autism, brain trauma, Parkinson's disease or other diseases caused by cerebral dysfunctions; for treating arthritis, rheumatism, poor circulation, arteriosclerosis, Raynaud's syndrome, angina pectoris, cardiac disorder, coronary heart disease, headache, dizziness, kidney disorder; cerebrovascular disease; inhibiting NF-Kappa B activation; for treating brain edema, sever acute respiratory syndrome, respiratory viral diseases, chronic venous insufficiency, hypertension, chronic venous disease, hemonhoids, peripheral edema formation, varicose vein disease, flu, post traumatic edema and postoperative swelling; for inhibiting blood clot, for inhibiting ethanol absorption; for lowering blood sugar; for regulating the adrenocorticotropin and corticosterone level. This invention provides a composition for AntiMS, antianeurysm, antiasthmatic, antibradykinic, anticapillarihemorrhagic, anticephalagic, anticervicobrachialgic, antieclamptic, antiedemic, antiencaphalitic, antiepiglottitic, antiexudative, antiflu, antifracture, antigingivitic, antihematomic, antiherpetic, antihistaminic, antihydrathritic, antimeningitic, antioxidant, antiperiodontic, antiphlebitic, antipleuritic, antiraucedo, antirhinitic, antitonsilitic, antiulcer, antivaricose, antivertiginous, anti-oedematous, anti inflammatory, cancerostatic, corticosterogenic, diuretic, fungicide, hemolytic, hyaluronidase inhibitor, lymphagogue, natriuretic, pesticide, pituitary stimulant, thymolytic, vasoprotective, inhibiting leishmaniases, modulating adhesion or angiogenesis of cancer cells, antiparasitics, or manufacturing an adjuvant composition and venotonic treatment.

This invention provides a use of compounds or methods for inhibiting the expression or secretion of adhesion proteins of cancers, cancer cell migration, metastasis or growth of cancers, wherein this invention comprises a process and method for administration of the an effective amount of composition, wherein administration is by intravenous injection, intravenous drip, intraperitoneal injection or oral administration; wherein administration is by intravenous drip: 0.003-0.03 mg/kg body weight of compound dissolved in 250 ml of 10% glucose solution or in 250 ml of 0.9%

NaCl solution, or by intravenous injection: 0.003-0.03 mg/kg body weight per day of compound dissolved in 10-20 ml of 10% glucose solution or of 0.9% NaCl solution, or 0.01-0.03 mg/kg body weight of compound dissolved in 250 ml of 10% glucose solution or in 250 ml of 0.9% NaCl solution, or by intravenous injection: 0.01-0.03 mg/kg body weight per day of compound dissolved in 10-20 ml of 10% glucose solution or of 0.9% NaCl solution, or 0.01-0.05 mg/kg body weight of compound dissolved in 250 ml of 10% glucose solution or in 250 ml of 0.9% NaCl solution, or by intravenous injection: 0.01-0.05 mg/kg body weight per day of compound dissolved in 10-20 ml of 10% glucose solution or of 0.9% NaCl solution, or 0.05-0.2 mg/kg body weight of compound dissolved in 250 ml of 10% glucose solution or in 250 ml of 0.9% NaCl solution, or by intravenous injection: 0.05-0.2 mg/kg body weight per day of compound dissolved in 10-20 ml of 10% glucose solution or of 0.9% NaCl solution, or by intravenous drip: 0.1-0.2 mg/kg body weight per day of compound dissolved in 250 ml of 10% glucose solution or in 250 ml of 0.9% NaCl solution, or by intravenous injection: 0.1-0.2 mg/kg body weight per day compound dissolved in 10-20 ml of 10% glucose solution or of 0.9% NaCl solution, or by intraperitoneal injection(I.P.): 2.5 mg/kg body weight per day compound dissolved in 10% glucose solution or of 0.9% NaCl solution, or by oral administration wherein the dosage of mammal is 0.01-3 mg/kg, 0.1-5 mg/kg, 1-10 mg/kg, 10-30 mg/kg, 30-60 mg/kg, or 60-90 mg/kg body weight of compound, or by intravenous injection or intravenous drip wherein the dosage of mammal is 0.01-0.1 mg/kg, 0.1-0.2 mg/kg, 0.2-0.4 mg/kg, or 0.4-0.6 mg/kg body weight of compound, or by intraperitoneal injection (I.P.) wherein the dosage of mammal is 1-3 mg/kg, 3-5 mg/kg, 4-6 mg/kg, or 6-10 mg/kg body weight of compound.

This invention provides a use of compounds or methods for inhibiting the expression or secretion of adhesion proteins of cancers, cancer cell migration, metastasis or growth of cancers, wherein the invention comprises a pharmaceutical composition comprising the compound of this invention or a pharmaceutically acceptable salt thereof, and a pharmaceutically acceptable carrier or diluent, wherein said compound is present in a concentration of 0.01 ug/ml to 65 ug/ml, or wherein said compound is present in a concentration of 0.01 ug/ml to 40 ug/ml, or wherein said compound is present in a concentration of 0.01 ug/ml to 30 ug/ml, or wherein said compound is present in a concentration of 0.01 ug/ml to 10 ug/ml, or wherein said compound is present in a concentration of 0.01 ug/ml to 5 ug/ml, or wherein said compound is present in a concentration of 5 ug/ml to 10 ug/ml, or wherein said compound is present in a concentration of 0.1 ug/ml to 5 ug/ml, or wherein said compound is present in a concentration of 0.1 ug/ml to 7.5 ug/ml, or wherein said compound is present in a concentration of 0.1 ug/ml to 10 ug/ml, or wherein said compound is present in a concentration of 0.1 ug/ml to 15 ug/ml, or wherein said compound is present in a concentration of 0.1 ug/ml to 20 ug/ml, or wherein said compound is present in a concentration of 0.1 ug/ml to 30 ug/ml, or wherein said compound is present in a concentration of 1 ug/ml to 5 ug/ml, or wherein said compound is present in a concentration of 1 ug/ml to 7.5 ug/ml, or wherein said compound is present in a concentration of 1 ug/ml to 10 ug/ml, or wherein said compound is present in a concentration of 1 ug/ml to 15 ug/ml, or wherein said compound is present in a concentration of 1 ug/ml to 20 ug/ml, or wherein said compound is present in a concentration of 1 ug/ml to 30 ug/ml, or wherein said compound is present in a concentration of 3 ug/ml to 5 ug/ml, or wherein said compound is present in a concentration of 3 ug/ml to 7.5 ug/ml, or wherein said compound is present in a concentration of 3 ug/ml to 10 ug/ml, or wherein said compound is present in a concentration of 3 ug/ml to 15 ug/ml, or wherein said compound is present in a concentration of 3 ug/ml to 20 ug/ml, or wherein said compound is present in a concentration of 3 ug/ml to 30 ug/ml, or wherein said compound is present in a concentration of 4 ug/ml to 5 ug/ml, or wherein said compound is present in a concentration of 4 ug/ml to 7.5 ug/ml, or wherein said compound is present in a concentration of 4 ug/ml to 10 ug/ml, or wherein said compound is present in a concentration of 4 ug/ml to 15 ug/ml, or wherein said compound is present in a concentration of 4 ug/ml to 20 ug/ml, or wherein said compound is present in a concentration of 4 ug/ml to 30 ug/ml, or wherein said compound is present in a concentration of 5 ug/ml to 8 ug/ml, or wherein said compound is present in a concentration of 5 ug/ml to 9 ug/ml, or wherein said compound is present in a concentration of 5 ug/ml to 10 ug/ml, or wherein said compound is present in a concentration of 5 ug/ml to 15 ug/ml, or wherein said compound is present in a concentration of 5 ug/ml to 20 ug/ml, or wherein said compound is present in a concentration of 5 ug/ml to 30 ug/ml, or wherein said compound is present in a concentration of 7 ug/ml to 8 ug/ml, or wherein said compound is present in a concentration of 7 ug/ml to 9 ug/ml, or wherein said compound is present in a concentration of 7 ug/ml to 10 ug/ml, or wherein said compound is present in a concentration of 7 ug/ml to 15 ug/ml, or wherein said compound is present in a concentration of 7 ug/ml to 20 ug/ml, or wherein said compound is present in a concentration of 7 ug/ml to 30 ug/ml.

This invention provides a use of compounds or methods for inhibiting the expression or secretion of adhesion proteins of cancers, cancer cell migration, metastasis or growth of cancers, wherein the invention comprises a pharmaceutical composition comprising the compound of this invention or a pharmaceutically acceptable salt thereof, and a pharmaceutically acceptable carrier or diluent, wherein said compound is present in a concentration of 0.008 uM to 80 uM, or wherein said compound is present in a concentration of 0.01 uM to 60 uM, or wherein said compound is present in a concentration of 0.01 uM to 50 uM, or wherein said compound is present in a concentration of 0.01 uM to 40 uM, or wherein said compound is present in a concentration of 0.01 uM to 30 uM, or wherein said compound is present in a concentration of 0.01 uM to 20 uM, or wherein said compound is present in a concentration of 0.01 uM to 10 uM, or wherein said compound is present in a concentration of 5 uM to 10 uM, or wherein said compound is present in a concentration of 0.1 uM to 5 uM, or wherein said compound is present in a concentration of 0.1 uM to 7.5 uM, or wherein said compound is present in a concentration of 0.1 uM to 10 uM, or wherein said compound is present in a concentration of 0.1 uM to 15 uM, or wherein said compound is present in a concentration of 0.1 uM to 20 uM, or wherein said compound is present in a concentration of 0.1 uM to 30 uM or wherein said compound is present in a concentration of 0.1 uM to 40 uM, or wherein said compound is present in a concentration of 0.1 uM to 50 uM or wherein said compound is present in a concentration of 0.1 uM to 60 uM, or wherein said compound is present in a concentration of 0.1 uM to 80 uM, or wherein said compound is present in a concentration of 1 uM to 5 uM, or wherein said compound is present in a concentration of 1 uM to 7.5 uM, or wherein said compound is present in a concentration of 1 uM to 10 uM, or wherein said compound is present in a concentration of 1 uM to 15 uM, or wherein said compound is present in a concentration of 1 uM to 20 uM, or wherein said compound is present in a concentration of 1 uM to 30 uM or wherein said compound is present in a concentration of 1 uM to 40 uM, or wherein said compound is present in a concentration of 1 uM to 50 uM or wherein said compound is present in a concentration of 1 uM to 60 uM, or wherein said compound is present in a concentration of 1 uM to 80 uM, or wherein said compound is present in a concentration of 3 uM to 5 uM, or wherein said compound is present in a concentration of 3 uM to 7.5 uM, or wherein said compound is present in a concentration of 3 uM to 10 uM, or wherein said compound is present in a concentration of 3 uM to 15 uM, or wherein said compound is present in a concentration of 3 uM to 20 uM, or wherein said compound is present in a concentration of 3 uM to 30 uM or wherein said compound is present in a concentration of 3 uM to 40 uM, or wherein said compound is present in a concentration of 3 uM to 50 uM or wherein said compound is present in a concentration of 3 uM to 60 uM, or wherein said compound is present in a concentration of 3 uM to 80 uM, or wherein said compound is present in a concentration of 5 uM to 8 uM, or wherein said compound is present in a concentration of 5 uM to 10 uM, or wherein said compound is present in a concentration of 5 uM to 15 uM, or wherein said compound is present in a concentration of 5 uM to 20 uM, or wherein said compound is present in a concentration of 5 uM to 30 uM or wherein said compound is present in a concentration of 5 uM to 40 uM, or wherein said compound is present in a concentration of 5 uM to 50 uM or wherein said compound is present in a concentration of 5 uM to 60 uM, or wherein said compound is present in a concentration of 5 uM to 80 uM. or wherein said compound is present in a concentration of 7 uM to 8 uM, or wherein said compound is present in a concentration of 7 uM to 10 uM, or wherein said compound is present in a concentration of 7 uM to 15 uM, or wherein said compound is present in a concentration of 7 uM to 20 uM, or wherein said compound is present in a concentration of 7 uM to 30 uM or wherein said compound is present in a concentration of 7 uM to 40 uM, or wherein said compound is present in a concentration of 7 uM to 50 uM or wherein said compound is present in a concentration of 7 uM to 60 uM, or wherein said compound is present in a concentration of 7 uM to 80 uM.

Alkenyl means unsaturated linear or branched structures and combinations thereof, having 1-7 carbon atoms, one or more double bonds therein. Non-limiting examples of alkenyl groups include vinyl, propenyl, isopropenyl, butenyl, s- and t-butenyl, pentenyl, hexenyl, butadienyl, pentadienyl, and hexadienyl.

An aryl is a functional group of organic molecule derived from an aromatic compound such as benzene, a 6-14 membered carbocyclic aromatic ring system comprising 1-3 benzene rings. If two or more aromatic rings are present, then the rings are fused together, so that adjacent rings share a common bond. Examples include phenyl and naphthyl. The aryl group may be substituted with one or more substitutes independently selected from halogen, alkyl or alkoxy.

Acyl is a functional group obtained from an organic acid by the removal of the carboxyl. Acyl groups can be written as having the general formula —COR, where there is a double bond between the carbon and oxygen. The names of acyl groups typically end in -yl, such as formyl, acetyl, propionyl, butyryl and benzoyl.

Benzoyl is one of acyls, $C_6H_5COR$, obtained from benzoic acid by the removal of the carboxyl.

Heterocyclic compound—a compound containing a heterocyclic ring which refers to a non-aromatic ring having 1-4 heteroatoms said ring being isolated or fused to a second ring selected from 3-to 7-membered alicyclic ring containing 0-4 heteroatoms, aryl and heteroaryl, wherein said heterocyclic comprises pyrrolidinyl, pipyrazinyl, morpholinyl, trahydrofuranyl, imidazolinyl, thiomorpholinyl.

Heterocyclyl groups derived from heteroarenes by removal of a hydrogen atom from any ring atom.

Alkanoyl is the general name for an organic functional group RCO—, where R represents hydrogen or an alkyl group. Preferably alkanoyl is selected from acetyl, propionoyl, butyryl, isobutyryl, pentanoyl and hexanoyl.

Alkenoyl is alkenylcarbonyl in which alkenyl is defined above. Examples are pentenoyl(tigloyl) and hexenoyl(angeloyl).

Alkyl is a radical containing only carbon and hydrogen atoms arranged in a chain, branched, cyclic or bicyclic structure or their combinations, having 1-18 carbon atoms. Examples include but are not limited to methyl, ethyl, propyl isopropyl, butyl, s- and t-butyl, pentyl, hexyl, heptyl, octyl, nonyl, undecyl, dodecyl, tridecyl, tetradecyl, pentadecyl, cyclopropyl, cyclobutyl, cyclopentyl and cyclohexyl.

Benzoyl alkyl substituted alkanoyl is refer to straight or branched C1-C6 alkanoyl substituted with at least one benzoyl and at least one alkyl, wherein the benzoyl is attached to a straight or branched C1-C6 alkyl. Preferably a benzoyl alkyl substituted alkanoyl is benzoyl methyl isobutanoyl.

A sugar moiety is a segment of molecule comprising one or more sugars or derivatives thereof or alduronic acid thereof.

Isobutyryl is Synonym of 2-Methylpropanoyl; (Y)Y3, Y and Y3 represent the same compound; YM and (ACH-Y) represent the same compound.

(Z)—O(C=O)C(CH3)=CH—C6H5 is an example of [O—C4 alkenoyl substituted with phenyl]

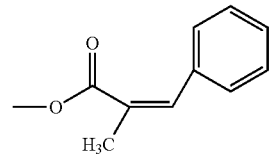

(Z)—O(C=O)CH=CH—C6H5 is an example of [O—C3 alkenoyl substituted with phenyl]

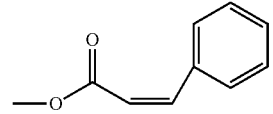

(E)-O(C=O)CH=CH—C6H5 is an example of [O—C3 alkenoyl substituted with phenyl]

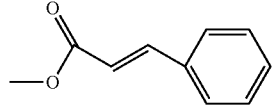

O(C=O)C6H5, Benzoyl is an example of [O—C1 alkanoyl substituted with phenyl]

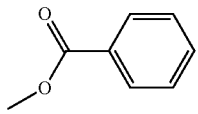

(2Z)-2-methyl-3-phenylacrylic acid

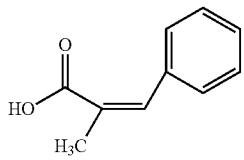

(2Z)-3-phenylacrylic acid

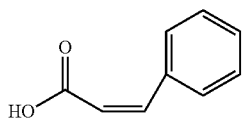 [SMILES: O=C(O)/C=C\c1ccccc1]

(2E)-3-phenylacrylic acid

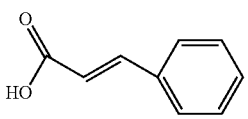 [SMILES: O=C(O)/C=C/c1ccccc1]

Benzoic acid

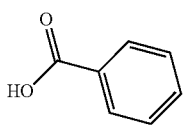

O-Angeloyl: O(C=O)C(CH3)=CH(CH3)

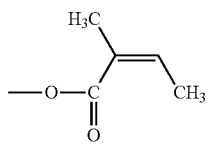

R— O-Tigloyl: O(C=O)C(CH3)=CH(CH3)

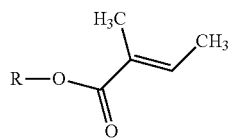

This invention provides a method of altering the characteristic of cancer cell membrane to block the migration, metastasis of cancer cells or inhibit the growth of cancers or anti-angiogenesis.

This invention provides a composition and method for inhibiting the growth, migration, metastasis of cancer by altering the adhesion characteristic of membrane of cancer cell, wherein the cancers comprise breast cancer, leukocyte cancer, liver cancer, ovarian cancer, bladder cancer, prostate cancer, skin cancer, bone cancer, brain cancer, leukemia cancer, lung cancer, colon cancer, CNS cancer, melanoma cancer, renal cancer or cervix cancer, wherein the method comprises administering to a subject or contacting the cells with Xanifolia Y0, Y1, Y2, Y, Y5, Y7, Y8, Y9, Y10, or a salt, ester, metabolite thereof. In an embodiment the method comprises administering to a subject or contacting the cells with the compound selected from formula in this application.

This application shows Xanifolia-Y is an alternate or supplemental agent to DNA-inhibition or microtubule-targeting drugs. It could be beneficial if it is used singly or in combination with other drugs of different mechanisms (block M-phase progression or DNA synthesis). Our inventions show combined effect of Xanifolia-Y and paclitaxel on inhibition of ES2 cells' growth (Details in Experiment 15).

Identify the binding target of Xanifolia-Y of adhesion proteins and signaling proteins in ovarian cancer cells.

In our animal studies, it was shown that Xanifolia-Y extended the life span of tumor bearing mice. (Reference Experiments 7, 8, 9 in U.S. Ser. No. 11/683,198, filed on Mar. 7, 2007,). The animals died sooner if the treatment of Xanifolia-Y was delayed (comparing results of treatments started from 1, 4 or 10 days after tumor inoculation). The results show that Xanifolia-Y inhibits migration or metastasis of the inoculated cancer cells. Ovarian carcinoma cells express high levels of adhesion molecules. Adhesion proteins are present in both cancer cells and mesothelial cells. While the lost of adhesion blocks of the protein accessibility due to a result of modulating by Xanifolia-Y, In an embodiment, the interaction of Xanifolia-Y with membrane alter the adhesion protein's binding site(s).

Fibronectin is a kind of glycoprotein that binds to membrane spanning receptor proteins comprising the integrins, collagen, fibrin and heparin sulfate. Fibronectin has been implicated in tumor development and metastasis. This application provides methods and compositions for modulating the gene expression of fibronectin, inhibiting the secretion of fibronectin, reducing the receptors of fibronectin, reducing the adhesion ability fibronectin, inhibiting the metastasis, or inhibiting cancer growth, wherein the method and composition comprises administering to the said subject as effective amount of compounds selected in this application.

Angiogenesis is a process involving the growth of new blood vessels. It is a normal process in growth and development. The angiopoietins are protein growth factors that modulate angiogenesis. The identified angiopoietins comprise angiopoietin 1, angiopoietin 2, angiopoietin 3, angiopoietin 4, angiopoietin 5, angiopoietin 6, angiopoietin 7, angiopoietin-like 1, angiopoietin-like 2, angiopoietin-like 3, angiopoietin-like 4, angiopoietin-like 5, angiopoietin-like 6, and angiopoietin-like 7. In an embodiment, the angiopoietin 1 is a positive factor to promote the new blood vessels. In embodiment, the angiopoietin 2 is antagonist of angiopoietin 1, which is a negative factor for the growth of new blood vessels. This application provides methods and compositions for modulating angiopoietin and inhibiting cancer growth; wherein the cancers comprise breast, leukocyte, liver, ovarian, bladder, prostate, skin, bone, brain, leukemia, lung, colon, CNS, melanoma, renal and cervix cancer, wherein the methods and compositions comprise administering to the said subject as effective amount of compounds selected in this application. The compounds in this application are positive regulating angiopoietin 2. The compounds in this application are negative regulating the angiopoietin 1. The results of the micro array experiment showed that compound Y and YM (ACH-Y) modulate the gene expression of angiopoietin family in ES2 cells. They promote angiopoietin 2 and inhibit angiopoietin 1 and angiopoietin-like 1 and angiopoietin-like 4.

The compounds in this application are used antiparasitics, enhancing an immune response, providing adjuvant activities or providing vaccine activities, anti-angiogenesis, inhibiting cancer cell metastasis and inhibiting cancer growth, wherein the compounds comprise Xanifolia Y0, Y1, Y2, Y, Y7, Y8, Y9, Y10, ACH-Y or a salt, ester, metabolite thereof and compounds selected from formula (1A), (1B), (1C), (1D), (1E), (1F), (1G), (1H), (1J), (1K), (1L). In an embodiment the method is administering contacting the compound in this application comprising Xanifolia Y0, Y1, Y2, Y, Y7, Y8, Y9, Y10, Xanifolia (x), Escin or Aescin or a salt, ester, metabolite thereof. In an embodiment the compound may be selected from formulas (1A), (1B), (1C), (1D) (1E), (1F), (1G), (1H), (1J), (1K), (14 In an embodiment, the compound comprises a triterpene backbone, two angeloyl groups and sugar moiety. In an embodiment the compound(s) are selected from Compound A to X and A1 to X1 in the application. In an embodiment the compound(s) are selected from Compound Z1 to Z7 in the application. In an embodiment the compound(s) are selected from ACH-Z4, ACH-Y10, ACH-Y2, ACH-Y8, ACH-Y7, ACH-Y0, ACH-X, ACH-E. In an embodiment the saponins comprise Ba1, Ba2, Ba3, Ba4, Ba5, Ba6, Ba7, Ba8, Ba9, Ba10, Ba11, Ba12, Ba13, Ba14, Ba15, Ba16, Ba 17.

The triterpene compounds of this invention can be administered to a subject in need thereof treating the subject, wherein including preventing cancer or has adjuvant effect to the subject, or inhibiting the initiation or promotion of cancer, or killing the cancer/tumor cells. In an embodiment the compounds inhibit the activation of nuclear factor-kB, wherein inhibiting the localization or wherein binding the DNA. In an embodiment the compounds induce apoptosis in cancer cells.

The triterpene compounds of this invention can reduce blood vessel in the tumor in a subject. (FIG. 44)

The following results are obtained from MicroArray experiments:

Y/D is the ratio (in folds) of gene expression in cells treated with compound Y as compared with those of the no drug control (D), YM/D is the ratio of gene expression in cells treated with compound YM (ACH-Y, Y without sugar moiety) compared with those of the no drug control (D)

TABLE 1

Effect of Y and YM on fibronectin expression in ES2 cells

| Probe Set ID | Y/D | YM/D | Gene.Symbol | Gene.Title |
|---|---|---|---|---|
| 212464_s_at | −2.7 | −1.1 | FN1 | fibronectin 1 |
| 216442_x_at | −2.6 | −1.1 | FN1 | fibronectin 1 |
| 211719_x_at | −2.6 | −1.2 | FN1 | fibronectin 1 |
| 210495_x_at | −2.5 | −1.1 | FN1 | fibronectin 1 |

The results of the microarray experiment showed that compound Y and YM(ACH-Y) inhibit fibronectin expression; The expression ratio of compound Y/Y3 to the control are −2.7, −2.6, −2.6, −2.5 folds detected by gene probes 212464_s_at; 216442_x_at; 211719x_at and 210495_x_at, respectively. These results indicate Y/Y3 inhibits fibronectin expression; wherein the YM/ACH-Y also show minor fibronectin inhibition with the inhibiting ratio of −1.1, −1.1, −1.2, −1.1 folds by gene probes 212464_s_at; 216442_x_at; 211719_x_at and 210495_x_at, respectively. The results indicate that while YM is active but is less potent than Y/Y3.

TABLE 2

Effects of Y and YM on integrin (vitronectin receptor) expression in ES2 cells

| Probe Set ID | Y/D | YM/D | Gene.Symbol | Gene.Title |
|---|---|---|---|---|
| 202351_at | −1.8 | −1.3 | ITGAV | integrin, alpha V (vitronectin receptor, alpha polypeptide, antigen CD51) |
| 236251_at | −1.4 | −1.4 | ITGAV | Integrin, alpha V (vitronectin receptor, alpha polypeptide, antigen CD51) |

The results of the micro array experiment showed that compound Y and YM(ACH-Y) inhibit integrin (vitronectin receptor) expression; wherein the inhibiting ratio of compound Y/Y3 to the control are −1.8, −1.4, folds as detected by different probes; wherein the inhibiting ratio of YM (ACH-Y) to the control are −1.3, −1.4 folds.

TABLE 3

Effects of Y and YM on laminin expression in ES2 cells

| Probe Set ID | Y/D | YM/D | Gene.Symbol | Gene.Title |
|---|---|---|---|---|
| 202202_s_at | −2.2 | −2.0 | LAMA4 | laminin, alpha 4 |
| 216264_s_at | −2.0 | −2.0 | LAMB2 | laminin, alpha 5 |
| 200770_s_at | −1.9 | −1.1 | LAMC1 | laminin, alpha 6 |
| 211651_s_at | −1.6 | −1.7 | LAMB1 | laminin, alpha 7 |
| 201505_at | −1.6 | −2.0 | LAMB1 | laminin, beta 1 |

The results of the micro array experiment showed that compound Y and YM(ACH-Y) inhibit laminin expression; The expression ratio of compound Y/Y3 to the control are −2.2, −2.0, −1.9, −1.6, −1.6 folds as detected by different probes; wherein the inhibiting ratio of YM/ACH-Y to the control are −2.0, −2.0, 1.1, −1.7, −2.0 folds.

TABLE 4

Effects of Y and YM on CAM expression in ES2 cells

| Probe Set ID | Y/D | YM/D | Gene.Symbol | Gene.Title |
|---|---|---|---|---|
| 201952_at | −1.9 | −1.4 | ALCAM | activated leukocyte cell adhesion molecule |
| 201951_at | −1.9 | −1.7 | ALCAM | activated leukocyte cell adhesion molecule |
| 212425_at | −1.7 | −1.5 | SCAMP1 | Secretory carrier membrane protein 1 |
| 240655_at | −1.6 | −1.3 | ALCAM | Activated leukocyte cell adhesion molecule |
| 212417_at | −1.4 | −1.4 | SCAMP1 | secretory carrier membrane protein 1 |
| 239431_at | −1.3 | −1.3 | TICAM2 | toll-like receptor adaptor molecule 2 |
| 212416_at | −1.3 | −1.1 | SCAMP1 | secretory carrier membrane protein 1 |

TABLE 4-continued

Effects of Y and YM on CAM expression in ES2 cells

| Probe Set ID | Y/D | YM/D | Gene.Symbol | Gene.Title |
|---|---|---|---|---|
| 228234_at | −1.3 | −1.3 | TICAM2 | toll-like receptor adaptor molecule 2 |
| 206667_s_at | −1.3 | −1.5 | SCAMP1 | secretory carrier membrane protein 1 |

The micro array experiment showed that compound Y and YM(ACH-Y) inhibit gene expression related to the adhesion molecule; wherein the inhibiting ratio of compound Y/Y3 to the control are −1.3 to −1.9 folds as detected by different probes; wherein the inhibiting ration of YM/ACH-Y to the control are −1.1 to −1.7 folds.

TABLE 5

Effects of Y and YM on collagen expression in ES2 cells

| Probe Set ID | Y/D | YM/D | Gene.Symbol | Gene.Title |
|---|---|---|---|---|
| 217428_s_at | −3.0 | −1.2 | COL10A1 | collagen, type X, alpha 1 (Schmid metaphyseal chondrodysplasia) |
| 231766_s_at | −2.8 | −2.4 | COL12A1 | collagen, type XII, alpha 1 |
| 201438_at | −2.4 | −1.5 | COL6A3 | collagen, type VI, alpha 3 |
| 1556138_a_at | −2.2 | −2.8 | COL5A1 | Collagen, type V, alpha 1 |
| 211809_x_at | −2.0 | −1.5 | COL13A1 | collagen, type XIII, alpha 1 |
| 207543_s_at | −2.0 | −1.5 | P4HA1 | procollagen-proline, 2-oxoglutarate 4-dioxygenase (proline 4-hydroxylase), alpha polypeptide I |
| 213992_at | −2.0 | −1.9 | COL4A6 | collagen, type IV, alpha 6 |
| 211343_s_at | −1.9 | −1.7 | COL13A1 | collagen, type XIII, alpha 1 |
| 211966_at | −1.8 | −1.7 | COL4A2 | collagen, type IV, alpha 2 |
| 200656_s_at | −1.8 | −1.2 | P4HB | procollagen-proline, 2-oxoglutarate 4-dioxygenase (proline 4-hydroxylase), beta polypeptide (protein disulfide isomerase-associated 1) |
| 209081_s_at | −1.7 | −1.5 | COL18A1 | collagen, type XVIII, alpha 1 |
| 202619_s_at | −1.7 | −1.2 | PLOD2 | procollagen-lysine, 2-oxoglutarate 5-dioxygenase 2 |
| 203325_s_at | −1.7 | −2.8 | COL5A1 | collagen, type V, alpha 1 |
| 200827_at | −1.7 | −1.2 | PLOD1 | procollagen-lysine 1,2-oxoglutarate 5-dioxygenase 1 |
| 221730_at | −1.6 | −1.6 | COL5A2 | collagen, type V, alpha 2 |
| 202311_s_at | −1.6 | −3.6 | COL1A1 | collagen, type I, alpha 1 |
| 213110_s_at | −1.6 | −2.2 | COL4A5 | collagen, type IV, alpha 5 (Alport syndrome) |
| 212091_s_at | −1.6 | −1.9 | COL6A1 | collagen, type VI, alpha 1 |
| 213290_at | −1.6 | −1.5 | COL6A2 | collagen, type VI, alpha 2 |
| 211981_at | −1.6 | −2.2 | COL4A1 | collagen, type IV, alpha 1 |
| 200654_at | −1.6 | −1.3 | P4HB | procollagen-proline, 2-oxoglutarate 4-dioxygenase (proline 4-hydroxylase), beta polypeptide (protein disulfide isomerase-associated 1) |
| 212489_at | −1.5 | −4.1 | COL5A1 | collagen, type V, alpha 1 |
| 202620_s_at | −1.4 | −1.3 | PLOD2 | procollagen-lysine, 2-oxoglutarate 5-dioxygenase 2 |
| 202733_at | −1.4 | −1.9 | P4HA2 | procollagen-proline, 2-oxoglutarate 4-dioxygenase (proline 4-hydroxylase), alpha polypeptide II |
| 208535_x_at | −1.4 | −1.2 | COL13A1 | collagen, type XIII, alpha 1 |
| 202185_at | −1.3 | −1.1 | PLOD3 | procollagen-lysine, 2-oxoglutarate 5-dioxygenase 3 |
| 202465_at | −1.3 | −1.6 | PCOLCE | procollagen C-endopeptidase enhancer |
| 221729_at | −1.3 | −1.8 | COL5A2 | collagen, type V, alpha 2 |
| 242324_x_at | −1.3 | −1.8 | CCBE1 | collagen and calcium binding EGF domains 1 |
| 1568611_at | −1.3 | −2.4 | P4HA2 | Procollagen-proline, 2-oxoglutarate 4-dioxygenase (proline 4-hydroxylase), alpha polypeptide II |

The results of the micro array experiment showed that compound Y and YM(ACH-Y) inhibit collagen expression. The expression ratio of compound Y/Y3 to the control range from −1.3 to −3.0 folds; wherein the expression ratio of YM/ACH-Y to the control range from −1.1 to −3.6 folds

TABLE 6

Effects of Y and YM on integrin expression in ES2 cells

| Probe Set ID | Y/D | YM/D | Gene.Symbol | Gene.Title |
|---|---|---|---|---|
| 205422_s_at | −1.9 | −2.0 | ITGBL1 | integrin, beta-like 1 (with EGF-like repeat domains) |
| 202351_at | −1.8 | −1.3 | ITGAV | integrin, alpha V (vitronectin receptor, alpha polypeptide, antigen CD51) |
| 1557080_s_at | −1.7 | −2.5 | ITGBL1 | Integrin, beta-like 1 (with EGF-like repeat domains) |
| 214927_at | −1.7 | −1.8 | ITGBL1 | Integrin, beta-like 1 (with EGF-like repeat domains) |
| 205885_s_at | −1.7 | −2.0 | ITGA4 | integrin, alpha 4 (antigen CD49D, alpha 4 subunit of VLA-4 receptor) |
| 213416_at | −1.6 | −1.7 | ITGA4 | integrin, alpha 4 (antigen CD49D, alpha 4 subunit of VLA-4 receptor) |
| 215177_s_at | −1.6 | 1.1 | ITGA6 | integrin, alpha 6 |
| 205884_at | −1.6 | −1.7 | ITGA4 | integrin, alpha 4 (antigen CD49D, alpha 4 subunit of VLA-4 receptor) |
| 1555349_a_at | −1.6 | −1.4 | ITGB2 | integrin, beta 2 (antigen CD18 (p95), lymphocyte function-associated antigen 1; macrophage antigen 1 (mac-1) beta subunit) |
| 227259_at | −1.6 | −1.1 | CD47 | CD47 antigen (Rh-related antigen, integrin-associated signal transducer) |
| 201474_s_at | −1.6 | −1.5 | ITGA3 | integrin, alpha 3 (antigen CD49C, alpha 3 subunit of VLA-3 receptor) |
| 214021_x_at | −1.5 | −2.2 | ITGB5 | Integrin, beta 5 |
| 201656_at | −1.5 | −1.1 | ITGA6 | integrin, alpha 6 |

The results of the micro array experiment showed that compound Y and YM(ACH-Y) inhibit gene expression related to the integrin family in ES2 cells. The expression ratio of compound Y/Y3 to the control are ranging from −1.5 to −1.9 folds; wherein the expression ratio of YM/ACH-Y to the control are ranging from −1.1 to −2.5 folds.

TABLE 7

Effects of Y and YM on myosin expression in ES2 cells

| Probe Set ID | Y/D | YM/D | Gene.Symbol | Gene.Title |
|---|---|---|---|---|
| 211926_s_at | −2.2 | −1.2 | MYH9 | myosin, heavy polypeptide 9, non-muscle |
| 212372_at | −1.7 | −1.4 | MYH10 | myosin, heavy polypeptide 10, non-muscle |
| 212338_at | −1.7 | −2.1 | MYO1D | myosin ID |
| 204527_at | −1.6 | −1.2 | MYO5A | myosin VA (heavy polypeptide 12, myoxin) |
| 202555_s_at | −1.6 | −1.2 | MYLK | myosin, light polypeptide kinase /// myosin, light polypeptide kinase |
| 203215_s_at | −1.6 | −1.6 | MYO6 | myosin VI |
| 225080_at | −1.5 | −1.4 | MYO1C | Myosin IC |
| 224823_at | −1.5 | −1.4 | MYLK | myosin, light polypeptide kinase |

The results of the micro array experiment showed that compound Y and YM(ACH-Y) inhibit gene expression related to the myosin family in ES2 cells. The expression ratio of compound Y/Y3 to the control are ranging from −1.5 to −2.2 folds; wherein the expression ratio of YM/ACH-Y to the control are ranging from −1.2 to −2.1 folds.

TABLE 8

Effects of Y and YM on cadherins expression in ES2 cells

| Probe Set ID | Y/D | YM/D | Gene.Symbol | Gene.Title |
|---|---|---|---|---|
| 244091_at | −2.0 | −1.7 | CDH13 | Cadherin 13, H-cadherin (heart) |
| 202468_s_at | −1.9 | −1.6 | CTNNAL1 | catenin (cadherin-associated protein), alpha-like 1 |
| 204726_at | −1.8 | −1.7 | CDH13 | cadherin 13, H-cadherin (heart) |
| 207149_at | −1.7 | −2.2 | CDH12 | cadherin 12, type 2 (N-cadherin 2) |
| 201533_at | −1.5 | 1.2 | CTNNB1 | catenin (cadherin-associated protein), beta 1, 88 kDa |

TABLE 8-continued

Effects of Y and YM on cadherins expression in ES2 cells

| Probe Set ID | Y/D | YM/D | Gene.Symbol | Gene.Title |
|---|---|---|---|---|
| 204677_at | −1.5 | −1.1 | CDH5 | cadherin 5, type 2, VE-cadherin (vascular epithelium) |
| 208407_s_at | −1.5 | −1.7 | CTNND1 | catenin (cadherin-associated, protein), delta 1 |
| 203440_at | −1.4 | 1.0 | CDH2 | cadherin 2, type 1, N-cadherin (neuronal) |
| 210844_x_at | −1.4 | −1.2 | CTNNA1 | catenin (cadherin-associated protein), alpha 1, 102 kDa |

The results of the micro array experiment showed that compound Y and YM(ACH-Y) inhibit gene expression of cadherins family in ES2 cells.

TABLE 9

Effects of Y and YM on tenascin-C expression in ES2 cells

| Probe Set ID | Y/D | YM/D | Gene.Symbol | Gene.Title |
|---|---|---|---|---|
| 201645_at | −3.2 | 1.0 | TNC | Tenascin C (hexabrachion) |

The results of the micro array experiment showed that compound Y inhibit gene expression of cadherins family in ES2 cells.

TABLE 10

Effects of Y and YM on heparin sulfate expression in ES2 cells

| Probe Set ID | Y/D | YM/D | Gene.Symbol | Gene.Title |
|---|---|---|---|---|
| 201655_s_at | −2.4 | −1.3 | HSPG2 | heparan sulfate proteoglycan 2 (perlecan) |
| 219403_s_at | −1.4 | −1.3 | HPSE | Heparanase |
| 203284_s_at | −1.3 | −1.7 | HS2ST1 | heparan sulfate 2-O-sulfotransferase 1 |

The results of the micro array experiment showed that compound Y inhibit gene expression of heparin sulfate family in ES2 cells.

TABLE 11

Effects of Y and YM on CD54 expression in ES2 cells

| Probe Set ID | Y/D | YM/D | Gene.Symbol | Gene.Title |
|---|---|---|---|---|
| 202638_s_at | 1.6 | 2.3 | ICAM1 | intercellular adhesion molecule 1 (CD54), human rhinovirus receptor |

The results of the micro array experiment showed that compound Y stimulate gene expression of CD54 in ES2 cells.

TABLE 12

Effects of Y and YM on angiopoietin expression in ES2 cells

| Probe Set ID | Y/D | YM/D | Gene.Symbol | Gene.Title |
|---|---|---|---|---|
| 205572_at | 3.5 | 1.4 | ANGPT2 | angiopoietin 2 |
| 211148_s_at | 2.5 | 1.4 | ANGPT2 | angiopoietin 2 |
| 205609_at | −1.1 | −1.2 | ANGPT1 | angiopoietin 1 |
| 221009_s_at | −1.2 | −1.4 | ANGPTL4 | angiopoietin-like 4 |
| 227533_at | −1.5 | −2.3 | ANGPTL1 | Angiopoietin-like 1 |

The results of the micro array experiment showed that compound Y and YM(ACH-Y) modulate the gene expression of angiopoietin family in ES2 cells. There is a up regulation of (positive regulating on) angiopoietin 2 and a down regulation of (negative regulating on) angiopoietin 1 and angiopoietin-like 1 and angiopoietin-like 4.

TABLE 13

Effects of Y and YM on Glypican expression in ES2 cells

| Probe Set ID | Y/D | Ym/D | Gene.Symbol | Gene.Title |
|---|---|---|---|---|
| 243865_x_at | −2.7 | −2.0 | GPC6 | Glypican 6 |
| 227059_at | −2.2 | −1.8 | GPC6 | Glypican 6 |

The results of the micro array experiment showed that compound Y and Ym inhibit gene expression of Glypican in ES2 cells.

TABLE 14

Effects of Y and YM on regulator of G-protein expression in ES2 cells

| Probe Set ID | Y/D | Ym/D | Gene.Symbol | Gene.Title |
|---|---|---|---|---|
| 204339_s_at | −3.5 | −1.2 | RGS4 | regulator of G-protein signalling 4 |
| 204337_at | −3.4 | −1.1 | RGS4 | regulator of G-protein signalling 4 |
| 204338_s_at | −2.5 | −1.1 | RGS4 | regulator of G-protein signalling 4 |

The results of the micro array experiment showed that compound Y and YM inhibit gene expression of G-protein in ES2 cells

TABLE 15

Effects of Y and YM on thrombospondin in ES2 cells

| Probe Set ID | Y/D | Ym/D | Gene.Symbol | Gene.Title |
|---|---|---|---|---|
| 201109_s_at | −2.0 | −6.2 | THBS1 | thrombospondin 1 |
| 201110_s_at | −1.8 | −4.5 | THBS1 | thrombospondin 1 |
| 201108_s_at | −1.7 | −2.2 | THBS1 | thrombospondin 1 |

The results of the micro array experiment showed that compound Y and YM inhibit gene expression of thrombospondin in ES2 cells

TABLE 16

Effects of Y and YM on insulin-like growth factor binding protein expression in ES2 cells

| Probe Set ID | Y/D | YM/D | Gene.Symbol | Gene.Title |
|---|---|---|---|---|
| 210095_s_at | −4.0 | −3.5 | IGFBP3 | insulin-like growth factor binding protein 3 |

TABLE 16-continued

Effects of Y and YM on insulin-like growth factor binding protein expression in ES2 cells

| Probe Set ID | Y/D | YM/D | Gene.Symbol | Gene.Title |
|---|---|---|---|---|
| 212143_s_at | −3.7 | −5.3 | IGFBP3 | insulin-like growth factor binding protein 3 |
| 201508_at | −1.7 | −2.4 | IGFBP4 | insulin-like growth factor binding protein 4 |
| 205302_at | −1.7 | −1.8 | IGFBP1 | insulin-like growth factor binding protein 1 |
| 201163_s_at | −1.4 | −2.7 | IGFBP7 | insulin-like growth factor binding protein 7 |
| 203851_at | −1.3 | −1.8 | IGFBP6 | insulin-like growth factor binding protein 6 |

The results of the micro array experiment showed that compound Y and YM inhibit gene expression of insulin-like growth factor binding protein in ES2 cells.

TABLE 17

Effects of Y and YM on RAB3B, member RAS oncogene family protein expression in ES2 cells

| ID | Y/D | YM/D | Gene.Symbol | Gene.Title |
|---|---|---|---|---|
| 242629_at | −3.5 | −1.8 | RAB3B | RAB3B, member RAS oncogene family |
| 205924_at | −1.7 | −1.8 | RAB3B | RAB3B, member RAS oncogene family |
| 227123_at | −1.6 | −1.2 | RAB3B | RAB3B, member RAS oncogene family |
| 205925_s_at | −1.2 | −1.2 | RAB3B | RAB3B, member RAS oncogene family |

The results of the micro array experiment showed that compound Y and Ym inhibit gene expression of RAB3B, member RAS oncogene family protein in ES2 cells.

TABLE 18

Effects of Y and YM on potassium channel, subfamily U, protein expression in ES2 cells

| ID | Y/D | YM/D | Gene.Symbol | Gene.Title |
|---|---|---|---|---|
| 237273_at | −4.0 | −1.9 | KCNU1 | potassium channel, subfamily U, member 1 |

The results of the micro array experiment showed that compound Y and Ym inhibit gene expression of family protein relate to potassium channel in ES2 cells.

TABLE 19

Effects of Y and YM on phosphatase, protein expression in ES2 cells

| | Y/D | YM/D | Gene.Symbol | Gene.Title |
|---|---|---|---|---|
| 37028_at | 2.4 | 5.6 | PPP1R15A | protein phosphatase 1, regulatory (inhibitor) subunit 15A |
| 202014_at | 2.6 | 6.2 | PPP1R15A | protein phosphatase 1, regulatory (inhibitor) subunit 15A |
| 215501_s_at | 3.2 | 7.1 | DUSP10 | dual specificity phosphatase 10 |
| 221563_at | 3.8 | 5.7 | DUSP10 | dual specificity phosphatase 10 |

The results of the micro array experiment showed that compound Y and Ym stimulate gene expression of family protein relate to phosphatase.

(Results of F1 and F3) In these experiments, we established and described the basic phenomenon that Y-treatment of ES2 cancer cells cause inhibition of fibronectin secretion. With a Western blot assay, we showed that ES2 cells without drug treatment (DMSO control) secret Fibronectin to medium and the amount of Fibronectin accumulated with time. However, no or only minimally secretion of Fibronectin was observed in cell culture treated with Xanifolia-Y. Inhibition of Fibronectin was observed as early as 8 hours after drug-treatment.

Inhibition of Fibronectin secretion is physiological and the determination of its quantity is based on the following criteria:

1. Fibronectin is secreted from viable cells. Only cell with over 85% viable cells after drug-treatment are employed in these experiments. The viable cells were determined by MTT assay.
2. For comparison, the immuno-band intensity from each samples are normalized with cell mass. The cell mass was determined by the MTT assay and is assigned as a MTT unit for each cell sample.

(Results of F4) Under a sub-lethal drug concentration (10 ug/ml Y), Over 95% of cells after 18 hours of Y-treatment was viable as determined by MTT assay. Western Blots show a reduction of Fibronectin secretion by cells into culture medium after Y-treatment. Scan of Fibronectin Western bands (average 6 pairs of blots) shows that there is a 40% reduction of Fibronectin secretion after 18 hours of Y-treatment.

(Results of F5) Similarly, 85% of cells after 24 hours of Y-treatment were viable as determined by the MTT assay. Western blot shows a reduction of Fibronectin bands of Y-treated samples. Based on 6 pairs of blots and after normalize them to MTT units, a 31% reduction of Fibronectin band intensity of Y-treated samples was observed. Accordingly, these results indicate that Fibronectin secretion by cells reduce 31% after 24 hours of Y-treatment.

(Results of F7) Effects of Paclitaxel on Fibronectin secretion by ES2 cells. To demonstrate that not all anticancer drugs can inhibit Fibronectin secretion from cells, we employed Paclitaxel, a well known anticancer drug that is effective for ovarian cancer. Our results showed that there is no inhibition of Fibronectin secretion with Paclitaxel treatment in ES2 cells (10 to 50 ng/ml, the IC50 of Paclitaxel is 1.5 ng/ml). This study also showed that Fibronectin secreted by ES2 cells reduced 30-40% after Y-treatment which agrees with previous results.

(Results of F8) In addition to ES2 cells, another human ovarian cancer cells (Hey8A) were employed in this study. It was found that Y-treated Hey8A cells secrete 31% Fibronectin as compared with the DMSO control, accordingly it has a inhibition of 69%.

Beside ovarian cancer, other human cancer cells were tested in the following experiments. These experiments show that the secretion of Fibronectin from cancer cells derived from lung, bladder, liver, brain and skin is inhibited by Xanifolia-Y treatment.

(F11) For lung carcinoma cells (H460), at concentration of 20 ug/ml, there are inhibitions of Fibronectin secretion ranged from 20-60%.

(F12A) For bladder carcinoma cells (HTB-9), Xanifolia-Y (10 ug/ml) inhibits 50% of Fibronectin secretion.

(F15) In liver HepG2 cells. 10 ug/ml of xanifolia-Y inhibits 42% secretion of Fibronectin.

(F16) Incubation of brain glioblastoma T98G cells with 10 ug/ml of xanifolia-Y inhibits 27% Fibronectin secretion and with 20 ug/ml Y inhibits 74% Fibronectin secretion.

(F17) For skin SK-Mel-5 cells, the inhibition is 40-57% with 20 ug/ml of Xanifolia-Y.

Studies of Xanifolia-Y Analogs and Other Saponin on Fibronectin Secretion from ES2 Cells.

(F 23) To study the inhibition effect with other saponins, we tested the compound O54, a triterpenoid saponin isolated from the same plant. With O54, there is no inhibition activity of Fibronectin secretion in ES2 cells, even at higher dose of 40 ug/ml (instead of the usual effective concentration of 10 ug/ml). This result indicates there is specificity in triterpenoid saponin that is responsible for the inhibition effect.

(F21) To research for functional groups that are effective for Fibronectin inhibition activity, we tested several derivatives of xanifolia-Y3. In these experiments, ES2 cells treated with ACH-Y (Y3 without sugars) and AKOH-Y (Y3 without the C21, C22 angeloyl group).

With 20 ug/ml Ach-Y, there is a reduction of Fibronectin secretion from ES2 cells (ranging from 53%-75% of the control). Inhibition of Fibronectin secretion was less (or not observed) when only 10 ug/ml Ach-Y was used. However, no effect was observed with AKOH even at 80 ug/ml.

(F 13) We also tested for inhibition activity with beta-Escin, a triterpenoid saponin with only one angeloyl group attached at C21.

The results show that 10 and 20 ug/ml of beta-Escin inhibit 7% and 48%, respectively, of Fibronectin secretion from ES2 cells. But 10 ug/ml of xanifolia-Y inhibits 49% Fibronectin secretion. Results indicate that beta-Escin also inhibits Fibronectin secretion but has half potency as xanifolia-Y.

(F14) (F24) We have determined the inhibition effect of different analogs of xanifolia-Y on ES2 cells. The results are shown in the following table.

| | ES2 cells | | | | | | | |
|---|---|---|---|---|---|---|---|---|
| | β-ES-10 | X-10 | Y0-10 | Y1-10 | Y3-10 | Y7-10 | ACH-Y-20 | AKOH-80 |
| % inhibition | 19 | 39 | 34 | 41 | 47 | 34 | 48 | No effect |

All samples (except AKOH) tested have effects of inhibition of Fibronectin secretion from ES2 cells. With 80 ug/ml of AKOH-Y which is 4 times higher concentration used in others saponins (10 ug/ml), it still has no effect on inhibition of Fibronectin secretion on ES2 cells.

In conclusion, saponins in general have effects in inhibition of Fibronectin secretion from ES2 cells. The fact that AKOH-Y (the Y3 without diangeloyl group) does not show any activity, indicating that acylation of C21, 22 positions is important for the inhibition activity.

| Studies of other saponins on Fibronectin secretion from ES2 and other cells | | | | | | |
|---|---|---|---|---|---|---|
| | ES2 cells | | | | | |
| | Mb12-10 | Mb5-10 | ACH-Mb5-10 | Ba1-10 | Ba4-10 | AKOH-Mb-40 |
| % inhibition | 30 | 35 | 30 | 30 | 28 | No effect |

| Liver | | | | | |
|---|---|---|---|---|---|
| HepG2 | Mb12-10 | Mb5-10 | ACH-Mb5-10 | Ba1-10 | Ba4-10 |
| % inhibition | 30 | 35 | 25 | 33 | 28 |

| Lung | | | | | |
|---|---|---|---|---|---|
| H460 | Mb12-10 | Mb5-10 | ACH-Mb5-10 | Ba1-10 | Ba4-10 |
| % inhibition | 20 | 25 | 22 | 19 | 18 |

| Bladder | | | | | |
|---|---|---|---|---|---|
| HTB-9 | Mb12-10 | Mb5-10 | ACH-Mb5-10 | Ba1-10 | Ba4-10 |
| % inhibition | 32 | 28 | 30 | 25 | 30 |

| Brain | | | | | |
|---|---|---|---|---|---|
| T98G | Mb12-10 | Mb5-10 | ACH-Mb5-10 | Ba1-10 | Ba4-10 |
| % inhibition | 40 | 33 | 35 | 26 | 24 |

| Skin | | | | | |
|---|---|---|---|---|---|
| SK-MEL-5 | Mb12-10 | Mb5-10 | ACH-Mb5-10 | Ba1-10 | Ba4-10 |
| % inhibition | 17 | 15 | 20 | 10 | 10 |

In addition to ES2 cells, other cancer cells derived from different organs were also investigated. Results are shown in following tables.

| (F25, 26, 31B) Liver | | | | | | |
|---|---|---|---|---|---|---|
| HepG2 | | | | | | |
| β-ES-10 | X-10 | Y0-10 | Y1-10 | Y3-10 | Y7-10 | ACH-Y-30 |
| % inhibition | | | | | | |
| 44 | 42 | 40 | 33 | 48 | 10 | 21 |

| (F27, 29) Lung | | | | | | |
|---|---|---|---|---|---|---|
| H460 | | | | | | |
| β-ES-20 | X-20 | Y0-10 | Y1-10 | Y3-10 | Y7-10 | ACH-Y-20 |
| % inhibition | | | | | | |
| No effect | 37 | 22 | 13 | 19 | 18 | 28 |

| (F28, 30) Bladder | | | | | | |
|---|---|---|---|---|---|---|
| HTB-9 | | | | | | |
| β-ES-10 | X-10 | Y0-10 | Y1-10 | Y3-10 | Y7-10 | ACH-Y-30 |
| % inhibition 47 | 38 | 32 | 50 | 51 | 60 | No effect |

| F 31, 32) Brain | | | | | | |
|---|---|---|---|---|---|---|
| T98G | | | | | | |
| β-ES-20 | X-20 | Y0-10 | Y1-10 | Y3-10 | Y7-10 | ACH-Y-20 |
| % inhibition 66 | 52 | 22 | 40 | 26 | 24 | 30 |

| (F 33) Skin | | | | | | |
|---|---|---|---|---|---|---|
| SK-MEL-5 | | | | | | |
| β-ES-20 | X-20 | Y0-10 | Y1-10 | Y3-10 | Y7-10 | ACH-Y-30 |
| % inhibition 17 | 15 | 27 | 10 | 11 | No effect | 21 |

(F20) Determination of cellular contents and secretion of Fibronectin after xanifolia-Y-treatment Results: This experiment shows that (1) there is a 46% reduction (54% of control) of Fibronectin secretion after xanifolia-Y-treatment and (2) the Fibronectin cellular content decrease 70% (30% of control) after the Y-treatment; (3) there is no change of the cellular beta-actin content in ES2 cells after the Y-treatment.

Up Regulation of Angiopoietin 2 (Ang2) in ES2 Cells with Xanifolia-Y Treatment.

Methods: ES2 (human ovarian carcinoma cells) were grew in RPMI 1640 medium. 4.5 million cells were seeded in a T75 flask and grown for 24 hours before drug-treatment.

Drug-treatment: Cells cultures were treated with 5, 10 and 15 ug/ml (final concentration) of Xanifolia-Y3 [Y3-5, Y3-10, Y3-15]. or DMSO control [D-10]. After 24 hours, cells were suspended in 1 ml of SDS sample buffer (cell-extract). Samples (80 ul/lane) were applied to 10% SDS gel and electrophoresis was conducted with 100 volts for 2 hours. Protein was transferred to a nitrocellulose membrane electrophoretically. The nitrocellulose blot was blocked with 5% non-fat dry milk in PBS. The blot was then incubated with the first antibodies (goat anti-Ang2, SIGMA A0851) and second antibody (donkey anti-goat AP conjugated, Promega V115A). The immuno-bands were developed with BCIP/NBT color development system (Promega S3771).

Results: As shown in FIG. 43, a Angiopoietin-2 immuno-band (M.W. 66K) was observed in cell extract from cells treated with 15 ug/ml Xanifolia-Y. No detectable or minimal immuno-band of Angiopoietin-2 was observed in control and low concentration of xanifolia-Y under these conditions. This results indicate that treatment of Xanifolia-Y in ES2 cells increase the cellular content of Angiopoietin-2. These results corroborate the results of Microarray studies.

This invention provides compositions and methods for modulating the gene expression in cancer cells, wherein the modulating comprises of positive and negative regulation, wherein genes being modulatated are adhesion proteins; wherein modulation includes expression, production and secretion of adhesion proteins, wherein the adhesion proteins comprise fibronectin, integrins family, Myosin, vitronectin, collagen, laminin, cadherin, heparin, tenascin, CD 54, CAM. This invention provides compositions and methods for modulating angiopoietins, wherein comprises positive regulating the angiopoietin 2, wherein comprises negative regulating angiopoietin 1. The composition and method of this invention comprises a triterpene wherein acylation group at carbon position 21 and/or 22 of the triterpene is necessary for the function and are selected from angeloyl, acetyl, alkanoyl, alkenoyl and acyl group. The sugar moiety (ies) at position 5 of the triterpene is important for enchancing activity of these compounds.

EXPERIMENTAL DETAILS

Experiment details of herb extraction, analysis of extract components by HPLC, determination of the cell-growth activity effected by Xanifolia Y with cells derived from different human organs using MTT Assay, purification of the bioactive components from plant extract, fractionation of plant extracts with FPLC, isolation of component Ys with preparative HPLC, determination of the chemical structure are disclosed in PCT/US05/31900, U.S. Ser. No. 11/289,142.

Experiment 1

Determination of the Hemolytic Activities of Compound Y from *Xanthoceras Sorbifolia*

Methods:
Human whole blood was obtained from the Houston Gulf Coast Blood Center.
Red blood cells were isolated by the following method: Human blood (in EDTA) was diluted 1:1 with PBS, underlay with 4 mL of Histopaque-1077 (SIGMA) and was centrifuged at 400 g for 30 min.
Red blood cells (RBC) were collected and washed three times with PBS.
10% suspensions of RBC were prepared with PBS before use.
50 µL of RBC suspension was added to 2 mL of saponins with different concentration.
The suspension was mixed by vortexing then left to sit at room temperature for 60 minutes.
The suspension was centrifuged at 3000 rpm for 5 min. Absorbance of the supernatant was measured at 540 nm.

Results:
In this experiment, hemolytic activities of human red blood cells by Xanifolia-Y (#63Y), Escin and SIGMA saponin standard were compared. Y contains two angeloyl groups, Escin has one angeloyl group and SIGMA saponin standard is a mixture of saponins from *Quillaia* bark. The results show that #63Y (compound Y) has higher hemolytic activity (IC50=1 µg/mL) than Escin or SIGMA saponin standard (IC50=5 µg/mL). See FIG. 5 A.

Experiment 2

Determination the Hemolytic and MTT Activities of Compound Y after Removal of the Angeloly Group or the Sugar Moiety by Alkaline or Acid Hydrolysis, Respectively Methods:
(A) Alkaline Hydrolysis of Xanifolia-Y: 20 mg of Xanifolia-Y was dissolved in 0.5 mL of 1M NaOH. The solution was incubated in an 80° C. water bath for 4 hours. It was cooled to room temperature before being neutralized with 0.5 mL 1 N HCl (adjusted pH to about 3). The mixture was extracted with 2 mL 1-butanol 3 times. The butanol fractions were collected and lyophilized. The hydrolyzed saponin was further purified with HPLC in a C-18 column eluted with 25% acetonitrile.

(B) Acid Hydrolysis of Xanifolia-Y: 15 mg Xanifolia-Y was dissolved in 1 mL of Methanol. 1 mL of 2N HCl was then added. The mixture was refluxed in an 80° C. water bath for 5 hours. The solution was then neutralized by adding 2 mL of 1N NaOH (to a final pH 3-4). The aglycone was then extracted with ethylacetate 3 mL×3. The extracts were collected and pooled. Further isolation of aglycone (sugar-removed Xanifolia-Y) was achieved by HPLC with isocratic elution of 80% acetonitrile.

Results:

The angeloly groups or the sugar moiety of the compound Y were removed by alkaline or acid hydrolysis respectively. The hemolytic activities of the hydrolysed products were then analyzed. Results of these studies indicate that removing sugars from the compound Y reduced hemolytic activity, but removing the angeloyl groups from the compound Y destroyed the hemolytic activity. It also suggested that sugars are helpful but not essential for hemolytic activity. See FIG. 3D. The experiment results show that compound-Y lost MTT activities if the angeloyl groups were removed. However, the MTT activities became very weak when the sugar moiety of the compound was removed. See FIG. 4 C, 4 D. Results of comparison of hemoyltic activities between Compound Y, Escin from SIGMA are shown in FIG. 6. Results of the comparison of hemolytic activities between compound Y, compound Y without sugar moiety or angeloly groups are shown in FIG. 5 A, 5B. Chemical structures of compound Y without sugar moiety (ACH-Y) or angeloly groups (AKOH-Y) are shown in FIG. 6 respectively.

Experiment 3

Effects of Xanifolia-Y on on Reduction of Venous Insufficiency, Particularly Hemorrhoids Methods:

SD rats, male, age-matched 7-8 weeks old weighing 163±18 g were in the experiment. The tested animals were allowed to acclimate for a week.

A cotton swab with a diameter of 4 mm soaked with 0.16 mL of inducer (deionized water:pyridine:ethyl ether:6% croton oil/ethyl ether, 1:4:5:10) was applied to the rat's anus for 12 seconds. The final concentration of croton oil was 3%. The edema developed linearly until 7-8 hours after application and the severity of the edema was sustained for more than 24 hours. Twenty-four hours later, recto-anus tissue (approx. 10 mm long) was isolated after the rats were euthanized. The weights of rat body and recto-anus were measured. The recto-anus coefficient (RAC) was calculated using the formula: weight of recto-anus (mg)/body weight (g).

RAC=weight of recto-anus (mg)/body weight (g)× 100%

The rates were randomly divided into 5 groups: control, positive control and 3 test groups, and each group had 8 rats. The dose for 3 groups of rats are 10, 20 and 40 mg/kg. The dose of 0.5% CMC-Na for control group is the same as the each test group. The tested drug was fed into the stomach on the morning, once a day before the animal modeling for 5 days. The anus suppository was applied to positive control once after the animal modeling (1 mL/100 g). The weights of recto-anus and RACs were calculated, compared with the controls and subject to a student t-test.

Results

The edema formed 30 minutes after the treatment. The rats were euthanized 22 hours after the last administration. The results showed that Xanifolia Y significantly reduced the swelling of the recto-anus of rats (Table A1).

TABLE A1

Effects of Xanifolia Y on reduction of swelling of the recto-anus of rats

| Group | Weight of recto-anus (g) | RAC | Reduction rate % |
|---|---|---|---|
| Modeling | 6.20 ± 0.77 | 2.33 ± 0.36 | |
| 10 mg/Kg | 4.68 ± 0.77* | 1.83 ± 0.36* | 21.5 |
| 20 mg/Kg | 4.28 ± 0.60** | 1.61 ± 0.24** | 30.9 |
| 40 mg/Kg | 3.97 ± 0.65** | 1.51 ± 0.23** | 35.1 |
| Anus suppository | 3.90 ± 0.80 | 1.54 ± 0.36 | 33.9 | n = 8, X ± SD, *p < 0.05, **p < 0.01

Experiment 4

Effects of Xanifolia Y on Reduction of the Swelling of Rats' Feet in the Carrageenin-induced Swollen Feet Model in Rats Method:

SD rats, male, weighing 163±18 g were used in the experiment. The tested animals are allowed to acclimate for a week. The rats drink water freely. The rats were randomly divided into 5 groups: control, positive control and 3 test groups, and each group had 8 rats. The dose for 3 groups of rats are 10, 20 and 40 mg/kg. Indometacin for the positive control is 10 mg/kg and fed once after modeling. The dose of CMC-Na for the control group is the same as each test group and fed into the stomach once a day before modeling for 5 days. The tested drug was fed into the stomach 10 minutes before the animal modeling (1 mL/100 g). The volumes of right foot of each rat were measured 0.5, 1, 2 and 4 hours before and after modeling. The volumes of the right hind feet were measured at a different time, 10 minutes after inflammation induced by subcutaneous injection (with syringe needle 7) of 0.05 mL of the 1% of Carrageenin/normal saline mixture into the feet. The Rate of swelling of the feet was calculated, compared with the controls and subject to a student t-test.

Rate of swelling $(E)$ (%)=$L_{tn}-L_{t0}/L_{t0}\times 100\%$ $L_{tn}$: volume of foot after the inflammation $L_{t0}$: volume of foot before the inflammation Results:

The results of this experiment showed Xanifolia Y significantly reduced swelling of the feet and the effect was related to the dosages. (Table A2).

TABLE A2

Effects of Xanifolia Y on reduction of swelling of rats' feet induced by Carrageenin

| Group | Dosage (mg/kg) | Swelling rate after administration (%) | | | |
|---|---|---|---|---|---|
| | | 0.5 hour | 1 hour | 2 hours | 4 hours |
| Modeling | | 22.6 ± 8.1 | 27.6 ± 8.2 | 23.0 ± 10.1 | 12.9 ± 6.1 |
| Test | 10 | 16.7 ± 3.8 | 18.5 ± 6.2 | 16.0 ± 5.9 | 10.5 ± 7.2 |
| Test | 20 | 10.5 ± 4.1** | 13.6 ± 4.2** | 12.4 ± 5.3* | 8.5 ± 5.4 |
| Test | 40 | 10.3 ± 3.3** | 12.6 ± 4.7** | 12.5 ± 6.2* | 6.5 ± 5.4 |
| Indometacin | 10.0 | 11.8 ± 4.3** | 14.7 ± 6.5* | 12.8 ± 7.0** | 10.7 ± 8.8 | n = 8, X ± SD, *p < 0.05, **p < 0.01 Student-t

Experiment 5

Purification of the Inhibition Components in the *Xanthoceras Sorbifolia* Extract (A) Fractionation of Plant Extracts with FPLC
Methods
Column. Octadecyl functionalized silica gel. Column dimension: 2 cm×28 cm; equilibrated with 10% acetonitrile—0.005% TFA before use.
Sample loading: 1-2 ml, concentration: 100 mg/ml in 10% acetonitrile/TFA.
Gradient elution condition: 10-80% acetonitrile in a total volume of 500 ml.
Monitor absorption wavelength: at 254 nm.
Fraction Collector: 5 ml/fractions (collect from 10% to 72% acetonitrile)
Instrument: AKTA-FPLC, P920 pump; Monitor UPC-900; Frac-900.
Results
The elution profile of the chromatography shows 4-5 broad fractions. These fractions were analyzed with HPLC. Specific components, corresponding to a-z in these FPLC fractions. FPLC fractions are then grouped into 7 pools and analyzed for cell growth activity with MTT assay. The fractions contain inhibition activity can be found. (See PCT/US05/31900, filed Sep. 7, 2006; U.S. Ser. No. 10/906, 303, filed Feb. 14, 2005; International Application No. PCT/US04/43465, filed Dec. 23, 2004; International Application No. PCT/US04/33359, filed Oct. 8, 2004 and U.S. Ser. No. 11/131,551, filed May 17, 2005, the contents of which are incorporated herein by reference).
(B) Isolation of Component Ys with Preparative HPLC
Methods
Column: A preparative HPLC column (Waters Delta Pak C18-300A);
Elution conditions: 45% acetonitrile isocratic elution with flow rate of 1 ml/min.
Fractions are monitored at 207 nm and were collected and lyophilized.
Results
Final separation of Y fractions was achieved by HPLC with a preparative column. These fractions, which include compound Y0, Y1, Y2, Y or Y3 and Y4, were collected. Re-chromatography of compound Y showed a single peak in HPLC with a C18 reverse phase column. Re-chromatography of the compound Y8, Y9 and Y10 showed a single peak in HPLC with a C18 reverse phase column.

(C) Appearance and Solubility
The pure compound Ys is an amorphous white powder, soluble in aqueous alcohol, i.e., methanol or ethanol, 50% acetonitrile and 100% pyridine.
(D) Inhibition Analysis of Compound Ys with MTT Assay
Inhibition analysis of compound Y was determined with MTT assay. FIG. 4A shows the inhibition activities of compound Y, Y8, Y9 and Y10 on the growth of ovarian cancer cells (OCAR-3). FIG. 22 shows the inhibition activities of compound Y(Y3), Y0, Y1 and Y2 on the growth of ovarian cancer cells (OCAR-3)

Experiment 6

Determination of the Chemical Structure

Methods
NMR analysis. The pure compound Y of *Xanthoceras sorbifolia* was dissolved in pyridine-D5 with 0.05% v/v TMS. All NMR spectra were acquired using a Bruker Avance 600 MHz NMR spectrometer with a QXI probe (1H/13C/15N/31P) at 298 K. The numbers of scans for 1D 1H spectra were 16 to 128, depending on the sample concentration. 2D HMQC spectra were recorded with spectral widths of 6000×24,000 Hz and data points of 2024×256 for t2 and t1 dimensions, respectively. The number of scans was 4 to 128. 2D HMBC were acquired with spectral widths of 6000×30,000 Hz and data points of 2024×512 for t2 and t1 dimensions, respectively. The number of scans was 64. The 2D data were zero-filled in t1 dimension to double the data points, multiplied by cosine-square-bell window functions in both t1 and t2 dimensions, and Fourier-transformed using software XWIN-NMR. The final real matrix sizes of these 2D spectra are 2048×256 and 2048×512 data points (F2×F1) for HMQC and HMBC, respectively.

Mass spectral analysis. The mass of samples was analyzed by (A) MALDI-TOF Mass Spectrometry and by (B) ESI-MS Mass spectrometry. (A) Samples for MALDI-TOF were first dissolved in acetonitrile, and then mixed with the matrix CHCA, i.e., Alpha-cyano-4-hydroxycinnamic acid, 10 mg CHCA/mL in 50:50 water/acetonitrile and 0.1% TFA in final concentration. The molecular weight was determined by the high resolution mass spectroscope analysis with standards. (B) For ESI, the sample was analyzed with LCQ DECA XP Plus machine made by Thermo Finnigan. It is ionized with ESI source and the solvent for the compound is acetonitrile.

Results

The profile of the proton NMR is presented in (application Ser. No. 11/683,198, US20070161580, filed Mar. 7, 2007) FIGS. 8A, 8B, 9A, 9B, 10A, 10B and. The NMR profiles of 1H, 13C, TOCSY, HMQC, HMBC and NOESY are shown respectively. FIG. 11 shows the MS of Y0. Based on these data and analysis, the structure of compound Y0 is assigned as shown below.

Structure of Compound Y0

This invention provides a bioactive compound Y0 and the chemical name is:

3-O-[β-D-galactopyranosyl(1→2)]-α-L-arabinofuranosyl (1→3)-β-D-glucuronopyranosyl-21-O-angeloyl, 22-O-(2-methylpropanoyl)-3β, 15α, 16α, 21β, 22α, 28-hexahydroxyolean-12-ene,

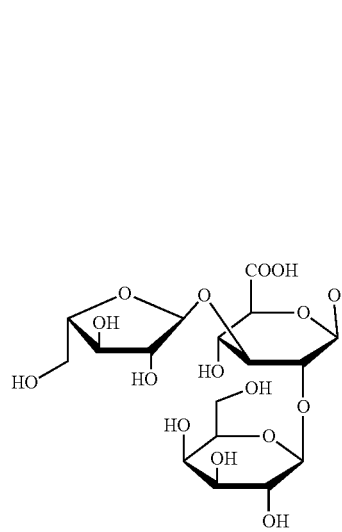
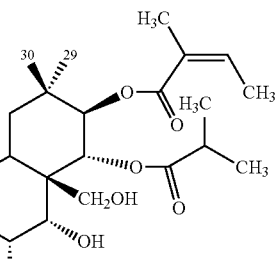

Experiment 7

Animal Study

Methods
Athymic Nu/Nu mice are divided into three groups (A, B and C) with four animals in each group.
On day 0, mice of group A and B were transplanted intra-peritoneally with ES2 (human ovarian cancer) cells.
On day 1, mice from B and C groups received drug (Xanifolia-Y, by i.p. route at dose of 5 mg/kg)
On days 2 to 4, and 7 to 11, B and C groups animals received daily drug administration of Xanifolia-Y, by i.p. route at dose of 2.5 mg/kg.
Group A mice have no drug-treatment.
Results:
Group A Mice—Died on day 19-22
Group B Mice—Survived over 50 days
Group C Mice—Survived over 50 days
Also See FIG. 23

Experiment 8

Animal Study

Methods
Athymic Nu/Nu mice were divided into three groups (A, D and E) with four animals in each group.
On day 0, all mice were transplanted intra-peritoneally with ES2 (human ovarian cancer) cells.
Group A mice received no drug-treatment.
Group D: From day 4, mice received a daily drug administration of Xanifolia-Y, via i.p. route for 9 days at dose of 2.5 mg/kg.
Group E: From day 10, mice received daily drug administration of Xanifolia-Y, via i.p. route for 10 days at dose of 2.5 mg/kg.
Result:
Group A, Mice implanted with tumor and no drug. All died within 24 days
Group D, Mice implanted with tumor and were given drug 9 times from 4th day. All survived
Group E Mice implanted with tumor and were given drug 10 times from 10th day. Half the number of mice survived
Also See FIG. 24

Experiment 9

Animal Study

Athymic Nu/Nu mice (2-3 months old) were transplanted sc with ES2 (human ovarian cancer) cells.
Five days after the transplant (day one), mice were divided into two groups (H and J) with two animals in each group.
Group H: On days 1-5, and 8-10 mice received daily drug administration of Xanifolia-Y, by i.p. route at dose of 2.5 mg/kg.
Group J mice received no drug-treatment.
Result:
Group H: Mice received drug-treatment, tumor size is 10 mm in 10 days
Group J: Mice received no drug-treatment, tumor size is 18 mm in 10 days
The tumor size is 45% smaller in mice with drug than the mice with no drug in 10 days period.
See FIG. 25

Experiment 10

Animal Study

Methods
Athymic Nu/Nu mice (5-6 weeks old) are divided into three groups (0, P and Q) with 5-6 animals in each group.
On day 0, all mice were transplanted intra-peritoneally with ES2 (human ovarian cancer) cells.
Group O: animals received no drug-treatment.
Group P: On days 4-8, 11-15, 18-22, 25-29, 32-36, 39-43, animals received daily drug administration of Xanifolia-Y, by i.p. route at dosage of 2.5 mg/kg
Group Q: On days 10-15, 18-22, 25-29, 32-36, 39-43, animals received daily drug administration of Xanifolia-Y, by i.p. route at dosage of 2.5 mg/kg.

The median survival time of tumor bearing mice with drug-treatment starting on day 4 after tumor inoculation is 58 days (extension of life span of 141%); and The median survival time of tumor bearing mice with drug-treatment started on day 10 after tumor inoculation is 31 days (extension of life span of 29%).

See FIG. 30

Experiment 11

Studies of Effect on Human Ovarian Cancer Cell Lines

Since we found that ovarian carcinoma cell lines are among the sensitive cells studied, we further investigated if other ovarian carcinoma cell lines are also susceptible to Xanifolia-Y.

Majority of ovarian cancers arise from the surface epithelium of ovary, most of them belong to the histological subtypes of clear cell and serous carcinoma. We obtained 10 more human ovarian carcinoma cell-lines of these histological subtypes for these studies. The inhibition activity exerted by Xanifolia-Y was determined with MTT assay. The following table shows the IC50 values of Xanifolia-Y on these cell lines.

Results:

TABLE B2

IC50 values of human ovarian carcinoma determined by MTT assay.

| Cell lines | Types | IC50 (uM) |
| --- | --- | --- |
| OVCAR3 | Serous | 2.2 |
| TOV-21G | Clear cell | 2.2 |
| ES2 | Clear cell | 4.4 |
| RMG2 | Clear cell | 8.8 |
| OVCA 429 | Serous | 7 |
| OVCA 432 | Serous | 4.4 |
| OVCA 433 | Serous | 8.8 |
| Caov 3 | Serous | 7 |
| SKOV 3 | Serous | 10.5 |
| Hey 8A | Serous | 10.5 |

The IC50 values of Xanifolia-Y in these cell-lines are ranging from 2 to 10 uM. These studies show that the effective concentration of Xanifolia-Y is in the micro-molar range which is comparable to those of other anti-cancer drugs.

Experiment 12

Study Apoptosis Induced by Xanifolia-Y

Experiment of apoptosis of OVCAR3 cells after treatment with Xanifolia-Y was assessed with flow cytometry of GFP-Annexin-V and propidium iodide.

Results were shown in FIG. 33 which indicates that induction of the early apoptosis (the lower right quadrant) and late a poptotic/necrosis (the upper right quadrant) were found in cells 24 h after exposure to Xanifolia-Y. By comparing the distribution of apoptotic/necrotic cells after the drug-treatment, a higher number of early apoptotic cells were observed as compare to those of the late apoptotic/necrosis cells. These results indicate that apoptosis is a major form of cell death induced by Xanifolia-Y.

See FIG. 26.

Experiment 13

Effect of Xanifolia-Y on Membrane Structure (EM Studies)

Xanifolia-Y has a potent hemolytic activity in red blood cells (FIG. 27). To study the effect of Xanifolia-Y on membrane structure, the morphology of cell membrane treated with Xanifolia-Y was examined with EM. In this experiment, K562 cells were treated with 5 uM of Xanifolia-Y for 60 min. Solvent DMSO and AKOH-Y (a derivative of Xanifolia-Y without the angeloyl group and it has no activity) served as controls. Cells were negative stained with 1% UAc and subsequently examined with EM.

FIG. 27 show that patches of pits were found in the membrane of Xanifolia-Y treated cells (FIG. 27B) but not in cells treated with the DMSO (FIG. 27A) or AKOH-Y (FIG. 27C) controls. These pits have the size from 80 A to 500 A (in diameter). The pits represent holes formed in the membrane. The pits are arranged in a characteristic pattern with smaller pits (80 A in diameter) located in the periphery and the bigger ones (500 A in diameter) in the center. The bigger holes are resulted from fusing of the smaller holes (FIG. 27D).

Membrane image of cells treated with A: DMSO solvent control, 60 min (magnification: ×60,000); B: Xanifolia-Y 5 uM, 60 min. (×60000); C: AKOH-Y, 20 uM, 60 min. (×60000); D: Xanifolia-Y 5 uM, 60 min. (×20000)

This experiments results show that the Xanifolia-Y alters the membrane of cell.

See FIG. 27

Experiment 14

Inhibition of Cell Adhesion by Xanifolia-Y

Methods and Results. ES2 or Hey8A cells were plated in T25 flasks with medium containing 5 ug/ml of Xanifolia-Y. Cultures were incubated for 5 hours. Attached cells were removed from flasks by trypsinization and the amounts were counted. Compare to no drug controls, 86±4% of ES2 cells and 67±8% of Hey8A cells were found attached to flasks under this condition. At 5 ug/ml Xanifolia-Y, over 90% of unattached cells are alive as determined by the trypan Blue exclusion assay and by their ability to re-attach to flasks when plating in medium without Xanifolia-Y. However, with 10 ug/ml Xanifolia-Y, less than 40% of cells attached to flasks and many of them are dead cells. This experiment shows that Xanifolia-Y inhibits cells adhesion process.

Experiment 15

Combined Inhibition Effect of Xanifolia-Y and Paclitaxel

Methods: ES2 cells were exposed to (i) Xanifolia-Y with concentrations of 40, 20, 10, 5, 2.5, and 1.25 ug/ml; or (ii) Paclitaxel with concentrations of 10, 5, 2.5, 1.25, 0.62 and 0.031 ng/ml; or (iii) Combined Xanifolia-Y and Paclitaxel with concentrations of each drug in same order (for example, 40 ug/ml Y plus 10 ng/ml T; 20 ug/ml Y plus 5 ng/ml T, etc. please see FIG. 28). Cells growth under these conditions was determined by the MTT assay.

Results: As shown in FIG. 28, The 1050 for Xanifolia-Y and Paclitaxel, is 5 ug/ml and 1.25 ng/ml, respectively.

Additive effect was observed when both drugs were used, because in this case, the 1050 value for Paclitaxel (0.625 ng/ml) and for Xanifolia-Y (2.5 ug/ml) is less than those when they are used singly.

See FIG. 28.

Experiment 16

Identify the Binding Target of Xanifolia-Y of Adhesion Proteins and Signaling Proteins in Ovarian Cancer Cells In our animal studies, it was shown that Xanifolia-Y extended the life span of tumor bearing mice (FIGS. 23 and 24). The animals died sooner if the treatment of Xanifolia-Y was delayed (comparing results of treatments started from 1, 4 or 10 days after tumor inoculation). The results show that Xanifolia-Y inhibits migration or metastasis of the inoculated cancer cells. Ovarian carcinoma cells express high levels of adhesion molecules. Adhesion proteins are present in both cancer cells and mesothelial cells. While the lost of adhesion is blocking of the protein accessibility due to direct binding to Xanifolia-Y, the interaction of Xanifolia-Y with membrane alter indirectly the adhesion protein's binding site(s).

A. We label Xanifolia-Y and use it as ligand to find the target molecules bind to it. Xanifolia-Y has carbohydrates (Galactose, arabinose and glucoronic acids). These carbohydrates can be $^3$H-labeled with peridodate-tritiated Borohydride (Cahmberg and Andersson, 1977). For the control, the non-reactive derivative of Xanifolia-Y (AKOH-Y) also is labeled. Labeled Xanifolia-Y is purified by HPLC and verified that it retains activity before use. Our studies indicate that the carbohydrates of Xanifolia-Y do not contribute a major role in its activity. Therefore, $^3$H-labeling of carbohydrate in Xanifolia-Y should not affect its activity.

B. We employ the following methods to study the direct binding between the labeled Xanifolia-Y and its target.

I. Detect binding of Xanifolia-Y on cell surface (by autoradiography): This autoradiographic method employs labeled Xanifolia-Y adding to culture cells (K562 suspension cells, or ES2 monolayer cells) and determine cells pick up label on cells surface. Cells are incubated in medium with labeled Xanifolia-Y with a concentration equal to the IC50 value (e.g. 4.4 ug/ml for ES2 cells). At this concentration, cells are alive. After incubation (30 min to 1 hour), cells are washed, fixed, dried and emulsified. Radioactive Xanifolia-Y is detected with autoradiography and microscopic analysis. Radioactive AKOH-Y (not active) serves as a negative control. This experiment shows that Xanifolia-Y binds to membrane.

II. Determine binding between selected protein and Xanifolia-Y by RIA: This experiment determines the known adhesion proteins bind to Xanifolia-Y. Binding of Xanifolia-Y to known purified adhesion proteins (or other signaling proteins) can be determined with RIA (Radio-Immuno Assay). Antibodies of many of these adhesion proteins (and protein itself) are available and can be employed in RIA assay. Binding of radioactive Xanifolia-Y (which compete with non-radioactive Xanifolia-Y) with specific protein is immuno-precipitated by specific antibodies. Affinity binding constant for these known proteins is determined by this method.

III. Immuno-precipitation (IP) analysis: Xanifolia-Y binds to molecules that associated with adhesion proteins. Many of known signaling proteins or adhesion protein form complex (spheroids). Spheroids are immuno-precipitated with the specific antibody to one of the adhesion protein. Cells are cultured with radioactive Xanifolia-Y. Membrane proteins or spheroids are isolated. Alternatively, isolated spheroids from cells are incubated with radioactive Xanifolia-Y in a cell-free system. Co-IP of the radioactive Xanifolia-Y in the spheroid indicates its association of Xanifolia-Y-binding protein. After the spheroid is identified, the contents of the spheroid are analyzed with biochemical methods, such as 2D gel electrophoresis.

IV. Purification and identification of Xanifolia-Y-binding protein: We employ the radioactive Xanifolia-Y as a tracer to identify and purify its target. The effective concentration for Xanifolia-Y in vitro assay is in the micro-molar range, suggesting that the binding to its target is relatively tight (or with high affinity). Therefore, it does able to detect its binding target in cell-free system. Membrane is isolated and proteins will be fractionated with ion-exchanger and gel filtration chromatography. Fractions from chromatography will be analyzed (by radioactive counting) for their association of Xanifolia-Y. Alternatively, proteins isolated from cancer cells or the membrane fraction are separated by 2D gel, blot the proteins in NC membrane and incubate with radioactive labeled Xanifolia-Y and determine the target protein that pick up radioactive Xanifolia-Y (tagged by the labeled-Xanifolia-Y). The tagged target is detected by autoradiography (beta-imager). The identity of protein is determined by Peptide Mapping and MALDI-TOF technique.

Our compounds interacting with target protein comprise integrins family, CD44, fibronectin, Myosin VI, collagen, laminin, Glycosylation cell surface proteins, polyglycans and FAK Adhesive molecules play an important role in migration and metastasis of ovarian cancer (Skubitz, 2002, Schaller, 1996; Zetter, 1993). A major route for the spread of ovarian cancer is by the attachment of tumor cells to the mesothelium lining in the peritoneal cavity (Gardner et al., 1995). For example, serous ovarian cancer cells invade through their membrane and released proteolytic enzymes or EMC molecules for attachment to mesothelial cells (Skubitz, 2002).

The integrins family and CD44—These proteins are detected on all mesothelial cells and ovarian cancer cells and play an important role in tumor/mesothelial interaction (Gardner et al., 1995).

Ovarian carcinoma cells form multicellular spheroids, in the peritoneal cavity of patients with advanced disease (Burleson et al., 2004). It was shown that adhesive proteins in ovarian carcinoma multicellular spheroids were involved in the adhesion process (Casey et al., 2001). The adhesive proteins are: integrins, CD44 and fibronectin.

Myosin VI, a motor protein that regulates border cell migration, is abundantly expressed in high-grade ovarian carcinomas including ES2 cells. Yoshida et al., (2004) reported that inhibition of myosin VI expression in ES2 cells impeded ovarian cells spreading and migration.

Casey et al., (2003) reported that Glycosylation cell surface proteins and polyglycans mediate the adhesion, migration and invasion of ovarian carcinoma cells. The major ligand for CD44 is the extra-cellular matrix glycosaminoglycan and hyaluronic acid (HA). Mesothelial cells contain large amount of HA (Catterall et al., 1997). These surface proteins also include: fibronectin, collagen and laminin.

FAK (focal-adhesion-associated kinase). FAK is a protein tyrosine kinase which involves in the regulation of cell cycle progression, cell survival and cell migration (Schaller, 2001). It was reported that FAK promote cell motility and invasion of ovarian cancer through distinct signaling pathway (Hsia et al., 2003). The role of integrins for adhesion is to activate intracellular signaling pathways (Schaller and Parsons, 1993). One of the affected kinase is (FAK). FAK expression inhibited by Xanifolia-Y-treatment.

Experiment 17

The Effect of Xanifolia-Y in Preventing Nodule Formation in Peritoneal Cavity

This experiment shows Xanifolia-Y blocks migration, invasion or growth of ovarian cancer in peritoneal cavity.

Our animal experiments indicate that the life span of the tumor bearing mice is extended after the Xanifolia-Y-treatment. The results show that a sooner treatment provides a better protection. The results show that Xanifolia-Y inhibits tumor cell's growth and reduce their attachments to mesothelium linings. We use Hey8A cells inoculated in peritoneal cavity produce tumor nodules (solid tumor mass) and the numbers of nodules increase during the tumor progression (Lander Jr., et al., 2005). The numbers of tumor nodules are determined by laparotomy. The growth of nodules (number and mass) before and after Xanifolia-Y-treatment is determined. The results show that Xanifolia-Y inhibits the growth number of nodule; and inhibits tumor growth after the Xanifolia-Y-treatment.

(A) Animal Model: Hey8A Cells are Inoculated into Peritoneal Cavity.

The relationship between the nodule formation and timelines during tumor progression are established. Usually, 4 to 6 nodules are formed during the entire period of tumor progression in this system (Lander Jr., et al., 2005). We start the drug-treatment at times equivalent to 20% and 50% of full tumor progression. At these times, the number of nodule is less and the size (weight) of the nodules is smaller. At the end of the drug-treatment, animals are euthanized and number of tumor nodules is determined and the tumor size (mass) is weighted.

Animals: 40 nu/nu mice are used per experiment.

2 groups of mice (20 each) (i) Drug-treatment start at time equivalent to 20% of full tumor progression (or on 4 days after tumor inoculation) (ii) Drug-treatment starts at time equivalent to 50% of full tumor progression (or on 10 days after tumor inoculation). On the day of starting drug-treatment, half of the animals (10) will be scarified and the number and weight of nodules will measured.

Drug-Treatments: Animals are administered daily for 5 days per week for two—three weeks. Dose: 0.25 mg/kg, through i.p. route.

Result: The numbers of tumor nodules are less in mice with drug treatment compare to mice without drug treatment. The size of tumor in drug treatment mice is smaller than tumor in no-drug treatment mice.

(B) Animal Model: ES2 Cells are Inoculated into Peritoneal Cavity.

The relationship between the nodule formation and timelines during tumor progression are established. Usually, 4 to 6 nodules are formed during the entire period of tumor progression in this system (Lander Jr., et al., 2005). We start the drug-treatment at times equivalent to 20% and 50% of full tumor progression. At these times, the number of nodule is less and the size (weight) of the nodules is smaller. At the end of the drug-treatment, animals are euthanized and number of tumor nodules is determined and the tumor size (mass) is weighted.

Animals: 40 nu/nu mice are used per experiment.

2 groups of mice (20 each) (i) Drug-treatment start at time equivalent to 20% of full tumor progression (or on 4 days after tumor inoculation) (ii) Drug-treatment starts at time equivalent to 50% of full tumor progression (or on 10 days after tumor inoculation). On the day of starting drug-treatment, half of the animals (10) will be scarified and the number and weight of nodules will measured.

Drug-Treatments: Animals are administered daily for 5 days per week for two—three weeks. Dose: 0.25 mg/kg, through i.p. route.

Result: The numbers of tumor nodules are less in mice with drug treatment compare to mice without drug treatment. The size of tumor in drug treatment mice is smaller than tumor in no-drug treatment mice.

We use two histological types of human ovarian cancer ES2 and Hey8A. These two are most common ovarian cancer types: clear cells carcinoma (ES2) and serous carcinoma (Hey8A). Hey and ES2 show high expression of integrins and other adhesion proteins (Ahmed et al., 2005).

Ovarian cancer cells that are resistant to drugs are chosen in this study. ES2 cells express low levels of P-glycoprotein and have multi-drug chemotherapy resistant character (resistant to doxorubicin, cisplatin, carmustine, etoposide and cyanomorpholinodoxorubicin).

Experiment 18

Determination of Aquaporin in HeLa and OVCAR3 Cells

Methods:
1. Hela or OVCAR3 cells were cultured in RPMI 1640 medium at 37 C in an incubator with 5% CO2.
2. Cells were harvested, washed with PBS.
3. Cellular protein was dissolved in SDS sample buffer with protease inhibitors (PMSF and Leupeptin) and was incubated at 70 C for 20 min before use.
4. Equal amounts of protein from Hela or OVCAR3 cells were separated with 12% SDS gel and subsequently blotted on nitrocellulose paper.
5. Western blot was performed with anti-AQ1 antibody (Chemicon/SIGMA) and second antibody which was conjugated with Alkaline phosphatase.

Results:

The following figure shows the results of Western blot.

Aquaporin-1 (indicated with an arrow) was observed in OVCAR3 cells but was minimally detected in HeLa cells.

Based on same amounts of protein loading into gel, it was found that OVCAR3 cells have higher concentration of Aquaporin-1 than in Hela cells.

Since OVCAR3 cells are more sensitive to Xanifolia-Y and it has a higher concentration of Aquaporin-1, these results show Xanifolia-Y is potent to inhibit the cancer cell growth wherein the Aquaporin is overexpressed.

See FIG. 31

Experiment 19

Analysis of Gene Expression of ES2 Cells after Y-Treatment by Microarray

In this invention, the microarray experiments were done in studying the gene expression. Total number of 54676 genes has been studied.

Cell culture and drug-treatment.: ES2 cells were seeded in a T-25 flask with 4.5 million cells per flask for 24 hours. Cell culture was replaced with fresh medium with xanifolia-Y (Y) or DMSO no drug control (D) for 24 hours. Cells were then harvested for RNA isolation. Three experiments were done.

RNA extraction, labeling, hybridization, and data analysis. RNA was extracted from tumor cells using the Qiagen RNeasy Kit. RNA quality and quantity was checked by the Agilent BioAnalyzer and the NanoDrop® ND-1000 spectrophotometer respectively before further manipulation. The first and second cDNA strands were synthesized from 20 ng of total RNA using the Affymetrix T7 oligo(dT) primer protocol and kit for the two-cycle amplification. To produce amplified biotin-labeled-cRNA, the cDNA was reverse transcribed by in vitro transcription using the MegaScript kit from Ambion. 15.0 µg of the labeled cRNA was fragmented and re-checked for concentration using the NanoDrop® ND-1000 spectrophotometer. A hybridization cocktail containing Affymetrix spike-in controls and fragmented labeled cRNA was loaded onto the Human U133 Plus 2.0 GeneChip® oligonucleotide array. The Affymetrix array (Affymetrix, Inc. Santa Clara, Calif.) is comprised of over 1,300,000 unique oligonucleotide features that represent greater than 38,500 well-substantiated human genes. The array was hybridized for 16 hours at 45° C. with rotation at 60 rpm then washed and stained with a strepavidin, R-phycoerythrin conjugate stain on the Affymetrix Fluidicis Station 450. Signal amplification was done using biotinylated antistreptavidin. The arrays were scanned using the GeneChip® 3000 confocal laser scanner with autoloader. The images were analyzed and quality control metrics recorded using Affymetrix GCOS software version 1.4. Lastly, the expression value for each gene was calculated using dChip PM-only model based or Plier algorithm.

Data Analysis Methods

Pairwise comparisons were made as follows: Treated vs. Control (Y vs. D), Modified Drug vs Control (YM/ACY-H vs. D) and Treated vs. Modified Drug (Y vs. YM/ACH-Y) Cel files analyzed using the Bioconductor package of R Statistical programming. Limma analysis generated a reasonable number of changing genes between the samples.

The raw data in the .CEL files were normalized by the GCRMA method (robust multi-array analysis). It is implemented in Bioconductor (http://www.bioconductor.org/). The raw signal intensity data were normalized, background corrected and summarized based on certain statistical models, and an expression value, in log 2-scale, is obtained per chip per probe set. Then the null hypothesis was tested that there's no significant changes in gene expression between the treatment pairs. This was done by LIMMA and is also implemented in Bioconductor. It uses empirical Bayes method to estimate the variance in gene expression. One comparison was made, namely, High Grade vs. Low Grade. The raw p-values were adjusted by the Benjamnin-Hochberg method for false discovery rate (FDR) control. All data sets contained a significant number of genes with a p-value less than 0.05, which is that the probability that a gene is NOT differential expressed (false positive) is 1:20.

All expression data is filtered by p-value (0.05).

The raw p-values were adjusted by the Benjamnin-Hochberg method for false discovery rate (FDR) control to yield an adjusted p-value.

Results: Please see Table 1 to 12

Inhibition of Fibronectin Secretion by Xanifolia-Y (Western Blot)

Experiment 20 (F1)

Methods

Cells: ES2 cells were grew in T-25 flask with RPMI 1640 medium over night before drug-treatment. Drug-treatment: cells cultures were replaced with fresh RPMI medium with Xanifolia-Y (10 ug/ml final concentration) or DMSO (as control) at 0 hour. At 1, 2, 4, 8 and 24 hour, aliquot of culture medium was taken out for Fibronectin determination. Fibronectin was determined by Western blot with monoclonal antibody (SIGMA) specific to human Fibronectin only.

Results (also see FIG. 39):
1. Cells treated with DMSO (as no drug control) secret Fibronectin to medium and the amount of Fibronectin accumulated with time. There is no or only minimally secretion of Fibronectin observed in cell culture treated with Xanifolia-Y.
2. For controls, Fibronectin immunoband was not observed in RPMI medium with fetal bovine serum, or employing the normal mouse serum (NS1).

Experiment 21(F3)

Methods:

Cells: ES2 cells were grew in RPMI 1640 medium over night before drug-treatment.

Drug-treatment: cells cultures were replaced with fresh RPMI medium containing Xanifolia-Y (10 ug/ml final concentration) or DMSO (as control) at 0 hour. At 4 hours (A) or 8 hour (B), culture medium was replaced with fresh culture medium without drug. At 2, 4, 8 and 24 hour, aliquot of culture medium was taken out for Fibronectin determination. Fibronectin (FN) was determined by Western blot with monoclonal antibody (SIGMA) specific only to human Fibronectin.

Results (also see FIG. 40):

(1) Compare the control and Y-treated cells before drug removal (at 4 and 8 hours), there is a reduction of FN secretion from Y-treated cells. There is no obvious cell morphology change during these times, suggesting cells are alive.

(2) Compare the control and Y-treated cells after the removal of drug at 24 hours, it was estimated that secretion of FN from Y-treated cells was reduced to over 50%.

(3) The amount of FN secreted by Y-treated cells at 24 hours is higher than those at 8 hours (before removal of Y) indicating that cells are still alive after Y-treatment.

Experiment 22 (F4)

Methods

Cells: ES2 cells were grew in RPMI 1640 medium over night before drug-treatment.

Drug-treatment: cells cultures were replaced with fresh RPMI medium containing Xanifolia-Y (10 ug/ml final concentration) or DMSO (as control) at 0 hour. At 2, and 18 hour, aliquot of culture medium was taken out for Fibronectin determination (Western blot method). Cell viability at 18 hours was determined by MTT assay. Cultures were replaced with RPMI medium with MTT and incubated for an hour. The formation of formazan was dissolved in DMSO and OD at 570 nm was measured.

Results (also see FIG. 40):
Over 95% of cells after 18 hours of Y-treatment were viable as determined by MTT assay.
Western Blots show a reduction of FN secretion by cells into culture medium after Y-treatment. Scan of FN Western bands (average 5 sets of blots) shows that there is a 40% reduction of FN secretion after 18 hours of Y-treatment.

Experiment 23(F5)

Methods:
Cells and Drug-treatment: same as previous experiments. After 7 or 24 hours, aliquot of culture medium was taken out for Fibronectin determination (Western blot method). Cell viability at 24 hours was determined by MTT assay.

Results:
93% and 85% of cells after 7 and 24 hours, respectively, of Y-treated cells was viable as determined by MTT assay.

Change in Fibronectin secretion during the first 7 hours of Y-treatment is not noticeable. However, after 24 hours, as compared with the control, the Fibronectin band of Y-treated samples is reduced. Based on same amount of live cells, the intensity of the immuno-bands were compared (per MTT O.D. unit). The scan of 3 pairs of blots shows a 31% reduction of Fibronectin band. Accordingly, these results indicate that Fibronectin secretion by cells reduce 31% after 24 hours of Y-treatment.

Experiment 24(F 7)

Effects of Paclitaxel on Fibronectin Secretion by ES2 Cells

Methods:
Cells: ES2 cells were grew in RPMI 1640 medium over night before drug-treatment. Drug-treatment: cells cultures were replaced with fresh RPMI medium containing DMSO (as control) [D]; Xanifolia-Y (10 ug/ml) [Y]; or Paclitaxel 10 or 50 ng/ml [T10, ro T50]. After 24 hours, aliquot of culture medium was taken out for Fibronectin determination (Western blot method). Cell viability at 24 hours was determined by MTT assay.

Results:
Based on the MTT units (cell basis) of treated cells and compared those with the DMSO control, 87%, 94% and 91% growth of Y, T10 and T50 cells, respectively, were viable after 24 hours of treatment.

The amount of Fibronectin secreted by cells into medium was determined by Western blot assay. The amount of Fibronectin secreted per cells basis was determined by dividing the Western-band intensity with the MTT unit.

By comparing with the DMSO control, ES2 cells treated with 10 ng/ml or 50 ng/ml Taxel secret 105% or 97%, respectively, of Fibronectin into medium during 24 hours of treatment. At the same time, Y-treated ES2 cells secreted 62% of control (a reduction of 38%).

Experiment 25(F 8)

Hey8A Cells Treated with Xanifolia-Y

Methods:
Cells: Hey8A (human ovarian carcinoma cells) were grew in RPMI 1640 medium to 90% confluent before drug-treatment. Drug-treatment: Cells cultures were replaced with fresh RPMI medium containing either DMSO (as control) [D1]; or Xanifolia-Y (10, 15, or 20 ug/ml) [Y1, Y2 and Y3]. Aliquot of medium was removed as 0 hours sample and no FN was detected at this time. After 24 hours, aliquot of culture medium was taken out for Fibronectin determination (Western blot method). Cell viability at 24 hours was determined by MTT assay. Cultures were replaced with RPMI medium (5 ml) with MTT and incubated for an hour. The formation of formazan was dissolved in DMSO and OD at 570 nm was measured.

Western Blot: Spent culture medium (0.6 ml) was mixed with SDS sample buffer (0.2 ml), boiled for 3 minutes before loading to SDS gel. Samples (60 ul/lane) were applied to a 6% SDS gel and electrophoresis was conducted with 100 volts for 2 hours. Protein was transferred to a nitrocellulose paper electrophoretically (30 min at 100 volts). The Western blot was incubated with the first antibody (mouse anti-FN, specific to human FN, SIGMA F0916) and second antibody (Anti-mouse IgG AP conjugated, Promega S3721). The immunobands were developed with BCIP/NBT color development system (Promega S3771).

Results:
After 24 hours of drug-treatment, cells with 15 ug/ml and 20 ug/ml were found dead (floating) and were not further proceeded. Cells with DMSO and 10 ug/ml Y were processed.

The MTT assay showed that the growths of cells with Y-treatment (10 ug/ml) are 83% of control.

The Western blot show that the band intensity of Y-treated samples (Y1) is much reduced compare to the DMSO control (D1)

The average band intensity after corrected with the MTT unit are: 1179 and 366, for DMSO control and Y-treated samples, respectively. Accordingly, Y-treated Hey8A cells secrete 31% Fibronectin (FN) as compared with the DMSO control, or a 69% inhibition.

Experiment 26(F 11)

Inhibition of Fibronectin Secretion by Xanifolia-Y in Human Lung Carcinoma Cells (H460)

Methods: please see Experiment 20.
Results: Lung cells (H460) are sensitive to Y in inhibition of FN secretion. Based on MTT results, cells are still viable at 20 ug/ml Y, but the inhibition of FN is over 60%.

Experiment 27(F 12)

Inhibition of Fibronectin Secretion by Xanifolia-Y in Bladder Carcinoma Cells (HTB-9)

Methods: please see Experiment 20.
Results:
The MTT assay showed that the growth of cells treated with 10 ug/ml Y reduced to 77%-91% compared to the DMSO control.

The Western blot shows that the FN band intensity of Y-treated samples are reduced. After corrected with the MTT unit (equivalent to cell mass) there is about 50% reduction of FN band intensity per cell mass.

These results indicate that Xanifolia-Y (10 ug/ml) inhibit 50% of FN secretion.

Experiment 28(F 13)

ES2 Cells Treated with Y and Beta-Escin

Methods: please see Experiment 20
Results:
The MTT assay showed that the growth of cells with Y, Es10 and Es20 are 89%, 90% and 82%, respectively as compared to the DMSO control.

The Western blot show that the FN band intensity of Es10 and Es20 samples are 93% and 52%, respectively, of DMSO control. The band intensity of Y10 sample is 51% of control.

These results show that 10 and 20 ug/ml of beta-escin inhibit 7% and 48%, respectively, of FN secretion. But 10 ug/ml of Y inhibits 49% FN secretion.

Results indicate that beta-escin also inhibits FN secretion but with half potency as Xanifolia-Y.

Experiment 29(F 14)

ES2 Cells Treated with Different Xanifolia-Ys

Methods: please see Experiment 20
Two experiments were done (FN14B and FN14C). Five gels per each experiment were run.
Results:
Except for AKOH-Y (the Y3 without diangeloyl group), all samples have some degrees of inhibition of FN secretion from ES2 cells. 80 ug/ml of AKOH-Y which is 4 times higher concentration used in others saponins (10 ug/ml), still have no effect on inhibition of FN secretion on ES2 cells.

| | ES2 cells | | | | |
|---|---|---|---|---|---|
| | β-ES-10 | X-10 | Y1-10 | Y3-10 | Y7-10 | AKOH-80 |
| % inhibition | 19 | 39 | 41 | 47 | 34 | No effect |

Conclusion:
It seems that saponins in general have effects in inhibition of Fibronectin secretion from ES2 cells. However, this experiment found that acylation of C21, 22 positions is important for the inhibition activity.

Experiment 30(F 23)

ES2 Cells Treated with 054

Methods: Please see Experiment 20.
Results: Based on these results, there is no inhibition of FN secretion in ES2 cells with 054 treatment at 40 ug/ml.

Experiment 31(F 24)

ES2 Treated with Y0 and Y5

Methods: please see Experiment 20.
Results: By comparing the immuno band's intensities of these samples the results of this experiment indicate that: (1) Y5 has same activity as Y3 for inhibition of FN secretion (both inhibit 68% at 10 ug/ml);
(2) Y0 is weaker as compare to Y3 for inhibition of FN secretion.(inhibit 34% at 10 ug/ml);
(3) Conclusion, both Y0 and Y5 have inhibition activity for FN secretion from ES2 cells.

Experiment 32(F 25, 26)

HepG2 Cells Treated with Ys

Methods: Please see Experiment 20.
Results: By comparing the immuno band's intensities of these samples (see table), it was found that at concentration of 10 ug/ml. X, ES, Y0, Y1, Y3, and Y5 have inhibition effect on Fibronectin secretion from HepG2 cells. Minimum or No effect was observed with Y7, Ach (10 ug/ml) and AKOH (80 ug/ml).

| | HepG2 | | | | | | |
|---|---|---|---|---|---|---|---|
| | β-ES-10 | X-10 | Y0-10 | Y1-10 | Y3-10 | Y7-10 | ACH-Y-30 |
| % inhibition | 44 | 42 | 40 | 33 | 48 | 10 | 21 |

Experiment 33(F 27, 29)

NCI-H460 Cells (Lung) Treated with Ys

Methods: please see Experiment 20

| | H460 | | | | | | |
|---|---|---|---|---|---|---|---|
| | β-ES-20 | X-20 | Y0-10 | Y1-10 | Y3-10 | Y7-10 | ACH-Y-20 |
| % inhibition | No effect | 37 | 22 | 13 | 19 | 18 | 28 |

Experiment 16 (F 28, 30)

HTB-9 Cells (Bladder) Treated with Ys

Methods: please see Experiment 20
(FN28, 30) Bladder

| | HTB-9 | | | | | | |
|---|---|---|---|---|---|---|---|
| | β-ES-10 | X-10 | Y0-10 | Y1-10 | Y3-10 | Y7-10 | ACH-Y-30 |
| % inhibition | 47 | 38 | 32 | 50 | 51 | 60 | No effect |

Experiment 34 (F31, 32)

T98G (Brain) Treated with Y2

Methods: please see Experiment 20

| | TG98G | | | | | | |
|---|---|---|---|---|---|---|---|
| | Y0-10 | Y1-10 | Y3-10 | Y7-10 | X-20 | ES-20 | ACH-20 |
| % inhibition | 22 | 40 | 26 | 24 | 52 | 66 | 30 |

Experiment 18(F 33)

SK-MEL-5 Cells Treated with Ys

Methods: please see Experiment 20

| | SK-MEL-5 | | | | | | |
|---|---|---|---|---|---|---|---|
| | β-ES-20 | X-20 | Y0-10 | Y1-10 | Y3-10 | Y7-10 | ACH-Y-30 |
| % inhibition | 17 | 15 | 27 | 10 | 11 | No effect | 21 |

Experiment 35 (F 20)

Determination of Cellular Contents and Secretion of FN After Y3-Treatment

Methods:
Cells: ES2 (human ovarian carcinoma cells) were grew in RPMI 1640 medium. 1.5 million cells were seeded in a T25 flask and grown for 24 hours before drug-treatment. Drug-treatment: Cells cultures were replaced with fresh RPMI medium containing either 2.5 ul of DMSO (as control) [D]; or 10 ug/ml (final concentration) of Xanifolia-Y3 [Y]. After 24 hours, aliquot of culture medium was taken out for Fibronectin determination (Western blot method). The attached cells were suspended in 1 ml of SDS sample buffer (cell-extract).

Western Blot: Spent culture medium (0.6 ml) was mixed with SDS sample buffer (0.2 ml), and the cell-extract was boiled for 3 minutes before loading to SDS gel. Samples (80 ul/lane) were applied to a 6%-10% SDS gel and electrophoresis was conducted with 100 volts for 2 hours. Protein was transferred to a nitrocellulose membrane electrophoretically (30 min at 100 volts). The nitrocellulose blot was blocked with 5% non-fat dry milk in PBS (1-2 hours). The blot was then incubated with the first antibodies (mouse anti-FN, specific to human FN, SIGMA F0916 and mouse anti-beta actin, SIGMA A5316) and second antibody (Anti-mouse IgG AP conjugated, Promega S3721). The immuno-bands were developed with BCIP/NBT color development system (Promega S3771). Determination of Western band intensity: The band-images of Western blot were captured with a digital camera (3-5 pictures were taken per gel) and the intensity of bands was determined using "Image J" software.

FN concentrations were normalized with the cellular beta-Actin concentrations. Fibronectin secreted into medium and inside Y-treated cells were determined and compare to controls (DMSO-treated cells).

Results: This experiment shows that (1) there is a 46% reduction (54% of control) of FN secretion after Y-treatment and (2) the FN cellular content decrease 70% (30% of control) after the Y-treatment; (3) there is no change of cellular beta-aecin concentration after the Y-treatment.

Experiment 36

Animal Study

Athymic Nu/Nu mice (2-3 months old) were transplanted sc with ES2 (human ovarian cancer) cells.
Five days after the transplant (day one), mice were divided into two groups (H and J) with two animals in each group.
Group H: On days 1-5, and 8-10 mice received daily drug administration of Xanifolia-Y, by i.p. route at dose of 2.5 mg/kg.
Group J mice received no drug-treatment.
Result:
Group H: Mice received drug-treatment, tumor size is 10 mm in 10 days
Group J: Mice received no drug-treatment, tumor size is 18 mm in 10 days
The tumor size is 45% smaller in mice with drug than the mice with no drug in 10 days period.

Experiment 37

Animal Study

Methods
Athymic Nu/Nu mice (5-6 weeks old) are divided into three groups (0, P and Q) with 5-6 animals in each group.
On day 0, all mice were transplanted intra-peritoneally with ES2 (human ovarian cancer) cells.
Group O: animals received no drug-treatment.
Group P: On days 4-8, 11-15, 18-22, 25-29, 32-36, 39-43, animals received daily drug administration of Xanifolia-Y, by i.p. route at dosage of 2.5 mg/kg
Group Q: On days 10-15, 18-22, 25-29, 32-36, 39-43, animals received daily drug administration of Xanifolia-Y, by i.p. route at dosage of 2.5 mg/kg.
Result:
The median survival time of tumor bearing mice without drug-treatment is 24 days. The median survival time of tumor bearing mice with drug-treatment starting on day 4 after tumor inoculation is 58 days (extension of life span of 141%); and The median survival time of tumor bearing mice with drug-treatment started on day 10 after tumor inoculation is 31 days (extension of life span of 29%).

Experiment 38

Inhibition of Cell Adhesion by Xanifolia-Y

Methods and Results: ES2 or Hey8A cells were plated in T25 flasks with medium containing 5 ug/ml of Xanifolia-Y. Cultures were incubated for 5 hours. Attached cells were removed from flasks by trypsinization and the amounts were counted. Compare to no drug controls, 86±4% of ES2 cells and 67±8% of Hey8A cells were found attached to flasks under this condition. At 5 ug/ml Xanifolia-Y, over 90% of unattached cells are alive as determined by the trypan Blue exclusion assay and by their ability to re-attach to flasks when plating in medium without Xanifolia-Y. However, with 10 ug/ml Xanifolia-Y, less than 40% of cells attached to flasks and many of them are dead cells. This experiment shows that Xanifolia-Y inhibits cells adhesion process.

Experiment 39

Increase Synthesis of Angiopoietin-2 in ES2 Cells by Xanifolia-Y

Methods: ES2 (human ovarian carcinoma cells) were grew in RPMI 1640 medium. 4.5 million cells were seeded in a T75 flask and grown for 24 hours before drug-treatment.
Drug-treatment: Cells cultures were treated with 5, 10 and 15 ug/ml (final concentration) of Xanifolia-Y3 [Y3-5, Y3-10, Y3-15]. or DMSO control [D-10]. After 24 hours, cells were suspended in 1 ml of SDS sample buffer (cell-extract). Samples (80 ul/lane) were applied to a 10% SDS gel and electrophoresis was conducted with 100 volts for 2 hours. Protein was transferred to a nitrocellulose membrane electrophoretically. The nitrocellulose blot was blocked with 5% non-fat dry milk in PBS. The blot was then incubated with the first antibodies (goat anti-Ang2, SIGMA A0851) and second antibody (donkey anti-goat AP conjugated, Promega V115A). The immuno-bands were developed with BCIP/NBT color development system (Promega S3771).

Results: As shown in this Western Blot, a Angiopoietin-2 immuno-band was observed in extract from cells treated with 15 ug/ml Xanifolia-Y. No or minimal immuno-band of Angiopoietin-2 was observed in control and low concentration of xanifolia-Y. This result indicates that treatment of Xanifolia-Y in ES2 cells increase the cellular content (or synthesis) of Angiopoietin-2. These results corroborate the results of Microarray studies.

Experiment 40

Removal of the Sugar Moiety from Saponin by Acid Hydrolysis

Method: 15 mg saponin was dissolved in 1 ml of Methanol. 1 ml of 2N HCl was then added. The mixture was refluxed in 80 C water bath for 5 hours. The solution was then neutralized by adding 2 ml of 1N NaOH (to final pH 4-6). The aglycone was then extracted with ethylacetate 3 ml×2. The extracts were collected and pooled. Further isolation of aglycone (sugar-removed saponin) was achieved by HPLC with isocratic elution of 80-100% acetonitrile.

Experiment 41

Removal of the Acyl Group by Alkaline Hydrolysis

Method: 20 mg of saponin was dissolved in 0.5 ml of 1M NaOH. The solution was incubated in 80 C water bath for 4 hours. It was cooled to room temperature before neutralized with 0.5 ml 1 N HCl (adjust pH to about 3). The mixture was extracted with 2 ml 1-butanol 3 times. The butanol fractions were collected and lyophilized. The hydrolyzed saponin with further purified with HPLC in a C-18 column eluted with 25% acetonitrile.

Experiment 42

Analysis of Genesis of Blood Vessel in Xenograft Tumor Treated with Compound Y

Method: Athymic Nu/Nu mice (5-6 weeks old) are divided into two groups (1 and 2) with 5 animals in each group. On day 0, all mice were transplanted intra-peritoneally with one million ES2 (human ovarian cancer) cells. Animals were randomly divided into two groups:

Group 1: Control group. Animals did not receive drug-treatment.

Group 2: Drug-treatment group. On days 10-15 and 18-22, animals received daily drug administration of Xanifolia-Y, by i.p. route at dosage of 2.5 mg/kg.

Results: Animals showed high tumor burden after 18 days. Animals with high tumor burden were euthanized and solid tumors were taken out from these mice (between 18-27 days). Tumor tissues fixed with formalin at room temperature. The fixed tissues were sectioned and stained with Haematoxylin and eosin (H&E). The red blood cells inside the micro blood vessels were identified under a microscope. FIG. 44 shows that more blood vessels were observed in the control Group1 than those in the drug-treated Group 2

Experiment 43

Determination of Cell Growth of *Leishmania* Parasites by MTT Assay

Method: *Leishmania* parasites (*Leishmania major*: MRHO/SU/59/P/LV39) were grown in culture medium in a T75 flask at room temperature. Promastigotes of *Leishmania major* (approximately 40 million per ml) were used in the experiment. 1.2 ml cell culture was transferred to a well of the 24-wells plate. Saponin Y10 (0.2 ml in medium) with different concentrations (final 6.25-200 ug/ml) was added to culture and cells were grown for 1-5 days at room temperature. At the end of drug-treatment, 150 ul of MTT (5 mg/ml in PBS) was added to each well and incubated for 4 hours. Formazan formed in cells was dissolved with DMSO and the OD at 490 nm was determined by an ELISA reader.

Results: this experiment shows that Y10 is cytotoxic to *Leishmania Major* (promastigotes) with IC50 approximately equal to 15 ug/ml. Experiments are repeated with Y, ACH-Y, AKOH-Y, Mb5, ACH-Mb5, AKOH-Mb5 and Ba1.

Experiment 44

Adding the Acyl Group to Triterpene by Esterification

Method: 40 mg of triterpene core (fraction IV) was dissolved in 1 ml pyridine in a 50 ml tube. Reaction is started by adding 0.2 ml of acyl chloride (including Tigloyl chloride, angeloyl chloride or benzoyl chloride). The mixture is stirred for 3 days at room temperature. At the end of reaction, 3 ml of NaHCO3 is slowly added to the reaction mixture. The solution is then extracted 3 times with 10 ml of ethyl acetate which is then evaporated under vacuum and at 45 C and lyophilization. The active esterification products are purified with HPLC.

Experiment 45

Adding the Acyl Group to Triterpene by Esterification

Method: 40 mg of triterpene core (fraction IV) was dissolved in 1 ml pyridine in a 50 ml tube. Reaction is started by adding 0.2 ml of acyl chloride (including Tigloyl chloride, angeloyl chloride or benzoyl chloride). The mixture is stirred for 0.5 hr, 1 hr, 2 hrs, 3 hrs, 4 hrs, 8 hrs or 1 day at room temperature. At the end of reaction, 3 ml of NaHCO3 is slowly added to the reaction mixture. The solution is then extracted 3 times with 10 ml of ethyl acetate which is then evaporated under vacuum and at 45 C and lyophilization. The active esterification products are purified with HPLC.

What is claimed is:

1. A compound for modulating the secretion or expression of adhesion proteins or angiopoietins of cells, for inhibiting the metastasis of cancer cell in a subject, wherein the compound is selected from the following:

a) A compound having structure (ACH-Z4):

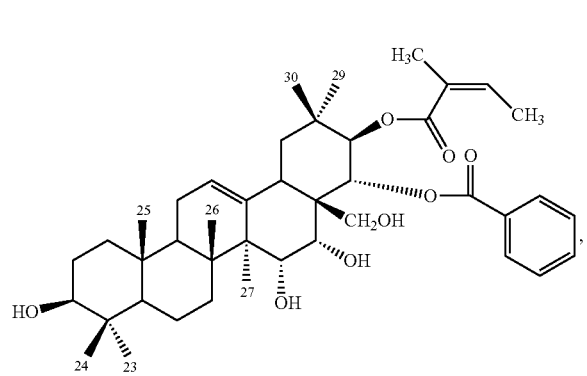

e) A compound having structure (ACH-Y7):

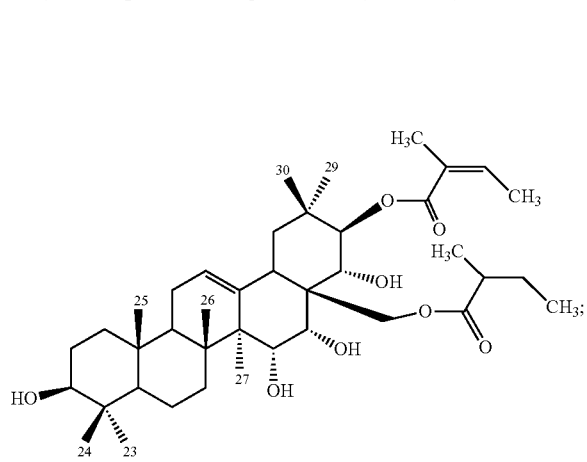

f) A compound having structure (ACH-Y0):

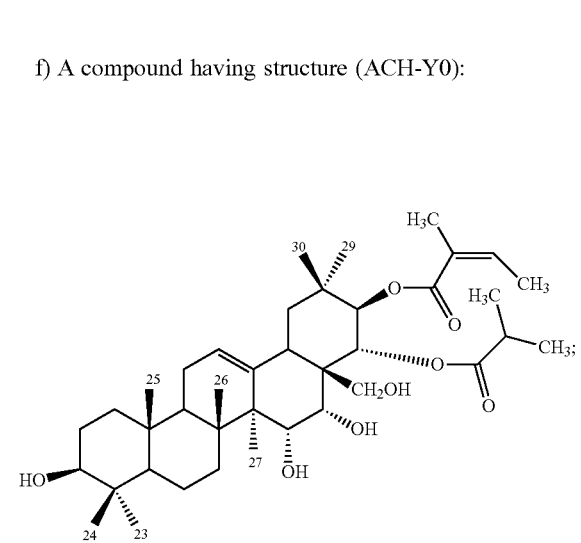

h) A compound having structure (ACH-X):

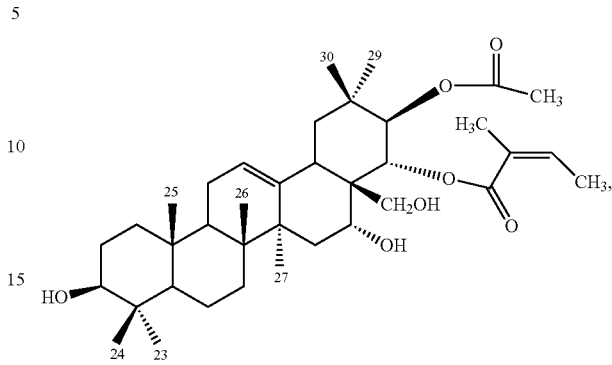

i) A compound having structure (ACH-Mb5):

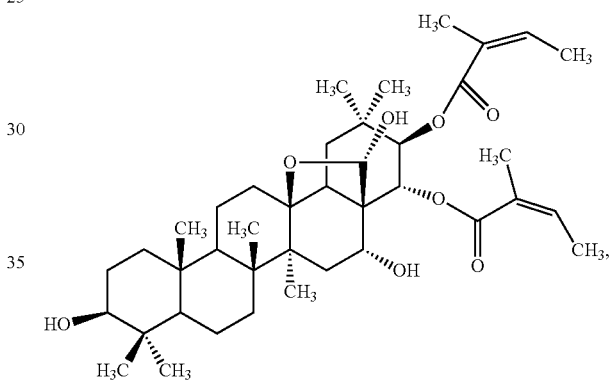

j) A compound having structure (ACH-Mb12):

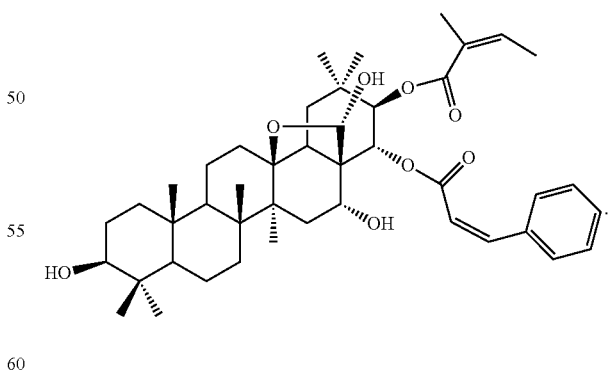

2. A method for modulating the secretion or expression of adhesion proteins or angiopoietins of cells, or for inhibiting the metastasis of cancer cells, in a subject, comprising contacting said subject with an effective amount of a compound selected from the following:

119
a) A compound having structure (ACH-Z4):
e) A compound having structure (ACH-Y7):
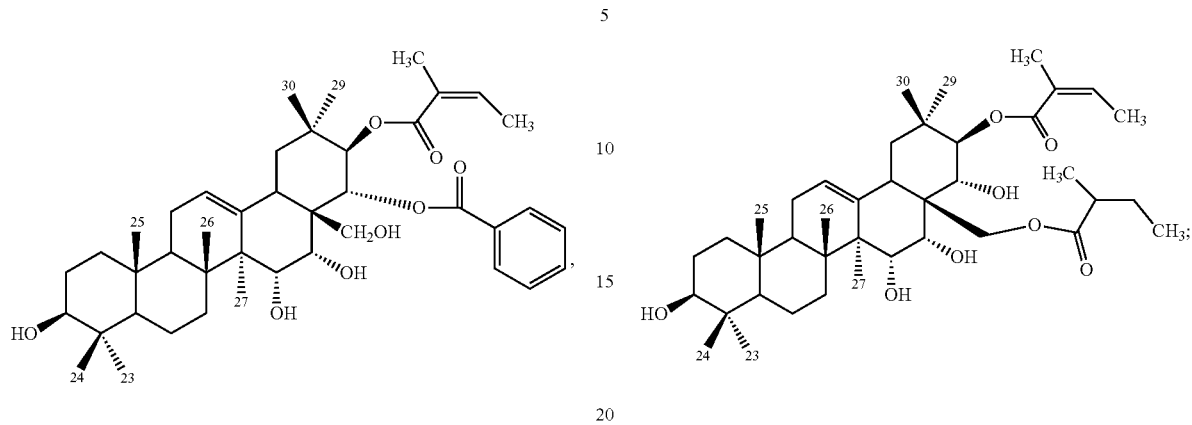
b) A compound having structure (ACH-Y10):
f) A compound having structure (ACH-Y0):
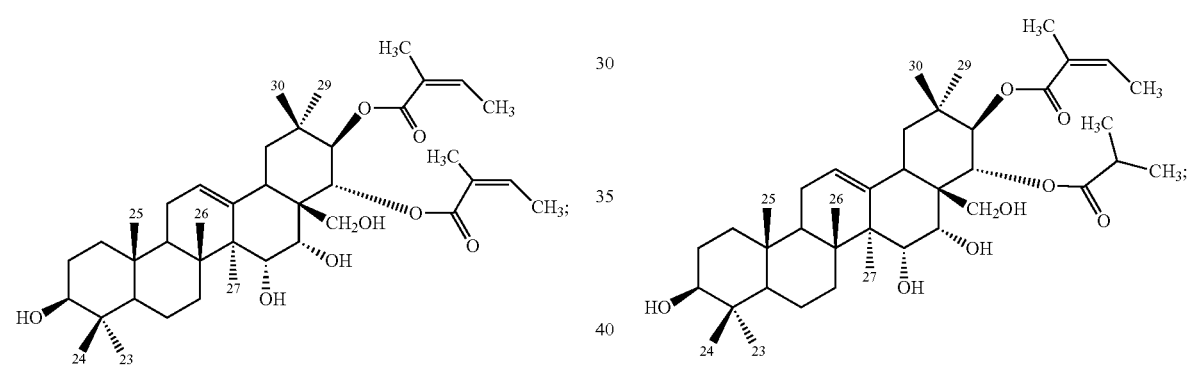
d) A compound having structure (ACH-Y8):
g) A compound having structure (ACH-E):
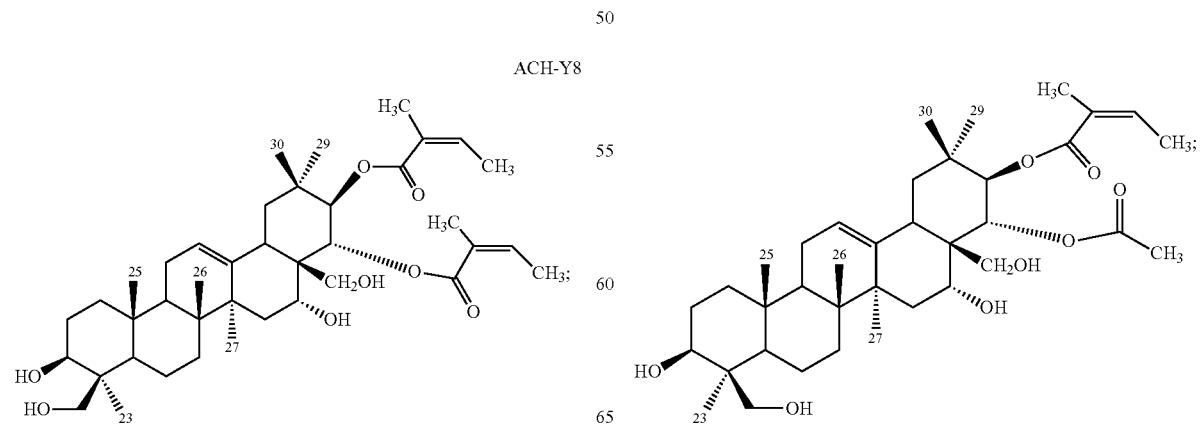

h) A compound having structure (ACH-X):

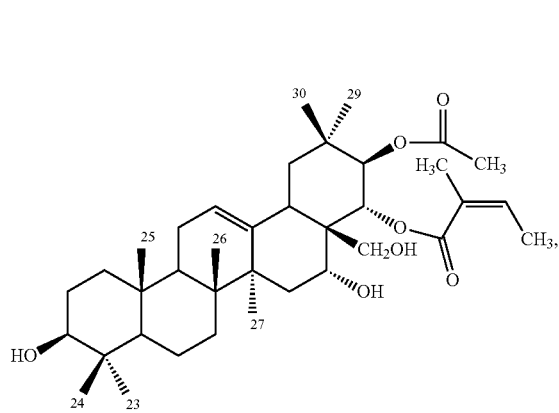

i) A compound having structure (ACH-Mb5):

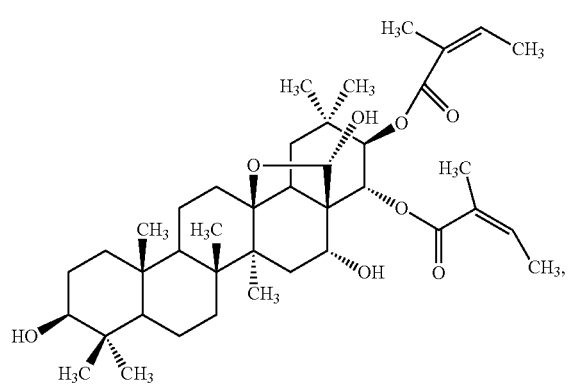

j) A compound having structure (ACH-Mb12):

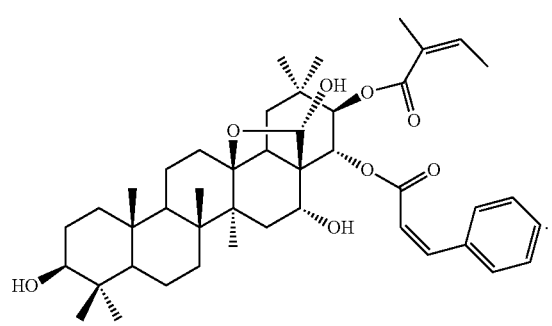

a) A compound having structure ((ACH-Y)):

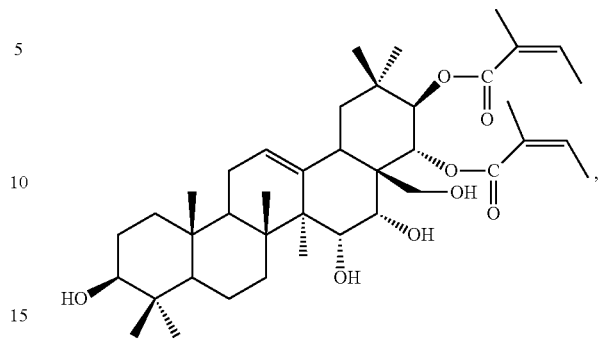

b) A compound having structure (ACH-Z4):

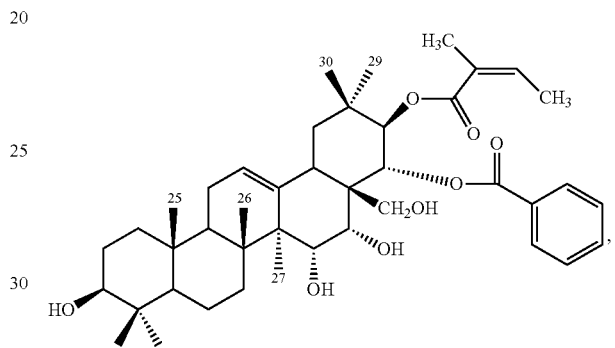

c) A compound having structure (ACH-Y10):

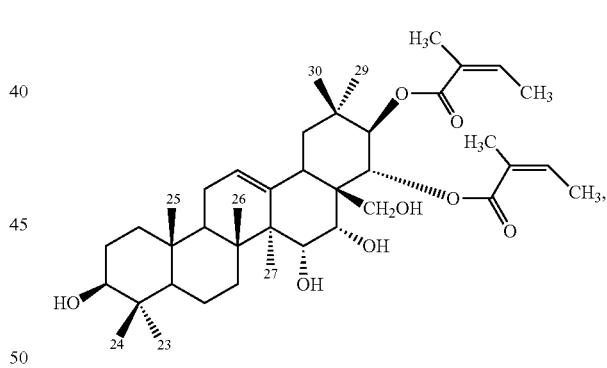

d) A compound having structure (ACH-Y2):

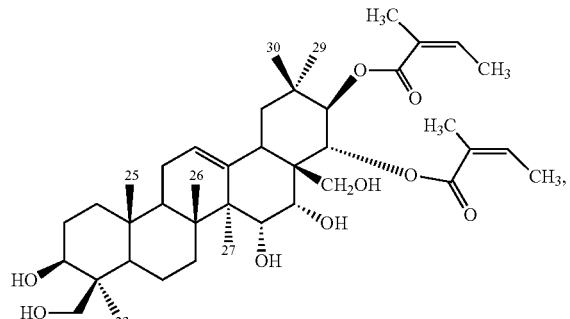

3. A method for treating parasites in a subject, comprising contacting said subject with an effective amount of compound, or its salt, or ester thereof, selected from the following:

e) A compound having structure (ACH-Y8):

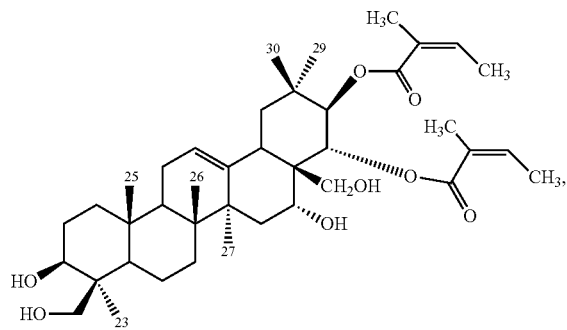

f) A compound having structure (ACH-Y7):

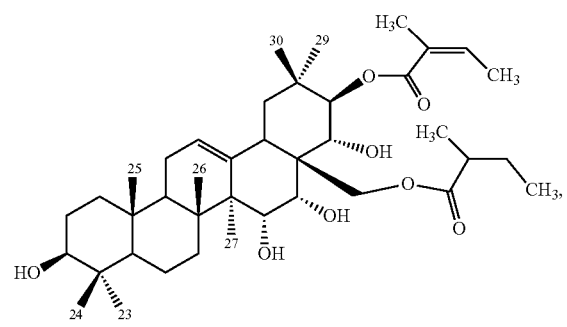

g) A compound having structure (ACH-Y0):

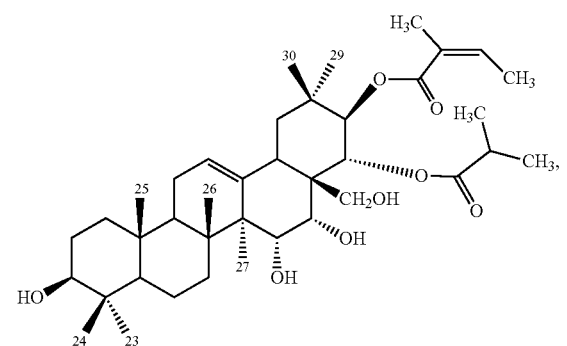

h) A compound having structure (ACH-E):

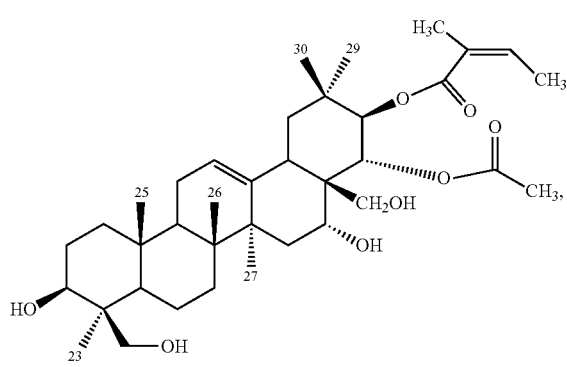

i) A compound having structure (ACH-X):

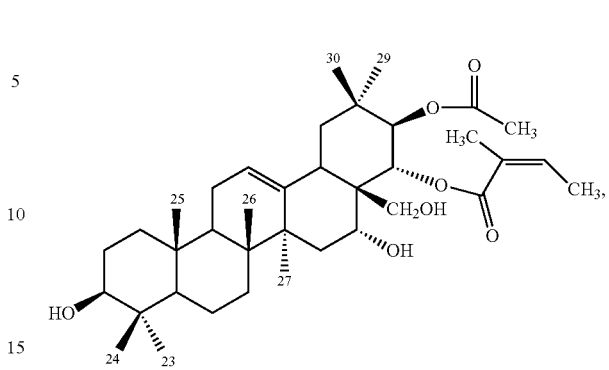

j) A compound having structure (ACH-Mb5):

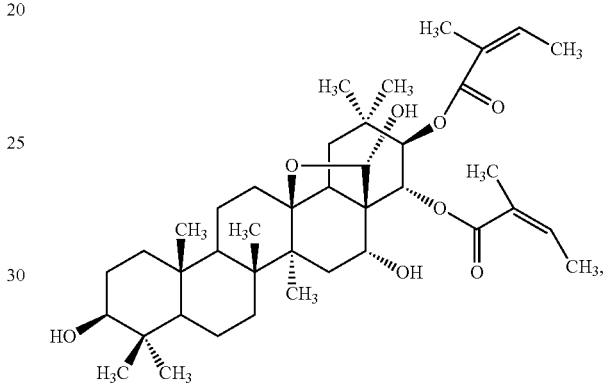

k) A compound having structure (ACH-Mb12):

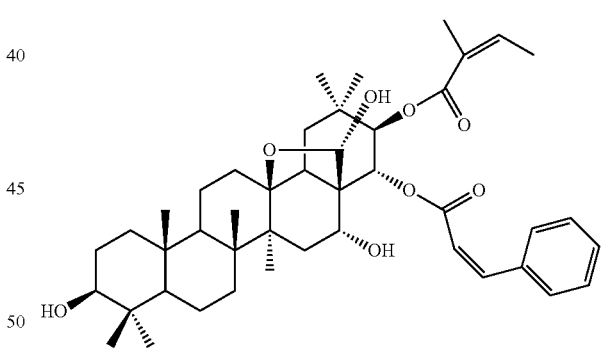

4. The method of claim 2 for inhibiting the metastasis of cancer cells, wherein the compound modulates the expression of: ABL2, ADAMTS1, AKR1C3, AMIGO2, ANGPT2, ANKRD11, AP2B1, APEH, APLP2, ARL10C, ARMC4, ARMCX1, ARMCX6, ARNTL2, ATF3, ATP6V0E, ATP6V1B2, ATP6V1C1, ATP6V1C1, BCL2A1, BCL6, BRI3, BTD, C14orf109, C14orf78, C17orf32, C6orf65, C9orf10, C9orf103, CAD, CAV1, CAV2, CBLL1, CCL20, CD33L3, CEBPB, CEP4, CFH /// CFHL1, CHRDL1, CITED2, CLDN14, CLN8, CLTA, CNAP1, COG6, COL18A1, COL4A2, COL5A1, COL5A2, COL6A3, COPG, CPM, CPNE3, CPSF1, CSRP2BP, CSTB, CTNS, CXCL2, DDB1, DDIT3, DDX20, DKFZP564I1171, DKFZP586J0619, DUSP10, DUSP10, DYRK3, EEF2K, EFEMP1, EMP1, EVC, EVI2A, EXT2, FAM62A, FER1L3, FLJ14466, FLNA, FN1, GANAB, GDF15, GEM, GNPDA1, GPAA1, GPC6, GPNMB, GPNMB, GUSB, H2AFV, H2AFV, HDAC9, HDLBP, HECW2, HMGA2, HMOX1, HSDL2, HSPBAP1, HSPC196, HYOU1, IDS, IGFBP3, IKBKAP, INSIG1, IPO4, IRS2, JAG1, KDELR3, KIAA0251, KIAA0586, KIAA1211, KIAA1462, KIAA1706, KIAA1754, KRT18, KRT7, KRTAP4-7, LAMP2, LEPR, LEPREL1, LHFPL2, LIF, LOC286044, LOC339229, LOC90693, LRRC8E, MAFG, MAGED2, MCTP1, MGC16291, MGC19764, MGC5618, MRPS30, MRPS31, MTERFD3, MYH9, NAGA, NAV2, NCSTN, NEK9, NEU1, NFKBIZ , NMT2, NPC2, NSUN5C, NTNG1, NUP188, OACT2, OS9P4HA1, P8, PALM2-AKAP2, PALM2-AKAP2, PARVA, PBX2, PDE4DIP, PDIA4, PDIA6, PEG10, PHF19, PIK4CA, PLEKHM1, PLOD1, PLOD2, PPP1R15A, PPP1R15A, PRKDC, PRSS23, PRSS23, PSEN2, PSMD1, PTPRF, PTPRJ, RAB32, RAB9A, RG9MTD1, RGS4, RHOQ, RND3, RNF25, RNPEP /// UBE2V1 /// Kua /// Kua-UEV, RNU17D, ROBO4, RRAGC, RRS1, SEC31L1, SERPINB2, SERPINB7, SESN2, SGEF, SGSH, SKIV2L, SLC25A21, SLC35A3, SLC3A2, SMARCA1, SNAPC1, SNF1LK, SPOCD1, SPTAN1, SQSTM1, ST3GAL6, STC2, STX3A, TFPI2, TGFBI, TGM2, THRAP1, TLN1, TMEM60, TNFAIP3, TRIB3, TRIO, TSC2, UAP1L1, UBAP2L, UPP1, URB, USP11, USP5, VDR, WDR4, YTHDF2, ZCCHC9, ZDHHC20, ZFHX1B, ZNF185, ZNF278, ZNF690, ZNF697, ITGAV, LAMA4, LAMB2, LAMC1, LAMB1, LAMA5, LAMC1, LAMA2, LAMB1, LAMAS, SCAMP1, TICAM2, CAMK2B, DL1, ICAM3, CEECAM1, ICAM5, CAMK1G, CAMSAP1, MCAM, CAMTA1, CKN1, ALCAM, DCAMKL2, CEACAM3, CAMK2D, CAMK2B, SCAMP5, CAMK4, NCAM1, CAMK2G, MYH10, MYO1D, MYO5A, MYO1C, MYLK, MYO6, MYLC2PL, MYO10, BECN1, MYO1E, TPM3, M-RIP, MYO1B, MYL6, MYOHD1, BECN1, TPM4, MYLK, MYOHD1, LOC221875, LOC402643, MYO15B, LOC129285, MYH11, MYO9B, CTNNAL1, CDH13, CDH12, CTNNB1, CDH5, CTNND1, CDH2, PCDHB16, CTNNA1, CELSR2, PCDHB6, PCDHB7, CTNND2, PCDHGC3, PCDHGB4, PCDHGA8, PCDHGA12, PCDHGC5, PCDHGC4, PCDHGB7, PCDHGB6, PCDHGB5, PCDHGB3, PCDHGB2, PCDHGB1, PCDHGA11, PCDHGA10, PCDHGA9, PCDHGA7, PCDHGA6, PCDHGA5, PCDHGA4, PCDHGA3, PCDHGA2, PCDHGA1, CTNND1, CDH23, PCDHB12, PCDHB10, PCDH18, CDH20, PCDH9, PCDHGA12, PCDHGA11, PCDHGA10, PCDHGA6, PCDHGA5, PCDHGA3, PCDH7, CDH18, CDH6, CCBE1, COL10A1, COL12A1, COL13A1, COL1A1, COL21A1, COL4A1, COL4A5, COL4A6, COL6A1, COL6A2, COL9A1, MMP9, P4HA1, P4HA2, P4HB, PCOLCE, PCOLCE2, PCOTH, PLODS, CIB1, ILK, ITGA2, ITGA3, ITGA4, ITGA6, ITGAV, ITGB1, ITGB1BP1, ITGB2, ITGB5, ITGBL1, TNC, EMILIN1, ICAM1, HSPG2, HPSE, HS2ST1, or SDC2.

5. The compound of claim 1, said compound having structure (ACH-Z4):

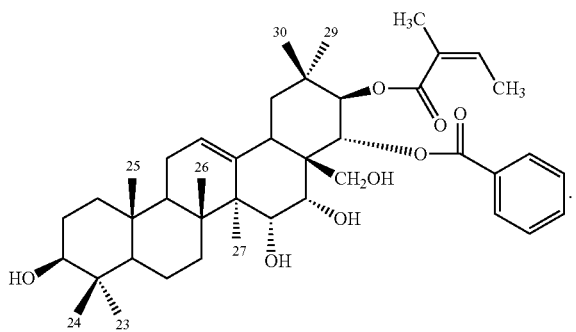

6. The compound of claim 1, said compound having structure (ACH-Y7):

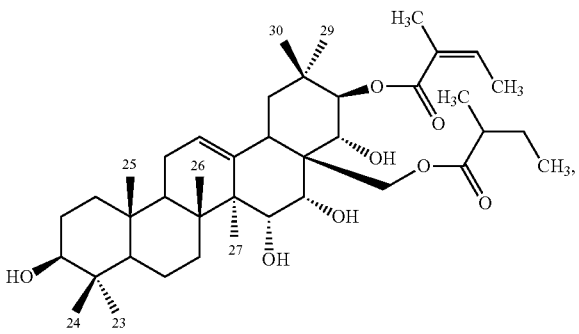

or structure (ACH-Y0):

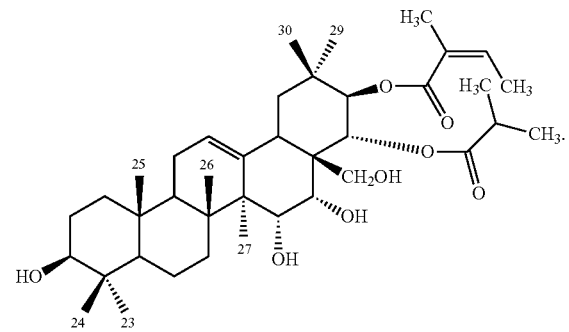

7. The compound of claim 1, said compound having structure (ACH-X):

8. The compound of claim 1, said compound having structure (ACH-Mb5):

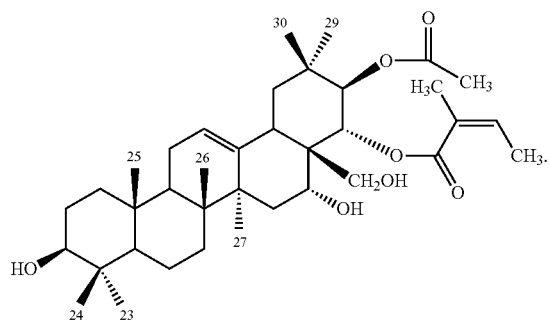

9. The compound of claim 1, said compound having structure (ACH-Mb12):

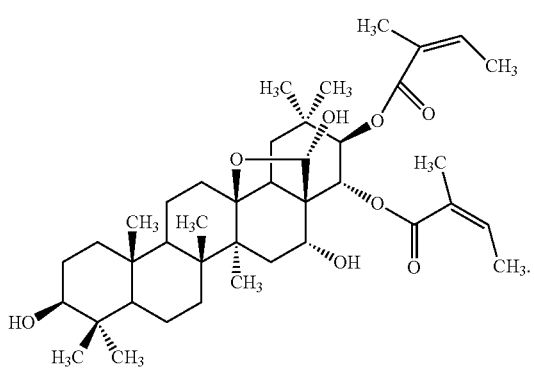

10. The method of claim 2, wherein the compound has structure (ACH-Z4):

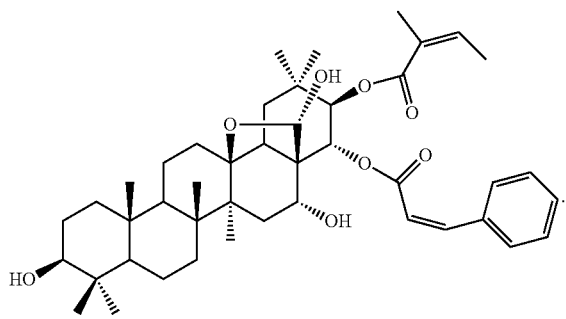

11. The method of claim 2, wherein the compound has structure (ACH-Y10):

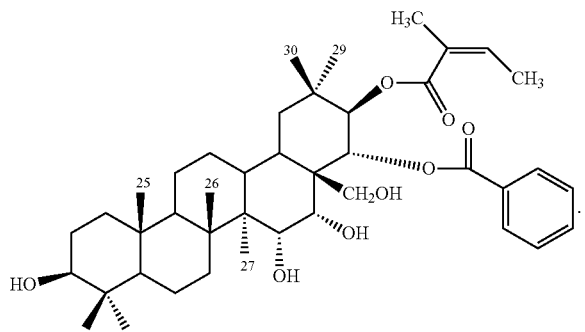

12. The method of claim 2, wherein the compound has structure (ACH-Y8):

ACH-Y8

13. The method of claim 2, wherein the compound has structure (ACH-Y7):

14. The method of claim 2, wherein the compound has structure (ACH-Y0):
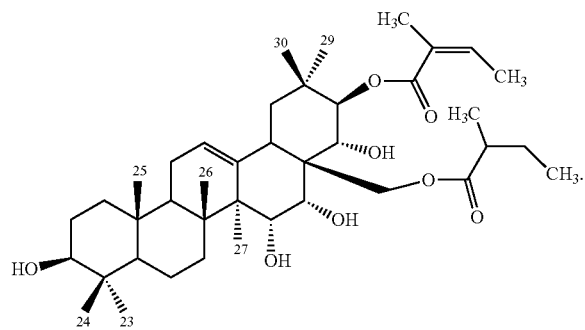
15. The method of claim 2, wherein the compound has structure (ACH-E):
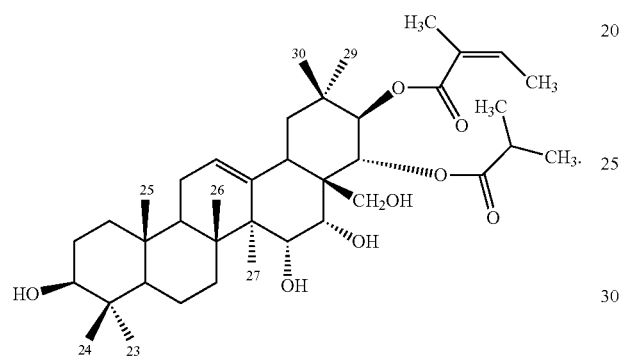
16. The method of claim 2, wherein the compound has structure (ACH-X):
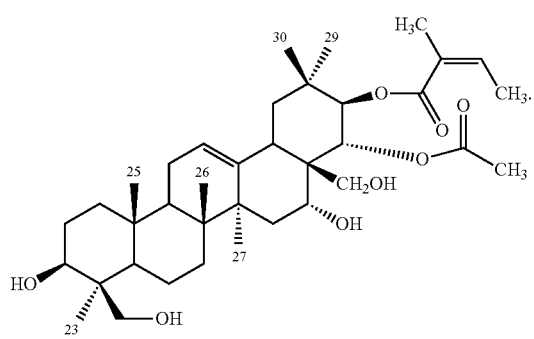
17. The method of claim 2, wherein the compound has structure (ACH-Mb5):
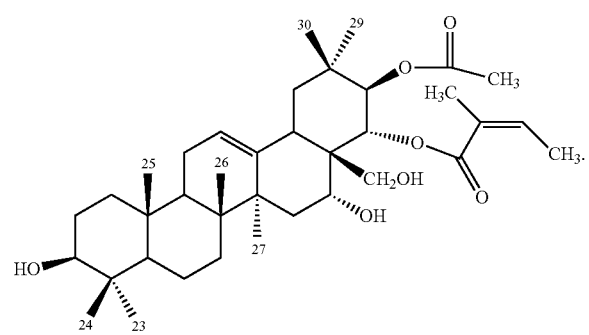
18. The method of claim 2, wherein the compound has structure (ACH-Mb12):
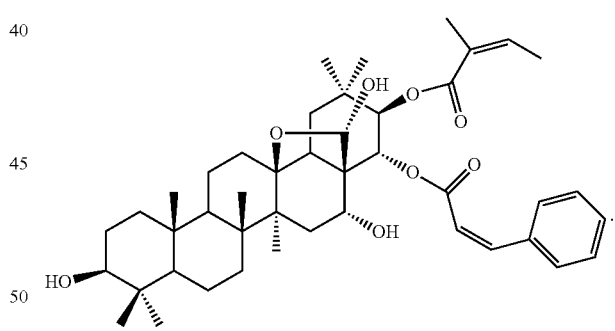
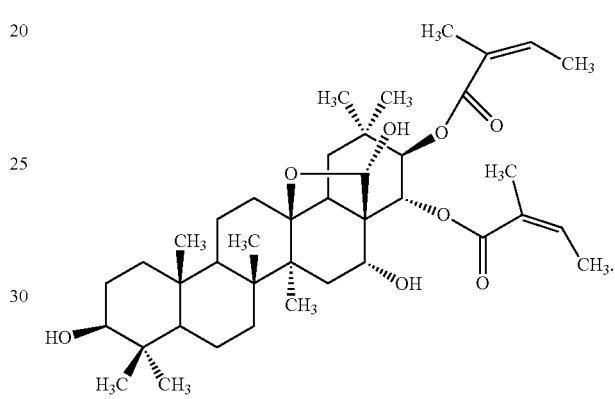
* * * * *